United States Patent
Putnam et al.

(10) Patent No.: US 9,651,568 B2
(45) Date of Patent: May 16, 2017

(54) METHODS AND SYSTEMS FOR EPI-FLUORESCENT MONITORING AND SCANNING FOR MICROFLUIDIC ASSAYS

(71) Applicant: CyVek, Inc., Wallingford, CT (US)

(72) Inventors: Martin A. Putnam, Cheshire, CT (US); Jeffrey T. Branciforte, Hartford, CT (US); Charles O. Stanwood, Durham, CT (US)

(73) Assignee: CyVek, Inc., Wallingford, CT (US)

( * ) Notice: Subject to any disclaimer, the term of this patent is extended or adjusted under 35 U.S.C. 154(b) by 180 days.

(21) Appl. No.: 14/479,290

(22) Filed: Sep. 6, 2014

(65) Prior Publication Data

US 2014/0377852 A1     Dec. 25, 2014

Related U.S. Application Data

(63) Continuation-in-part of application No. PCT/US2013/030052, filed on Mar. 8, 2013, and a
(Continued)

(51) Int. Cl.
*G01N 33/00* (2006.01)
*G01N 35/00* (2006.01)
(Continued)

(52) U.S. Cl.
CPC .. *G01N 35/00029* (2013.01); *B01L 3/502738* (2013.01); *G01N 21/6458* (2013.01);
(Continued)

(58) Field of Classification Search
CPC ................ G01N 35/29; G01N 21/6458; B01L 2200/021; B01L 2300/631; B01J 2219/286
See application file for complete search history.

(56) References Cited

U.S. PATENT DOCUMENTS

| 3,555,143 A | 1/1971 | Axen et al. |
| 3,867,517 A | 2/1975 | Ling |

(Continued)

FOREIGN PATENT DOCUMENTS

| CA | 1189449 | 6/1985 |
| CN | 1173776 | 11/2004 |

(Continued)

OTHER PUBLICATIONS

Chaudhury and Whitesides, 1991,"Direct Measurement of Interfacial Interactions Between Semispherical Lenses and Flat Sheets of Poly(dimethylsiloxane) and Their Chemical Derivatives", p. 1021:Interaction between Oxidized PDMS Surfaces.

(Continued)

*Primary Examiner* — Sam P Siefke
(74) *Attorney, Agent, or Firm* — McCormick, Paulding & Huber LLP

(57) ABSTRACT

An operating and reading instrument for performing an assay employing a portable microfluidic assay cartridge, the instrument comprising a translatable table under automated control, the translatable table carrying a receiving region for the portable cartridge and carrying a port system connectable to the cartridge that includes at least one remotely automated valve carried by the translatable table, the valve arranged to apply pressurized flowable substance at selected times to the cartridge while the cartridge is on the translatable table.

20 Claims, 146 Drawing Sheets

Related U.S. Application Data continuation-in-part of application No. PCT/US2013/033610, filed on Mar. 22, 2013, and a continuation-in-part of application No. 13/427,857, filed on Mar. 22, 2012, now Pat. No. 9,216,412, and a continuation-in-part of application No. 13/511,593, filed as application No. PCT/US2010/057860 on Nov. 23, 2010, now Pat. No. 9,229,001.

(60) Provisional application No. 61/608,570, filed on Mar. 8, 2012, provisional application No. 61/754,377, filed on Jan. 18, 2013, provisional application No. 61/465,688, filed on Mar. 22, 2011, provisional application No. 61/263,572, filed on Nov. 23, 2009.

(51) Int. Cl.
  *G01N 21/64* (2006.01)
  *B01L 3/00* (2006.01)

(52) U.S. Cl.
  CPC ............. *B01J 2219/00286* (2013.01); *B01J 2219/00522* (2013.01); *B01J 2219/00585* (2013.01); *B01J 2219/00596* (2013.01); *B01L 3/502707* (2013.01); *B01L 2200/021* (2013.01); *B01L 2200/025* (2013.01); *B01L 2200/028* (2013.01); *B01L 2200/0631* (2013.01); *B01L 2300/0636* (2013.01); *B01L 2300/087* (2013.01); *B01L 2300/0816* (2013.01); *B01L 2300/0838* (2013.01); *B01L 2300/1805* (2013.01); *B01L 2400/049* (2013.01); *B01L 2400/0487* (2013.01); *B01L 2400/0655* (2013.01); *G01N 2035/00039* (2013.01); *G01N 2035/00108* (2013.01); *G01N 2035/00752* (2013.01)

(56) References Cited

U.S. PATENT DOCUMENTS

| | | |
|---|---|---|
| 3,876,376 A | 4/1975 | Bauman et al. |
| 3,939,350 A | 2/1976 | Kronick et al. |
| 4,222,744 A | 9/1980 | McConnell |
| 4,254,096 A | 3/1981 | Monthony et al. |
| 4,368,047 A | 1/1983 | Andrade et al. |
| 4,425,438 A | 1/1984 | Bauman et al. |
| 4,447,546 A | 5/1984 | Hirschfeld |
| 4,517,288 A | 5/1985 | Giegel et al. |
| 4,690,907 A | 9/1987 | Hibino et al. |
| 4,716,121 A | 12/1987 | Block et al. |
| 4,717,545 A | 1/1988 | Morris |
| 4,797,259 A | 1/1989 | Matkovich et al. |
| 4,820,490 A | 4/1989 | Morris |
| 4,844,869 A | 7/1989 | Glass |
| 4,857,453 A | 8/1989 | Ullman et al. |
| 4,923,819 A | 5/1990 | Fernandez et al. |
| 5,004,923 A | 4/1991 | Hillman et al. |
| 5,009,998 A | 4/1991 | Chow et al. |
| 5,041,181 A | 8/1991 | Brackett et al. |
| 5,118,608 A | 6/1992 | Layton et al. |
| 5,164,598 A | 11/1992 | Hillman et al. |
| 5,296,375 A | 3/1994 | Kricka et al. |
| 5,302,349 A | 4/1994 | Dandliker et al. |
| 5,304,487 A | 4/1994 | Wilding et al. |
| 5,311,275 A | 5/1994 | Taniguchi et al. |
| 5,376,252 A | 12/1994 | Ekstrom et al. |
| 5,376,522 A | 12/1994 | Takiguchi et al. |
| 5,427,946 A | 6/1995 | Kricka et al. |
| 5,500,350 A | 3/1996 | Baker et al. |
| 5,508,200 A | 4/1996 | Tiffany et al. |
| 5,512,151 A | 4/1996 | Hayamizu et al. |
| 5,517,778 A | 5/1996 | Simson |
| 5,534,328 A | 7/1996 | Ashmead et al. |
| 5,593,290 A | 1/1997 | Greisch et al. |
| 5,622,871 A | 4/1997 | May et al. |
| 5,624,850 A | 4/1997 | Kumar et al. |
| 5,637,469 A | 6/1997 | Wilding et al. |
| 5,725,363 A | 3/1998 | Bustgens et al. |
| 5,837,546 A | 11/1998 | Allen et al. |
| 5,842,787 A | 12/1998 | Kopf-Sill et al. |
| 5,856,174 A | 1/1999 | Lipshutz et al. |
| 5,861,265 A | 1/1999 | Perry |
| 5,866,345 A | 2/1999 | Wilding et al. |
| 5,876,675 A | 3/1999 | Kennedy |
| 5,882,465 A | 3/1999 | McReynolds |
| 5,885,470 A | 3/1999 | Parce et al. |
| 5,885,527 A | 3/1999 | Buechler |
| 5,886,345 A | 3/1999 | Koster et al. |
| 5,922,591 A | 7/1999 | Anderson et al. |
| 5,932,799 A | 8/1999 | Moles |
| 5,942,443 A | 8/1999 | Parce et al. |
| 5,965,237 A | 10/1999 | Bruin et al. |
| 5,976,896 A | 11/1999 | Kumar et al. |
| 6,008,057 A | 12/1999 | Glass et al. |
| 6,020,209 A | 2/2000 | Narang et al. |
| 6,046,056 A | 4/2000 | Parce et al. |
| 6,048,498 A | 4/2000 | Kennedy |
| 6,068,751 A | 5/2000 | Neukermans |
| 6,068,752 A | 5/2000 | Dubrow et al. |
| 6,073,482 A | 6/2000 | Moles |
| 6,082,185 A | 7/2000 | Saaski |
| 6,083,763 A | 7/2000 | Balch |
| 6,086,740 A | 7/2000 | Kennedy |
| 6,103,537 A | 8/2000 | Ullman et al. |
| 6,123,798 A | 9/2000 | Gandhi et al. |
| 6,143,152 A | 11/2000 | Simpson et al. |
| 6,167,910 B1 | 1/2001 | Chow |
| 6,197,595 B1 | 3/2001 | Anderson et al. |
| 6,214,560 B1 | 4/2001 | Yguerabide et al. |
| 6,235,241 B1 | 5/2001 | Catt et al. |
| 6,238,538 B1 | 5/2001 | Parce et al. |
| 6,245,296 B1 | 6/2001 | Ligler et al. |
| 6,251,343 B1 | 6/2001 | Dubrow et al. |
| 6,267,858 B1 | 7/2001 | Parce et al. |
| 6,274,337 B1 | 8/2001 | Parce et al. |
| 6,293,012 B1 | 9/2001 | Moles |
| 6,306,669 B1 | 10/2001 | Yano et al. |
| 6,321,791 B1 | 11/2001 | Chow |
| 6,361,958 B1 | 3/2002 | Shieh et al. |
| 6,366,924 B1 | 4/2002 | Parce |
| 6,383,748 B1 | 5/2002 | Carpay et al. |
| 6,391,622 B1 | 5/2002 | Knapp et al. |
| 6,408,878 B2 | 6/2002 | Unger et al. |
| 6,479,299 B1 | 11/2002 | Parce et al. |
| 6,494,230 B2 | 12/2002 | Chow |
| 6,495,104 B1 | 12/2002 | Unno et al. |
| 6,497,155 B1 | 12/2002 | Feygin et al. |
| 6,507,989 B1 | 1/2003 | Bowden et al. |
| 6,517,778 B1 | 2/2003 | Kumar et al. |
| 6,520,753 B1 | 2/2003 | Grosjean et al. |
| 6,524,830 B2 | 2/2003 | Kopf-Sill et al. |
| 6,532,997 B1 | 3/2003 | Bedingham et al. |
| 6,533,914 B1 | 3/2003 | Liu |
| 6,534,013 B1 | 3/2003 | Kennedy |
| 6,541,213 B1 | 4/2003 | Weigl et al. |
| 6,551,841 B1 | 4/2003 | Wilding et al. |
| 6,573,089 B1 | 6/2003 | Vann |
| 6,576,478 B1 | 6/2003 | Wagner et al. |
| 6,648,015 B1 | 11/2003 | Chow |
| 6,649,358 B1 | 11/2003 | Parce et al. |
| 6,649,403 B1 | 11/2003 | McDevitt et al. |
| 6,680,206 B1 | 1/2004 | McDevitt et al. |
| 6,719,868 B1 | 4/2004 | Schueller et al. |
| 6,729,352 B2 | 5/2004 | O'Connor et al. |
| 6,747,285 B2 | 6/2004 | Schueller et al. |
| 6,756,019 B1 | 6/2004 | Dubrow et al. |
| 6,767,194 B2 | 7/2004 | Jeon et al. |
| 6,767,706 B2 | 7/2004 | Quake et al. |
| 6,875,619 B2 | 4/2005 | Blackburn |
| 6,899,137 B2 | 5/2005 | Unger et al. |
| 6,908,737 B2 | 6/2005 | Ravkin et al. |
| 6,908,770 B1 | 6/2005 | McDevitt et al. |
| 6,929,030 B2 | 8/2005 | Unger et al. |

(56) References Cited

U.S. PATENT DOCUMENTS

| | | |
|---|---|---|
| 6,951,632 B2 | 10/2005 | Unger et al. |
| 6,960,467 B2 | 11/2005 | Shieh et al. |
| 6,994,826 B1 | 2/2006 | Hasselbrink, Jr. et al. |
| 7,005,292 B2 | 2/2006 | Wilding et al. |
| 7,018,830 B2 | 3/2006 | Wilding et al. |
| 7,028,536 B2 | 4/2006 | Karp et al. |
| 7,033,476 B2 | 4/2006 | Lee et al. |
| 7,040,338 B2 | 5/2006 | Unger et al. |
| 7,087,181 B2 | 8/2006 | Schmidt et al. |
| 7,122,153 B2 | 10/2006 | Ho |
| 7,125,510 B2 | 10/2006 | Huang |
| 7,128,910 B2 | 10/2006 | Tucker et al. |
| 7,143,785 B2 | 12/2006 | Maerkl et al. |
| 7,144,616 B1 | 12/2006 | Unger et al. |
| 7,164,533 B2 | 1/2007 | Moon et al. |
| 7,169,314 B2 | 1/2007 | Unger et al. |
| 7,186,383 B2 | 3/2007 | Webster et al. |
| 7,189,358 B2 | 3/2007 | Beach et al. |
| 7,192,559 B2 | 3/2007 | Chow et al. |
| 7,192,629 B2 | 3/2007 | Lammertink et al. |
| 7,216,671 B2 | 5/2007 | Unger et al. |
| 7,238,269 B2 | 7/2007 | Gason et al. |
| 7,241,421 B2 | 7/2007 | Webster et al. |
| 7,250,128 B2 | 7/2007 | Unger et al. |
| 7,258,837 B2 | 8/2007 | Yager et al. |
| 7,285,411 B1 | 10/2007 | Parce et al. |
| 7,294,503 B2 | 11/2007 | Quake et al. |
| 7,326,561 B2 | 2/2008 | Goodman et al. |
| 7,343,248 B2 | 3/2008 | Parce et al. |
| 7,349,158 B2 | 3/2008 | Moon et al. |
| 7,351,376 B1 | 4/2008 | Quake et al. |
| 7,378,280 B2 | 5/2008 | Quake et al. |
| 7,396,674 B2 | 7/2008 | Miyakawa et al. |
| 7,399,643 B2 | 7/2008 | Moon et al. |
| 7,410,809 B2 | 8/2008 | Goix et al. |
| 7,419,639 B2 | 9/2008 | Osterfeld et al. |
| 7,445,926 B2 | 11/2008 | Mathies et al. |
| 7,473,562 B2 | 1/2009 | Van Beuningen et al. |
| 7,476,363 B2 | 1/2009 | Unger et al. |
| 7,491,552 B2 | 2/2009 | McDevitt et al. |
| 7,507,588 B2 | 3/2009 | Mehrpouyan et al. |
| 7,601,270 B1 | 10/2009 | Unger et al. |
| 7,622,081 B2 | 11/2009 | Chou et al. |
| 7,622,083 B2 | 11/2009 | Amirkhanian et al. |
| 7,666,687 B2 | 2/2010 | Webster et al. |
| 7,682,565 B2 | 3/2010 | Linton et al. |
| 7,682,817 B2 | 3/2010 | Cohen et al. |
| 7,691,333 B2 | 4/2010 | McBride et al. |
| 7,695,683 B2 | 4/2010 | Quan et al. |
| 7,736,890 B2 | 6/2010 | Sia et al. |
| 7,736,891 B2 | 6/2010 | Nelson et al. |
| 7,745,207 B2 | 6/2010 | Jovanovich et al. |
| 7,754,010 B2 | 7/2010 | Unger et al. |
| 7,754,148 B2 | 7/2010 | Yu et al. |
| 7,759,067 B2 | 7/2010 | Andersson et al. |
| 7,766,033 B2 | 8/2010 | Mathies et al. |
| 7,766,055 B2 | 8/2010 | Unger et al. |
| 7,799,553 B2 | 9/2010 | Mathies et al. |
| 7,833,708 B2 | 11/2010 | Enzelberger et al. |
| 7,837,946 B2 | 11/2010 | McBride et al. |
| 7,843,567 B2 | 11/2010 | Moon et al. |
| 7,846,676 B2 | 12/2010 | Yang et al. |
| 7,887,750 B2 | 2/2011 | Blatt et al. |
| 7,887,753 B2 | 2/2011 | Quake et al. |
| 7,892,493 B2 | 2/2011 | Weekamp |
| 7,919,172 B2 | 4/2011 | Schueller et al. |
| 7,935,489 B2 | 5/2011 | O'Neill et al. |
| 7,943,089 B2 | 5/2011 | Yang et al. |
| 7,947,492 B2 | 5/2011 | Niehaus |
| 8,002,933 B2 | 8/2011 | Unger et al. |
| 7,445,926 C1 | 9/2011 | Mathies et al. |
| 8,049,893 B2 | 11/2011 | Moon et al. |
| 8,101,403 B2 | 1/2012 | Yager et al. |
| 8,104,515 B2 | 1/2012 | Unger et al. |
| 8,110,407 B2 | 2/2012 | Tsukada et al. |
| 8,124,015 B2 | 2/2012 | Diercks et al. |
| 8,129,176 B2 | 3/2012 | Quake et al. |
| 8,147,774 B2 | 4/2012 | Hagiwara et al. |
| 8,168,139 B2 | 5/2012 | Manger et al. |
| 8,211,657 B2 | 7/2012 | Li et al. |
| 8,236,573 B2 | 8/2012 | Tokhtuev et al. |
| 8,273,574 B2 | 9/2012 | Quake et al. |
| 8,277,759 B2 | 10/2012 | Sundberg et al. |
| 8,999,131 B2 | 4/2015 | Ikegami et al. |
| 9,180,453 B2 | 11/2015 | Chiu et al. |
| 9,207,236 B2 | 12/2015 | Cary |
| 2001/0005489 A1 | 6/2001 | Roach et al. |
| 2002/0081744 A1 | 6/2002 | Chan et al. |
| 2002/0102742 A1 | 8/2002 | Parce et al. |
| 2002/0115225 A1 | 8/2002 | Wagner et al. |
| 2002/0144738 A1 | 10/2002 | Unger et al. |
| 2002/0180963 A1 | 12/2002 | Chien |
| 2002/0187560 A1 | 12/2002 | Pezzuto et al. |
| 2003/0012693 A1 | 1/2003 | Otillar et al. |
| 2003/0032191 A1 | 2/2003 | Hilson et al. |
| 2003/0054376 A1 | 3/2003 | Mullis et al. |
| 2003/0134431 A1 | 7/2003 | Parce et al. |
| 2003/0185713 A1 | 10/2003 | Leonard et al. |
| 2004/0072278 A1 | 4/2004 | Chou et al. |
| 2004/0101444 A1 | 5/2004 | Sommers et al. |
| 2004/0110199 A1 | 6/2004 | Montemagno et al. |
| 2004/0126875 A1 | 7/2004 | Putnam et al. |
| 2004/0189311 A1 | 9/2004 | Glezer et al. |
| 2004/0200909 A1 | 10/2004 | McMillan et al. |
| 2004/0219661 A1 | 11/2004 | Chen et al. |
| 2004/0228770 A1 | 11/2004 | Gandhi et al. |
| 2004/0231986 A1 | 11/2004 | Rossier |
| 2005/0098750 A1 | 5/2005 | Sobek |
| 2005/0100943 A1 | 5/2005 | Kambara et al. |
| 2005/0214173 A1 | 9/2005 | Facer et al. |
| 2005/0221385 A1 | 10/2005 | Nikiforov et al. |
| 2005/0249633 A1 | 11/2005 | Blatt et al. |
| 2005/0266582 A1 | 12/2005 | Modlin et al. |
| 2006/0057576 A1 | 3/2006 | Paszkowski et al. |
| 2006/0063271 A1 | 3/2006 | Putnam et al. |
| 2006/0073035 A1 | 4/2006 | Sundararajan |
| 2006/0073484 A1 | 4/2006 | Mathies et al. |
| 2006/0076068 A1 | 4/2006 | Young et al. |
| 2006/0207877 A1 | 9/2006 | Schmidt et al. |
| 2006/0233668 A1 | 10/2006 | Resch-Genger et al. |
| 2006/0234298 A1 | 10/2006 | Chiu et al. |
| 2006/0257956 A1 | 11/2006 | Basset et al. |
| 2006/0263818 A1 | 11/2006 | Scherer et al. |
| 2006/0263914 A1 | 11/2006 | Sando et al. |
| 2006/0289059 A1 | 12/2006 | Krylov et al. |
| 2007/0017633 A1 | 1/2007 | Tonkovich et al. |
| 2007/0061093 A1 | 3/2007 | Angelescu et al. |
| 2007/0149863 A1 | 6/2007 | Padmanabhan et al. |
| 2007/0224084 A1 | 9/2007 | Holmes et al. |
| 2007/0248958 A1 | 10/2007 | Jovanovich et al. |
| 2008/0017512 A1 | 1/2008 | Bordunov et al. |
| 2008/0035499 A1 | 2/2008 | Weng |
| 2008/0131327 A1 | 6/2008 | Van Dam |
| 2008/0241858 A1 | 10/2008 | Metzger et al. |
| 2008/0280285 A1* | 11/2008 | Chen ............... B01L 3/502715 435/5 |
| 2008/0311585 A1 | 12/2008 | Gao et al. |
| 2008/0311665 A1 | 12/2008 | Ryan et al. |
| 2009/0053732 A1 | 2/2009 | Vermesh et al. |
| 2009/0071833 A1 | 3/2009 | Gorfinkel et al. |
| 2009/0074623 A1 | 3/2009 | Park et al. |
| 2009/0087884 A1 | 4/2009 | Beerling et al. |
| 2009/0148933 A1 | 6/2009 | Battrell et al. |
| 2009/0181411 A1 | 7/2009 | Battrell et al. |
| 2009/0215158 A1 | 8/2009 | Sekizawa et al. |
| 2009/0253181 A1 | 10/2009 | Vangbo et al. |
| 2009/0257920 A1 | 10/2009 | Facer et al. |
| 2009/0325171 A1 | 12/2009 | Hirt et al. |
| 2009/0325276 A1 | 12/2009 | Battrell et al. |
| 2010/0081216 A1 | 4/2010 | Yager et al. |
| 2010/0101670 A1 | 4/2010 | Juncker et al. |
| 2010/0167384 A1 | 7/2010 | Clemmens et al. |
| 2010/0173394 A1 | 7/2010 | Colston, Jr. et al. |
| 2010/0186841 A1 | 7/2010 | Mukaddam et al. |

(56) References Cited

U.S. PATENT DOCUMENTS

| | | |
|---|---|---|
| 2010/0216248 A1 | 8/2010 | Wardlaw |
| 2010/0221814 A1 | 9/2010 | Asogawa et al. |
| 2010/0233791 A1 | 9/2010 | Sim et al. |
| 2010/0303687 A1 | 12/2010 | Blaga et al. |
| 2010/0304494 A1 | 12/2010 | Tokhtuev et al. |
| 2011/0008776 A1 | 1/2011 | Warthoe et al. |
| 2011/0020947 A1 | 1/2011 | Bedingham et al. |
| 2011/0076735 A1 | 3/2011 | Jovanovich et al. |
| 2011/0105361 A1 | 5/2011 | Moon et al. |
| 2011/0195260 A1 | 8/2011 | Lee et al. |
| 2011/0206557 A1* | 8/2011 | Phan ............... B01F 5/0614 422/68.1 |
| 2011/0262940 A1 | 10/2011 | Hisamoto et al. |
| 2011/0306081 A1 | 12/2011 | Szita et al. |
| 2012/0070833 A1 | 3/2012 | Wang |
| 2012/0164036 A1 | 6/2012 | Stern et al. |
| 2012/0266986 A1 | 10/2012 | Wimberger-Friedl et al. |
| 2012/0301903 A1 | 11/2012 | Putnam et al. |
| 2013/0011859 A1 | 1/2013 | Putnam et al. |

FOREIGN PATENT DOCUMENTS

| | | |
|---|---|---|
| CN | 1957254 | 5/2007 |
| CN | 1964789 | 5/2007 |
| CN | 101067642 | 11/2007 |
| CN | 101263392 | 9/2008 |
| DE | 3226407 | 1/1984 |
| EP | 0401033 | 12/1990 |
| EP | 1415788 | 5/2004 |
| EP | 1404448 | 9/2006 |
| EP | 1936382 | 6/2008 |
| EP | 2284538 | 2/2011 |
| EP | 2463666 | 6/2013 |
| GB | 2155152 | 9/1985 |
| GR | 94100467 | 6/1996 |
| JP | 9-288089 | 11/1997 |
| JP | 2001-157855 | 6/2001 |
| JP | 2003-507737 | 2/2003 |
| JP | 2005-140681 | 6/2005 |
| JP | 2007-516419 | 6/2007 |
| RO | 122612 | 9/2009 |
| WO | 9204613 | 3/1992 |
| WO | 9737803 | 10/1997 |
| WO | 9911754 | 3/1999 |
| WO | 9944217 | 9/1999 |
| WO | 0107889 | 1/2001 |
| WO | 0114865 | 3/2001 |
| WO | 03004160 | 1/2003 |
| WO | 03042677 | 5/2003 |
| WO | 2004000721 | 12/2003 |
| WO | 2004034028 | 4/2004 |
| WO | 2004041061 | 5/2004 |
| WO | 2004059299 | 7/2004 |
| WO | 2004061085 | 7/2004 |
| WO | 2005066613 | 7/2005 |
| WO | 2005107938 | 11/2005 |
| WO | 2006071470 | 7/2006 |
| WO | 2007021813 | 2/2007 |
| WO | 2007032316 | 3/2007 |
| WO | 2007033385 | 3/2007 |
| WO | 2007044091 | 4/2007 |
| WO | 2007092713 | 8/2007 |
| WO | 2007093939 | 8/2007 |
| WO | 2007106579 | 9/2007 |
| WO | 2007117987 | 10/2007 |
| WO | 2007136715 | 11/2007 |
| WO | 2008032128 | 3/2008 |
| WO | 2008043041 | 4/2008 |
| WO | 2008043046 | 4/2008 |
| WO | 2008075253 | 6/2008 |
| WO | 2008089493 | 7/2008 |
| WO | 2008115626 | 9/2008 |
| WO | 2008154036 | 12/2008 |
| WO | 2009012340 | 1/2009 |
| WO | 2009029177 | 3/2009 |
| WO | 2009088408 | 7/2009 |
| WO | 2009105711 | 8/2009 |
| WO | 2010017210 | 2/2010 |
| WO | 2010027812 | 3/2010 |
| WO | 2010057078 | 5/2010 |
| WO | 2010071045 | 6/2010 |
| WO | 2010077618 | 7/2010 |
| WO | 2010148252 | 12/2010 |
| WO | 2011040884 | 4/2011 |
| WO | 2011053845 | 5/2011 |
| WO | 2011063408 | 5/2011 |
| WO | 2012071069 | 5/2012 |
| WO | 2012129455 | 9/2012 |

OTHER PUBLICATIONS

Cooksey et al., "A vacuum manifold for rapid world-to-chip connectivity of complex PDMS microdevices," Lab on a Chip, vol. 9, No. 9 (Jan. 1, 2009)!

Delamarche et al, "Patterned Delivery of Immunoglobulins to Surfaces Using Microfluidic Networks", Science, vol. 276, p. 779-781, (submitted Dec. 30, 1996).

Duffy, et al, "Rapid Prototyping of Microfluidic Systems in Poly (dimethylsiloxane)", Anal. Chem vol. 70, No. 23, 1998, 4974-4984.

Effenhauser et al, "Integrated Capillary Electrophoresis on Flexible Silcione Microdevices; Analysis of DNA . . . ", Analytical Chemistry, vol. 69, No. 17, 3451-7.

Fayram, Sandra L., "Fluorescence Immunoassay and Passive Latex Agglutination as Alternatives to Hemagglutination Inhibition for Determining Rubella Immune Status," from "Journal of Clinical Microbiology," vol. 17, No. 4, Apr. 3, 1983, pp. 685-688 (4 pages).

Folta et al, "Design, Fabrication and Testing of a Miniature Peristaltic Membrane Pump", 1992, Technical Digest IEEE Solid-State Sensors and Actuators Workshop, pp. 186-189.

Fujii et al., Bulk- and Surface-Modified Combinable PDMS Capillary Sensor Array as an Easy-to-Use Sensing Device with Enhanced Sensitivity to Elevated Concentrations of Multiple Serum Sample Components, Lab Chip 12:1522 (2012).

Grover et al., "Teflon films for chemically-inert microfluidic valves and pumps," Lab on a Chip, vol. 8, No. 6 (Jan. 1, 2008).

Henares et al., "Current Development in Microfluidic Immunosensing Chip," Analytica Chimica Acta 611:17-30 (2008).

Henares et al., "Development of Single-Step Heterogenous Sandwich Capillary Immunosensor for Capillary-Assembled Microchip (CAs-CHIP) Integration," Twelfth International Conference on Miniaturized Systems for Chemistry and Life Sciences, San Diego, California (Oct. 12-16, 2008.

Henares et al., "Enzyme-Release Capillary as a Facile Enzymatic Biosensing Part for a Capillary-Assembled Microchip," Analytical Sciences 25:1025-1028(Aug. 2009).

Henares et al., "Multiple Enzyme Linked Immunosorbent Assay System on a Capillary-Assembled Microchip Integrating Valving and Immuno-Reaction Functions," Analytica Chimica Acta 589:173-179 (2007).

Henares et al., "Single-Drop Analysis of Various Proteases in a Cancer Cell Lysate Using a Capillary-Assembled Microchip," Anal Bioanal Chem 391:2507-2512 (2008).

Henares et al., "Single-Step ELISA Capillary Sensor Based on Surface-Bonded Glucose Oxidase, Antibody, and Physically-Adsorbed PEG Membrane Containing Peroxidase-Labeled Antibody," Sensors and Actuators B 149:319-324 (2010).

Hicks, Jocelyn M., "Fluorescence Immunoassay," from "Human Pathology", vol. 15, No. 2, Feb. 1984, pp. 112-116 (5 pages).

Hisamoto et al., "Capillary-Assembled Microchip as an On-Line Deproteinization Device for Capillary Electrophoresis," Anal Bioanal Chem 386:733-738 (2006).

Hisamoto et al., "Capillary-Assembled Microchip for Universal Integration of Various Chemical Functions onto a Single Microfluidic Device," Anal. Chem. 76:3222-3228 (2004).

Hisamoto et al., "Integration of Multiple-Ion-Sensing on a Capillary-Assembled Microchip," Analytica Chimica Acta 556:164-170 (2006).

(56) References Cited

OTHER PUBLICATIONS

Hisamoto et al., "Integration of Valving and Sensing on a Capillary-Assembled Microchip," Anal. Chem. 77:2266-2271 (2005).
Hosokawa, K, and Maeda, R., "A pneumatically-actuated three-way microvalve fabricated with polydimethysiloxane using the membrane transfer technique", J. Mickromecjh. Microeng. 10 (2000) 415-420.
Hosokawa, K. and Maeda, R., "A normally closed PDMS (polydimethylsiloxane) microvalve", T.Iee Japan, vol. 120-E, No. 4, 2000.
International Search Report and Written Opinion from PCT/US10/57860, dated Apr. 6, 2011.
International Search Report and Written Opinion from related PCT/US2012/030216, dated Oct. 10, 2012.
Invitation to Pay Additional Fees and, Where Applicable, Protest Fee, including Communication Relating to the Results of the Partial International Search from corresponding PCT/US2013/030054 dated Jul. 17, 2013.
Lammerink, et al "Modular Concept for Fluid Handling Systems—A demonstrator Micro Analysis System", 1996, Proc. IEEE Micro Electro Mechanical Systgems Workshop, San Diego CA, Feb. 1996, pp. 389-394.
Macdonald and Whitesides, "Poly(dimethylsilocane) as a Material for Fabricating Microfluidic Devices", 2002.
Madou, Fundamentals of Microfabrication, CRC Press, 1997, pp. 382-394 especially p. 390.
Notification of Transmittal of the International Search Report and the Written Opinion of the International Searching Authority, or the Declaration from corresponding PCT/US2013/030057 dated Jul. 8, 2013.
Notification of Transmittal of the International Search Report and the Written Opinion of the International Searching Authority, or the Declaration from corresponding PCT/US2013/000062 dated Jul. 1, 2013.
Ozinskas, Alvydas J., "Principles of Fluorescence Immunoassay," from "Topics in Fluorescence Spectroscopy, vol. 4: Probe Design and Chemical Sensing," 1994, pp. 449-496 (48 pages).
Shoji et al, "Microflow Devices and Systems", 1994, J. Micromech. Microeng. 4 (1994) 157-171.
Smits, "Piezoelectric Micropump with Three Valves Working Peristaltically", 1990, Sensors and Actuators, A21-23 (1990) 203-206.
Supplementary European Search Report from corresponding European Appn. No. 10832371.8 dated Jul. 22, 2013.
Yacoub-George et al., "Automated 10-Channel Capillary Chip Immunodetector for Biological Agents Detection," Biosensors and Bioelectronics 22:1368-1375 (2007).
International Search Report for International Application No. PCT/US1333610 dated Jun. 10, 2013.
International Search Report for International Application No. PCT/US2013030051 dated Jul. 8, 2013.
International Search Report for International Application No. PCT/US2013030052 dated Jun. 26, 2013.
International Search Report for International Application No. PCT/US2013030053 dated Nov. 6, 2013.
International Search Report for International Application No. PCT/US2013030056 dated Nov. 27, 2013.

\* cited by examiner

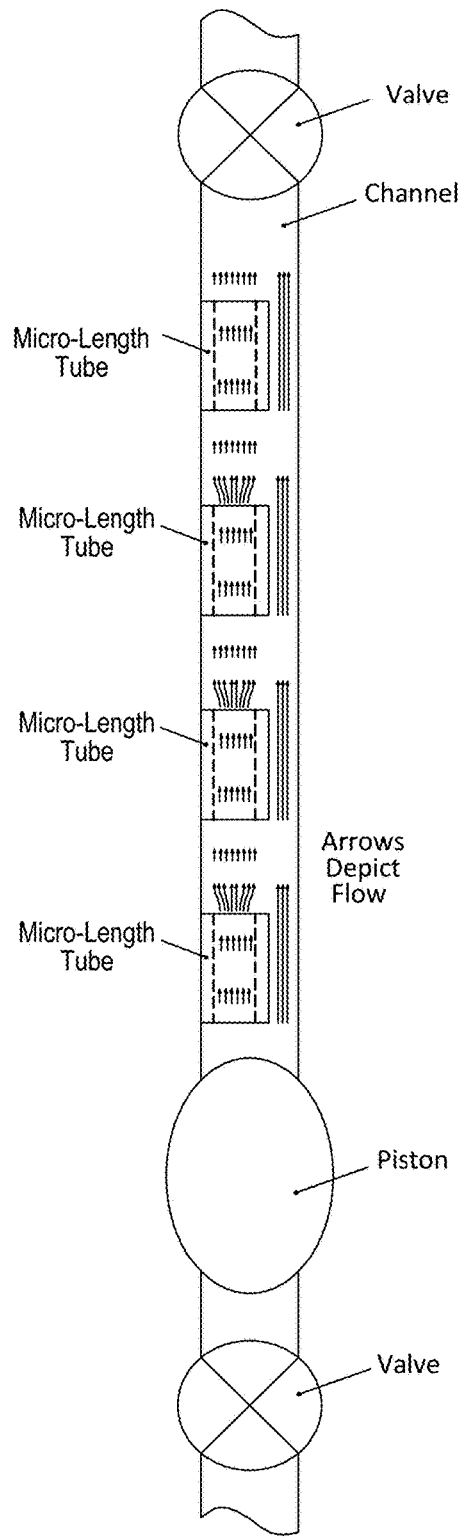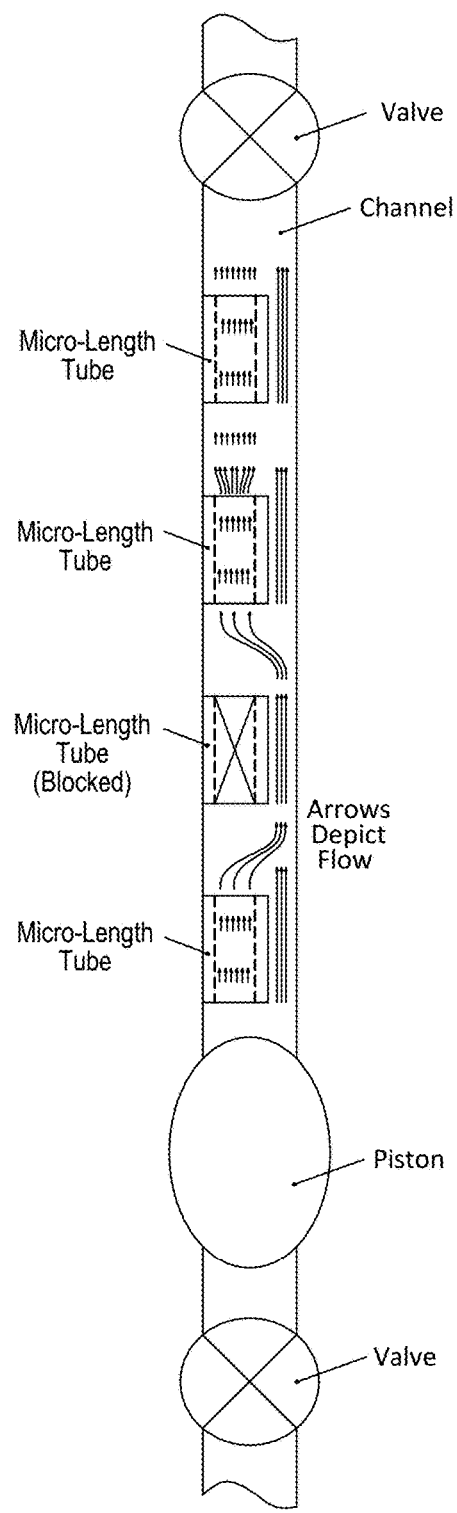
FIG. 2A
FIG. 2B

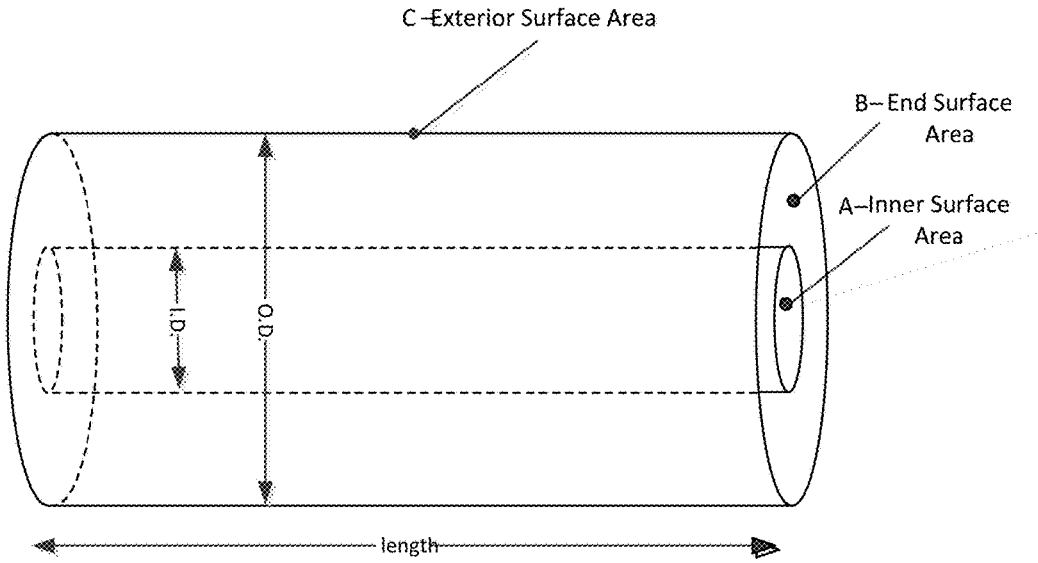

Total Surface Area, T = A + 2*B + C

%Reduction of Surface Area without exterior coating= 1- (A+2*B)/T

%Reduction of Surface Area without exterior and ends coating 1- A/T

%Reduction of Surface Area without exterior and ends coating= 1- (A*0.5)/T

Example: O.D. = 125μm, I.D. = 75μm, Length= 250μm
   Without Exterior: 57% Reduction of surface area
   Without Exterior & Ends: 66% Reduction of surface area
   Without Exterior & Ends & with 50% code: 83% reduction of surface area

FIG. 5

Pick and place

Pick and place

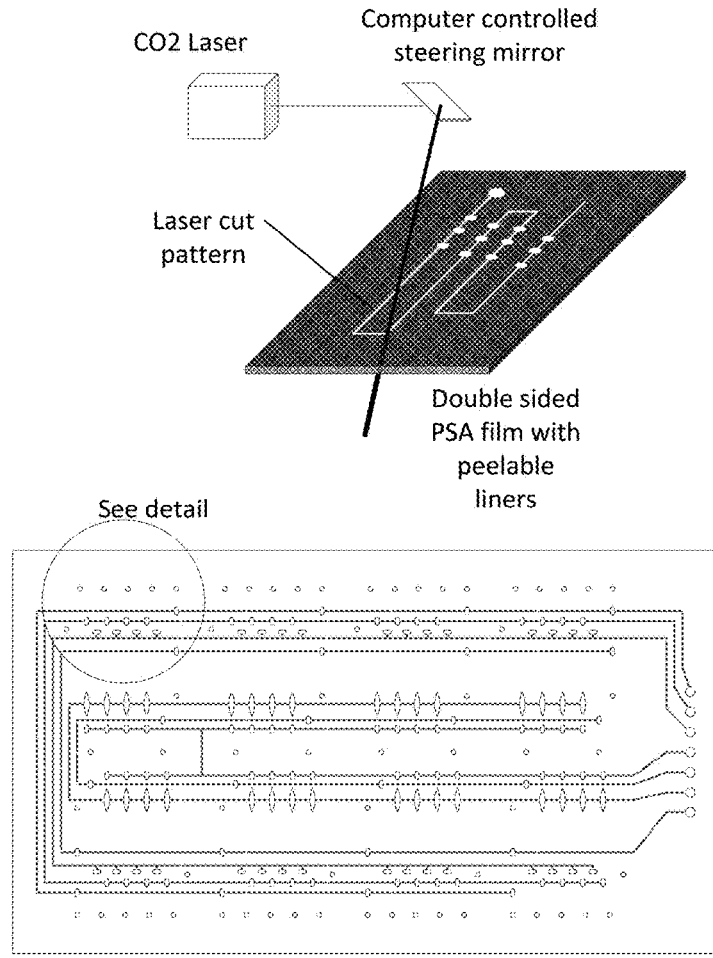
FIG. 20A
FIG. 20B
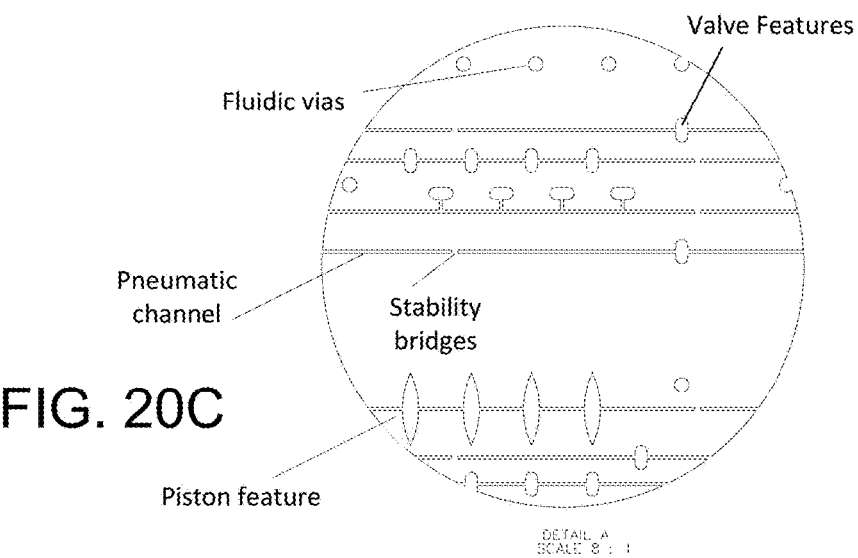
FIG. 20C

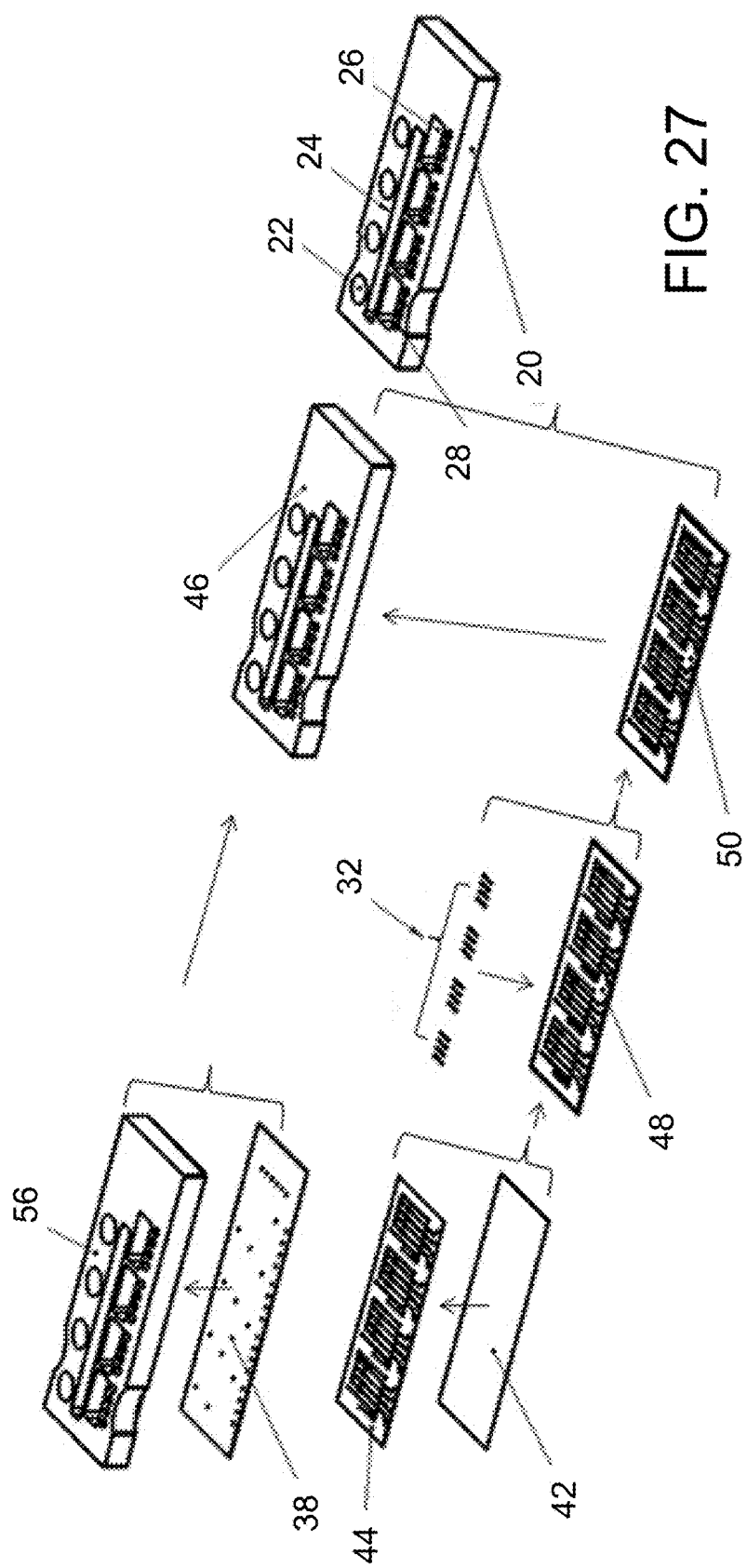

50

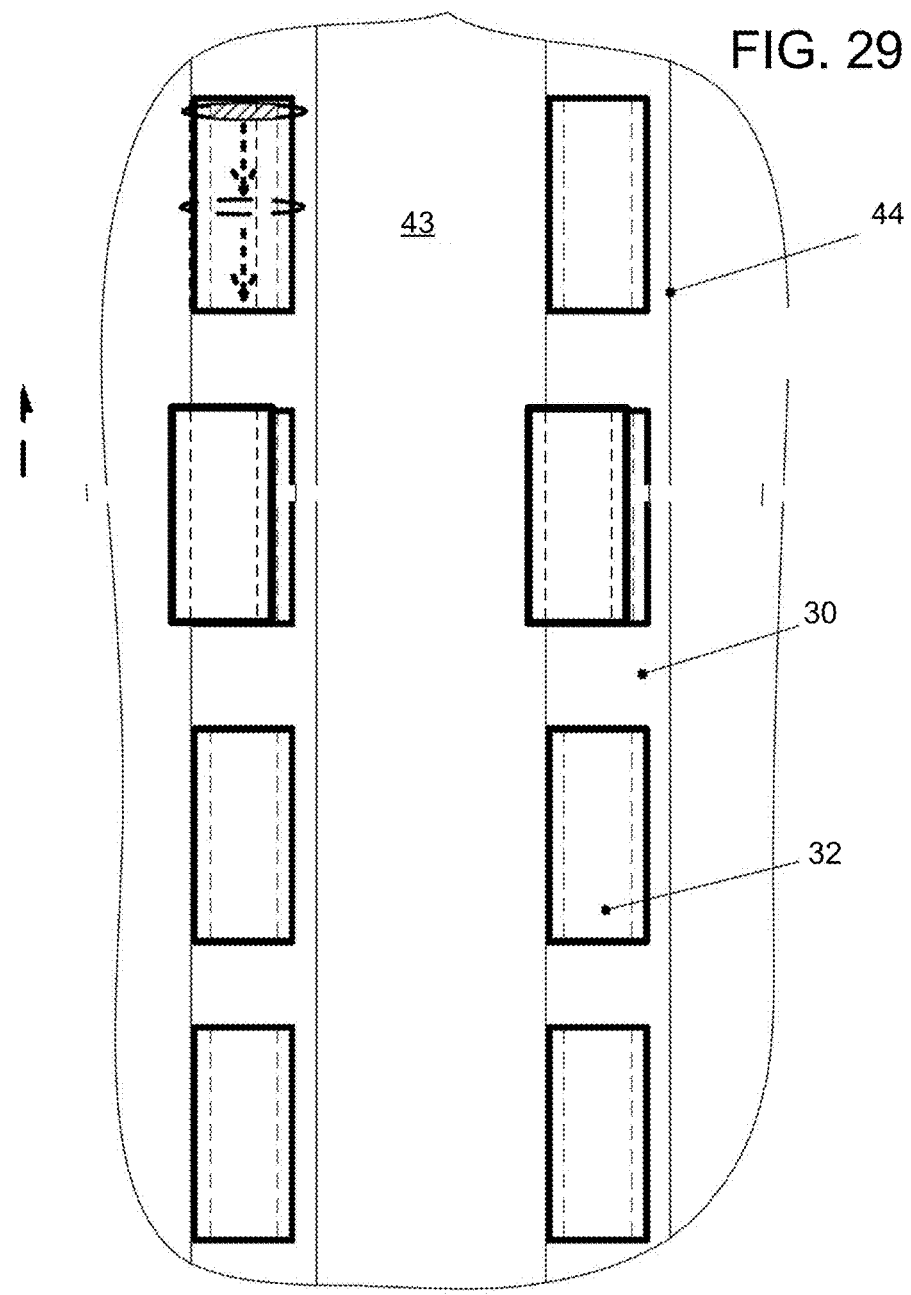

Pick & Place – Top View

Pick and place
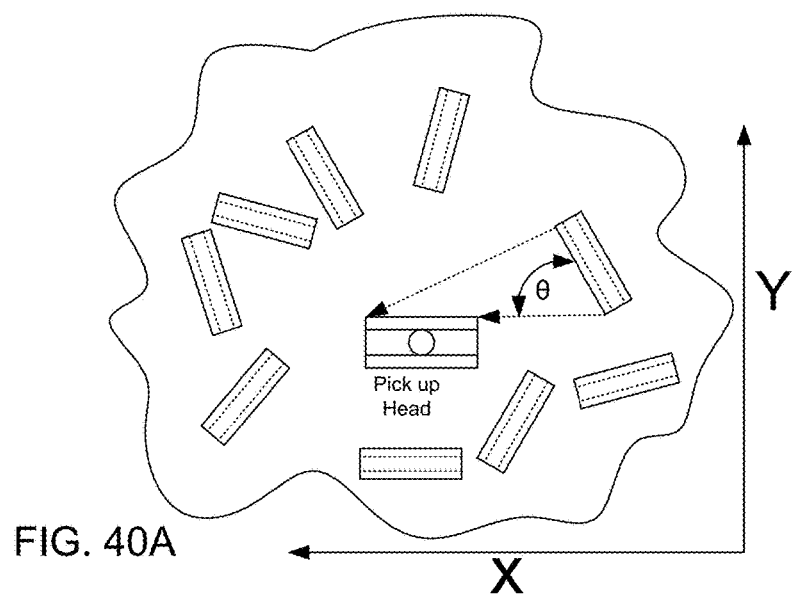
FIG. 40A
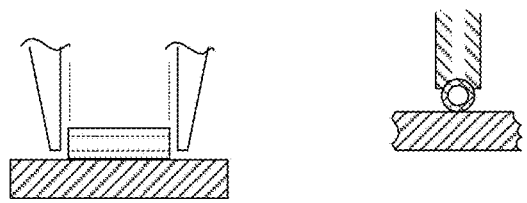
FIG. 40E
FIG. 40C
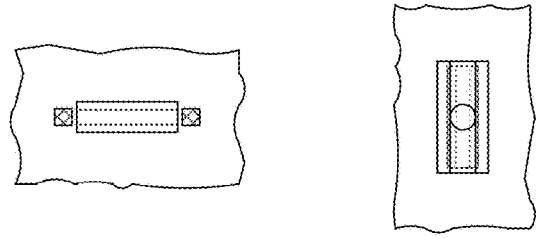
FIG. 40F
FIG. 40D
FIG. 40B
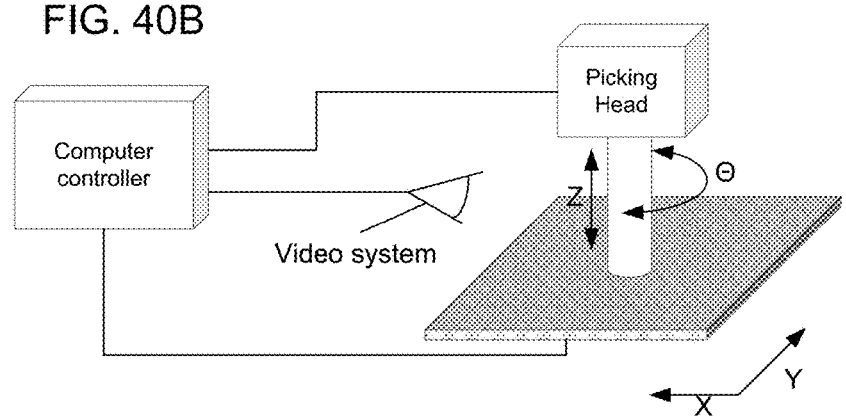

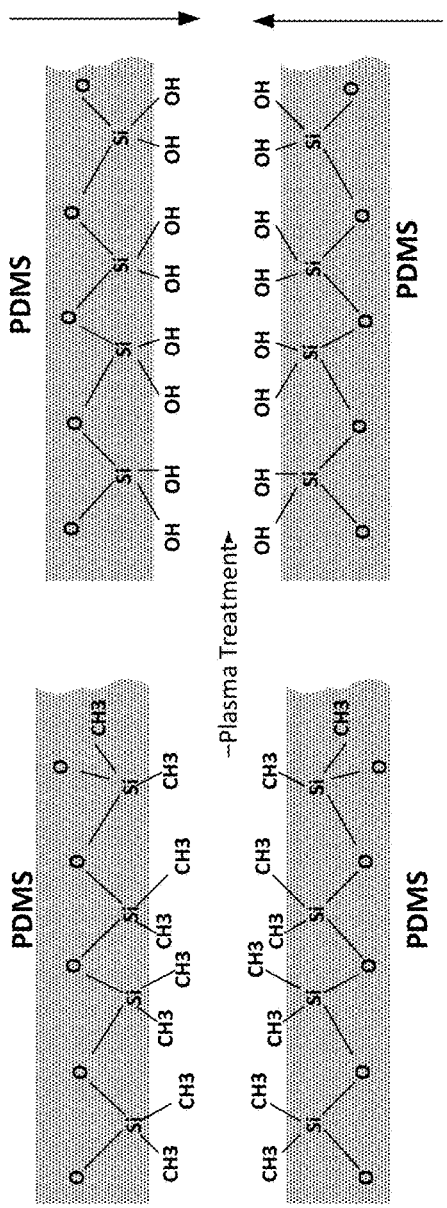
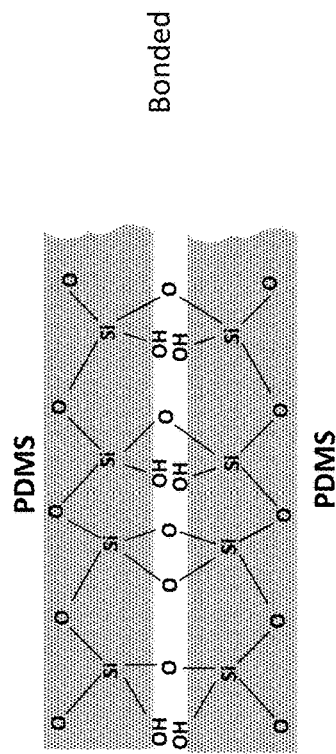
FIG. 42A
FIG. 42B
FIG. 42C

Make and Break
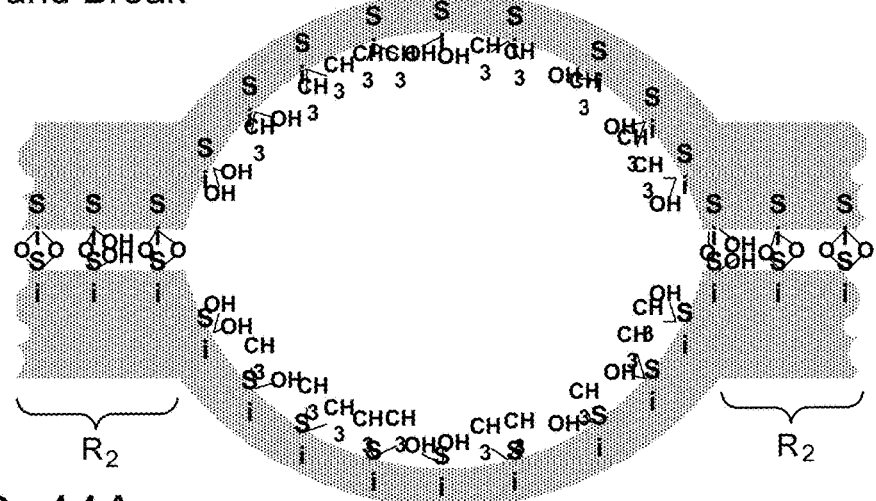
FIG. 44A
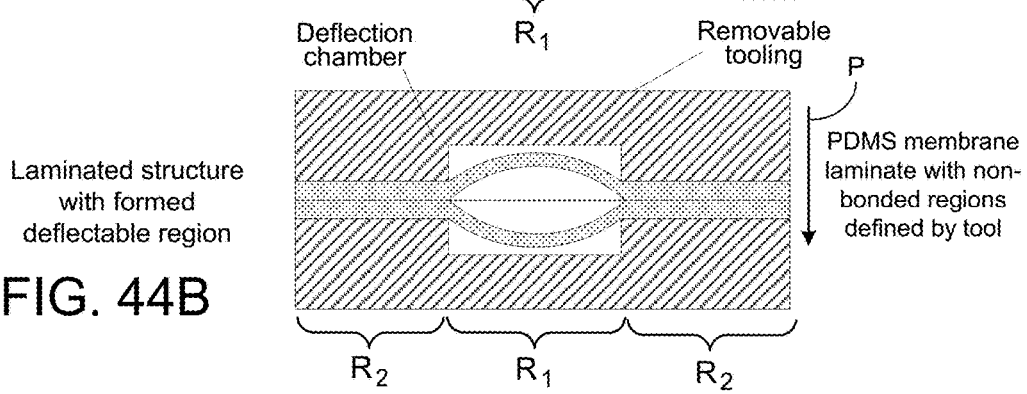
Laminated structure with formed deflectable region
FIG. 44B
Deflection chamber   $R_1$   Removable tooling   P
PDMS membrane laminate with non-bonded regions defined by tool
FIG. 45A
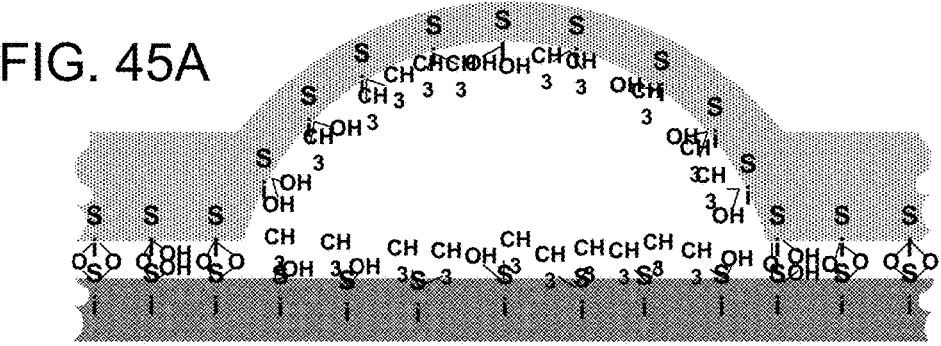
FIG. 45B
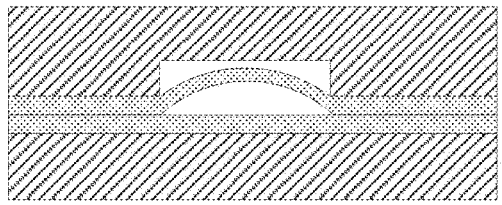

Make and Break     Composite membrane
  Thin flexible sheet (PET ~ 10 um thick)
PDMS Film (50-200 um )
  Thin flexible sheet (PET ~ 10 um thick)
PDMS coating (0.5-5 um )
PET/PDMS Lamination     FIG. 46C
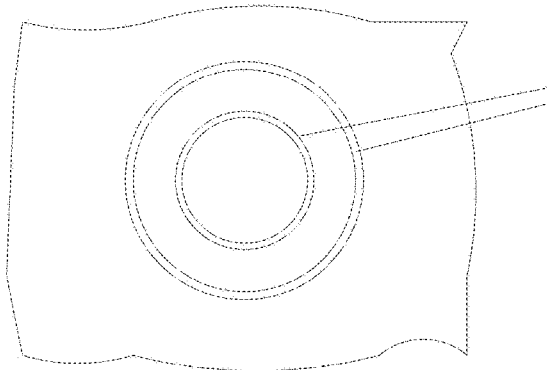
Stress relief channels formed in PET film (~ 25 um wide)
Circular stress relief slots
Thin flexible sheet (PET ~ 10 um thick)
PDMS Film (50-200 um )
FIG. 46D
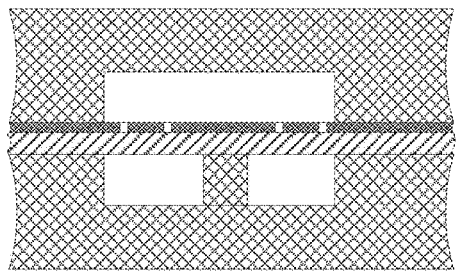 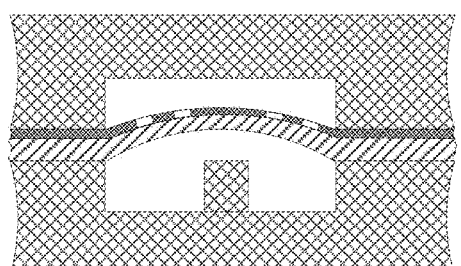
FIG. 46E            FIG. 46F Silicon based rigid materials ex. Silicon, silica or silicates Intermediate bifunctional layer such as
Organofunctional silane or oxide layer

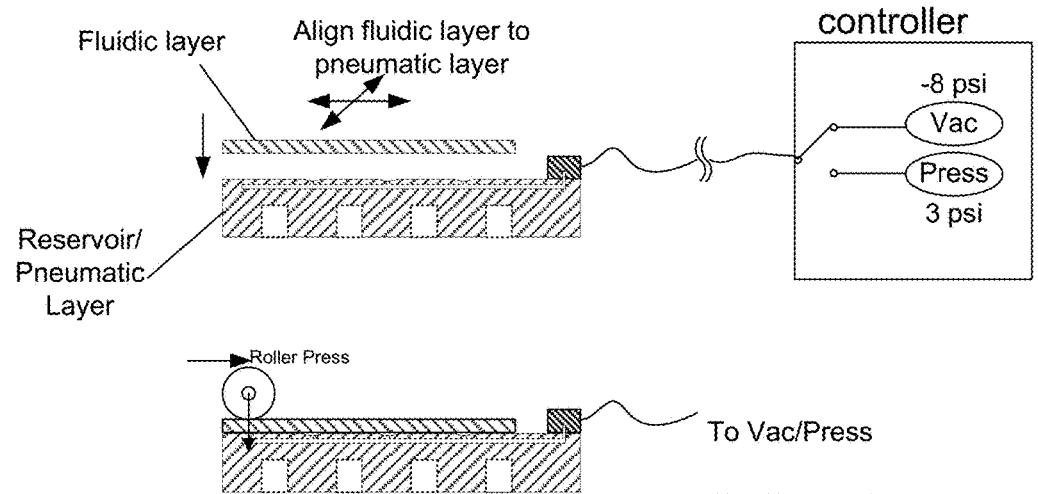
FIG. 50A
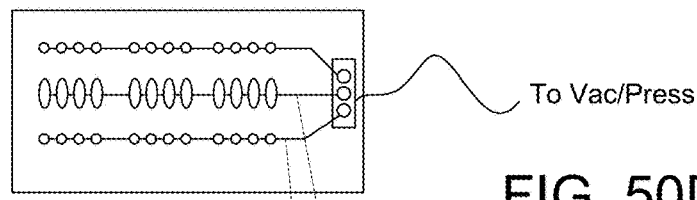
FIG. 50C
FIG. 50D
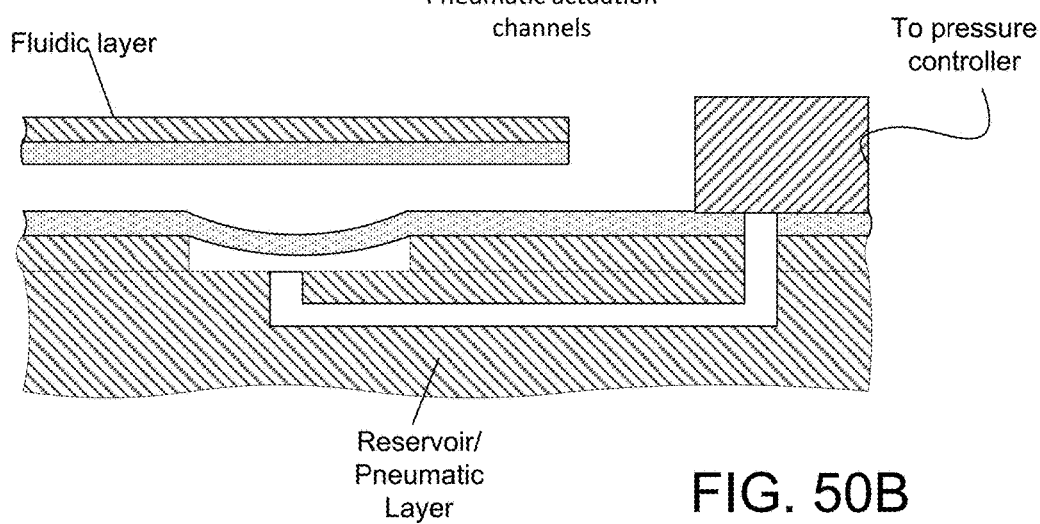
FIG. 50B

Make and break Process Illustration – used to prepare multiple valves at once on a device Make and Break No leak path exists outside chamber boundary B

Pneumatic chamber

Planar surface (fully bonded between membrane and fluidic layer)

Fluidic channel

Membrane sealed tightly around perimeter of pneumatic chamber

Pneumatic supply channel

FIG. 56A
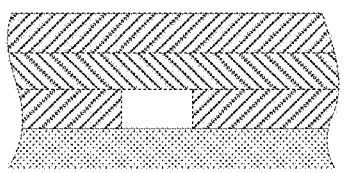
Close channel
FIG. 56B
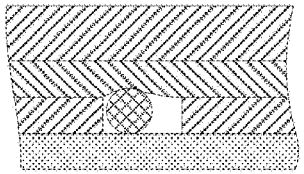
Fix micro-particle in channel
FIG. 56C
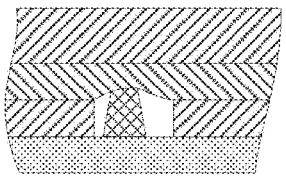
Fix micro-particle in channel
FIG. 56D
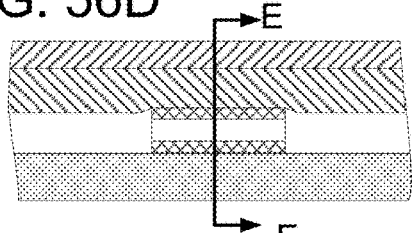
Fix micro-length tube detection element in channel
FIG. 56E
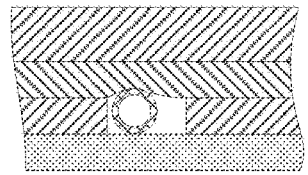
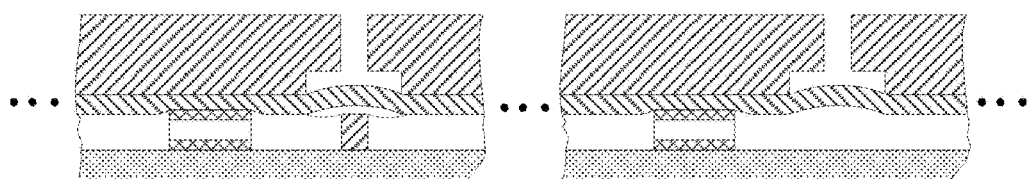
Fix micro-length tubes, define membrane for valves and pistons, close channel
FIG. 56F

FIG. 60
Fluidic Architecture and Protocol
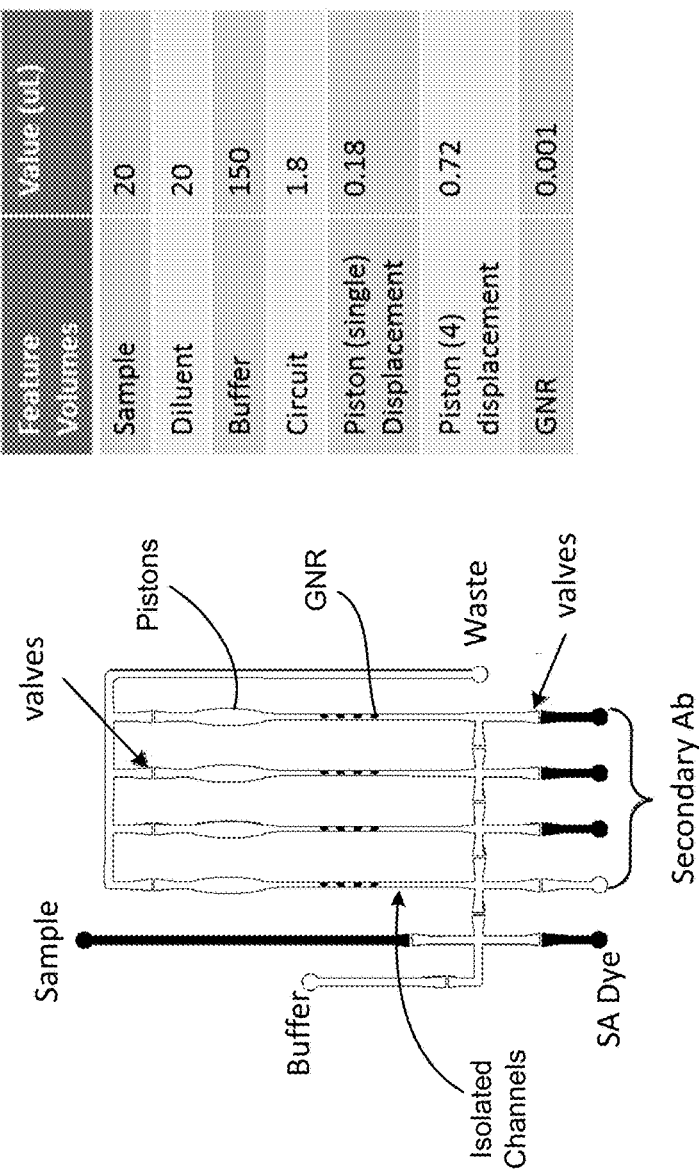
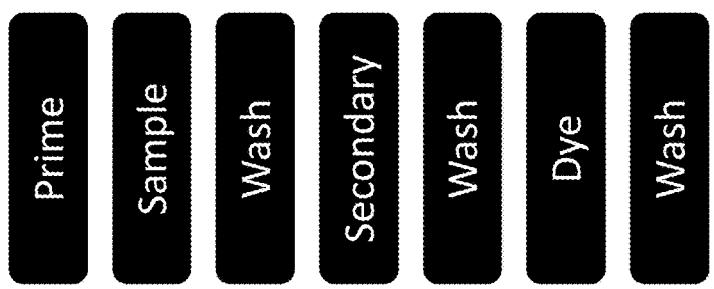

Automatic Scan Setup
- Sample Circuit Layout
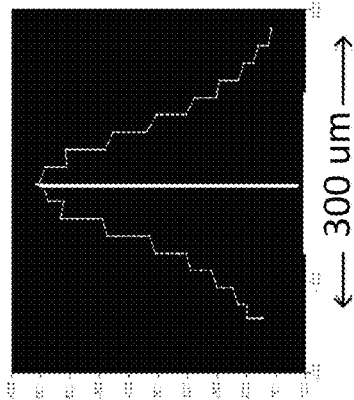
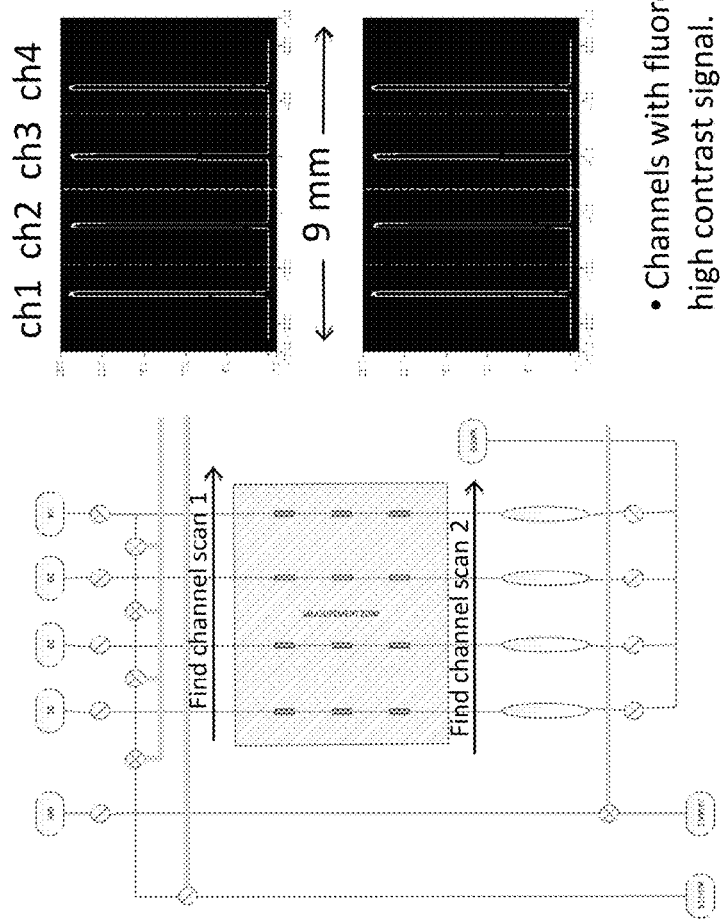
- Channels with fluorescent dye present produce high contrast signal.
- Channel locations and chip orientation is precisely determined from scan profiles
- Optimal focus is determined by sweeping z
FIG. 61

General Schematic for Epifluorescent
Scanning Microscope

Laser Beam Shape Isometric View

Laser Beam Shape Layout View

Micro-length tube element scan schematic

Overall Scan Sequence

FIG. 73

Reading Code from Micro-length tube flow element

Provide micro-length tube element with a code pattern written in capture agent on inside surface of the element; the code represents the identity and/or concentration of capture agent on the element

↓

Pick and place micro-length tube element into flow channel(s)

↓

Conduct analyte capture step by sample flow Through a channel(s), attaching analyte Molecules to capture agent in the code Pattern on inside surface of the micro-length tube element

↓

Attach fluorophore tag to capture analyte molecules by flow through the channel and micro-length tube element, completing the fluid assay

↓

Scan the channel(s) to conduct pattern analysis, identify pattern of light emission from captured analyte and match the read pattern to stored code table

↓

Use the coded information associated with the specific code pattern of the micro-length tube element; present e.g. by print-out or associated the data with stored or transmitted assay data

FIG. 74
Preferred Implementation of previous figures first block

Provide micro-length tube element uniformly coated with capture agent on the inside cylindrical surface with no active capture agent on Outside cylindrical surface

With laser beam, deactivated or remove the capture agent according to the blank spaces of a predetermined code pattern, preferably a bar-code pattern Reading Code Consolidated

FIG. 77
Bar Code in Micro-Length Tube Element
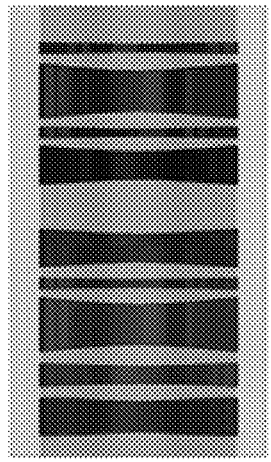
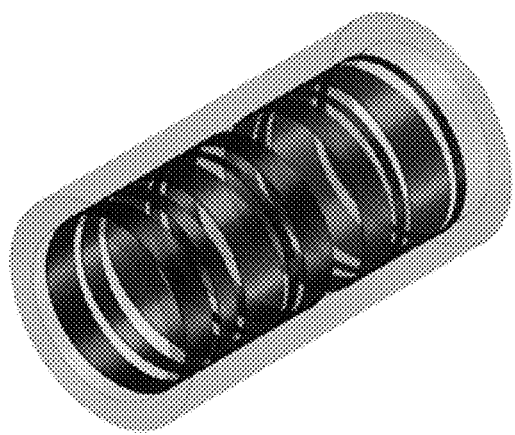
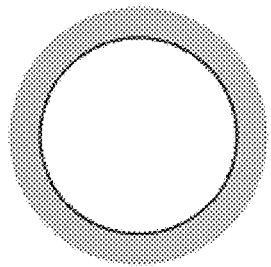
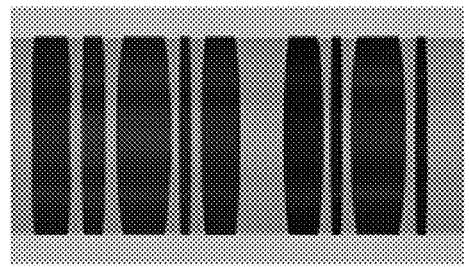

FIG. 78  Scan Data File Snippet

| Timestamp | Gain | Exposure | xPos | yPos | Center | Median | RMS | Mean | StdDev | Max | Min | Channel | Velocity |
|---|---|---|---|---|---|---|---|---|---|---|---|---|---|
| 25:18.6 | 1 | 10 | 561 | -207 | 11 | 12 | 12.59831 | 12.41033 | 2.168574 | 20 | 6 | 1 | 200 |
| 25:18.6 | 1 | 10 | 561 | -207 | 11 | 12 | 12.59977 | 12.41679 | 2.139898 | 19 | 6 | 1 | 200 |
| 25:18.7 | 1 | 10 | 1099 | -207 | 11 | 12 | 12.59977 | 12.41679 | 2.139898 | 19 | 6 | 1 | 200 |
| 25:18.7 | 1 | 10 | 1099 | -207 | 16 | 13 | 12.71469 | 12.54103 | 2.094641 | 21 | 5 | 1 | 200 |
| 25:18.7 | 1 | 10 | 1093 | -207 | 14 | 13 | 12.74004 | 12.56383 | 2.111963 | 19 | 5 | 1 | 200 |
| 25:18.7 | 1 | 10 | 1093 | -207 | 14 | 13 | 12.74004 | 12.56383 | 2.111963 | 19 | 5 | 1 | 200 |
| 25:18.7 | 1 | 10 | 1086 | -207 | 18 | 13 | 12.96235 | 12.78609 | 2.130713 | 20 | 6 | 1 | 200 |
| .... | | | | | | | | | | | | | |
| 25:44.9 | 1 | 10 | -3906 | -207 | 12 | 11 | 11.29127 | 11.12588 | 1.908924 | 18 | 4 | 2 | 200 |
| 25:44.9 | 1 | 10 | -3906 | -207 | 12 | 11 | 11.29127 | 11.12588 | 1.908924 | 18 | 4 | 2 | 200 |
| 25:44.9 | 1 | 10 | -3906 | -207 | 12 | 11 | 11.29127 | 11.12588 | 1.908924 | 18 | 4 | 2 | 200 |
| 25:44.9 | 1 | 10 | -3906 | -207 | 9 | 11 | 11.34321 | 11.19035 | 1.856259 | 17 | 5 | 2 | 200 |
| 25:44.9 | 1 | 10 | 1100 | 2585 | 11 | 11 | 11.25899 | 11.11056 | 1.822494 | 18 | 4 | 2 | 200 |
| 25:44.9 | 1 | 10 | 1100 | 2585 | 11 | 11 | 11.25899 | 11.11056 | 1.822494 | 18 | 4 | 2 | 200 |
| 25:44.9 | 1 | 10 | 1100 | 2585 | 11 | 11 | 11.25899 | 11.11056 | 1.822494 | 18 | 4 | 2 | 200 |
| .... | | | | | | | | | | | | | |
| 27:02.5 | 1 | 10 | -3892 | 8169 | 13 | 12 | 11.94034 | 11.78989 | 1.889861 | 18 | 4 | 3 | 200 |
| 27:02.5 | 1 | 10 | -3892 | 8169 | 13 | 12 | 11.94034 | 11.78989 | 1.889861 | 19 | 4 | 3 | 200 |
| 27:02.6 | 1 | 10 | -3892 | 8169 | 13 | 12 | 11.94034 | 11.78989 | 1.889861 | 18 | 4 | 3 | 200 |
| 27:02.6 | 1 | 10 | -3898 | 8169 | 13 | 12 | 11.78514 | 11.63564 | 1.871547 | 18 | 5 | 3 | 200 |
| 27:02.6 | 1 | 10 | -3898 | 8169 | 10 | 12 | 11.68101 | 11.52888 | 1.879474 | 18 | 4 | 3 | 200 |
| 27:02.6 | 1 | 10 | -3898 | 8169 | 10 | 12 | 11.68101 | 11.52888 | 1.879474 | 18 | 4 | 3 | 200 |
| 27:02.6 | 1 | 10 | -3904 | 8169 | 12 | 12 | 11.76859 | 11.61512 | 1.894712 | 19 | 5 | 3 | 200 |

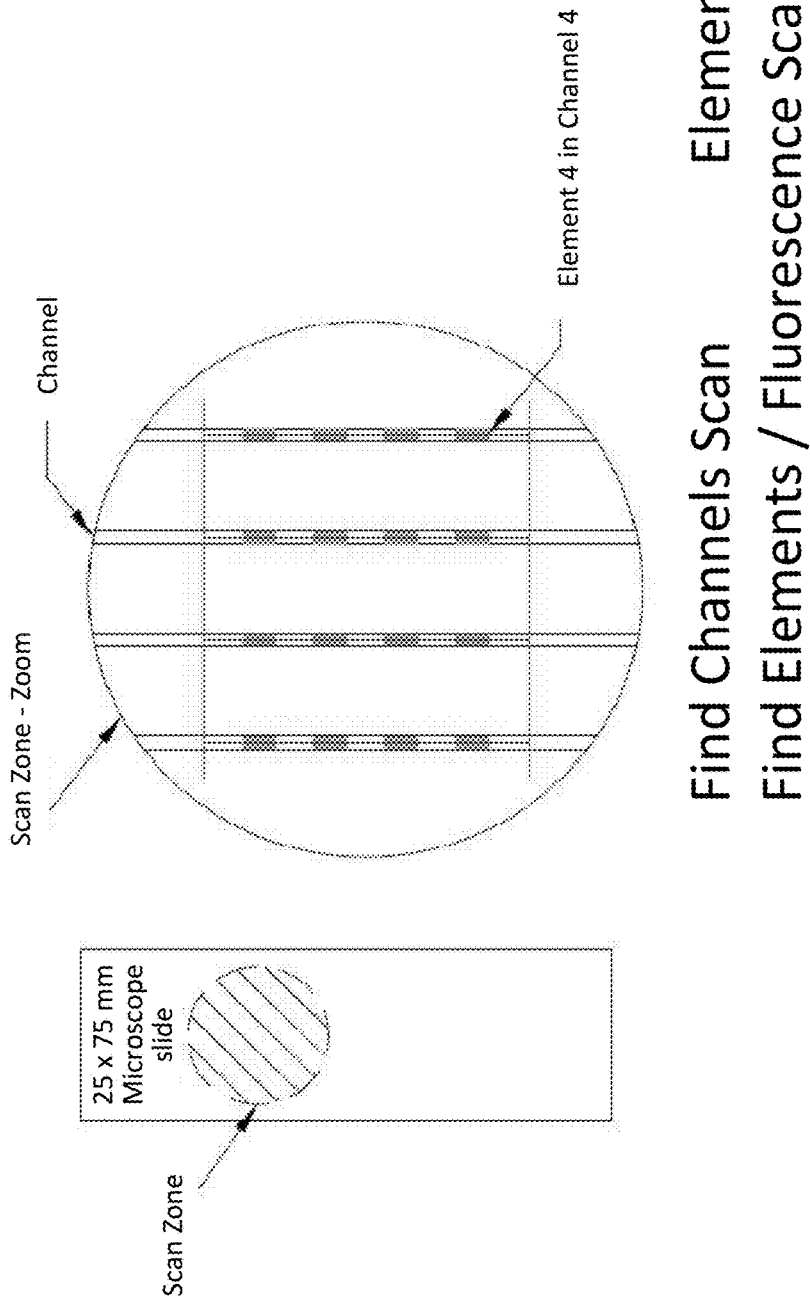

Find Channels ROI

Find Channels Scan Plot

Find Channels Processing Flowchart

Find Elements ROI

Find Elements Scan Plot

Find Elements Processing Flowchart

Auto Focus Scan Plot

Auto-Focus Processing Flowchart

Auto-Expose Schematic

Auto-Exposure Procedure Flowchart

Laser/ROI Alignment

Fluorescence Scan ROI, bright field

Fluorescence scan data processing

Oscillator flow monitored at single location
Refer to FIG. 1

FIG. 103
Fluidic Architecture and Protocol
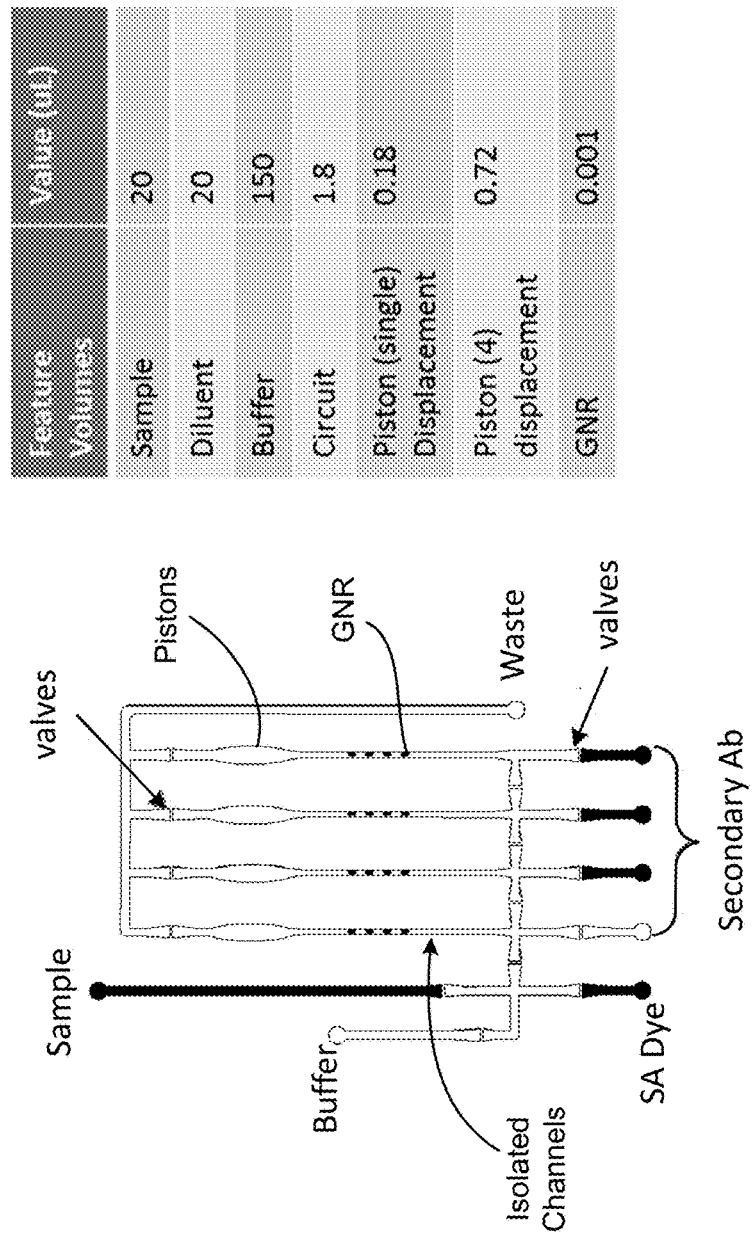
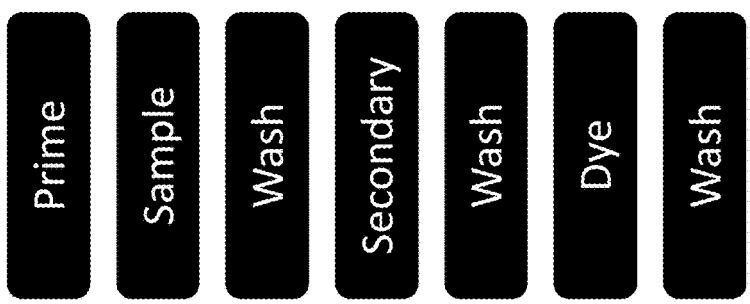

METHODS AND SYSTEMS FOR EPI-FLUORESCENT MONITORING AND SCANNING FOR MICROFLUIDIC ASSAYS

CROSS REFERENCE TO RELATED APPLICATIONS

This application is a Continuation in Part of International Application No. PCT/US2013/030052, filed Mar. 8, 2013; which claims priority to Provisional Application No. 61/608,570, filed Mar. 8, 2012; and Provisional Application No. 61/754,377, filed Jan. 18, 2013; and a Continuation in Part of International Application No. PCT/US2013/033610, filed Mar. 22, 2013, which claims priority to Provisional Application No. 61/754,377, filed Jan. 18, 2013. This application hereby incorporates by reference, in its entirety, each and every application referred to above, to the extent of matter related to any of the features defined in the "Summary" section of this application. This application is also a Continuation in Part of U.S. application Ser. No. 13/427,857, filed Mar. 22, 2012, which claims priority to U.S. Provisional Application No. 61/465,688, filed Mar. 22, 2011 and U.S. Provisional Application 61/608,570, filed Mar. 8, 2012; and is a Continuation in Part of U.S. application Ser. No. 13/511,593, filed Sep. 24, 2012, which claims priority to International Application No. PCT/US2010/057860, filed Nov. 23, 2010, which claims priority to U.S. Provisional Application No. 61/263,572, filed Nov. 23, 2009. This application hereby incorporates by reference, in its entirety, U.S. application Ser. No. 13/427,857, filed Mar. 22, 2012 to the extent of matter related to any of the features defined in the "Summary" Section of this application.

TECHNICAL FIELD

The invention concerns assays in microfluidic systems, including systems that employ portable microfluidic devices. Some versions of microfluidic devices are in the form of microfluidic cartridges (cassettes) that are actuated and read by an associated apparatus such as a bench-top instrument that both conducts the assay protocol within the cartridge and reads the results.

The invention also concerns multiplex microfluidic assays in which multiple assays performed in a microfluidic system are read or scanned with epi-fluorescence.

The invention in particular relates to monitoring assays performed within microfluidic systems, to detecting assay results after microfluidic assays have been run (performed), and to determining the precise relative location of a microfluidic system to a precise detection system, for conducting monitoring or detection with precision.

The invention has broad aspects that are applicable to microfluidic assay systems, in general, and more specific aspects that concern the assays conducted within portable microfluidic cartridges, and particularly cartridges in which the relative position of the cartridge and a precise outside scanning system is not precisely determined. Particularly important applications of the invention concern microfluidic assay cartridges that are inserted into a multi-function apparatus that both causes the assay to be performed within the cartridge and the results detected.

BACKGROUND

As is well understood, with any microfluidic assay system there is the potential for failure, and with complex systems, typically, there are numerous potential failure modes. Examples of failure modes for microfluidic assay systems relate to flows in microfluidic channels and to valves and pistons that control the flows according to a pre-determined assay protocol. The failure modes occur with any microfluidic system, but can be of particular concern when the assay is performed within a microfluidic cartridge. Blockage of a microfluidic channel and inability of a valve to open or close are examples of failure. If a valve does not open, flow is prevented; if it does not close completely, valve leakage may occur at an inopportune time. There is also the possibility of a contaminant in the microfluidic channels.

There are also potential for human errors. For example, most samples for immunoassays, e.g., human plasma or human serum samples, are diluted with a diluent at a prescribed ratio, for example one-to-one (one part sample to one part diluent) or one to five. It is important for the proper ratio to be supplied, but personnel may improperly prepare the samples.

With microfluidic assays in general, and especially automated microfluidic immunoassays performed within portable cartridges, there are many steps in the assay protocol that need to occur with specific timing and specific reagents. For instance it is necessary to know when a buffer liquid or reagent is being flowed through a microfluidic channel and when a sample is being flowed, and whether, in each case, it is flowed at the proper rate and/or for the proper duration. It is also necessary to know whether there is leakage or flow into regions where no flow can be permitted. Further, when a liquid volume is displaced in a pulsed flow type microfluidic system, for instance as a reciprocating piston pump pushes small slug (portions) of liquid sequentially through a channel, it is important to have a precisely determined quantity of fluid in each slug.

Problems in attempting to obtain this information arise. For instance, because liquids flow in microfluidic channels are very tiny (e.g., 100-200 microns cross section width and depth, only millimeters in length) flows are difficult to visualize. The channels are so small that it is difficult for the human eye to observe the fact that liquid is not flowing where it is desired. The assay reagents are typically transparent, compounding the difficulty of visual or optical observation.

The problems are especially acute when seeking highly accurate quantification in a microfluidic assay. In quantifying assays it is desired that a given amount of immobilized capture agent be exposed to a given amount of various fluids to enable reactions over defined times so that results can be compared to a standard to enable the quantification. Results need to be determined with an overall coefficient of variation of less than 10% (accuracy within 10%), preferably much less.

Thus, to be quantitative, assays require consistent run-to-run performance. For example in an assay employing a fluorescent dye conjugated with immobilized, captured moieties, the concentration and the volume of the buffer or wash liquid, of secondary reagents such as antibodies, and of fluorescent dye all need to be the same from run to run if one is to compare the result to a standard calibrating curve precisely generated from previous calibrating runs. This is particularly true in blood testing in which a patient human plasma or serum sample is measured for the presences or the quantity of specific health-related analytes, for instance, antibodies such as interleukins (a class of antibodies called cytokines), e.g., IL5 or IL6. There are many other classes of antibodies to be measured in plasma or serum.

For these reasons it is important to verify that at the end of an assay when a result is generated, that the result has been produced precisely according to the desired protocol.

The result of an assay is typically measured by detecting an emanation, e.g., a fluorescence intensity, from a reaction site. The emanation may come from a bead, a micro particle or an immobilized spot. As presently preferred, it comes from an immobilized glass nano-reactor (GNR) in the form of a small hollow tube or micro-tube, of length no more than 1000 micron, typically less than 500 micron, with capture agent, e.g., antibody, immobilized on its inside surface.

The fluorescence intensity from the region of the capture agent is essentially all that is measured at the completion of many assays. That fluorescence intensity is compared to a calibration curve. From the calibration curve the unknown concentration of the analyte is determined. For the calibration curve to be valid to a particular run, it is necessary that all of the conditions for that assay are repeated specifically and reproducibly from run to run. Improved means to measure such conditions are to be greatly desired.

For the following description of novel techniques for monitoring microfluidic assays, it is important that the exact location of features on a microfluid cassette be known. Novel techniques for doing this are described later herein.

SUMMARY

In a first aspect, the invention features an operating and reading instrument for performing an assay employing a portable microfluidic assay cartridge, the instrument comprising a translatable table under automated control, the translatable table carrying a receiving region for the portable cartridge and carrying a port system connectable to the cartridge that includes at least one remotely automated valve carried by the translatable table, the valve arranged to apply pressurized flowable substance at selected times to the cartridge while the cartridge is on the translatable table.

In preferred implementations of this aspect of the invention may incorporate one or more of the following:

The instrument may have pneumatically-actuatable micro-valves and the flowable substance may be air at positive or negative pressure. There may be a plurality of controllable valves on the translation table adapted to apply positive and negative pressure to the cartridge to operate micro-valves thereon. The valve or valves on the translatable table may be solenoid operated. A flexible hose or hoses may connect the valve or valves on the translatable table to a fixed source. The port system on the translatable table may comprise a raised rigid boss with an engaging rim constructed to engage a compliant surface at the receiving port of the portable cartridge to form a fluid tight seal. There may be a plurality of adjacent receiving ports on the portable cartridge and the port system on the translatable table may comprise a ganged set of rigid bosses having engaging rims lying in the same plane, constructed to engage a planar compliant surface on the cartridge. The instrument may include clamping means for clamping the portable cartridge against the porting system carried on the translatable table. The clamping means may comprise a lever mounted on a pivot axis, may have a manual operating portion and a load applying portion for pressing the cartridge against the porting system, the manual operating portion may be spaced substantially further from the pivot axis than the load applying portion. The instrument may include a stationary optical system constructed to inspect the cartridge during movement of the table, the optical system may have a fixed optical axis and the table may be constructed to move the cartridge across this axis to enable imaging different regions of the cartridge. The optical instrument may be constructed to read the cartridge by epi-fluorescence. The table may be movable in X and Y orthogonal coordinates. The instrument may include a planar radiant heater plate mounted in close proximity to, and parallel with, a planar surface of the cartridge, adjacent its enclosed microfluidic channels, the plate of size sufficiently larger than the portable cartridge so that the fluidic portion of the cartridge may always be adjacent the radiant surface throughout its range of translation. The heater pate and an optical system for inspecting the cartridge may lie on the same side of the cartridge, wherein there may be an aperture through the heater plate through which the optical inspection axis extends. The instrument with the optical system may have an objective lens mounted in close proximity to or within the aperture of the heater plate. The instrument may be constructed and programmed to translate the cartridge for inspection during conduct of the fluid flow portions of the assay for monitoring or determining location of portions of the microfluidic system. The instrument may be constructed and programmed to translate the cartridge for inspection after conduct of the fluid flow portions of the assay for reading the results of the assay. The instrument may be constructed and programmed to perform an immunoassay on the cartridge. The instrument may be constructed and programmed to perform ELISA on the cartridge. Only fluid connections to the cartridge may be pneumatic connections.

In some aspects, a method of conducting an assay may employ any of the method or apparatus disclosed herein.

In a second aspect, the invention features an operating and reading instrument for performing an assay employing a portable microfluidic assay cartridge, the instrument comprising a translatable table under automated control, the translatable table carrying a receiving region for the portable cartridge and carrying a port system connectible to the cartridge that includes at least one remotely automated valve arranged to apply pressurized flowable substance at selected times to the cartridge while the cartridge is on the translatable table, the instrument including a stationary optical system constructed to inspect the cartridge during movement of the table, the optical system having a fixed optical axis and the table constructed to move the cartridge across this axis to enable imaging different regions of the cartridge.

Preferred implementations of this aspect of the invention may incorporate one or more of the following:

The optical instrument may be constructed to read the cartridge by epi-fluorescence. The table may be movable in X and Y orthogonal coordinates. The instrument may include a planar radiant heater plate mounted in close proximity to, and parallel with, a planar surface of the cartridge, adjacent its enclosed microfluidic channels, the plate of size sufficiently larger than the portable cartridge so that the fluidic portion of the cartridge may always be adjacent the radiant surface throughout its range of translation. The heater pate and an optical system for inspecting the cartridge may lie on the same side of the cartridge, wherein there may be an aperture through the heater plate through which the optical inspection axis extends. The optical system may have an objective lens mounted in close proximity to or within the aperture of the heater plate. The instrument may be constructed and programmed to translate the cartridge for inspection during conduct of the fluid flow portions of the assay for monitoring or determining location of portions of the microfluidic system. The instrument may be constructed and programmed to translate the cartridge for inspection after conduct of the fluid flow portions of the assay for reading the results of the assay. The instrument may be constructed and programmed to perform an immunoassay on the cartridge. The instrument may be constructed and programmed to perform ELISA on the cartridge. The only fluid connections to the cartridge may be pneumatic connections. In certain implementations, any method or device disclosed herein may be used in conjunction with a method of conducting an assay. The instrument may be provided with an operating program adapted to translate the table, and the table is so movable, prior to completion of the fluid portions of the assay for purposes of precisely determining the position of microfluidic channels for use during monitoring the fluidic portions of the assay or reading the results.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 2A and 2B are diagrammatic plan views, on enlarged scale, depicting 4 micro-length tube elements fixed in series in a flow channel, FIG. 2A illustrating substantial liquid flow both through the flow elements and as by-pass flow through by-pass passages on the outside of the elements, while FIG. 2B illustrates the continued flow condition in the case in which one micro-length tube becomes blocked.

FIG. 5 depicts a flow element and a micro-length tube element example, illustrating the percentage reduction of active capture agent under differing conditions of the surfaces of the element;

FIG. 9G shows an element being introduced with interference fit into a channel, the width of which is less than the diameter of the element, while

FIGS. 19A and 22B illustrate the flow cross-sections of a flow channel with micro-length tube element in place in a channel;

FIG. 20A is a diagram of a laser and computer controlled steering mirror cutting a pattern in double sided PSA film with peelable liners;

FIG. 20B is a plan view of a laser-cut pattern in the material of FIG. 20A, defining pneumatic control channels and features for integrated valves and pumps while FIG. 20C is a magnified view of a portion of FIG. 20B;

FIG. 27 is a schematic diagram in perspective of assembly steps for a microfluidic assay device, a Figure very similar to FIG. 1 except for numeral references instead of legends;

FIG. 29 is a greatly magnified plan view of a portion of the channel structure, showing two channels, with four hollow flow elements disposed in each (see FIG. 68) and indicating scanning;

FIG. 40A, in plan view, illustrates hollow micro-particles (here, micro-length tubes) distributed in random fashion onto a flat surface, and a pick up head is shown;

FIG. 40B is a three dimensional diagram showing a picking head with video system and computer controller for effecting relative movements X, Y, Z and angular orientation theta between a surface element and the picking head;

FIGS. 40C and 40D are side cross-sectional and plan views of a placement tool in form of a vacuum tip;

FIGS. 40E and 40F are side and horizontal cross section views of a tweezer pick up tool;

FIG. 42A is a diagrammatic showing of two opposed layers of PDMS, showing them in the natural state of the PDMS which is a hydrophobic state with methyl group endings exposed;

FIG. 42B is a similar Figure following plasma oxygen plasma treatment showing the separated layers are terminated in OH groups;

FIG. 42C is a similar Figure illustrating permanent bonds between the hydroxyl groups producing oxygen covalent bridging;

FIG. 44A is similar to FIG. 43B, but shows each PDMS layer deflected outwardly from the other in the central region; and it illustrates two regions of PDMS following plasma activation, steady contact in region $R_2$ and cyclical contact and activation or separation in what is referred to as the valve region, $R_1$, illustrating the initiation of permanent bonding through the hydroxyls and the condensation reaction resulting in bridging oxygen in the region $R_2$, and in region $R_1$, where contact had occurred only temporarily and then removed, the surface having a number of methyl groups or non-bonding or lower energy state species;

FIG. 45A, similar to FIG. 44A, is a figure illustrating a single deflected surface opposing a planar surface.

FIGS. 44B, 43C and 45B show deflection chambers useful with, respectively, the devices of FIGS. 44A, 43A and 43B, and 45A;

FIGS. 46A, 46B, 46C, 46D, 46E and 46F illustrate composite membranes useful with the Make and Break process: FIG. 46A illustrates, in cross-section, a composite membrane comprising a thin flexible sheet (PET) and a PDMS film of greater thickness; FIG. 46B illustrates, in cross-section, a thin flexible sheet (PET) and a PDMS coating of lesser thickness; FIG. 46C illustrates, in plan view, a PET/PDMS lamination having circular stress relief channels formed in PET film; FIG. 46D illustrates, in cross-section, a composite membrane similar to that of FIG. 46A, but having stress relief slots formed in the thin flexible sheet (PET); FIGS. 46E and 46F, similar to FIGS. 41 and 43C, illustrate in cross-section a composite corresponding to that of FIG. 46D, in respectively un-deflected and deflected states;

FIG. 50A shows, diagrammatically, a pneumatic tool (the reservoir/pneumatic layer) to which a fluidic layer is to be brought into contact and joined, the system capable of applying pressure or vacuum to the pneumatic tool, FIG. 50B being a magnified view of a portion of FIG. 50A;

FIG. 50C shows the pneumatic tool in cross-section with the fluidic layer pressed against it, while FIG. 50D is a plan view, with the connections to supply ports for selective application of vacuum and pressure to the pneumatic tool;

FIG. 54A is a cross-section similar to FIG. 43C, but indicating an un-bonded area beyond the limit lines B of the pneumatic chamber, while FIG. 54B is a magnified view of a portion of FIGS. 54A and 54C is a plan view (top view), each denoting a leak path beyond the pneumatic chamber; FIG. 54D is a protocol flow diagram including cross-sectional views associated with states within the pneumatic chamber during the make and break protocol; FIGS. 54E and 54F and 54G are views similar, respectively, to FIGS. 54A, 54B and 54C, but showing no leak path exists outside the chamber boundary; and FIGS. 54H and 54I are similar respectively to FIGS. 53A and 53B but have an initial phase using constant −3 psi deflection pressure, followed by positive and negative pressure cycling.

FIGS. 56A, 56B, 56C, 56D, 56E, 56F, 56G, 56H, 56I, 56J, and 56K illustrate functions performable by the membrane layer: FIG. 56A, close channel; FIG. 56B, close channel, fix micro-particle in channel, particle shown as round in cross-section; FIG. 56C, close channel, fix micro-particle in channel, particle shown of another shape; FIGS. 56D (a lengthwise cross-section) and 56E (a transverse cross-section), close channel, fix micro-particle element in the shape of a micro-length tube in channel; FIG. 56F, close channel, fix multiple micro-length tubes (e.g., GNRs) in channel, define flexible membrane for a valve and a piston; FIG. 56G, fix micro-length tube (GNR) in channel in fluidic layer and define valves and piston that can be operated to constitute a pneumatically-actuated membrane-pump; FIG. 56H, close channel and in conjunction with fixing micro-length tube in channel and defining flexible membrane of pneumatically actuated valve, form via for liquid to be pumped from or to reservoir; FIG. 56I, in conjunction with closing fluidic channel and fixing micro-length tube in the fluidic channel, bounding a pneumatic channel and forming a pneumatic shunt at blockage of the pneumatic channel; FIG. 56J, close channel, fix micro-length tube in channel, at other side, bound a pneumatic channel, pneumatic shunt formed in the reservoir layer about a blockage of the pneumatic channel; and FIG. 56K, in a fluidic layer of a device, close channel, fix tube in channel and form membrane portion of micro-valve, and by exposed portion of membrane beyond the fluidic layer, define planar compliant surface for engagement with narrow lip of boss at pneumatic interface.

FIG. 57B shows solenoid-actuated three-way valves 9 on moving X,Y stage selectively apply Pneumatic Conditions at Supply Ports defined by raised bosses of FIG. 57C. Conditions supplied are: (1) atmospheric pressure, (2) positive (+) actuating pressure, (3) negative (−) actuating pressure. Only connections to moving X, Y stage assembly are positive and negative pressure line to manifolds feeding valves 9 and electrical control lines for solenoid coils of the valves;

FIG. 60 outlines the fluidic architecture of a single microfluidic subunit of the cartridge of FIGS. 57 and 57A, and, in tabular form, presents the steps of an immunoassay protocol conducted within the cassette (FIGS. 21, 28C and 103);

FIG. 61 diagrammatically illustrates the procedure of precisely determining the location of channels of a microfluidic cartridge, for instance when fixed within the precise X, Y stage system of FIGS. 57, 57A, 57B and 58;

FIG. 73—Reading Code from Micro-length tube flow element;
FIG. 74—Preferred Implementation of previous Figures first block;
FIG. 77—Bar Code in Micro-length tube Element;
FIG. 78—Scan Data File Snippet;
FIG. 79—Chip (microfluidic channel system) Layout.

FIG. 103 outlines the fluidic architecture of a single microfluidic subunit of the cartridge of FIGS. 57 and 57A, and, in tabular form, presents the steps of an immunoassay conducted within the cassette;

FIG. 104 is a diagrammatic view of a microfluidic channel containing micro-length tubes, on the insides of which are immobilized capture agents in the form of DNA (on some) and antibody (on others), while

FIG. 105 is a similar diagrammatic view of a microfluidic channel containing micro-length tubes, on the insides of which are immobilized capture agents;

Figure 121:
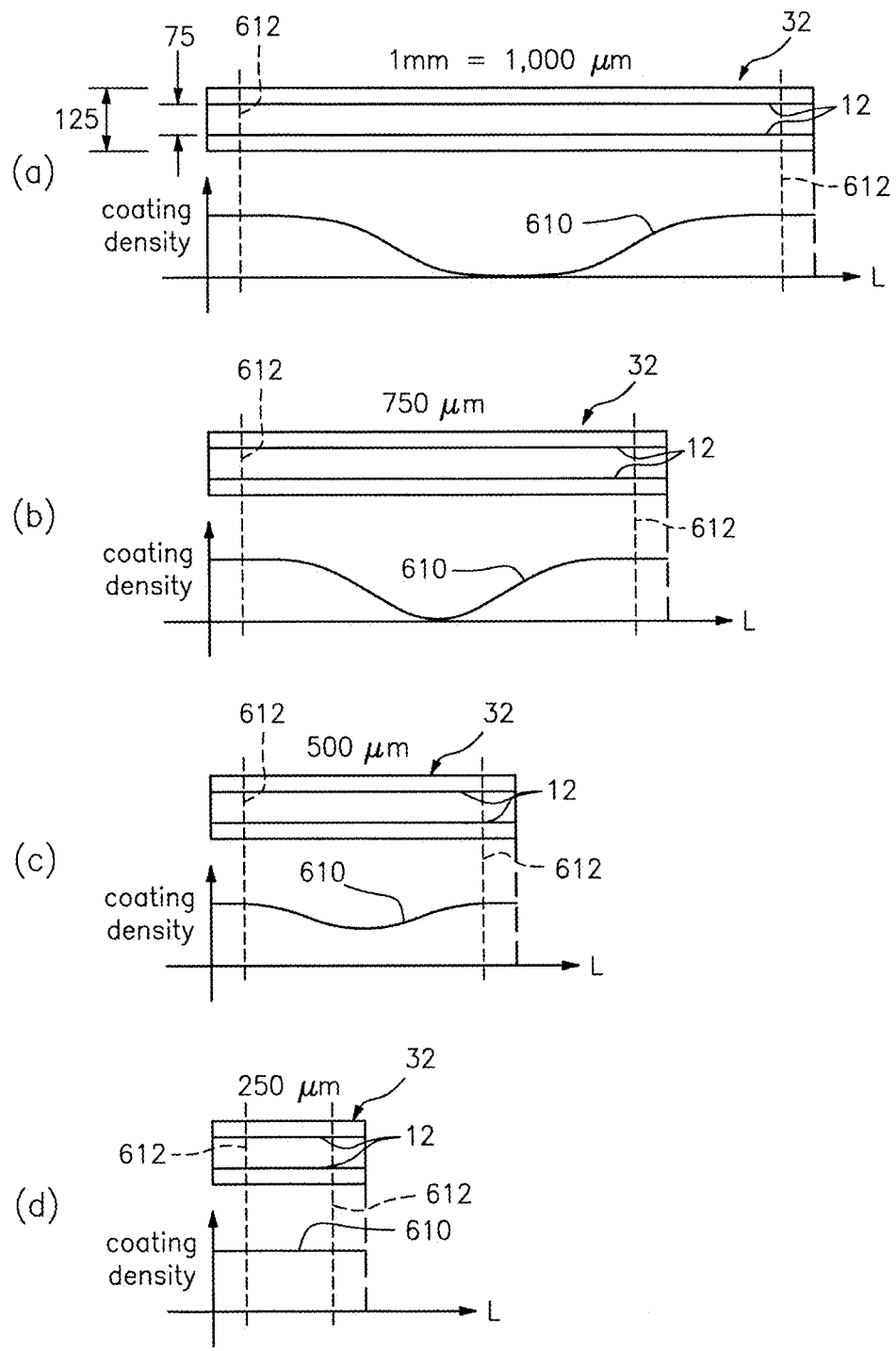

FIG. 121, illustrations (a)-(d), are side views four GNRs at different lengths and the associated GNR internal coating density curves, in accordance with embodiments of the present invention.

Figure 122:
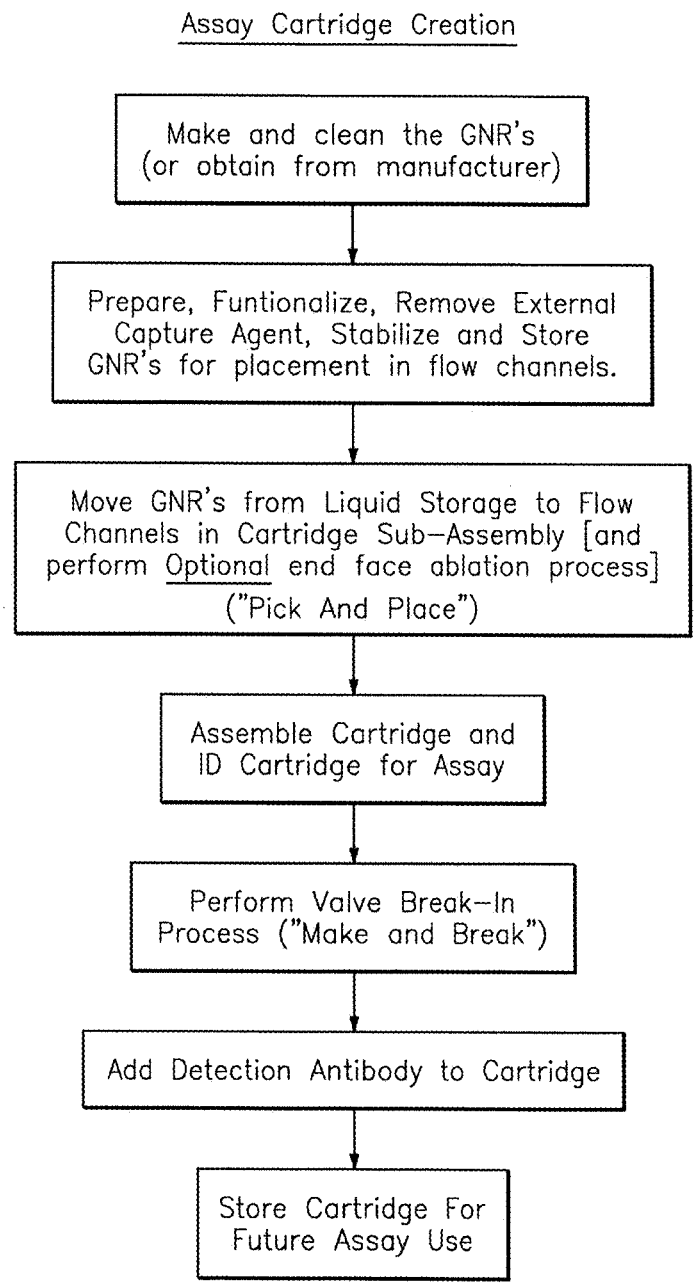

FIG. 122 is a flowchart of an assay cartridge creation process, in accordance with embodiments of the present invention.

Figure 123:
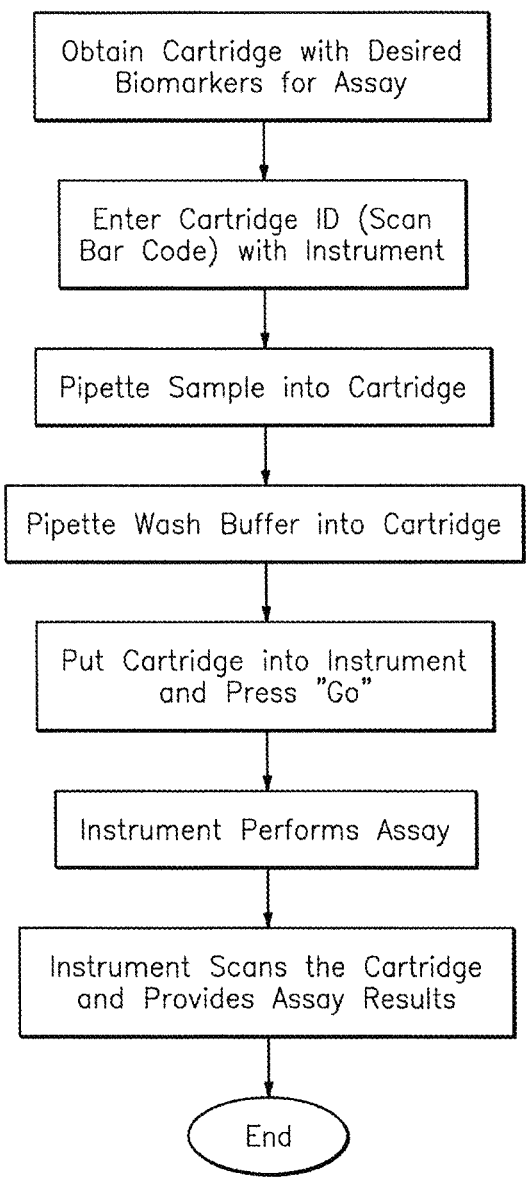

FIG. 123 is a flowchart of a process for running an assay, in accordance with embodiments of the present invention.

Figure 124:
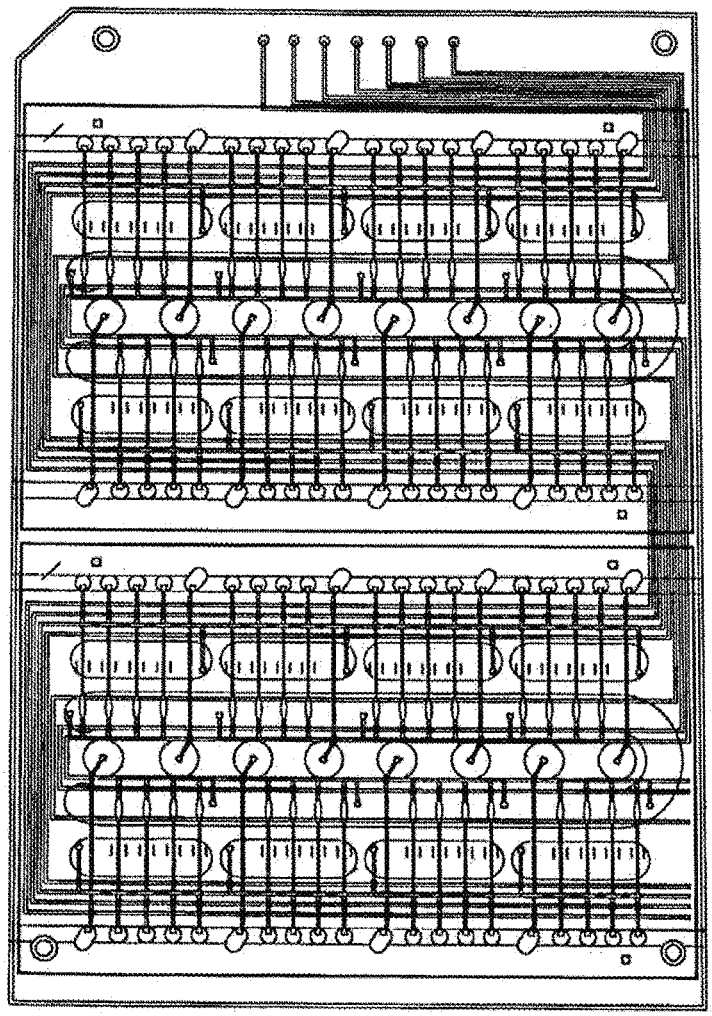

FIG. 124 is a top view of a portion of the assay cartridge, showing fluidic and pneumatic channels, in accordance with embodiments of the present invention.

Figure 125:
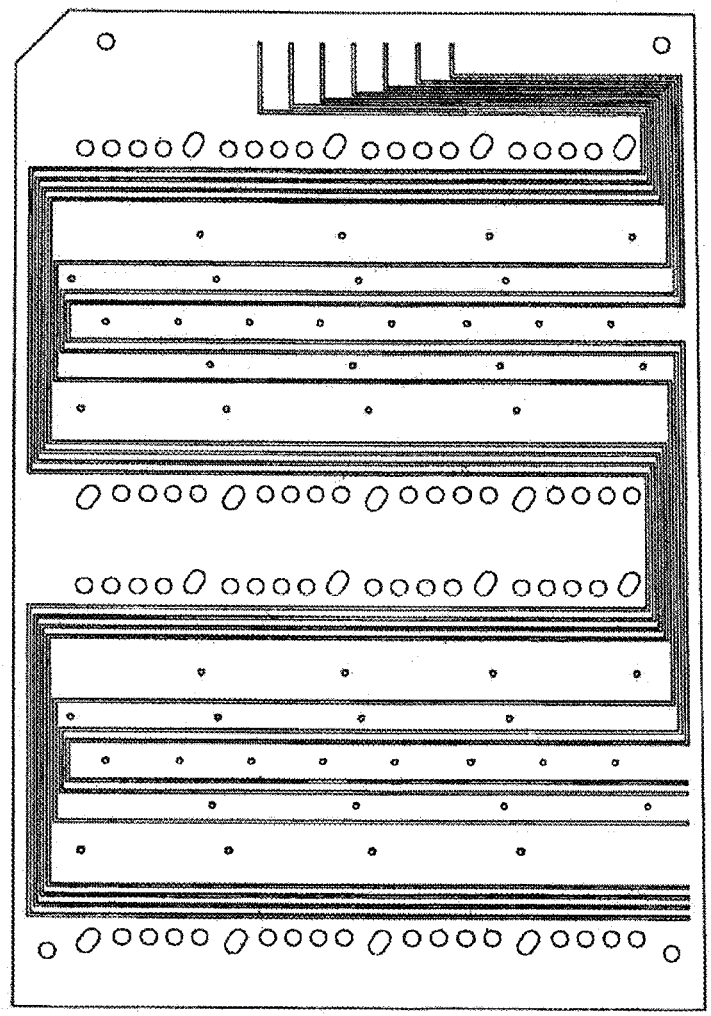

FIG. 125 is a top view of a portion of the assay cartridge showing the pneumatic channels, in accordance with embodiments of the present invention.

This application is a stylistically edited version of a corresponding PCT application which has been incorporated by reference. The edits have included some changes to the figure designations. A table of the new designations and corresponding figure designations in the earlier PCT application publication is given below. Any use of the old designation in the text of this application, if it appears, should be referred to this table for identifying the figure (or numeral) intended.

Figure 9:
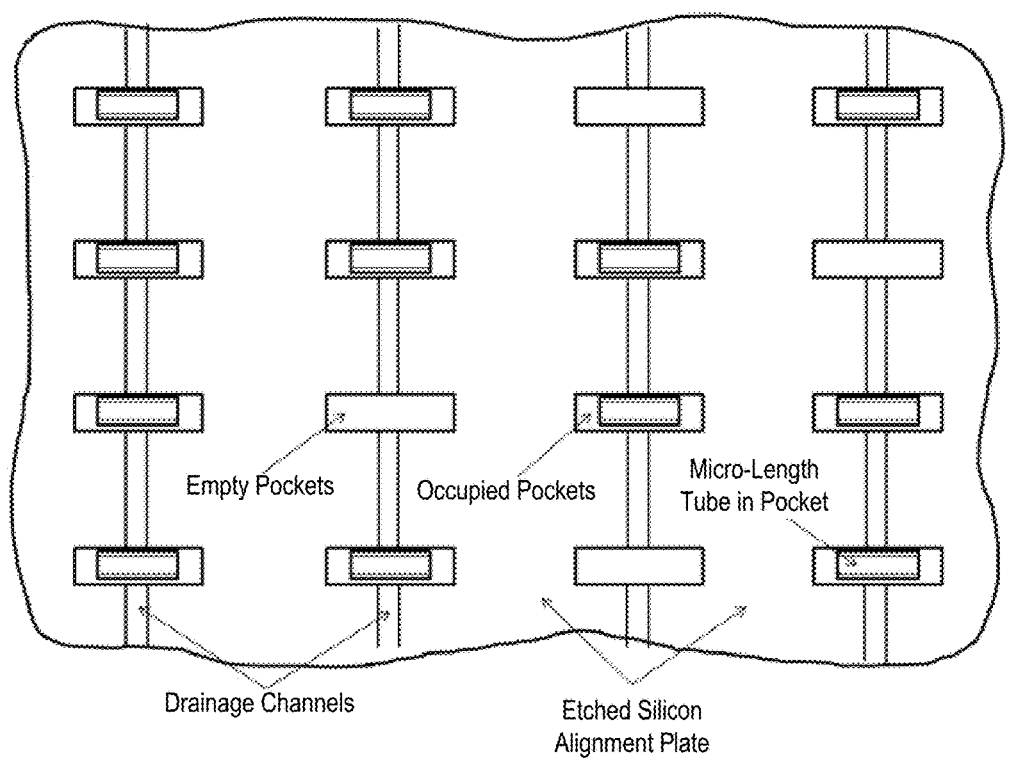
FIG. 9 is a plan view of portion of an alignment plate for micro-tubular elements.
Figure 9A:
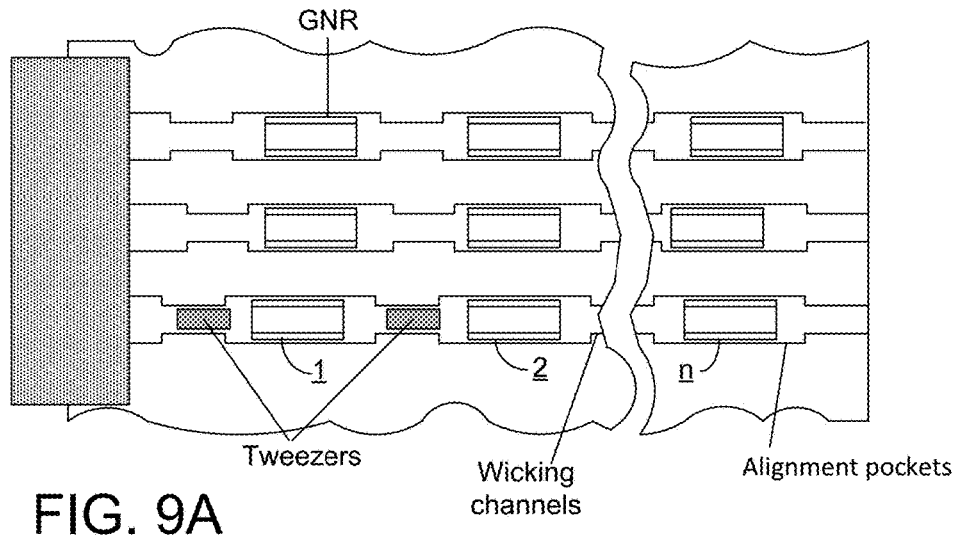
FIG. 9A, under the heading "pick and place", is a plan (top) view of alignment pocket, GNRs (micro-length tubes) in the pockets, wicking channels, and tweezers.
Figure 9B:
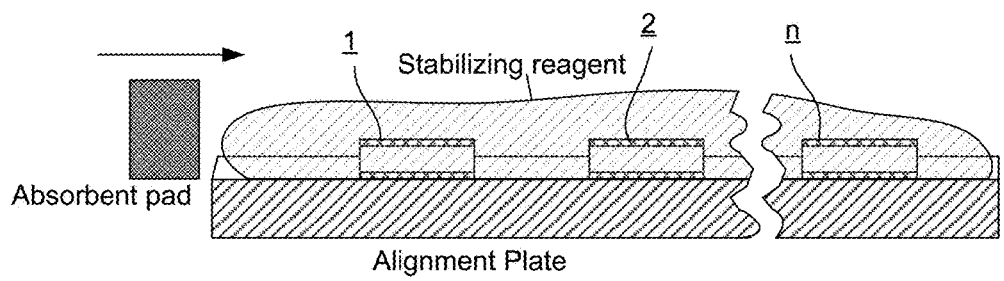
FIG. 9B is a cross-sectional view of GNRs covered with stabilizing reagent and an absorbent pad approaching the alignment plate, while FIG. 9C, similar to FIG. 9B, shows the absorbent pad positioned on the alignment plate and stabilizing reagent greatly reduced, and FIG. 9D, similar to FIG. 9C, shows the absorbent pad removed and tweezers positioned at opposite ends of a GNR.
Figure 9C:
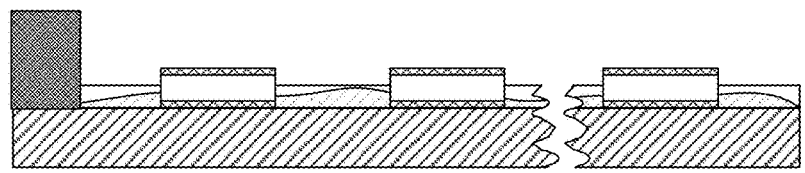
Figure 9D:
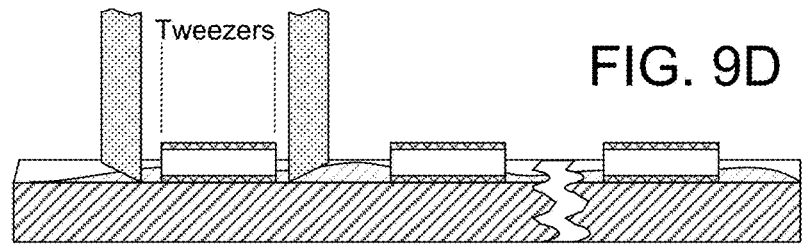
FIGS. 9D and 9E are plan (top) and vertical cross-sectional views, respectively, of a circular absorbent pad surrounding GNRs on a flat plate.
Figure 9E:
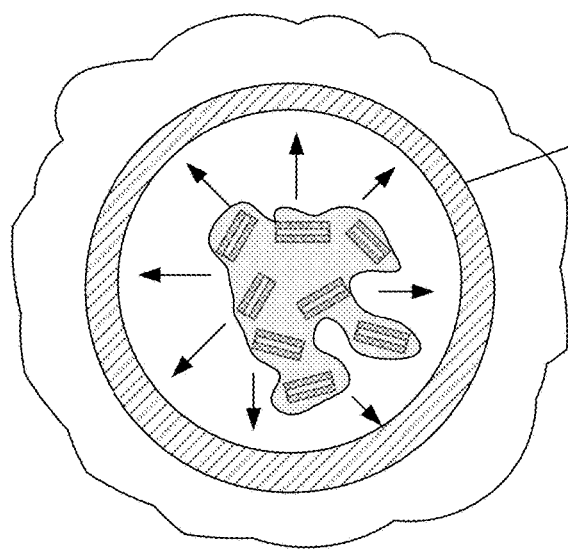
Figure 9F:
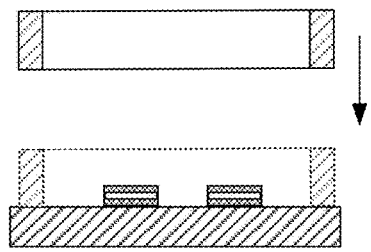
Figure 9H:
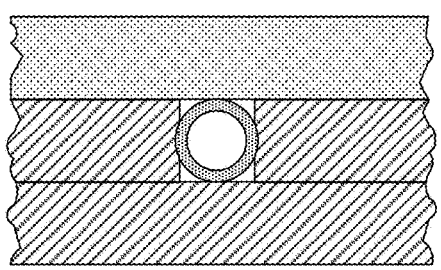
FIG. 9H shows the element in a channel closed by a top layer.
Figure 9G:
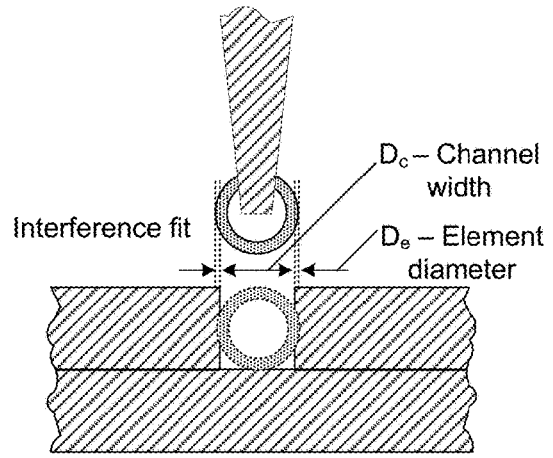
Figure 10:
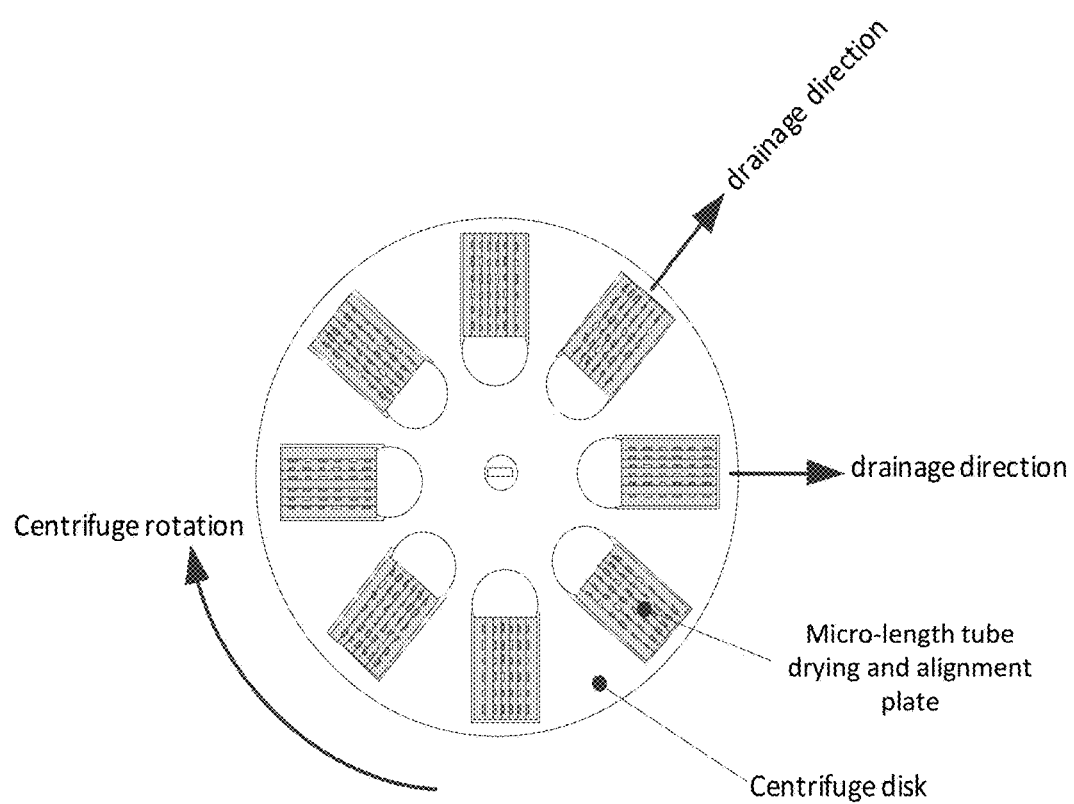
FIG. 10 illustrates a centrifugal dryer cooperating with a drying and alignment plate to dry the micro-length tube elements.
Figure 11:
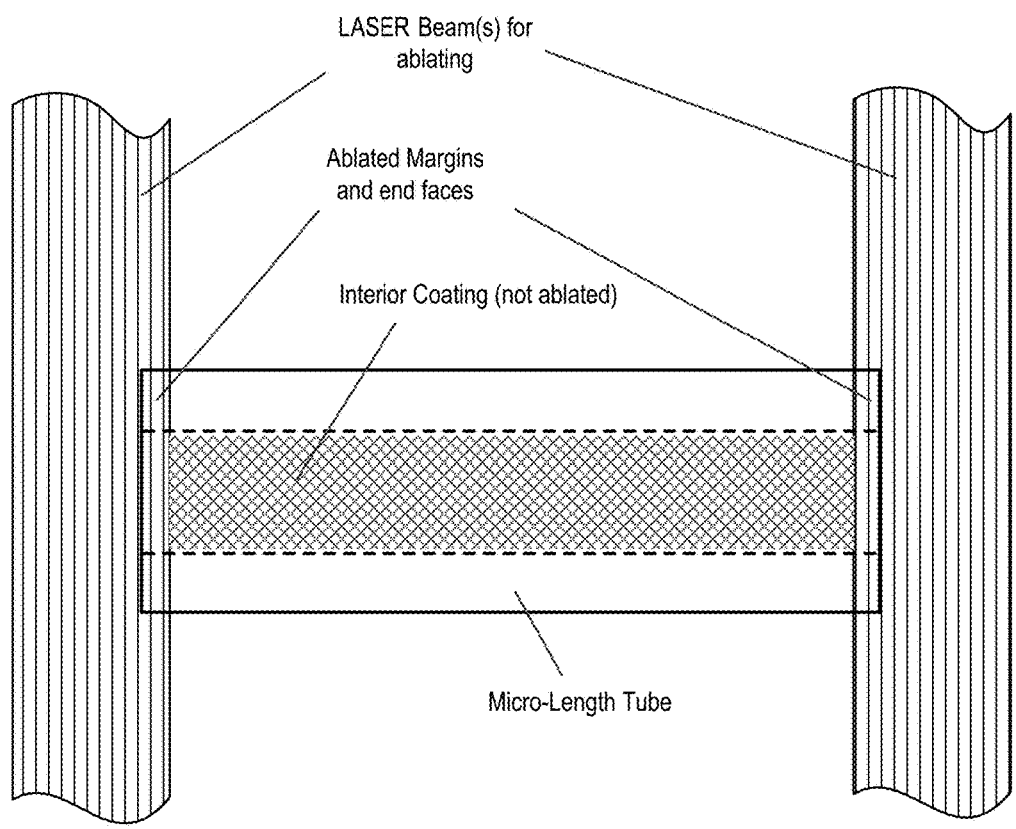
FIG. 11 is, on enlarged scale, a diagrammatic representation of laser beams ablating (removing or rendering inactive) selected regions of capture agent on end and inside surfaces of a micro-length tube element.
Figure 12:
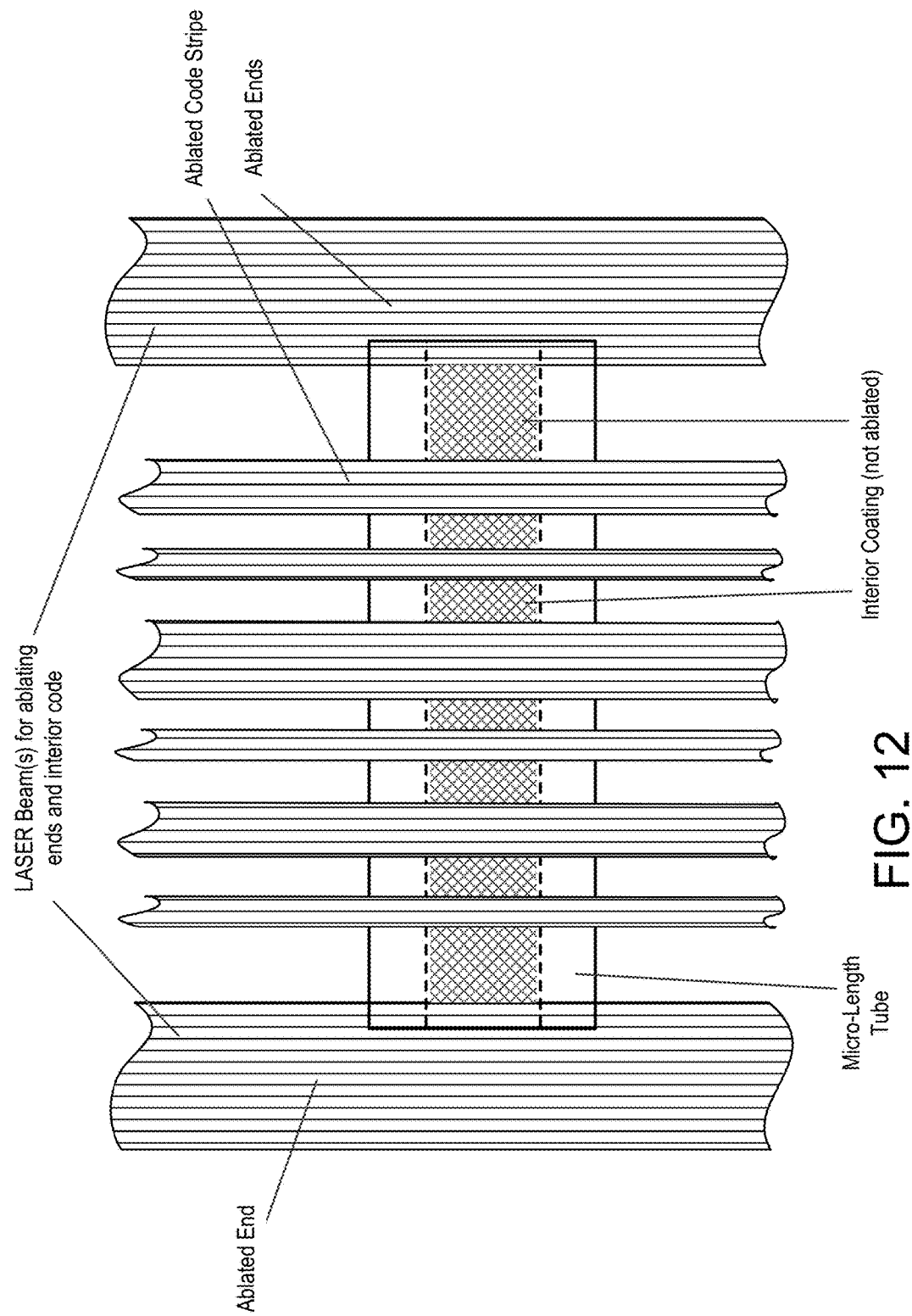
FIG. 12 is a view similar to FIG. 11, depicting the formation of a code of capture agent on the inside surface of a micro-length tube flow element.
Figure 13:
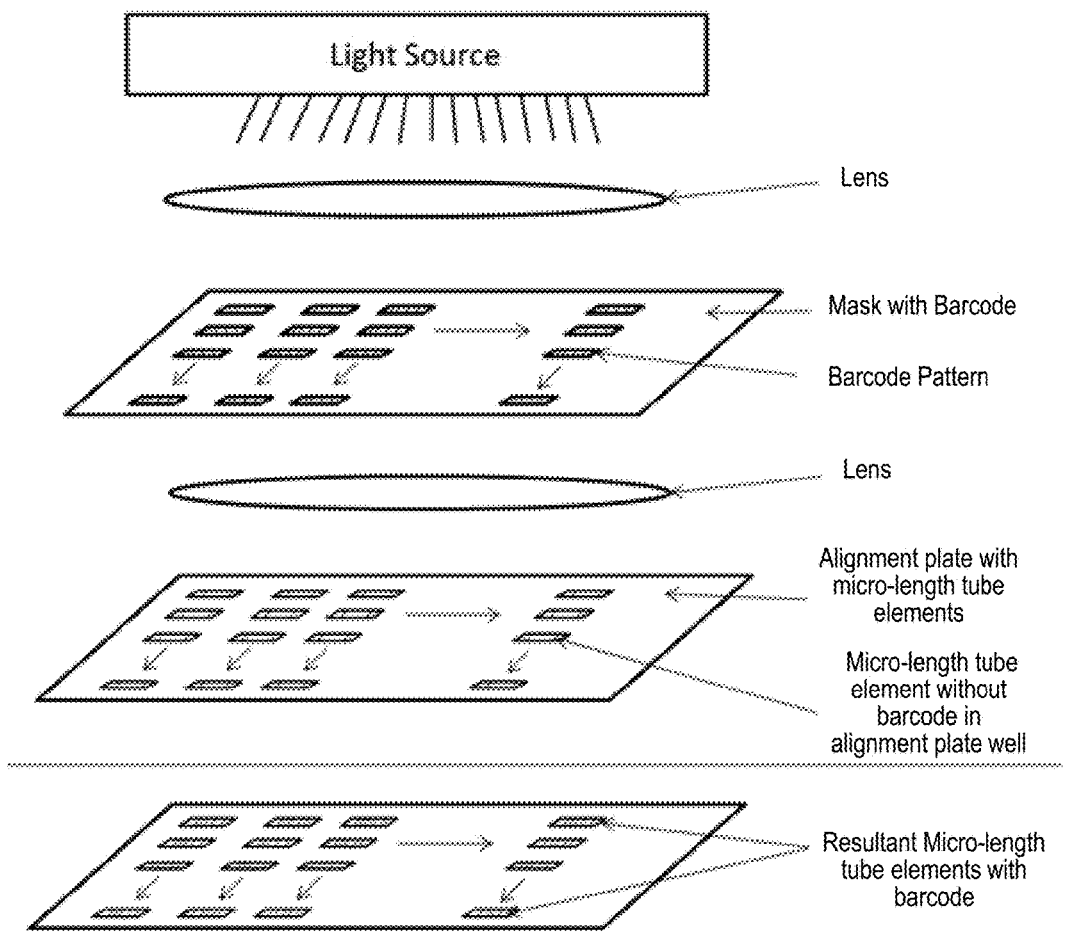
FIG. 13 depicts a photo mask exposure scheme for forming a large laser beam into beamlets that perform the steps of FIG. 11 or 12.
Figure 14:
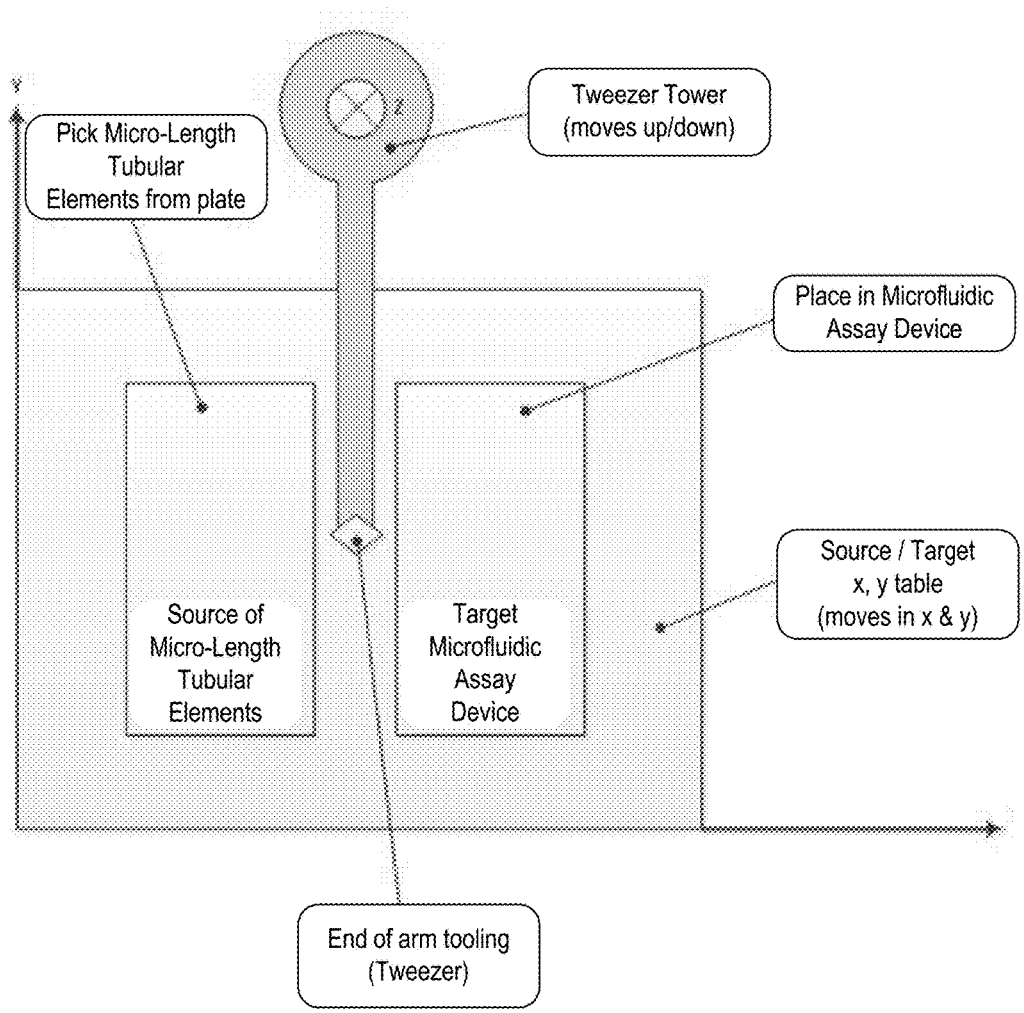
FIG. 14 is a diagrammatic top view of a system for placing discrete micro-length tube elements into open channels of a microfluidic assay device (see also FIG. 33)
Figure 15:
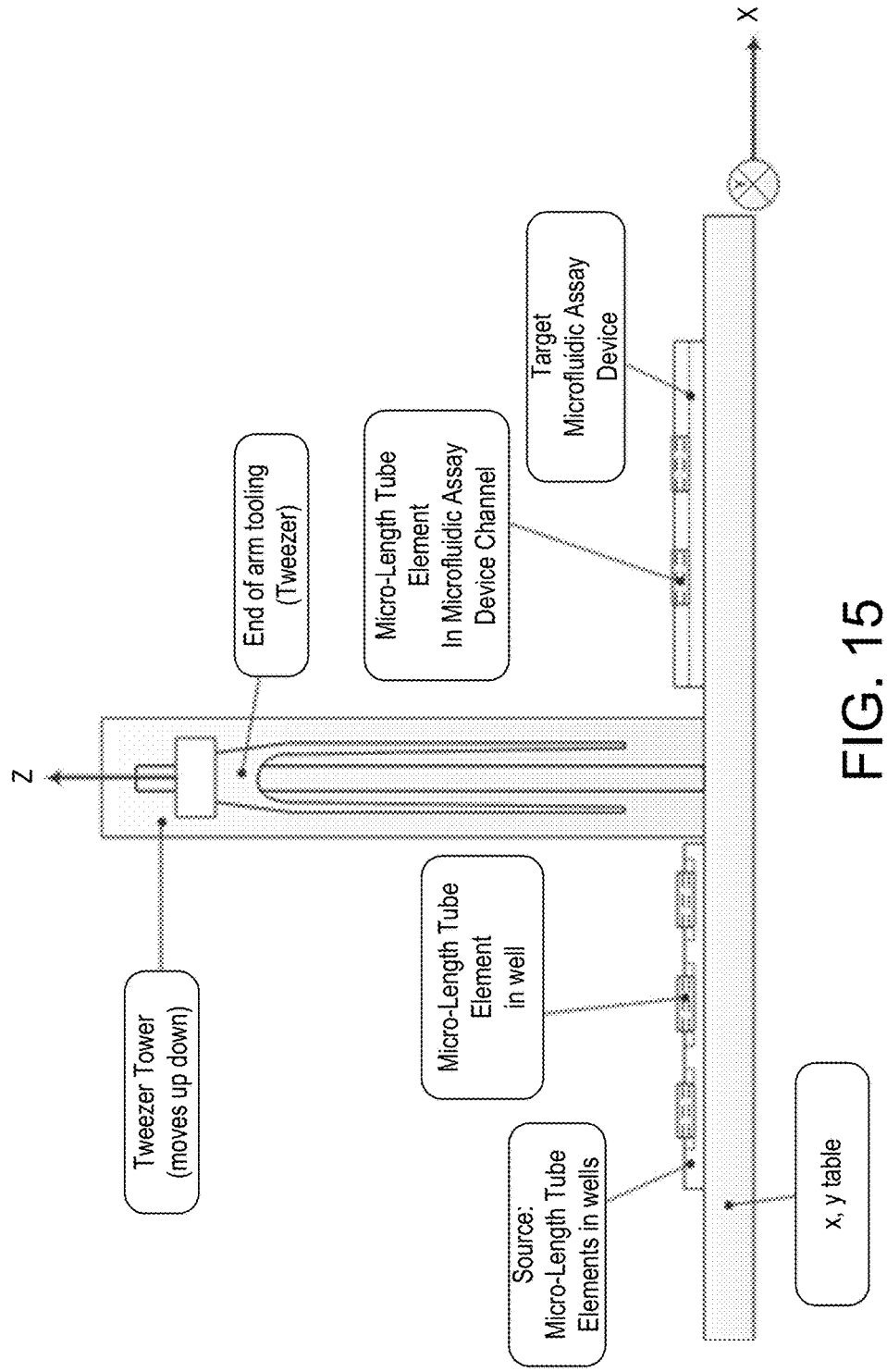
FIG. 15 is a side view of a pick and place apparatus employing a tweezer instrument for engaging end surfaces of the micro-length tube elements (see also FIG. 34)
Figure 16:
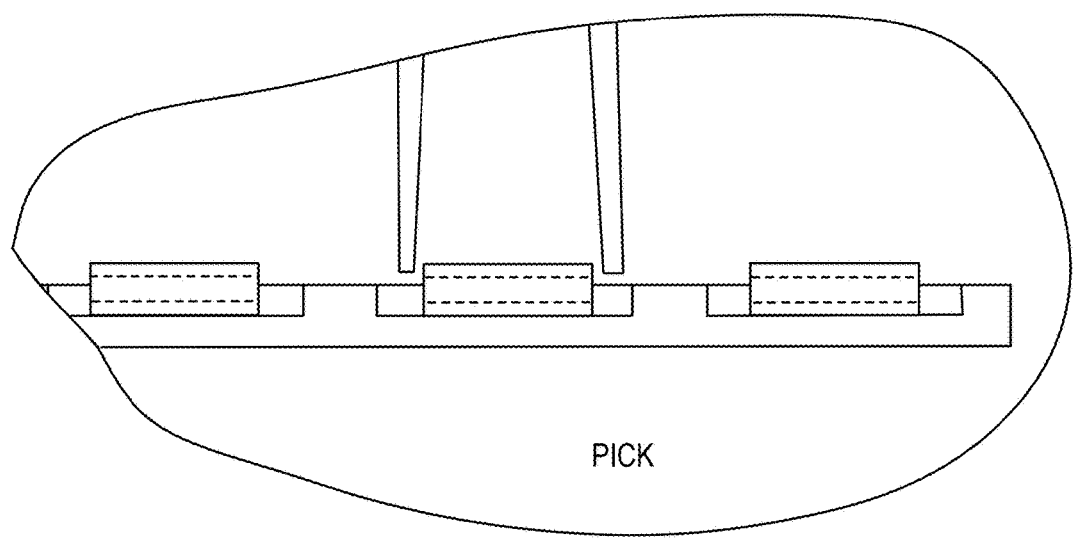
FIG. 16 "PICK", depicts the ends of tweezer tines approaching the oppositely directed end surfaces of a micro-length tube element positioned in the alignment plate.
Figure 17:
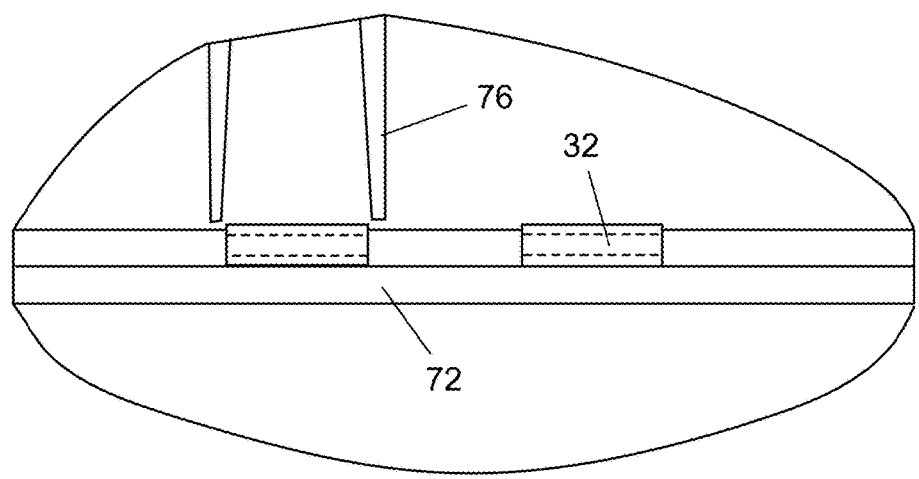
FIG. 17 "PLACE with tweezer", depicts the ends of tweezer tines leaving the oppositely directed end surfaces of a micro-length tube element positioned in a flow channel of the microfluidic device.
Figure 18A:
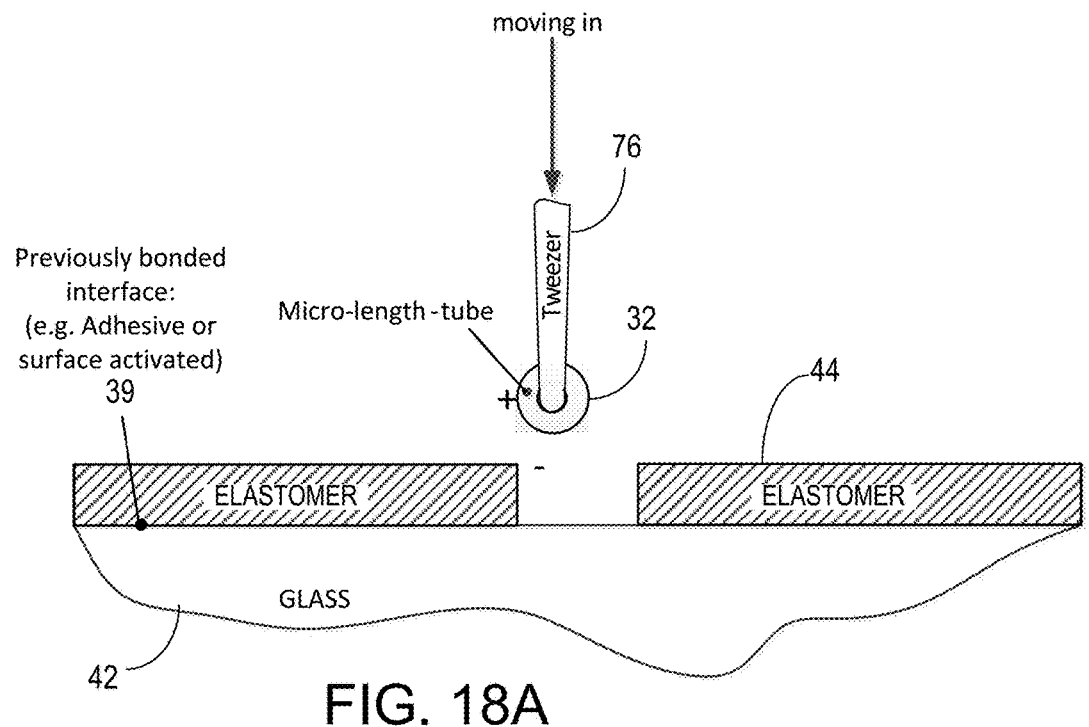
FIGS. 18A, 18B, 18C, 18D and 18E represent, in large scale end cross-section views, a sequence of steps involved in placing and fixing the position of micro-length tube elements in an assay device and completing the enclosure of a flow channel in the device.
Figure 18B:
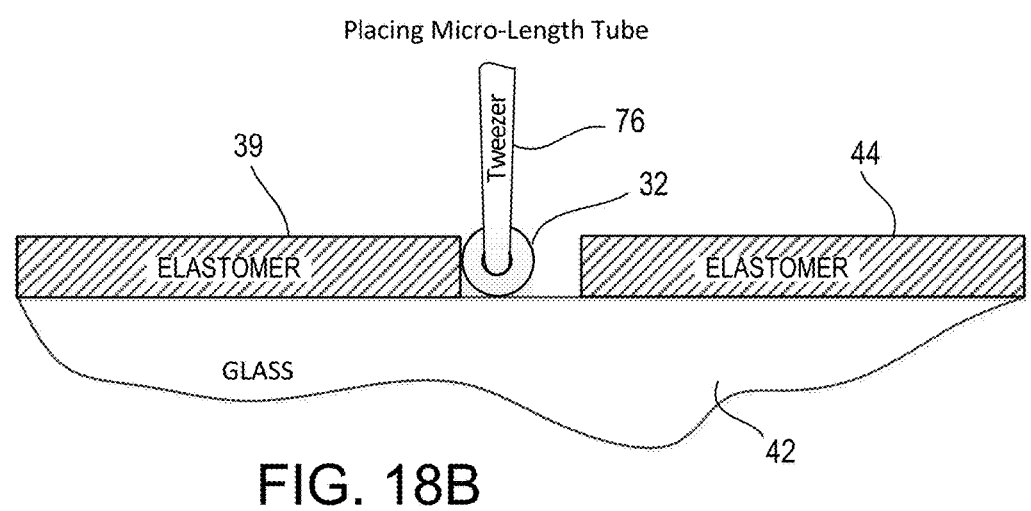
Figure 18C:
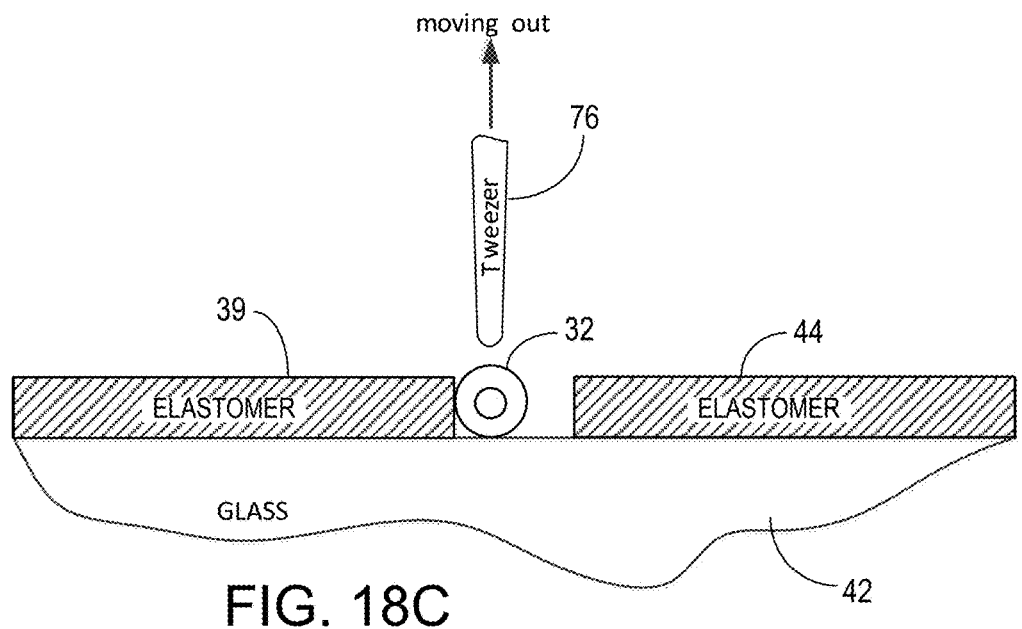
Figure 18D:
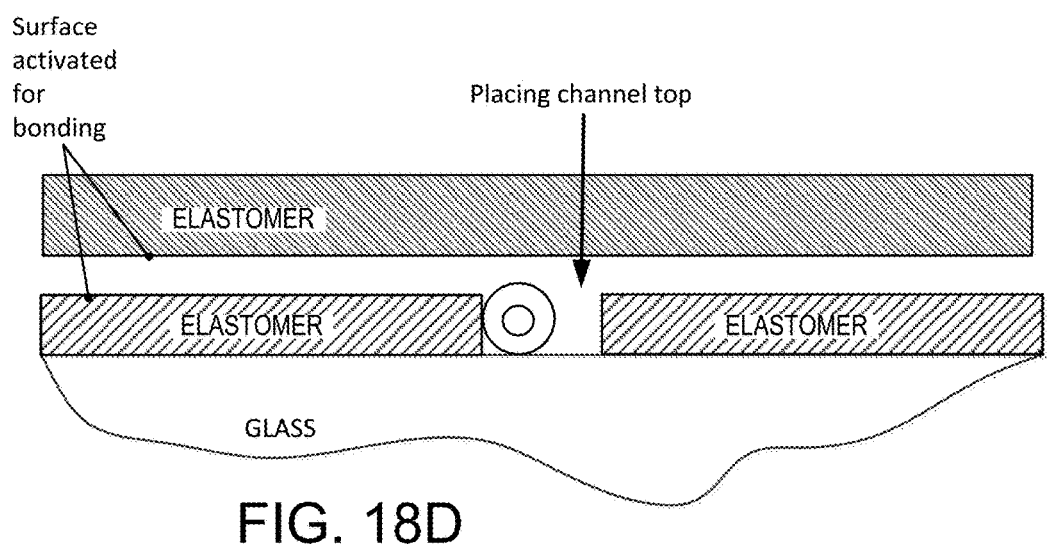
Figure 18E:
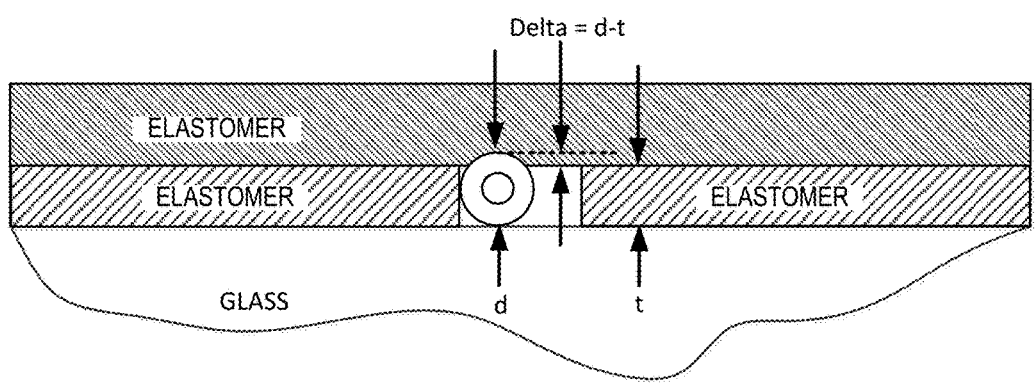
Figure 30:
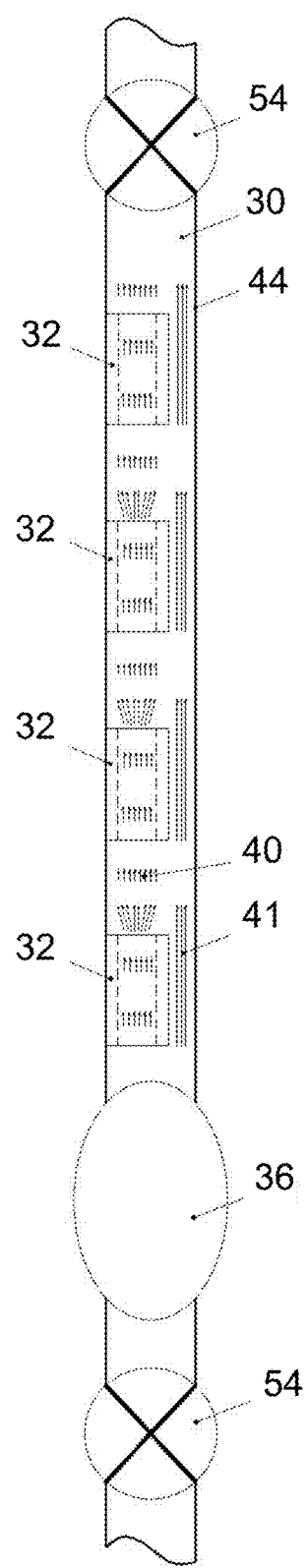
FIG. 30 is a plan view of a single channel, with schematic illustration of on-board pump and valve, and showing flow paths through and alongside hollow flow elements.
Figure 30A:
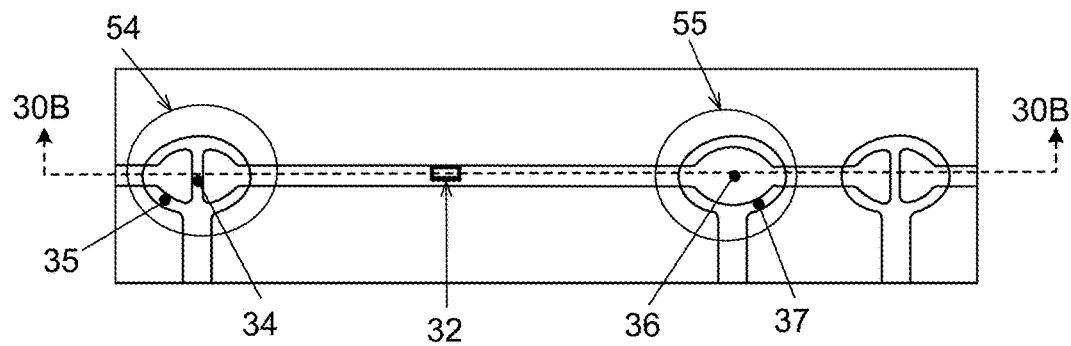
FIG. 30A is Similar to FIG. 30, a plan view, but in greater detail, of a microfluidic channel having a hollow flow element and a micro-piston located between two micro-valves.
Figure 30B:
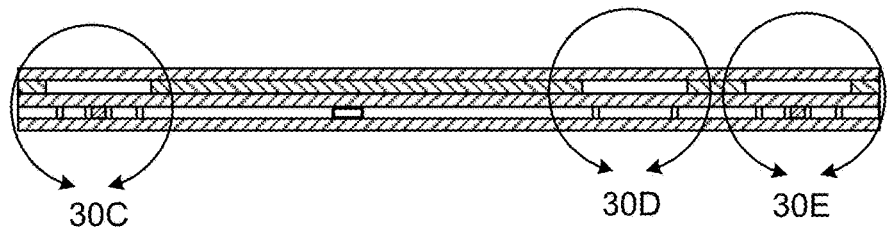
FIG. 30B is a cross section of the assembly of FIG. 30A taken on line 30B of FIG. 30A.
Figure 30C:
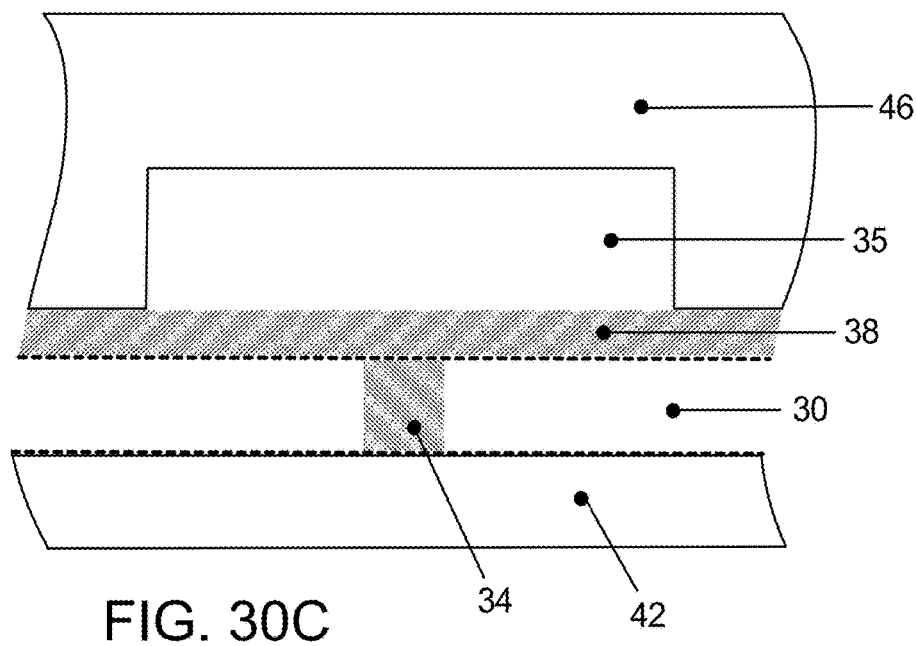
FIGS. 30C, 30D and 30E are magnified views of portions of FIG. 30B as respectively designated by circles in that figure, FIGS. 30C and 33E showing the membrane engaged upon a valve seat.
Figure 30D:
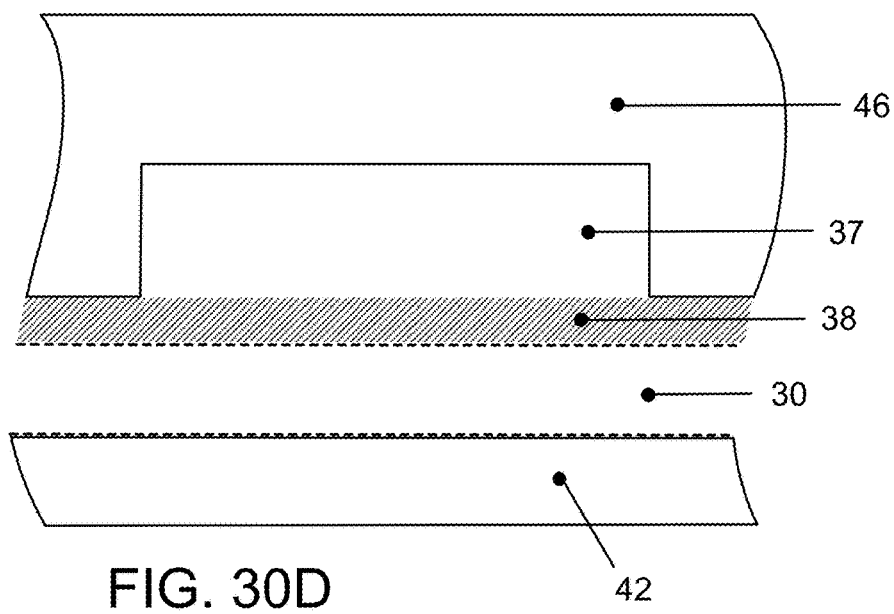
Figure 30E:
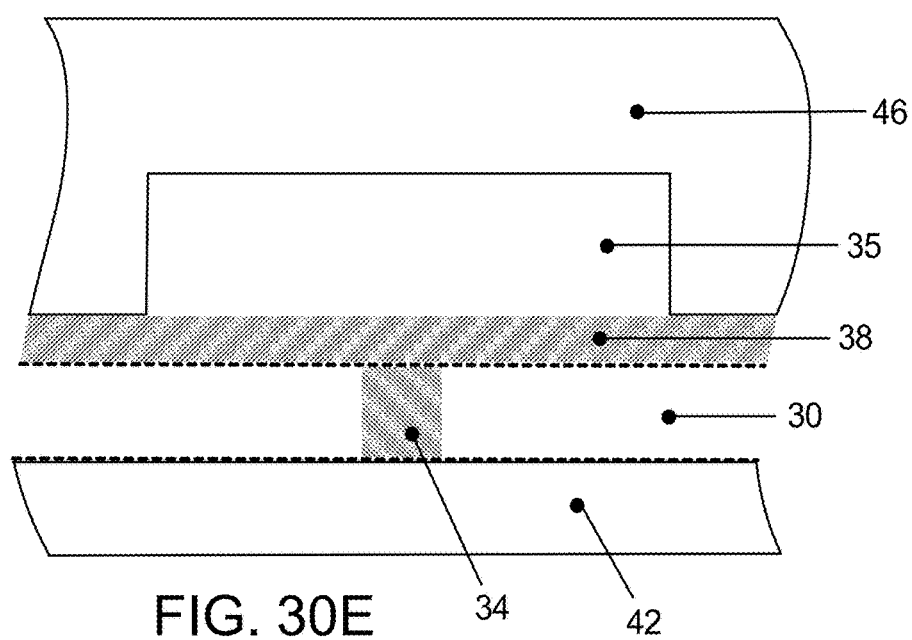
Figure 30F:
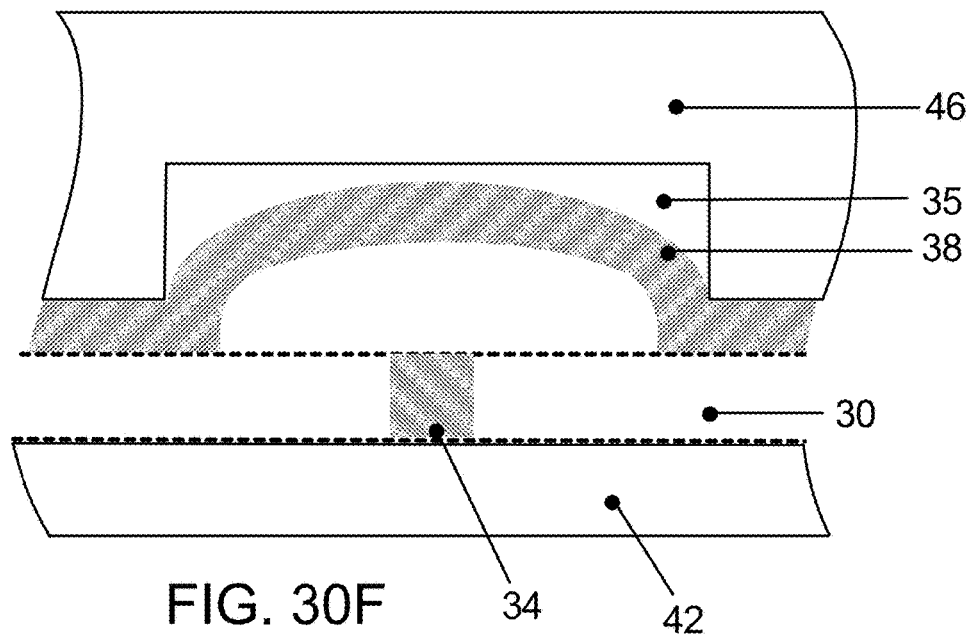
FIG. 30F is a view like the magnified cross-sections of FIGS. 30C and 30E, except with the membrane deflected away from the valve seat.
Figure 30G:
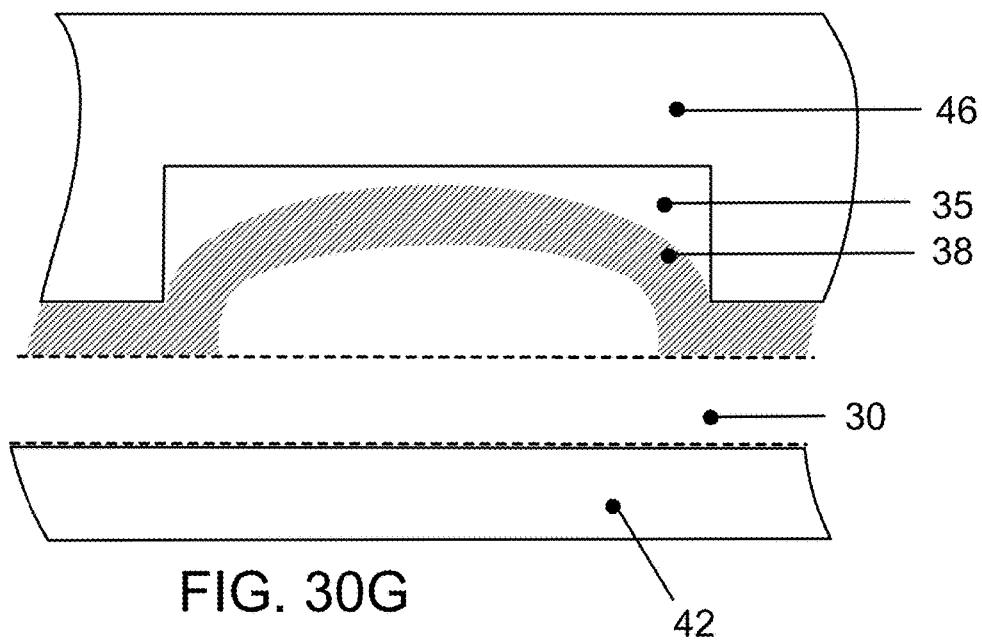
FIG. 30G is like the magnified cross-section of FIG. 30D, except with the membrane deflected.
Figure 33:
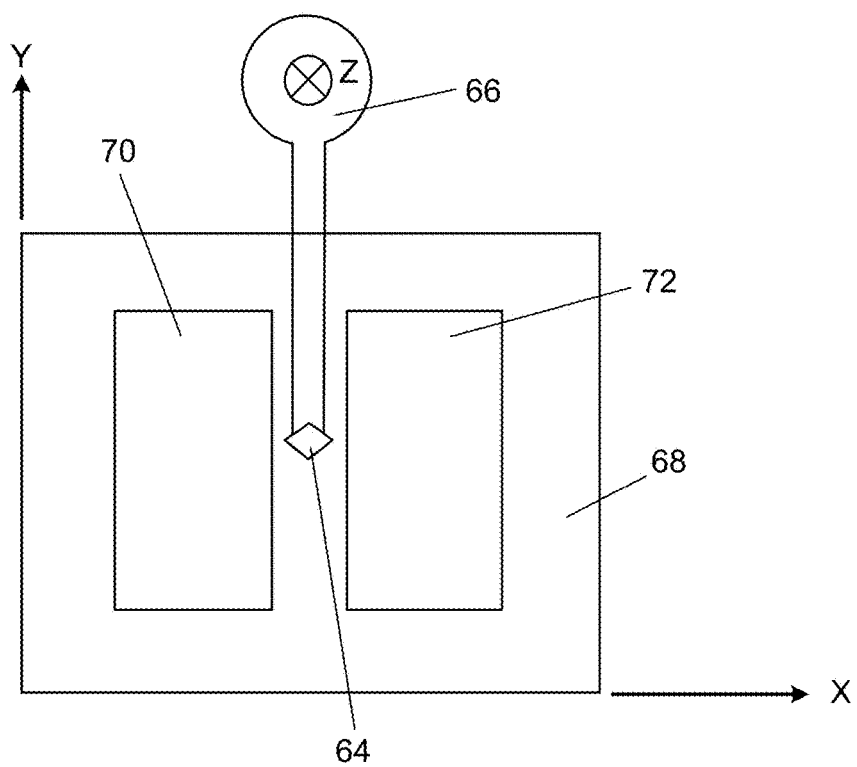
FIG. 33 is a diagram in plan view of a pick-and-place instrument positioned above an X,Y translation table, a delivery plate for discrete, extremely small hollow flow elements and a receiving channel of multiplex micro-fluidic assay devices of the preceding figures (see also FIG. 14)
Figure 34:
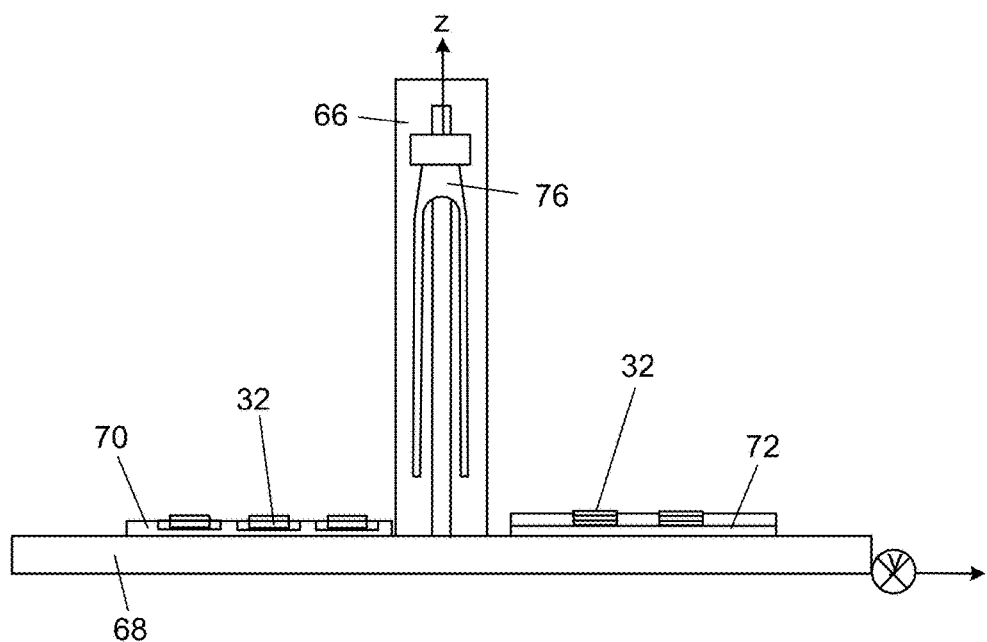
FIG. 34 is a diagrammatic front view of a tweezer type pick and place device, and its support tower (see also FIG. 15)
Figure 35:
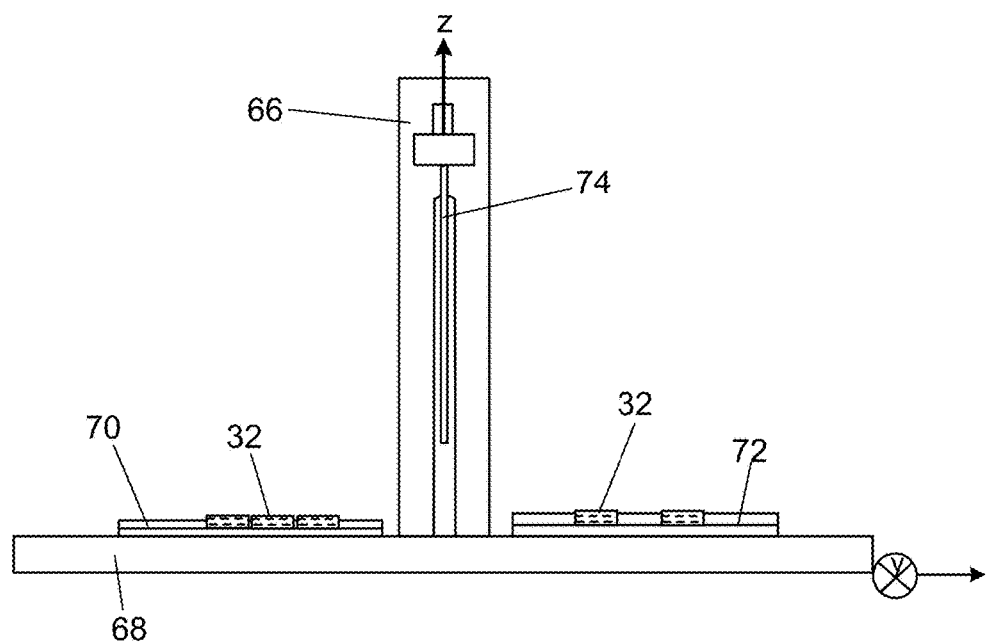
FIG. 35 is a diagrammatic front view, similar to that of FIG. 34, of a vacuum type pick and place device, and its support tower.
Figure 36:
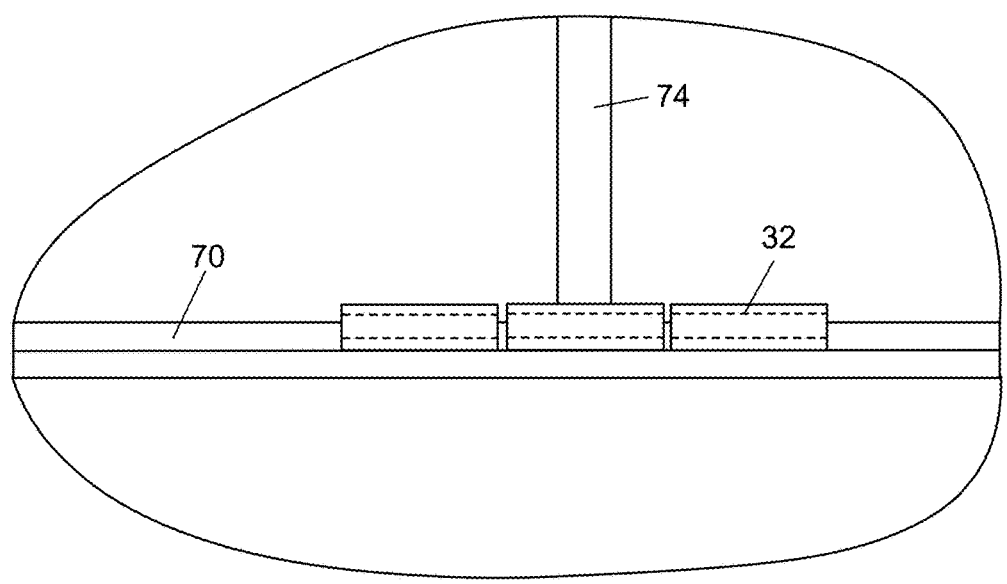
FIGS. 36 and 37 depict, respectively, picking, and placing side views of a vacuum pick up device.
Figure 37:
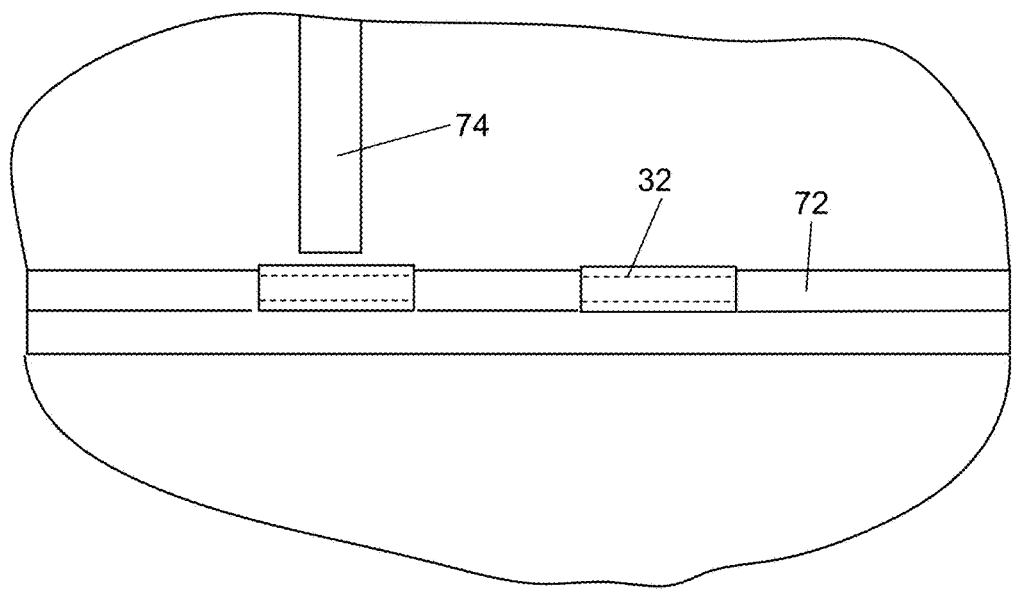
Figure 38:
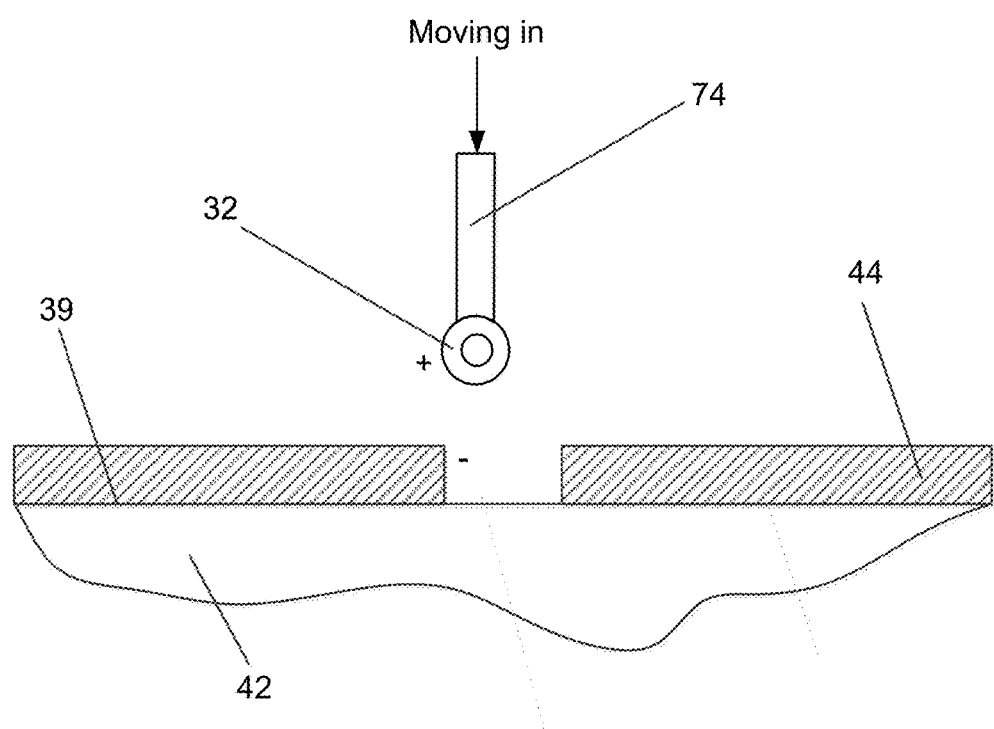
FIGS. 38, 39 and 39A depict a sequence of positions during placing of a flow element with a pick-and-place device, the + and − signs diagrammatically illustrating the use of close-space electrostatic attraction between the channel wall and the element being delivered that facilitaties placement of the element and withdrawal of the tool.
Figure 39:
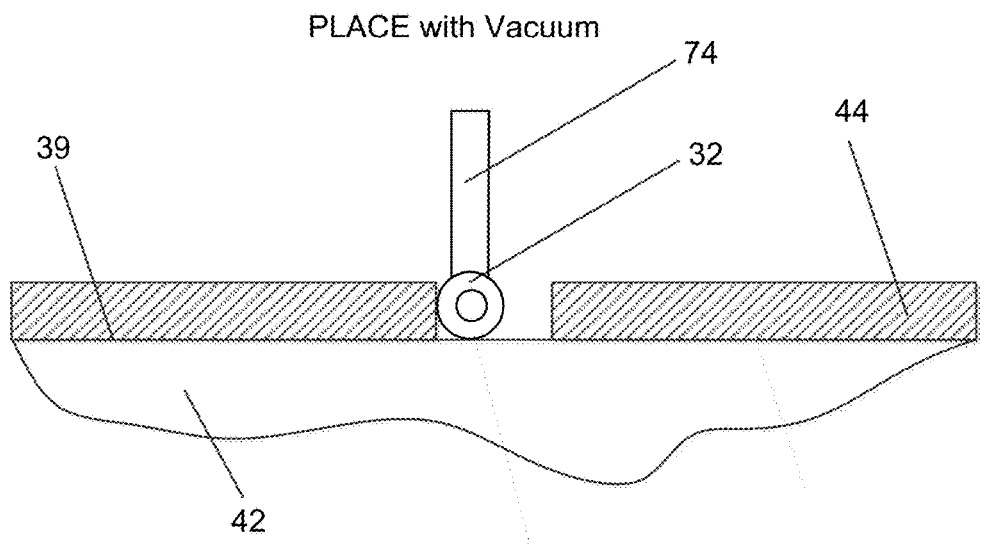
Figure 39A:
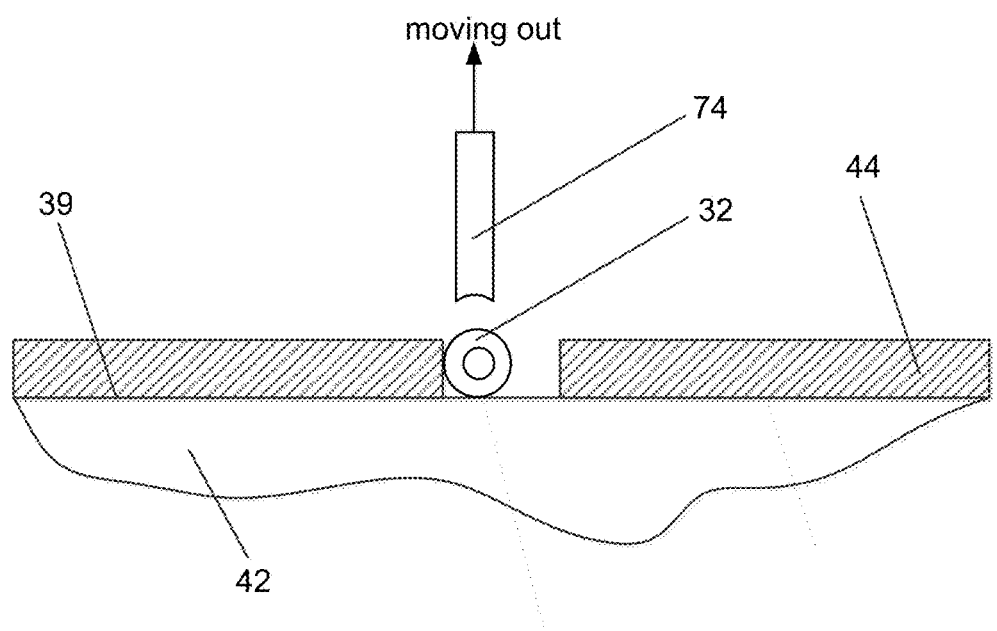
Figure 39B:
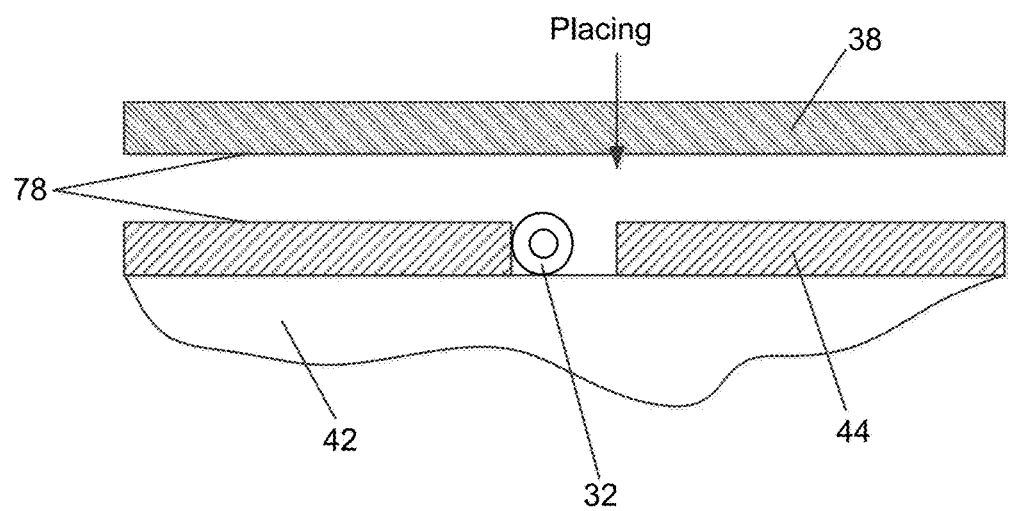
FIGS. 39B and 40 illustrate element-securing and channel-sealing actions occurring during assembly of the device of preceding figures.
Figure 40:
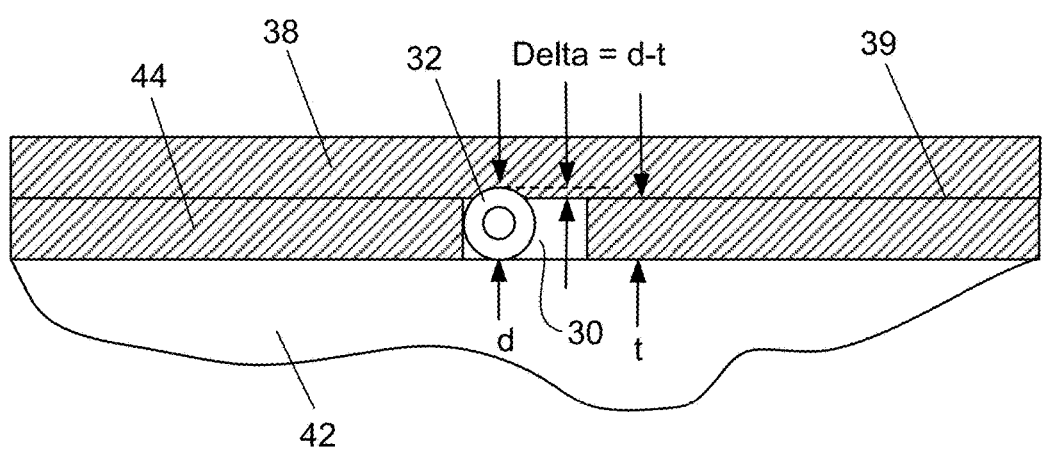
Figure 41:
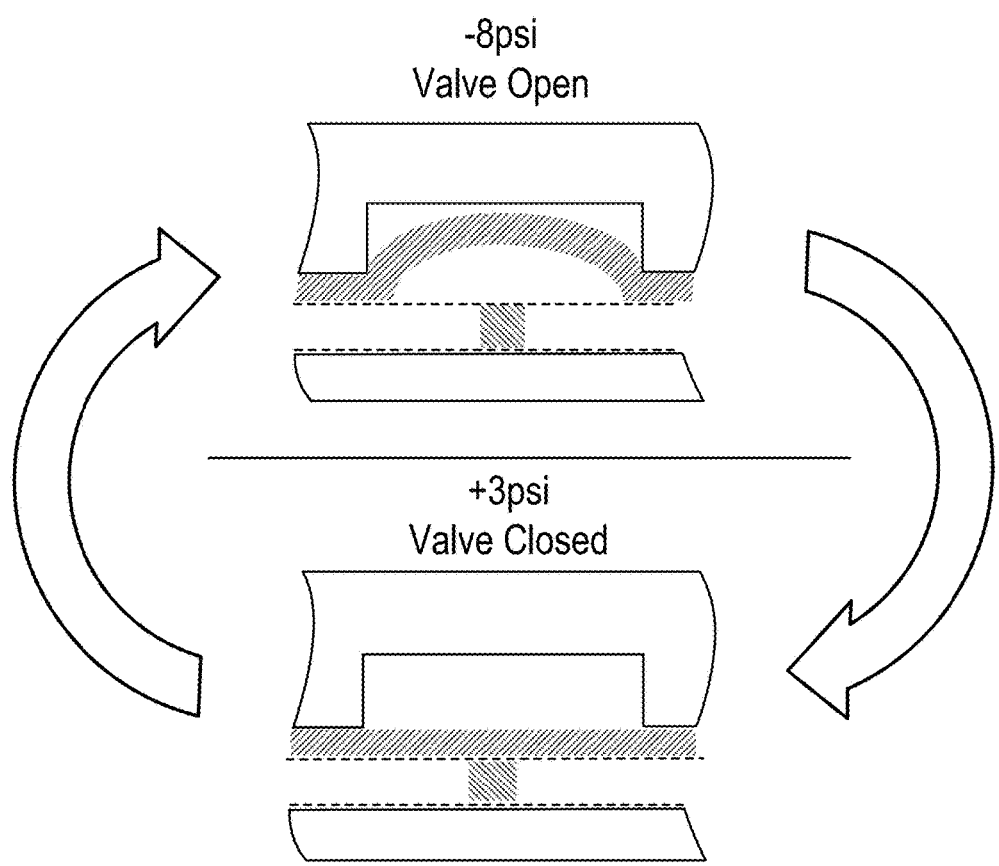
FIG. 41 is a diagrammatic view, showing the repeated cycling during manufacture of a diaphragm valve formed by an overlying portion of a PDMS layer, which is bonded to the opposed structure at each side, the diaphragm valve, repeatedly closed with 3 psi positive pressure and opened with negative 8 psi pressure (vacuum), is found to overcome the molecular bonds being formed between diaphragm and valve seat, thus over time, neutralizing the tendency for permanent co-valent bonds to form between contacting surface-activated surfaces, thus enabling the thus-formed valve to properly operate.
Figure 46A:
Figure 47A:
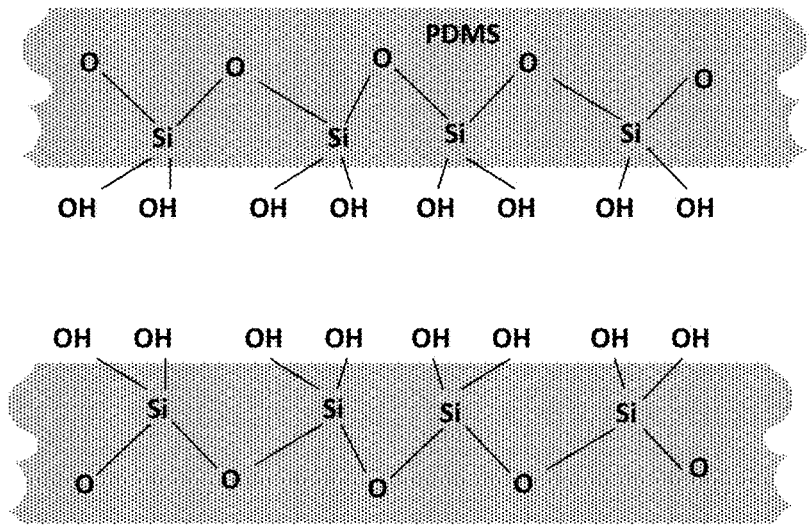
FIG. 47A is a view similar to that of FIG. 42B, but showing one layer of PDMS with OH groups exposed and an opposed layer of silicon based rigid materials with OH groups exposed facing the PDMS layer.
Figure 47B:
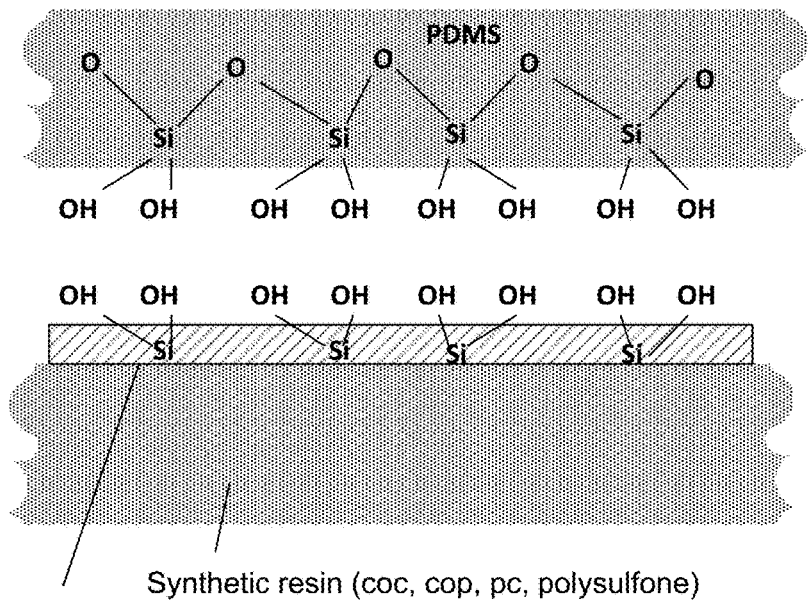
FIG. 47B is a view similar to that of FIG. 42B but showing one layer of PDMS with OH groups exposed, and an opposed layer comprised of synthetic resin, carrying an intermediate bi-functional layer with OH groups exposed facing the PDMS layer.
Figure 48A:
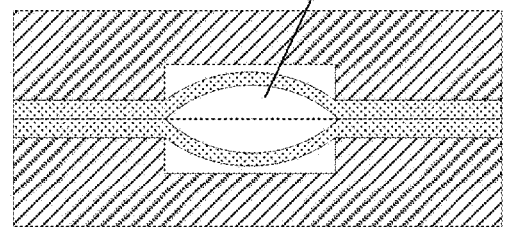
FIGS. 48A, 48B, and 48 show a fluidic channel, FIG. 48, having two different cross-sections, FIGS. 48A and 48B taken, respectively on the detail lines A and B of FIG. 48, the details correspondingly respectively with previous FIGS. 44B and 45B.
Figure 51A:
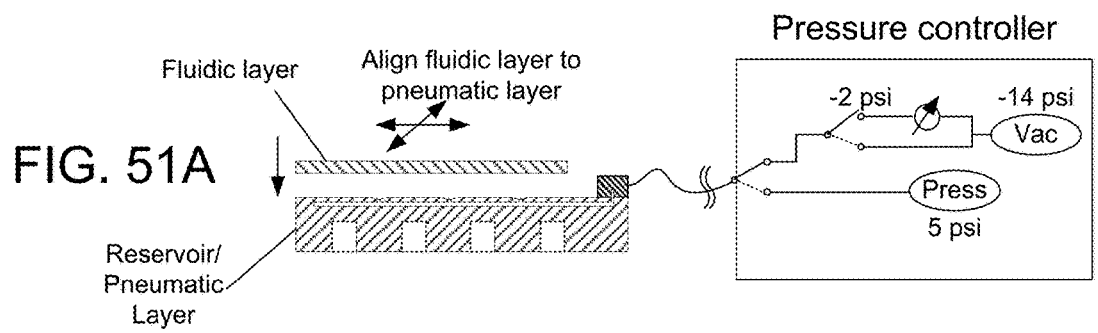
FIGS. 51A, 51B and 51C correspond respectively with the foregoing for a system that is the same except the pressure controller is constructed to selectively apply vacuum at two values, −2 and −14 psi)
Figure 51C:
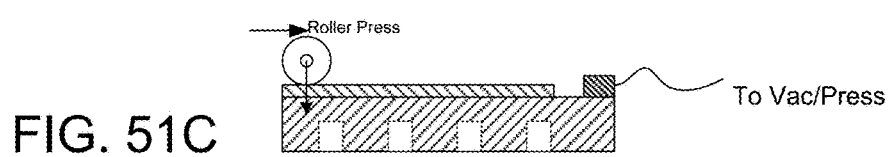
Figure 51D:
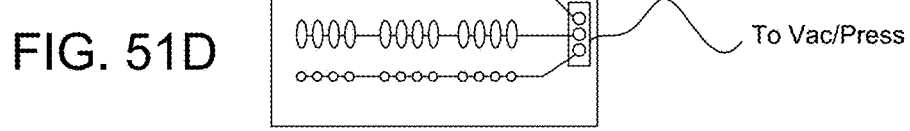
Figure 51B:
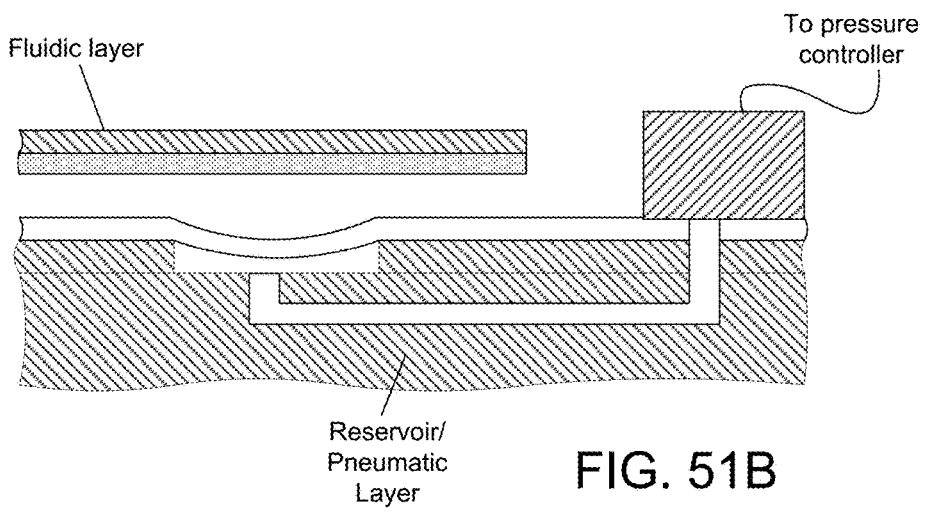

| PCT Publication | Current Application |
| --- | --- |
| FIG. 50H (Sheet 12) | FIG. 9H |
| FIG. 50G(i) (Sheet 12) | FIG. 9G |
| FIG. 33A' Numeral 12B (Sheet 42) | FIG. 30B Numeral 30C |
| FIG. 33A' Numeral 12C (Sheet 42) | FIG. 30B Numeral 30D |
| FIG. 33A' Numeral 12D (Sheet 42) | FIG. 30B Numeral 30E |
| FIG. 51 A-11 (Sheet 66) | FIGS. 46C, 46D, 46E, and 46F |
| FIG. 51A-12 (Sheet 67) | FIGS. 47A and 47B |
| FIG. 51B(ii) (sheet 68) | FIGS. 51B, 51C and 51D |
| FIG. A-16 Detail A (Sheet 69) | FIG. 48A |

-continued

Figure 1:
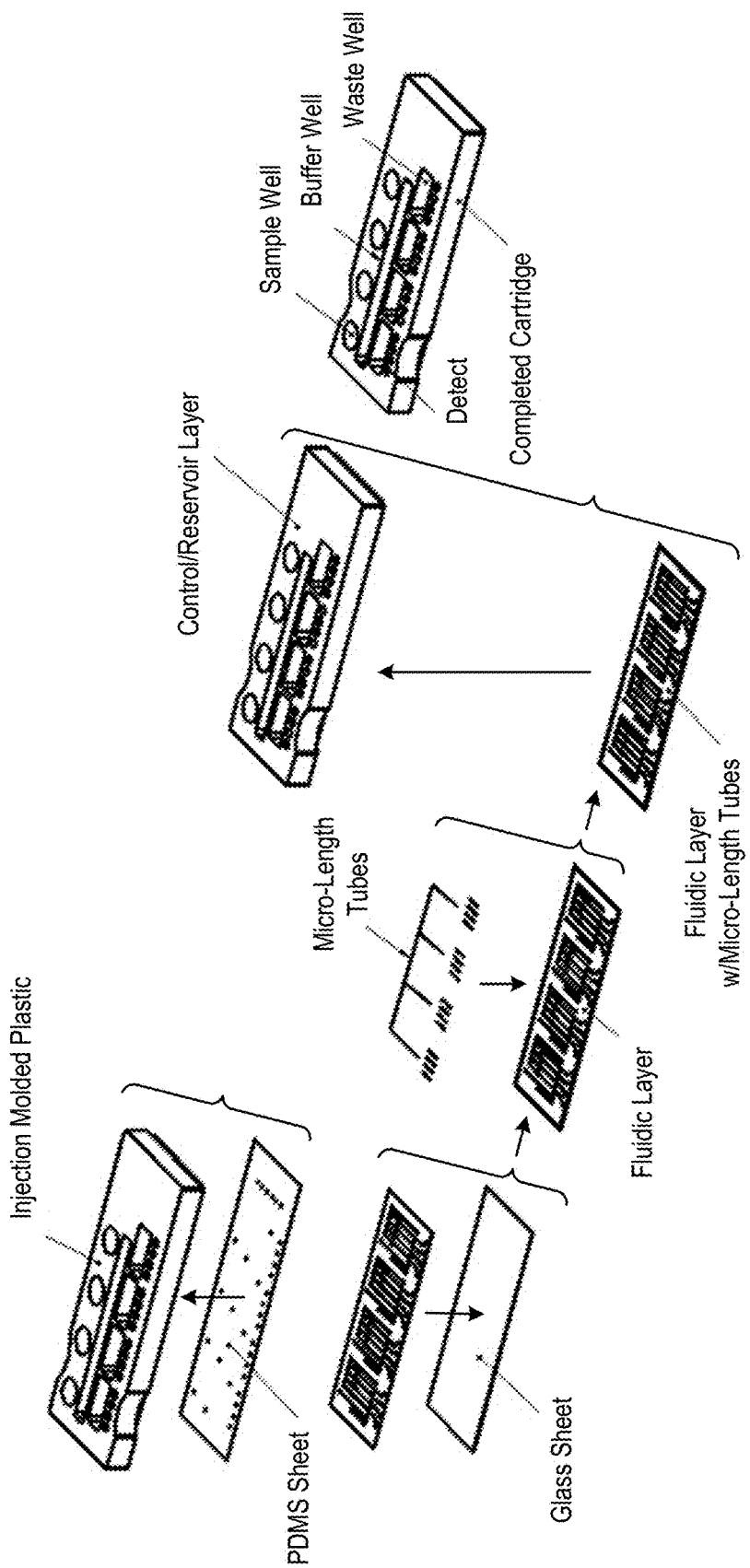
FIG. 1 is an illustration of assembly steps for an assay cassette having flow channels in which discrete micro-length tube flow elements (e.g., GNRs) are fixed between a Fluidic Layer subassembly and a PDMS sheet of a Control/Reservoir Layer subassembly (see also FIG. 30)
Figure 2C:
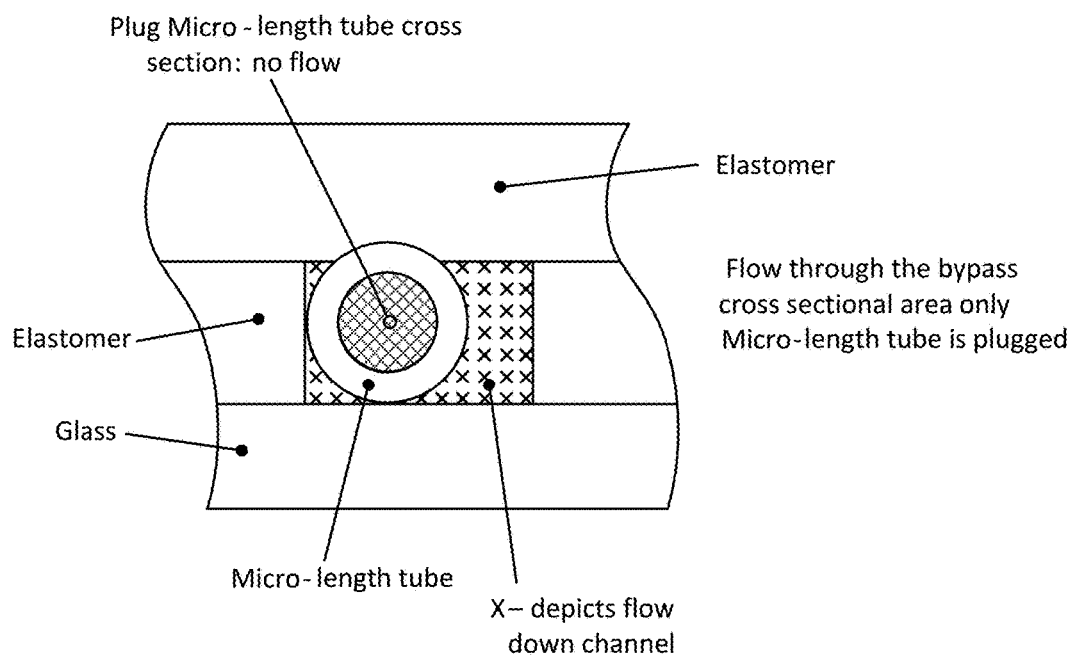
FIG. 2C is a cross-section, on enlarged scale, depicting flow conditions in which a micro-length tube element becomes plugged (i.e. blocked)
Figure 19A:
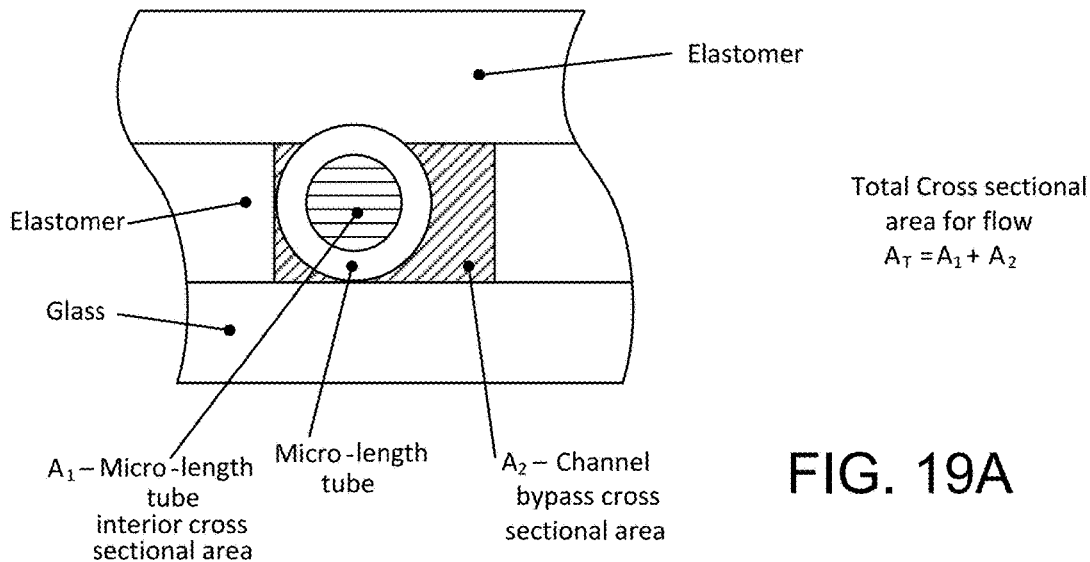
Figure 19B:
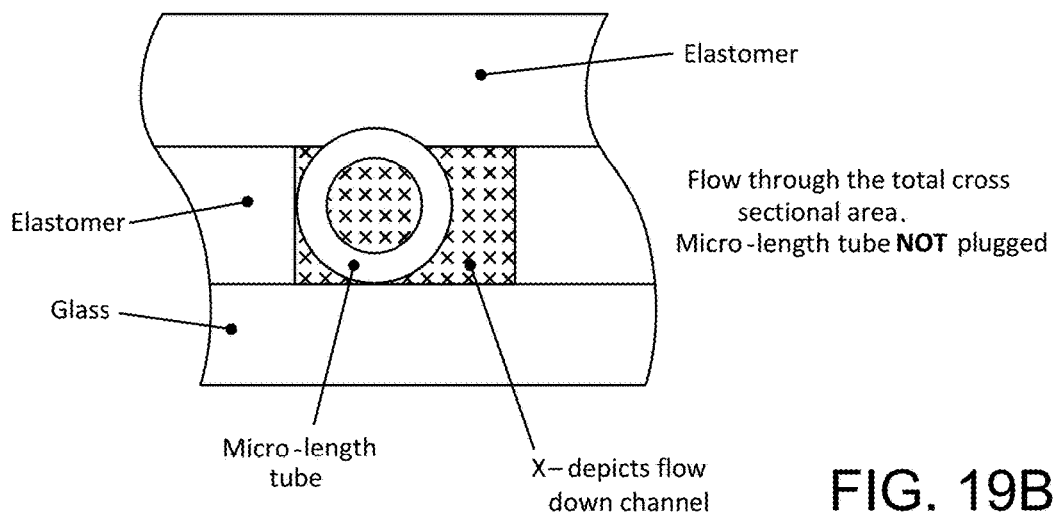
Figure 20D:
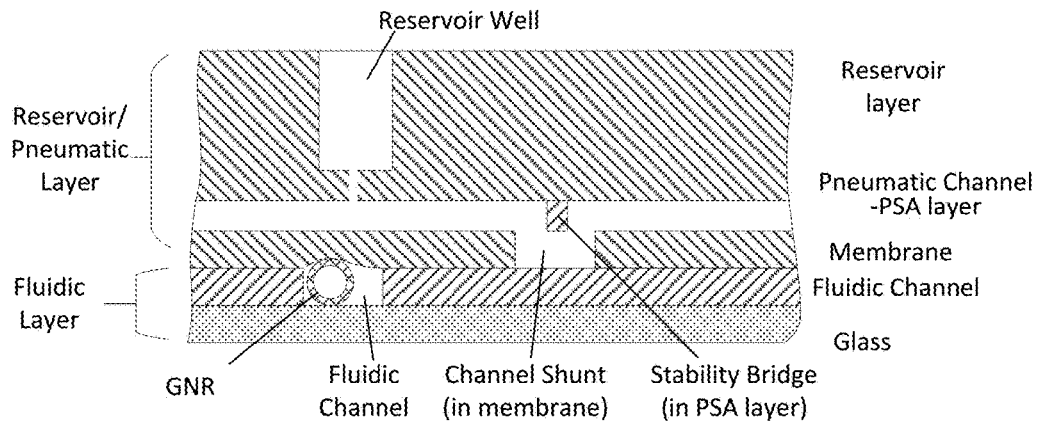
FIG. 20D is a vertical cross section, with parts broken away, on a magnified scale, of a microfluidic device comprising a reservoir layer, a pneumatic channel-PSA layer, a membrane, a fluidic layer containing a GNR in a fluidic channel and a glass layer, with a channel shunt formed in the membrane layer at the location of a stability bridge in the pneumatic channel-PSA layer, the membrane also closing a fluidic channel and containing a GNR placed in the channel (see also FIG. 56I)
Figure 20E:
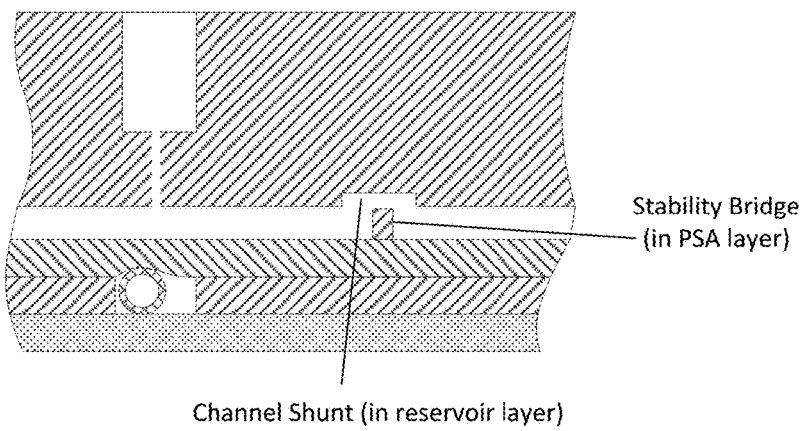
FIG. 20E is a vertical cross section, with parts broken away, on a magnified scale, similar to FIG. 20D, except that the channel shunt is formed in the reservoir layer, the membrane also closing a fluidic channel and containing a GNR placed in the channel (see also FIG. 56J)
Figure 20F:
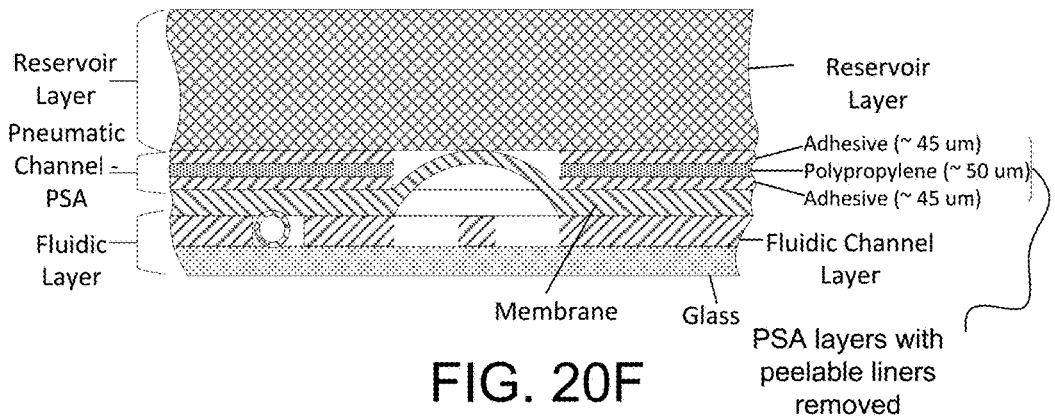
FIG. 20F is a cross-section similar to FIGS. 20D and 20E, depicting a valve portion ofxthe membrane deflected into a recess cut in the pneumatic channel—PSA layer, the membrane also closing off a fluidic channel and containing a GNR placed in the channel.
Figure 48B:
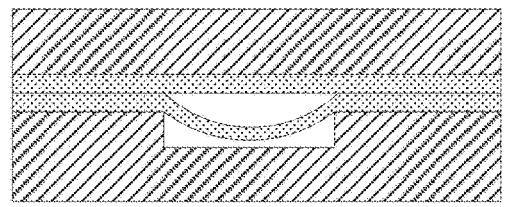
Figure 48:
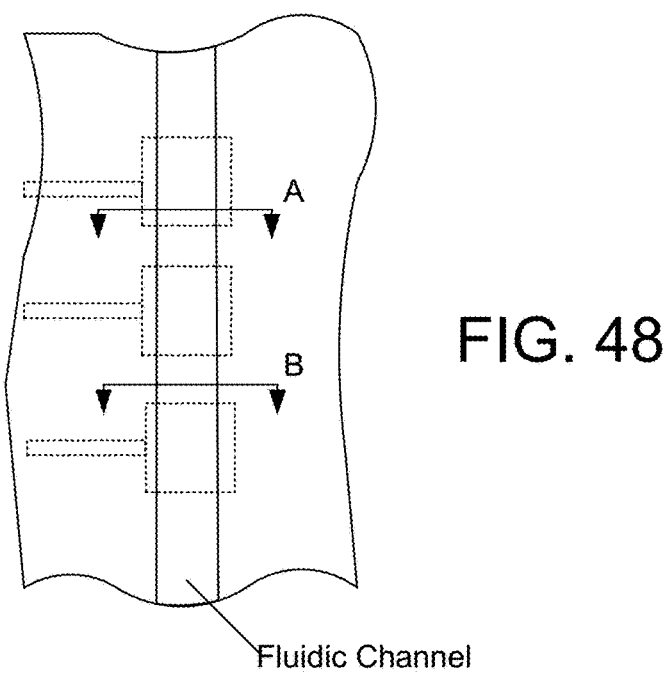
Figure 49A:
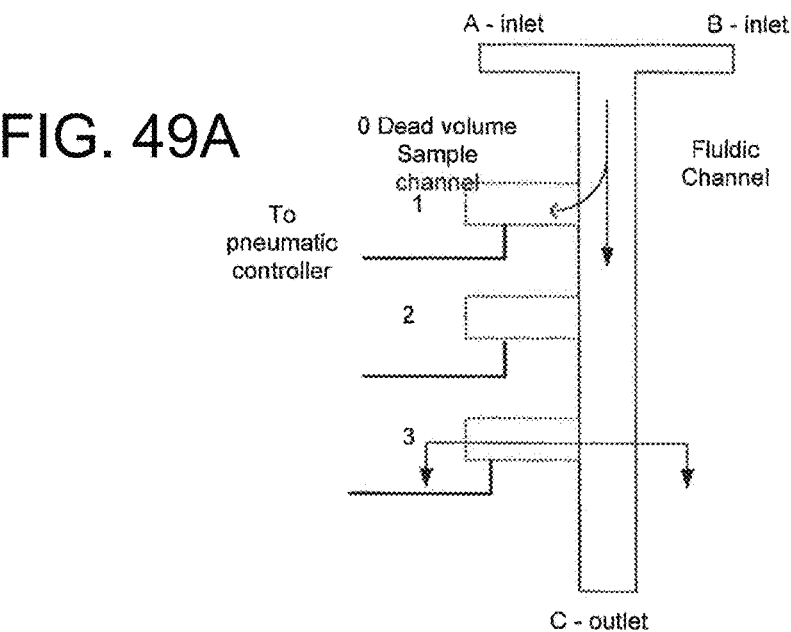
FIG. 49B (taken on line 3 of FIG. 49A) and FIG. 49A show in respective cross-section and plan views, a fluidic channel arrangement including a channel that extends from two inlets to an outlet, and, in communication with it, a zero dead volume sample channel; the cross section shows a pneumatic chamber in which the membrane is shown in deflected open position in solid lines, and closed by dashed line.
Figure 49B:
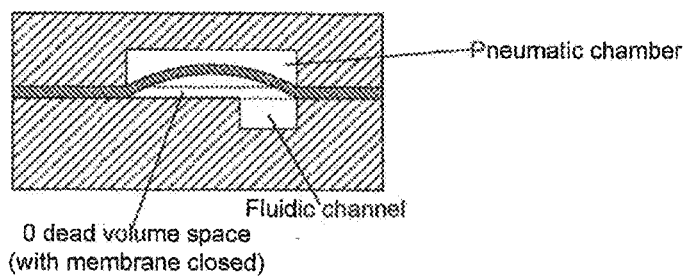
Figure 52:
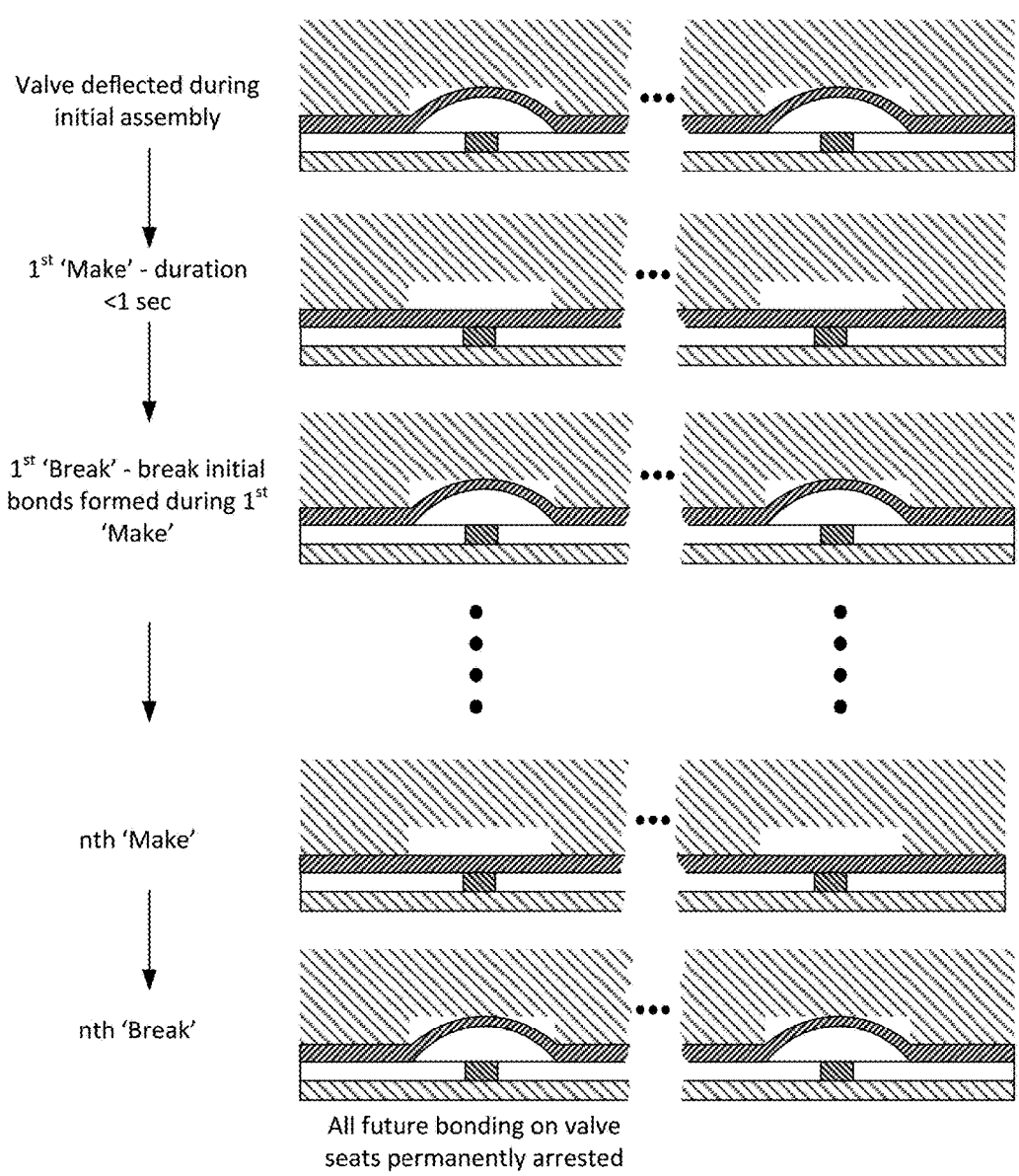
FIG. 52 is a view similar to FIG. 41, illustrating stages of the system applied to multiple valves simultaneously.
Figure 53A:
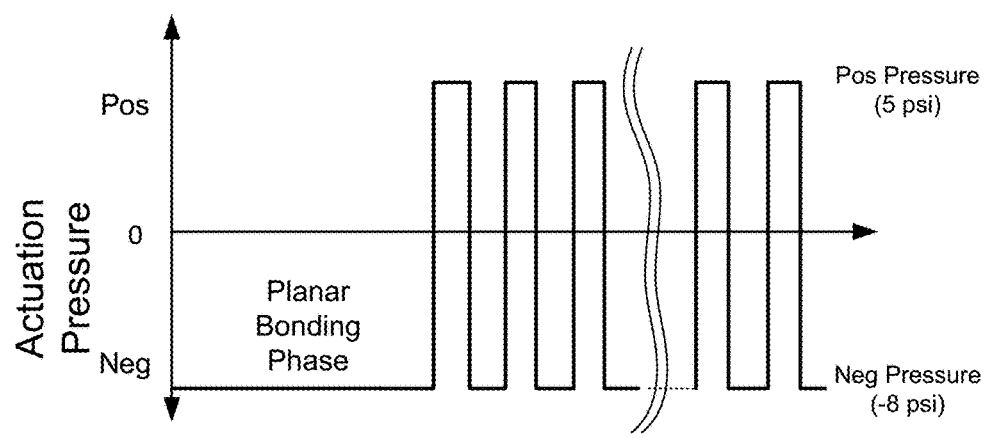
FIGS. 53A and 53B are graphs illustrating the selected pressures over time and the development of properties of the contacting surfaces during the make and break process.
Figure 53B:
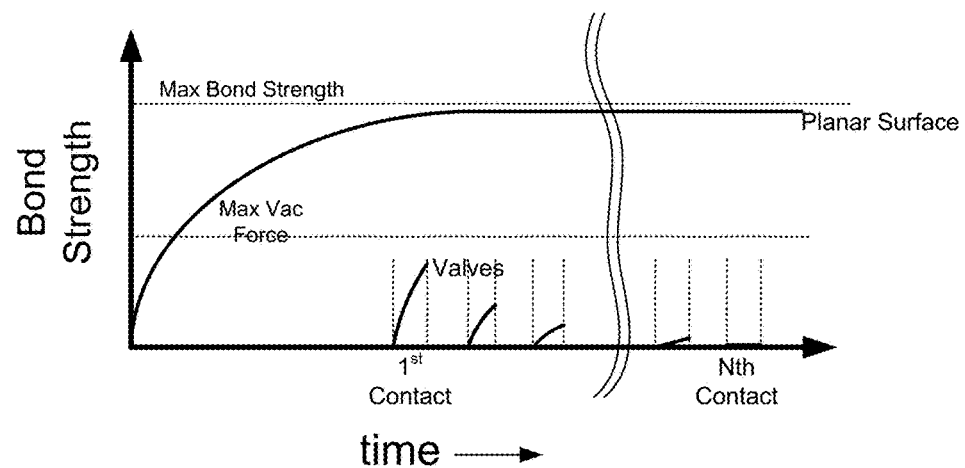
Figure 54A:
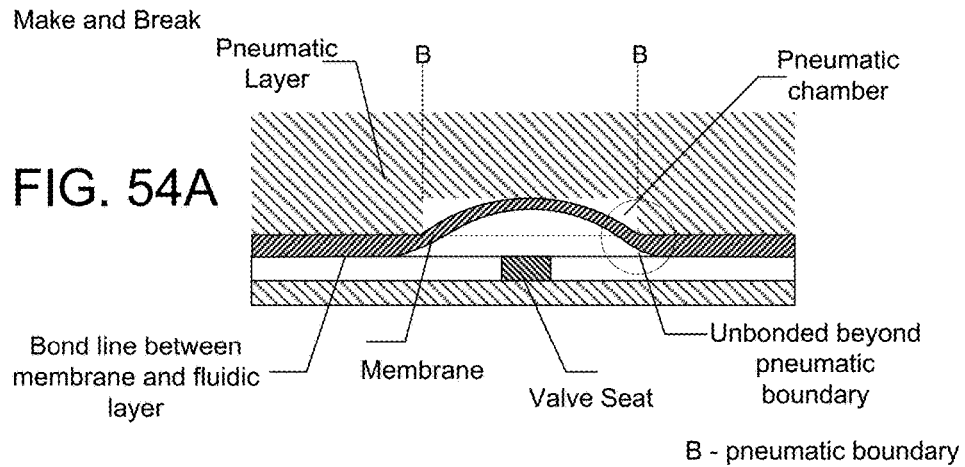
FIGS. 54A, 54B, 54C, 54D, 54E, 54F, 54G, 54H, and 54I concern another make and break protocol having similarities with that of FIG. 41 to FIG. 53B.
Figure 54B:
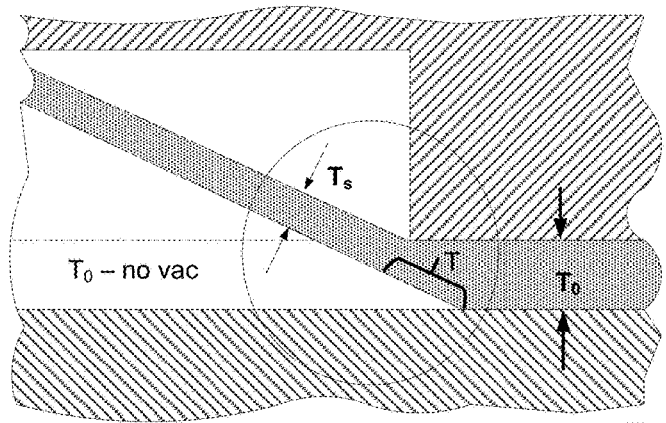
Figure 54C:
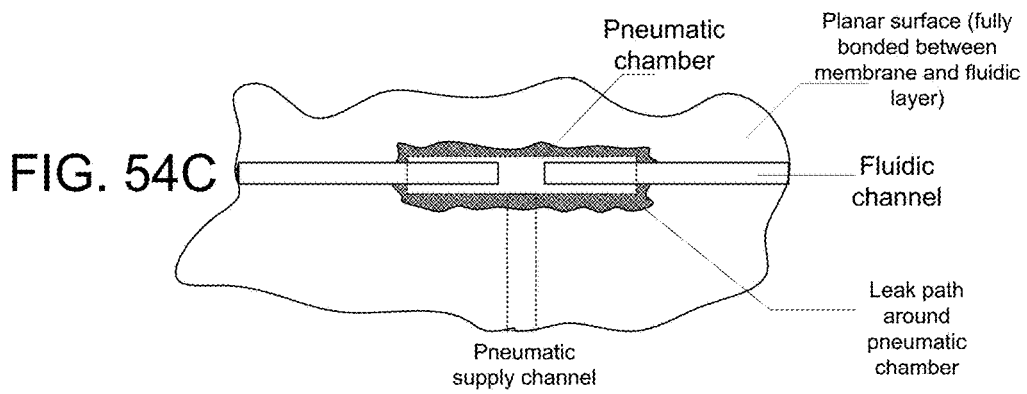
Figure 54D:
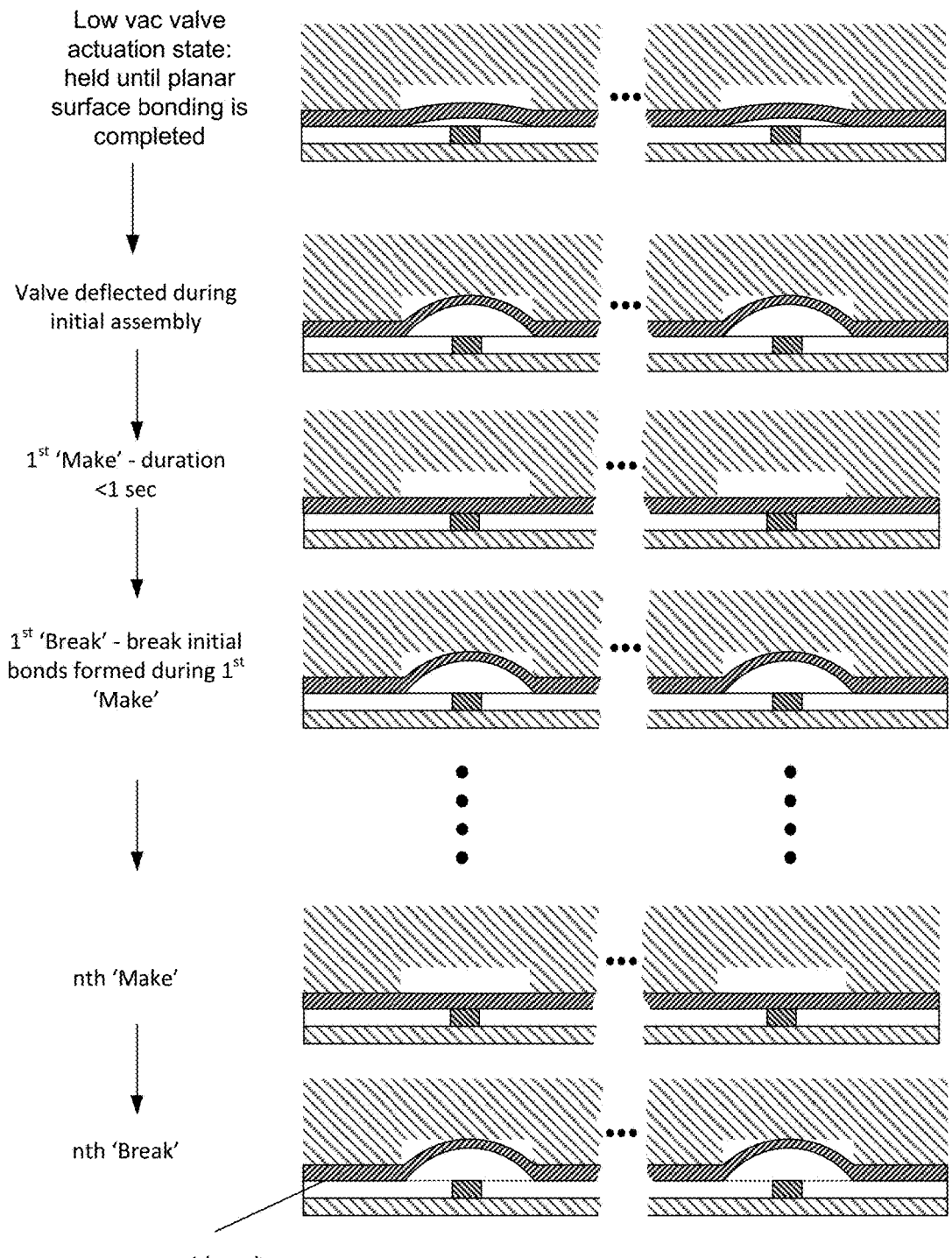
Figure 54E:
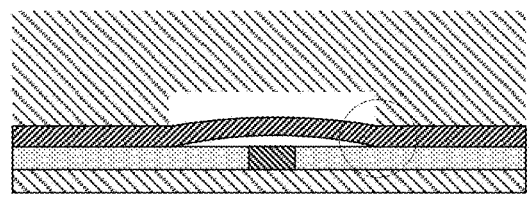
Figure 54F:
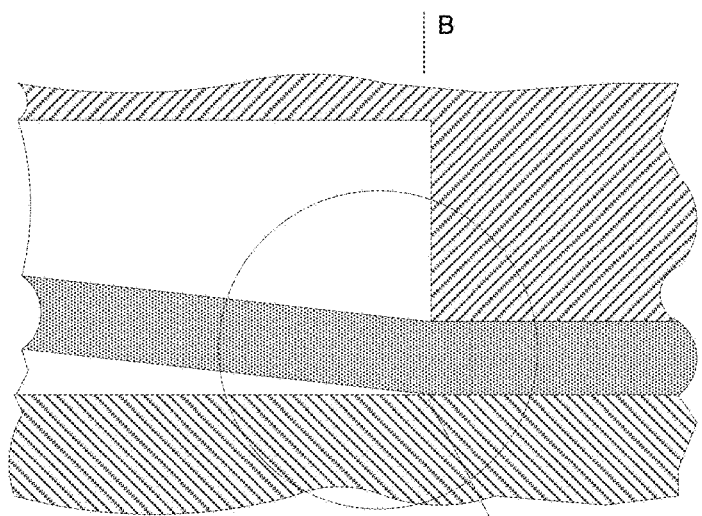
Figure 54G:
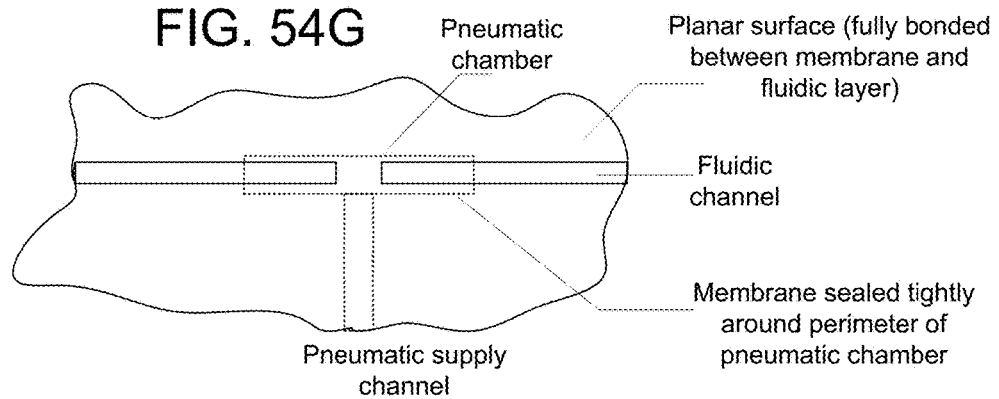
Figure 54H:
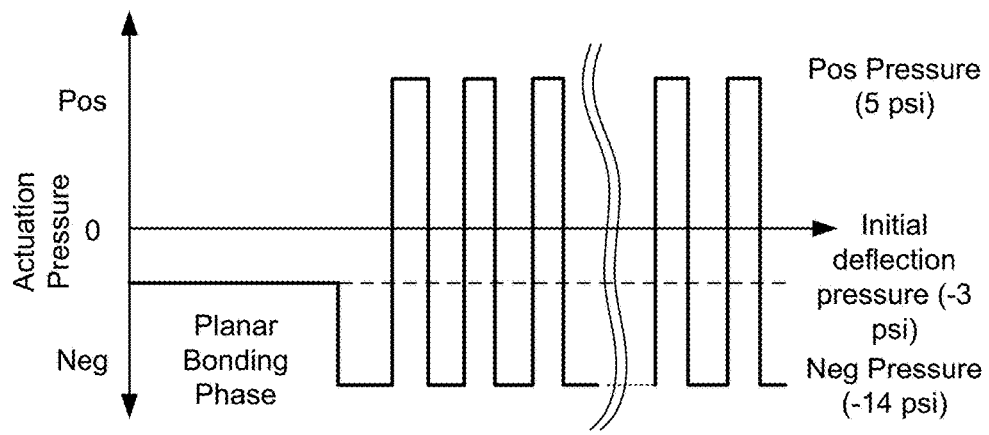
Figure 54I:
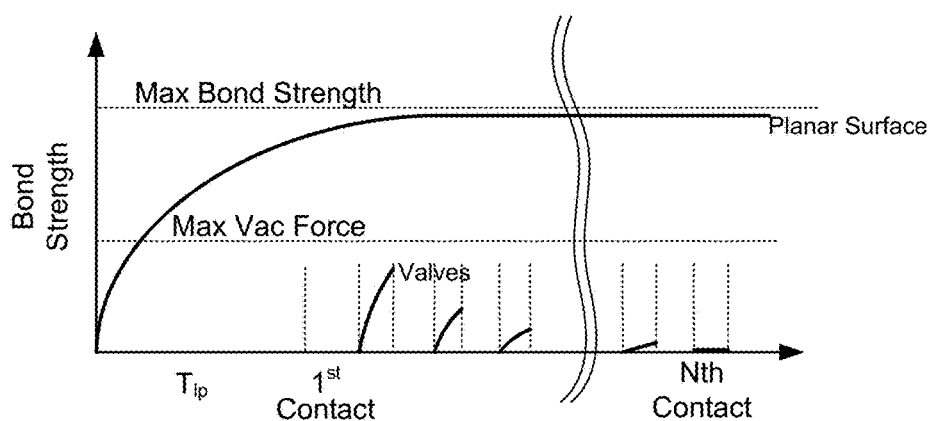
Figure 55:
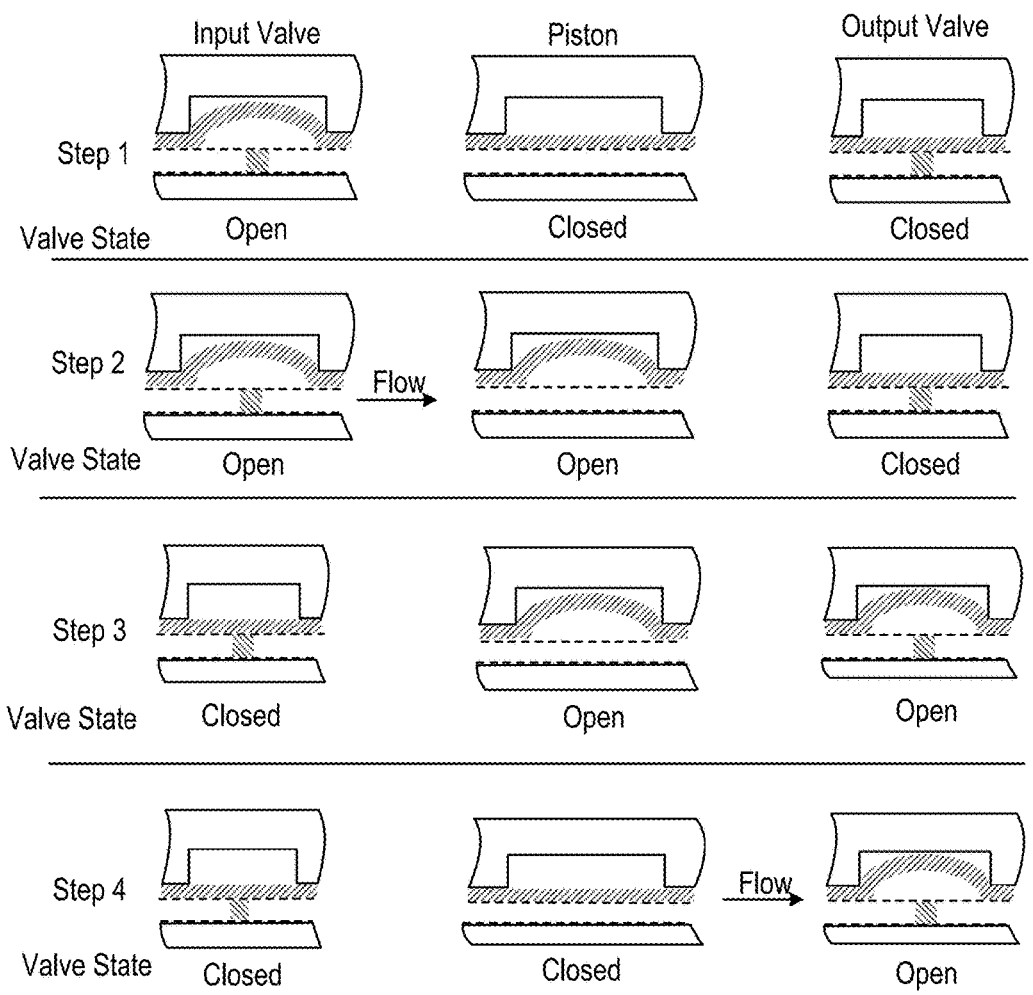
FIG. 55 pictures diagrammatically a pumping and valve state sequence by which liquid flow can be drawn into the piston from the left and expelled to the right to produce a desired directional, pulsating flow.
Figure 56G:
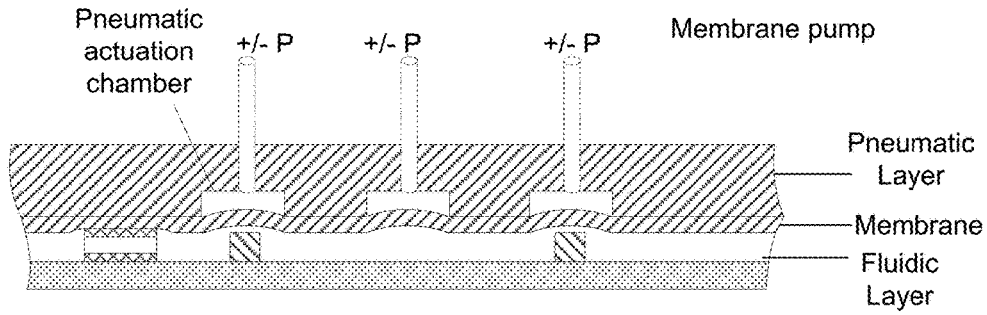
Figure 56H:
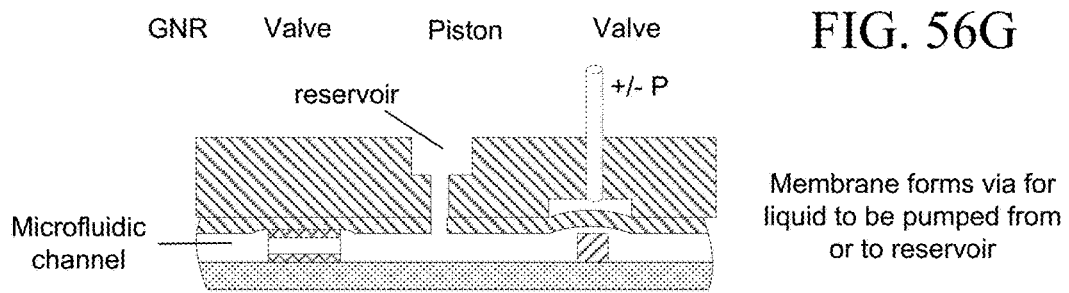

| PCT Publication | Current Application |
| --- | --- |
| FIG. A-16 Detail B (Sheet 69) | FIG. 48B |
| FIG. 51A-18 (Sheet 70) | FIG. 49A |
| FIG. 51A-19 (Sheet 70) | FIG. 49B |
| FIG. 52A1 (Sheet 71) | FIG. 54A |
| FIG. 52A1$_m$ (Sheet 71) | FIG. 54B |
| FIG. 52A plan (Sheet 71) | FIG. 54C |
| FIG. 52 A 1N (Sheet 72) | FIG. 54D |
| FIG. 52A2 (Sheet 73) | FIG. 54E |
| FIG. 52A2$_m$ (Sheet 73) | FIG. 54F |
| FIG. 52A2 plan (Sheet 73) | FIG. 54G |
| FIG. 52A2N (Sheet 74) | FIGS. 54H and 54I |
| FIG. 53 Drawing A (Sheet 76) | FIG. 56A |
| FIG. 53 Drawing B (Sheet 76) | FIG. 56B |
| FIG. 53 Drawing C (Sheet 76) | FIG. 56C |
| FIG. 53 Drawing D (Sheet 76) | FIG. 56D |
| FIG. 53 Drawing E (Sheet 76) | FIG. 56E |
| FIG. 53 Drawing F (Sheet 76) | FIG. 56F |

DETAILED DESCRIPTION

One of the problems addressed concerns the surface area associated with a micro-length tube element, i.e., an element having length less than 700 micron and a micro-bore diameter between about 75+/−50 micron that is fixed in a flow channel and exposed to flow of liquid sample, e.g., a glass nano reactor "GNR" Such devices are typically made of endlessly drawn micro-bore filament such as used to form capillary tubes, but in this case, the filament is finely chopped in length to form discrete, shorter micro-flow elements. It is realized that capture agent immobilized on the surface of such a device, applied by immersion techniques, can raise a significant depletion problem. This occurs, for instance, when attempting to characterize concentrations of an analyte at low levels such as a few pico-grams per milliliter, as is desired. The phenomenon referred to as "depletion" occurs in which the concentration of analyte in the sample being measured can be disadvantageously depleted volumetrically as a result of binding to a large active area of the flow element. This results in reduction of sensitivity of the assay, and therefore its usefulness. To explain further, any analyte in an ELISA or sandwich type of amino assay on antigen will bind to a capture antibody in a way that is governed by a kinetic reaction, a dynamic process. While analyte such as an antigen binds to capture agent such as an antibody, the reverse also occurs, the bound analyte molecules unbind from the capture agent. The kinetics concern an "on" rate and an "off" rate—analyte being captured and analyte being released. The capture reaction will continue, depleting the analyte in the ambient volume, and reducing its net rate of capture, until the system reaches equilibrium in which the rate of binding is equal to the rate of unbinding. The gradual action occurs according to a substantially exponential curve.

The absolute value of the equilibrium condition depends on the original concentration of the analyte in the volume of sample being assayed. Increase in concentration results in a higher signal, decrease in concentration results in a lower signal. In cases in which assay depletion occurs, the concentration of the analyte in the sample is detrimentally decreased over time. It is realized that micro-length tubes fixed in flow channel may present an excess of capture agent in the volume of liquid sample to which the element is exposed, decreasing the effective concentration of the analyte. The concentration decreases at an excessive rate, relative to initial, starting point concentration sought to be measured. While efforts to calibrate for this are helpful, such depletion ultimately lowers the sensitivity of the assay because, as the signal goes down r, it approaches the noise level, and results in a lower signal-to-noise ratio, i.e. an inherent reduction of effectiveness of the assay. (Already there are significant contributors to noise i.e., background, nonspecific binding of capture antibody, fluorescence noise, electronic noise, etc.). Therefore, especially for detecting small concentrations, it is desired not to deplete the initial volume of the analyte in manner that does not contribute positively to the assay measurement. Efficient ways to do that, as by somehow limiting the amount of exposed surface have not been apparent. This may be seen as an inherent problem with use of micro-flow elements of various descriptions that are coated by immersion or the like and used in an immunoassay or sandwich assay or even a molecular diagnostic type of assay. One typically wishes to immerse the elements in capture agent, e.g. an antibody or some type of moiety that is a capture molecule for the analyte to be sensed or detected, to uniformly coat all surfaces of the element. One object of invention is to overcome this problem with respect to micro-length tube elements characterized by an inside surface and an outside surface, or often also with two end surfaces. Adding up all surface area over which a density of capture molecules is coated can add up to a surface area on the order of over 100,000 square microns. This is the case for a preferred form of micro-length tube, having on the order of about: a length of 200 microns, an external diameter or width of 125 microns, and an internal diameter or width of 70 microns. A particular problem addressed here is to find practical approaches for accurately reducing active surface area of immersion-coated flow assay elements in general, and in particular, micro-flow elements, and in particular micro-length tube elements.

A further problem being addressed here concerns treated micro-flow-elements that are to be in fixed positions in channels for exposure to flow of sample. It is desirable to expose the elements in batch, in free state to an immobilization process for applying the capture agent or antibody to the element surface, and then transfer each element mechanically to its fixed position in a channel, for instance in a channel of a multiplex micro-fluidic "chip" (or "cassette"). It is desired to use a quick and accurate placement process, for instance a pick and place device mounted on an accurate X, Y stage. For such purpose, it is desirable to physically contact the tiny element for picking it up from a surface and placing it in an open channel, which is then closed to form a micro-fluidic passage. It is desirable to employ grippers, e.g. a tweezer instrument that contacts the outer surface of the device. The pick and place action is made possible by pre-aligning open channels to receive the micro-flow elements and the surface on which the free elements are supplied with the automated pick-and-place instrument. This enables the grippers to pick up and place the micro-flow elements precisely in desired flow channel positions in which they are to be fixed. We recognize a problem arises with having an active capture agent, e.g. antibody, immobilized on outer surfaces of an element. Such a coating is susceptible to mechanical damage as a result of the mechanical manipulation process. Outside surfaces of micro-flow elements come in contact with (a) a supply surface, e.g. an aligning pocket or groove, (b) the transferring grippers, and (c) surfaces of the channel in which it is being deposited. All of these contacts give rise to possible damage to the fragile coated capture agent, which typically is a very thin layer of antibody or the like adsorbed to the surface of the flow element. This coating is often only a few molecules thick, thickness of the order of nanometers or tens of nanometers, and is quite fragile. The net result of damaging a capture surface of the placed micro-element is seen during read out of the assay. If the surface has been scratched or perturbed in any way, that can give rise to an irregular concentration or presentation of captured analyte, the signal can be irregular, and contribute to irreproducibility or poor performance of the assay.

We thus realize it is desirable not to have immobilized active capture agent on the outside surface of a micro-flow element, and especially micro-length tube element, where it is susceptible to damage and where it contributes to increasing the total surface area of the capture agent or antibody that contributes to depletion.

The features described in the claims and hereafter address these and other important problems.

Discrete micro-flow elements are immersed in liquid containing capture agent, such as antibodies or antigens, and, after coating by the liquid, are picked, and placed into channels for flow-through assays. The micro-flow elements are in preferred form of discrete micro-length tubes, defined as micro-flow elements of length less than about 700 micron, and bore diameter of 70+/−50 micron. The flow elements are surface-treated so active capture agent, e.g. capture antibody, is not on the outside, or is of limited outside area. For this effect, micro-flow elements, or in particular, micro-length tubes, are disposed in a bath of active agent and violently agitated, resulting in coating of protected inside surface, but due to extreme shear forces, a clean area on the outside surface, for instance the entire outside cylindrical surface of a round cross-section discrete micro-length tube. In lieu of or in addition to this shear procedure, a special filament-manufacturing process is conceived that results in preventing coating an exterior surface of flow elements with a predetermined capture agent. Capture agent on selected coated areas are ablated or deactivated with precisely positioned laser beam, such as can be produced by a mask for simultaneous treatment of a large number of elements, leaving residual active agent of defined area on the inside surface of micro-flow elements. Residual capture agent, itself, on the inside of the elements, usefully defines a readable code related to the desired assay. Flow channel shape is sized relative to flow elements fixed in the channel to allow (a) bypass channel flow along the exposed outside of a micro-flow element to reach and flow through later elements in the channel in case of clogging of the first element, along with (b) sample and assay liquid flow through the micro-flow element to expose the surface to capture agent and other assay liquids. Lacking the need to attempt to seal the outside, the element can simply be gripped, as by an elastomeric sheet pressed against the element. Electrostatic attraction between flow element and channel wall is employed to fix the element in position, overcoming any disturbing force of the placing instrument as it is drawn away after delivery of the element. After assay, fluorescence is excited and read by special scanning confined to micro-flow element geometry. Locators are seeded in the recorded data, and used to locate the regions of interest in detected fluorescence data, e.g. from micro-length tubes. Code, written with the capture agent substance inside the micro-flow element is read through a transparent wall of the element. Efficient assembly and tooling features are disclosed. All features are applicable to micro-length tubes, enabling their efficient use. A number of the features are or will be found to be useful with other hollow elements, for example, longer micro-flow elements.

In respect of scanning, the purpose of this invention to deliver a method for performing a fluorescence measurement of multiple immobilized elements contained in a microfluidic chip. This method provides for determining the paths to be followed during the scanning, as well as the proper focus, and camera exposure. The method is based on a known general chip layout. The method provided results in the ability to place the chip to be measured into the scanner and then start the scan without any additional manual settings required. The method does the rest, and produces the desired fluorescence measurements as the results.

Certain aspects of invention involve eliminating or preventing the occurrence of active capture agent on outside surfaces of micro-flow elements, e.g. extended outside cylindrical surface, and/or end surfaces, while leaving active capture agent on the inside surface unperturbed, or of a desirable area or pattern. Features addressing this aspect include techniques to selectively limit the capture agent on the interior surface and steps that act in combination with outside and inside surfaces to achieve the desired result.

For the specific advantage of reducing the overall capture surface area, two aspects of invention will first be described, and the effect of their combination. A first technique is employed to eliminate or prevent capture agent, e.g. antibody, from immobilizing to the outside surface of hollow flow elements, especially, micro-length tube elements. That is done during a batch coating process, and involves suspending discrete hollow elements, especially micro-length tube elements, in an Eppendorff tube or other tube with the capture agent of interest and aggressively agitating fluid to impart disrupting shear forces to the exterior surface of the elements. Preferably, this is achieved by vortexing the fluid at high speed, for instance employing an instrument that orbits the container at approximately 2000 rpm of the orbiter, about an orbital path of the supporting shaft of diameter of about 25 mm.

The micro-tub elements are placed with a volume, e.g. a milliliter of capture agent, e.g. antibody. The appropriate vortexing speed, is dependent e.g. on the nature of the suspension, e.g. the viscosity of the liquid chosen, and can be easily determined experimentally. It is set by observing whether the capture agent is effectively non-existent on the outside, long surface of the micro-length tube elements, e.g. the outside cylindrical surface in the case of the body being of circular cross-section.

The physical principle involved concerns shearing force on the outside surface of the micro-length tube element that acts to prevent binding of the capture agent to the surface through an adsorption process. One can observe whether the vigorous agitation is sufficient to shear off any capture agent, e.g. antibody that has already been bound to that surface. At the same time, the inside surface is environmentally shielded from this shearing by virtue of the geometry which is tubular, and the micro-size of the bore of the tube. This prevents vortexing from causing any turbulence to occur within the element. Only laminate flow conditions exist. With micro bore elements the Reynolds number is always low enough to ensure that that laminar flow condition exists on the inside surface. Under these conditions, the velocity of fluid traversing in the micro-length tube element at the interior wall interface is by definition zero. So there is no shear force involved there, whereas the outside is in a highly turbulent, high shear force environment.

The observed result of aggressive agitation, e.g. vortexing, is that fluorescence which is observed by performing a sandwich assay is completely absent from the outer cylindrical surface of a micro-length tube element, whereas it is present in an observable way on the inside surface. In the case of square-end micro-length tube elements, fluorescence is also present on the end faces of elements.

Vortexing is the presently preferred technique for producing the shear forces. The case showed here employs orbitally rotating the micro tube in a very rapid manner back and forth in small circles at a rate of approximately a couple thousand rotations per minute, and an excursion of about 25 mm.

However, any type of rapid oscillation that creates a high degree of turbulence can be employed, so a back and forth motion, a circular rotation, anything that would very rapidly mix the fluids and create high shear forces will suffice.

In summary, micro-length tube elements in the presence of aggressive agitation leads to removal of capture agent, e.g. antibodies, from outside surface of the elements, and prevention of their coating with the agent, but leaves the inside surface of the micro-length tube element in condition to immobilize capture agent, e.g. capture antibodies, for subsequent interaction with analyte of the sample.

As an alternative to the high shear technique, we conceive an alternate process in which, during the original drawing of the small bore tube, and prior to the point along the draw path that the usual removable protective polymer coating is applied to the filament, that a non-stick coating, e.g. sputtered gold, silver or graphite, is applied to the filament, e.g. by passing through a sputtering chamber. Silane or similar coating must be applied to receiving surfaces before capture agent, e.g. antibodies will attach. However, due to the properties of the sputter coating, or the like, the surface will not receive the silane or equivalent, then likewise, the active capture agent.

Another feature of invention concerns realizing the desirability and technique of removing coated capture agent from selected end surfaces of the flow elements and a margin portion or other portion of the interior surface. Preferably, following the aggressive agitation process, the micro-length tube elements are further processed using a laser elimination process that removes or de-activates capture agent, e.g. antibodies, from surface from which the agent was not removed by the high shear process. Those surfaces include transverse end surfaces and a selected portion of the inside surface, leaving only an annular stripe on the inside surface sized sufficient to process the assay, but small enough to reduce depletion of the analyte from the sample.

In a preferred form an ablating laser is arranged transversely to the axis of elongation of the micro-length tube elements with the effect that the energy arrives though parallel to the end faces has a neutralizing or removal effect on the capture agent that is on those end faces, as a result of incidence of substantially parallel radiation, but also of internal reflection scattering of the radiation by the transparent substance that defines those end faces.

The net effect of two novel processes described, if used in novel combination, is to leave only a band of selected dimension, which can be small, of capture agent immobilized on the inside surface of the micro-length tube element. This can be done in a way that leaves one or more bands separated by a space of no capture agent. Thus one can generate a single band in the center or a single band closer to one end or multiple bands distributed along the length of the micro-length tube element. These bands can be of different widths, can have different spacing, and can be of the form of a code, e.g. a bar code, which is useful to encode the particular flow element, e.g. micro-length tube element.

Further is a description of manufacturing techniques that have important novel features.

The micro-length tube elements are first cut, i.e. chopped, from previously supplied continuous small-bore filament into the short, discrete micro-length tube elements. They are then treated in batch manner.

A bulk of the micro-length tube elements is then exposed in an Eppendorff tube to wash buffer. After washing processing is performed, the buffer is removed, and replaced with a silane. By use of this simple, low-cost immersion step, the silane is allowed to bind to all of the surfaces of the micro-length tube elements. Excess silane after a period of time is washed away with water in a buffer. Then a capture agent, e.g. antibody, in solution is added to the Eppendorff tube with the bulk of micro-length tube elements and allowed to incubate overnight. The incubation is performed on the orbital vortexer for approximately 16 hours at 2000 rotations per minute, with of the order of one-centimeter diameter orbital motion. The orbital plate that contains the numerous Eppendorff tubes is approximately 6 inches in diameter, but the orbital motion is a circular pattern counterclockwise and then clockwise motion in a circular pattern of diameter of approximately 2 centimeters.

After the vortexing process is completed, the net result is that the capture agent has been immobilized on the inside surface of the micro-length tube element and also on the end faces but it is not present on the outside cylindrical surface of the tubular element. The capture gent solution is removed from the Eppendorff tube, which is replaced with a wash buffer, a wash buffer solution, and the wash buffer solution is then further replaced with a stabilizing buffer, what we call a blocking buffer. In the preferred embodiment, a commercial material called StabilCoat® solution is used.

StabilCoat® blocking solution is introduced to the Eppendorff tube along with micro-length tube elements, then a portion of those elements is aspirated in a pipette along with some of the StabilCoat®, and dispensed onto an alignment plate. The alignment plate contains a series of rectangular shaped pockets, each designed to accommodate and position a single micro-tube element within a small space, preferably with clearance tolerance sized in microns, a space of 10 to 50 microns between the micro-length tube element and the walls of the pocket. After the elements are allowed to roam on the plate, they fall into these pockets still in the presence of the solution of the buffer solution. The excess buffer solution is removed from the alignment plate containing the micro-length tube elements by placing their plates with elements into a centrifuge or centrifuge holder and centrifuging at approximately two thousand rpm, for 30 seconds, thereby removing all excess StabilCoat® solution from the plate and the micro-length tube elements. This process is facilitated by the novel design of the plate shown, in which drain channels extend radially from the pockets.

The process of creating immobilized antibodies or other active biological species to serve as assay capture agent on micro-particles, and particularly the inside of hollow glass micro-particle elements, and then transferring the functionalized micro-particles to the channel of a microfluidic device, according to the invention, involves a number of critical steps. Long spools of continuous capillary tubing of approximately 125 micron OD, 70 micron ID, with a few microns thick polyamide protective coating on the exterior are obtained from a manufacturer. Typically these are drawn, fiber-like filaments, with highly polished and accurately dimensioned inner and outer surfaces. The spools are rewound onto a mandril in a tight mono-layer wrapping fashion such that each turn or strand, wound around the mandril is in contact with adjacent strands. The wrapped series of strands consists of for instance a hundred strands. It is then wrapped with an adhesive tape by which the strands are captured in an assembled unit. The tape is then slit parallel to the mandrill axis and the tape removed bringing the strands with them. This produces a thin linear array of monofilaments in close contact with one another. The relatively long array of monofilaments is then presented to a wafer dicing saw (as used in the semiconductor industry for dicing thin ceramic wafers), the filaments are diced at repeat distances of approximately 250 microns, producing cylindrical tubular micro-particles of that length.

After the dicing process, the individual micro-particle elements still retained on the tape are liberated using a hot aqueous detergent solution which liberates the individual elements from the tape. They are allowed to settle into the bottom of a beaker, the tape is removed from the solution, then the aqueous solution is removed and replaced with a hot sulfuric acid and peroxide solution, used to dissolve the polyamide coating from the outside surface of the glass elements. This is followed by a substantial washing cycle, a number of flushings with de-ionized water to remove the residual sulfuric acid solution. After the hollow glass elements have been thoroughly washed, they are silanized using a silane reagent such as APTES which stands for aminopropyltriethoxysilane ("silane"). The micro-particles are allowed to incubate in the silane solution for approximately an hour after which they are rinsed and cured in an oven for another hour after which they're then stored in an ethanol solution. To ensure the silane reaches the inside surface of the tubular micro-particles, vigorous vortexing is used to uniformly distribute the silane throughout the interior of the hollow elements. The micro-particles are then transferred to a reagent solution containing the capture molecule of interest, for example a capture antibody.

For this purpose the silanized micro-particles are transferred to a vial containing the capture agent for example a capture antibody. The capture antibody is allowed to bind to the active silane surface for a period of 16 to 24 hours after which a rinsing cycle is performed to remove any loosely bound capture agent and then finally the functionalized micro-particle elements are transferred to another vial containing a stabilizing compound such as SurModics' brand StabilCoat®. They remain in the StabilCoat® solution until it is desired for them to be transferred to a microfluidic device, such as a microfluidic cartridge. They are stored in the StabilCoat solution in a refrigerator until ready to be used.

Thus, after the immobilization process is complete wherein the surface of the micro-particle, or inside surface of the hollow glass micro-particle elements have the active species immobilized to the surface, the particles are re-suspended in a stabilizing compound such as StabilCoat (trademark of SurModics, Inc.) for storage until needed. The purpose of the stabilizing compound is to protect the activity of the immobilized species when the micro-particles are taken out of the reagent and exposed to atmosphere. We have discovered that the antibodies immobilized to a surface without a protective coating, during storage, have a tendency to degrade in their functionality (become partially denatured) with the result of a higher coefficient of variation of assay execution, severely affecting the precision (repeatability) and sensitivity of the assay, and thus preventing an accurate quantification assay.

The stabilizing reagent consists of high concentrations of sugars and proprietary compounds. We have found that when the water component is allowed to evaporate, thick residue of this sugary compound is left behind, which under low humidity conditions has a tendency to crystallize and become a fairly rigid structure which can cause particles in this compound to become almost irreversibly stuck to any surface that it comes in contact with and has been allowed to dry in.

According to a preferred step in the process of moving the micro-particles from the liquid state to the dry state involves dispensing the micro-particles in a solution of the protective coating liquid, e.g., StabilCoat, onto an alignment plate such as a precisely micro-machined grooved pocketed plate such as a silicon micro-machined plate with pockets configured to accept the micro-particles in an array pattern. The shaped pockets are, e.g., rectangular in the case of short segments of capillary tubing forming hollow micro-particle elements. The excess liquid compound is either spun off in a centrifuge or wicked away using an absorbent pad, leaving behind a small residue of protective compound about the micro-particle, e.g., both inside the hollow glass micro-particle element and around the outside of the element in the pocket capturing the element.

We have discovered that allowing the stabilizing compound to dry in an environment of relative humidity less than approximately 60% relative humidity has a deleterious effect of retaining the micro-particles through a sugar crystalline structure that bonds the elements into the pocket. It has been found maintaining the humidity of 55 to 60% relative humidity or higher softens (hydrates) the stabilizing compound to the point at which the viscosity approaches nears that of water enabling a pick and place process to proceed for placing the micro-particles in channels of a microfluidic device. Under these conditions, one may use automated tweezers or a vacuum picking head to grab the micro-particles out of the capturing pockets and place them into their final destination, a microfluidic channel of a microfluidic device.

The steps of assembly of the micro-particles is summarized as follows.

When ready to assemble the pick and place technique previously described in U.S. Application Nos. 61/608,570 and Ser. No. 13/427,857 is employed in which the micro-particles are placed in a groove locator plate.

There is, however, an alternative way that this could be done. This involves distributing the micro-particles in random fashion onto a flat surface not having grooves or alignment pockets. The advantage of this process is not requiring a micro machined component for the manufacturing process. The disadvantage is that the micro-particles are randomly distributed in a pile. The tendency is for them to come to rest in a monolayer on the surface, but with random orientation. Further, as a result of removing the excess StabilCoat by centrifuge or wicking away the excess stabilizing solution, it has been observed that the micro-particles have a tendency to agglomerate into dense pack of the randomly oriented elements.

We realize a solution exists to this problem. Individual micro-particles can be picked from this dense pack by use of a placement tool, e.g., a vacuum tip, that engages the top surface of the elements, in combination with a vision system used to identify an individual element and a motion system responsive to the vision system, which orients the relative relation of the vacuum pickup tip and the micro-particles in both X and Y coordinates, and angular orientation. The placement tool can be moved in minute movement, slightly laterally within channel, to bring GNR against one side wall. Preferably a table carrying the fluidic layer, preferably channel side up, moves in computer-controlled X, Y and Z, and the placement tool is stationary, with only the grippers (e.g. tweezers) moving under computer control.

CyVek temporarily secures the micro-particles in open channels prior to this fluidic component with open-sided channels being turned upside down for bonding to the flexible membrane. The membrane is carried by the pneumatic component of the cartridge, to complete the assembly.

Currently this is done in over-width, under-depth open micro channels. Electrostatic attraction draws the GNRs from the placement tool (enabling tool withdrawal) and holds them against one side of the over-sized channel with sufficient certainty that the assembly can be overturned for bonding against the membrane. Compressive force of the elastically compressible membrane permanently then fixes the GNRs permanently in position.)

An alternative technique is contemplated that would avoid need for the placement tool to move laterally against one side of the over-size channel. In this case the open channel in a resilient PDMs (silicone rubber) channel-defining layer is slightly undersize in width and may be oversize in depth relative to the GNR.

In this case the placement tool thrusts the GNR down with force-fit into the channel, and the sides of the channel are slightly, resiliently deformed to accept the GNRs. The sides then grip the micro-particles tightly. The GNRs may even be thrust so deep into the channels that they are submerged below the face plane of the fluidic layer.

Final assembly then proceeds: the fluidic layer is turned upside down and bonded to this up-facing membrane.

In a typical system the GNRs are short segments of fine capillary tubing, e.g., outside diameter, e.g., 125 micron, inside diameter 70 micron and length 250 micron).

The accepting microfluidic channels in one instance are (uniquely) wider than the micro-particles, and shallower. Successful placing depends upon electrostatic force associated with silicone rubber (PDMS, an electric insulator material) to attract the micro-particles from the placing instrument, and retain them in position during the completion of the assembly process, which even involves turning the over-size channels upside down. In this case elastic deformation of the covering membrane at the sites of the raised top surface of the micro-particles permanently fixes the location of the micro-particles.

In alternative technique, the microfluidic channels are undersize, widthwise, relative to the micro-particle width, and the placing tool forces the micro-particles into the channels, to obtain a mechanical grip by elastomeric material forming the sides of the channel. Again, the microfluidic channels can have depth less than the micro-particles, so that the membrane stretches over them to further fix their location. In another instance, the channel depth may exceed the depth of the micro-particles, and the placement submerges the particles such that the overlying membrane is not locally disturbed by the presence of the micro-particles.

The novel process of creating immobilized antibodies or other active assay capture agents on micro-particles, and particularly on the inside of hollow micro-particle elements (micro-length tube elements) will now be described by reference to a specific example. This will be followed by examples of novel transfer of functionalized micro-particles to an operative position within a microfluidic device, for instance to a microfluidic channel.

In the preferred case of micro-length glass tube elements, long spools of continuous glass capillary tubing of approximately 125 micron OD, 70 micron ID, with a few microns thick polyamide protective coating on the exterior are obtained from a manufacturer. Typically these are drawn, fiber-like filaments, with highly polished and accurately dimensioned inner and outer surfaces. The spools are rewound onto a mandrel in a tight mono-layer wrapping fashion such that turns or strands wound around the mandrel are in contact with adjacent strands. The wrapped series of strands comprises, for instance, one hundred strands. The strands are then wrapped on their outside with an adhesive tape by which the strands are captured in an assembled unit. The tape is then slit at one point parallel to the mandrel axis and the tape with the strands is removed. This produces a thin linear array of monofilaments in close contact with one another. The relatively long array of monofilaments is then presented to a wafer dicing saw (as used in the semiconductor industry for dicing thin ceramic wafers). The filaments are diced at repeat distances of the order of 1000 micron or less, to produce micro-length tube elements. Preferably, the repeat distances are less than 700 micron, and in preferred instances, of the order of 250 microns, producing cylindrical micro-length glass tube particles of that length. Those tubes having internal volume of the order of a nanoliter and are referred to as "glass nano reactors", or "GNR"s).

After the dicing process, the individual micro-length particles or elements, still retained on the tape, are liberated from the tape using a hot aqueous detergent solution. They are allowed to settle into the bottom of a beaker and the tape is removed from the solution. Then the aqueous solution is removed and replaced with a hot sulfuric acid and peroxide solution, to dissolve the polyamide coating from the outside surface of the glass elements. This is followed by a substantial washing cycle, employing a number of flushings with de-ionized water to remove the residual sulfuric acid solution. After the hollow glass elements have been thoroughly washed, they are silanized using a silane reagent such as APTES (aminopropyltriethoxysilane, "silane"). The micro-particles are allowed to incubate in the silane solution for approximately an hour. To ensure the silane reaches the inside surface of the tubular micro-particles, vigorous vortexing is used to uniformly distribute the silane throughout their interior to form a silane coating. The micro-length tubes are then rinsed and cured in an oven for another hour after which they are stored in an ethanol solution, ready for being functionalized, (i.e., treated to surface-immobilize a capture molecule of interest, for example a capture antibody).

For functionalizing, the silanized micro-particles are transferred to a vial containing the capture agent, for example a capture antibody. Again, to ensure the capture agent reaches the inside surface of the tubular micro-particles, vigorous vortexing is used, which is found to be capable of substantially uniformly distributing the capture agent throughout the tubular interior of the micro-length particles to produce substantially uniform immobilization of the capture agent over the length of the interior surface. The capture antibody under these conditions is allowed to bind to the active silane surface for a period of 16 to 24 hours. Advantageously, as herein further described, it is found, that the vortexing conditions of the process, prevent immobilization of the capture agent to occur to longitudinally-extending outer surfaces of the violently agitated micro-length particles.

After the immobilization process is complete, with inside surfaces of the hollow elements carrying a substantially uniform coating of immobilized active species, the functionalized micro-particle elements are re-suspended by transfer to another vial. The vial contains a stabilizing compound such as SurModics brand StabilCoat™. We have discovered that antibodies or other biological capture agents immobilized to a surface without a protective coating, during storage have a tendency to degrade in their functionality (become partially denatured) with the result of a higher coefficient of variation of assay execution. This can severely affect the precision (repeatability) and sensitivity of many assays, and thus prevent quantification to the desired degree. Thus the purpose of the stabilizing compound is to protect the activity of the immobilized species when the micro-particles are taken out of the reagent and exposed to ambient conditions.

The functionalized micro-length tube elements remain in the stabilizing solution stored in a refrigerator until ready to be used, i.e. until it is desired for them to be transferred to a dry state within a microfluidic device, such as a microfluidic cartridge.

A preferred step in the process of moving the micro-particles from the liquid state to the dry state involves dispensing the micro-length particles in a solution of the protective coating liquid, e.g., StabilCoat, onto a so called "pick-up plate", for presenting the micro-particles for subsequent picking and placing in microfluidic channels. A preferred example of a pick-up plate is a precisely micro-machined grooved locator plate, preferably a pocketed locator plate such as a silicon micro-machined plate, with pockets configured to capture individual micro-particles in an array pattern. The shaped pockets are, for example, rectangular in the case of short segments of capillary tubing forming hollow micro-particle elements (micro-length tubes). The excess liquid compound is either spun off in a centrifuge or wicked away using an absorbent pad, as described herein. Either technique leaves behind a small residue of protective compound about the micro-particle, e.g., both inside the hollow glass micro-particle element and around the outside of the element, i.e. in the pocket capturing the element. In cases later described in using a planar pick up plate, a small residue remains with the elements in a puddle on the plane surface on which the elements are displayed. In mass manufacture, it is typically desired, after applying the micro-particles to a pick up plate, to store the plate and particles prior to installation into the microfluidic device.

We have discovered that allowing the stabilizing compound to dry in an environment of relative humidity less than approximately 55% has a deleterious effect of retaining the micro-particles through a sugar crystalline structure that bonds the elements to their supporting surface. As previously noted, the stabilizing reagent consists of high concentrations of sugars and proprietary compounds. We have found that when the water component is allowed to evaporate, thick residue of this sugary compound is left behind, which under low humidity conditions has a tendency to crystallize and become a fairly rigid structure which can cause micro-particles in this compound to become almost irreversibly adhered to any surface with which it comes in contact and allowed to dry.

It has been found maintaining relative humidity of a minimum of about 55%, preferably about 60% or higher, softens (hydrates) the stabilizing compound to the point at which the viscosity approaches that of water, and enables a pick and place process to proceed for placing the micro-particles in a microfluidic device. Under these conditions, one may use automated tweezers or a vacuum picking head to grasp the micro-particles, e.g. withdrawing them from the capturing pockets or the supporting surface of the pick-up plate, and placing them in their final destination, e.g. a microfluidic channel of a microfluidic device.

When ready to assemble, the pick and place technique elsewhere described herein is employed in which the micro-particles are first disposed in a groove or pocket of a locator plate, from which they are picked by tweezer or vacuum tool.

An alternative, novel technique involves distributing the micro-particles in random fashion onto a flat surface not having grooves or alignment pockets. The advantage of this process is not requiring a micro machined plate component for the manufacturing process. The disadvantage is that the micro-particles are randomly distributed in a pile. The tendency is for them to come to rest in a monolayer on the surface, but with random orientation. Further, as a result of removing the excess StabilCoat by centrifuge or wicking away the excess stabilizing solution, it has been observed that the micro-particles have a tendency to agglomerate into a dense monolayer concentration of randomly oriented elements. However we realize that there are solutions to this problem. Individual micro-particles can be picked from this dense concentration by use of an automated vacuum tip that engages the top surface of the elements, such as previously described herein, in combination with a computer-control vision system used to identify an individual element and its orientation from a detected image, and a motion system responsive to the vision system, which orients the relative relation of the vacuum pickup tip and the plate supporting the micro-particles in both X and Y coordinates and angular orientation. Similarly, automated tweezers may be operated with controlled motions in X and Y coordinates, and angular orientation, as described herein.

The GNRs immediately after immobilization are stabilized in a reagent that is capable of protecting or stabilizing the catcher antibody on the surface of the GNRs, e.g., StabilCoat®. GNRs are transferred to an alignment plate and dispensed on to the alignment plate in a puddle with the stabilizing reagent and the liquid form of the stabilizing reagent is used to aid in the assembly or the self-assembly of the GNRs into certain alignment pockets. Because the stabilizing compound has a very high sugar and salt content it is desirable to remove as much of the mass of the liquid from the surface or around the surface of the GNRs prior to allowing any residual reagent to evaporate. As evaporation causes a concentration of sugar content and salt content nearby a crystallization process occurs which acts to hold or cement the GNRs into or onto whatever surface they are presented to. It is important therefore to remove as much of the residual reagent as possible and a technique involving centrifugation was previously described wherein the excess material is spun in a centrifuge and spun off of the plate and away from the GNRs as shown in FIG. 9D. An alternative process that is considerably easier to implement a manufacturing process involves using an absorbent pad placed at the edge of the channels associated with the pockets holding the GNRs wherein a capillary working process is used to soak up residual StabilCoat® into the absorbent pad and draw out of the channels through the channels and out of the channels and away from the GNRs.

Typical dimensions for the channels are shown in FIGS. 9A, 9B, 9C and 9D. The plane view of the channels retaining the GNRs. The GNRs are located in pockets approximately 125 microns wide by 400 microns in length separated from each other by a narrower channel approximately 75-80 microns in width by 200 microns in length. The Figure is broken away, showing microtubes 1, 2 and n, where n may be as large as about 50. The narrow channel is provided to aid in the flow of the excess reagent through the channels and away from the GNRs to the wicking pad and narrower to prevent GNRs from migrating out of the retaining pocket that they are intended to fall into. The length of the channels can range typically from 5 millimeters to 25 millimeters depending on the or even 75 millimeters depending on the size or the scale of the manufacturing process involved. The number of GNRs ranges from a few hundred to a few thousand depending on the cross-section area. Per channel, the number of GNRs is on the order of 50.

FIG. 2 is a side view of the GNRs on a surface or in a channel with a puddle StabilCoat® surrounding the channels and contained on the plate around the plate. It depicts a wicking pad in the process of being moved toward the end of the channels full of the stabilizing solution. The GNRs are completely submerged under the material.

Figure 3:
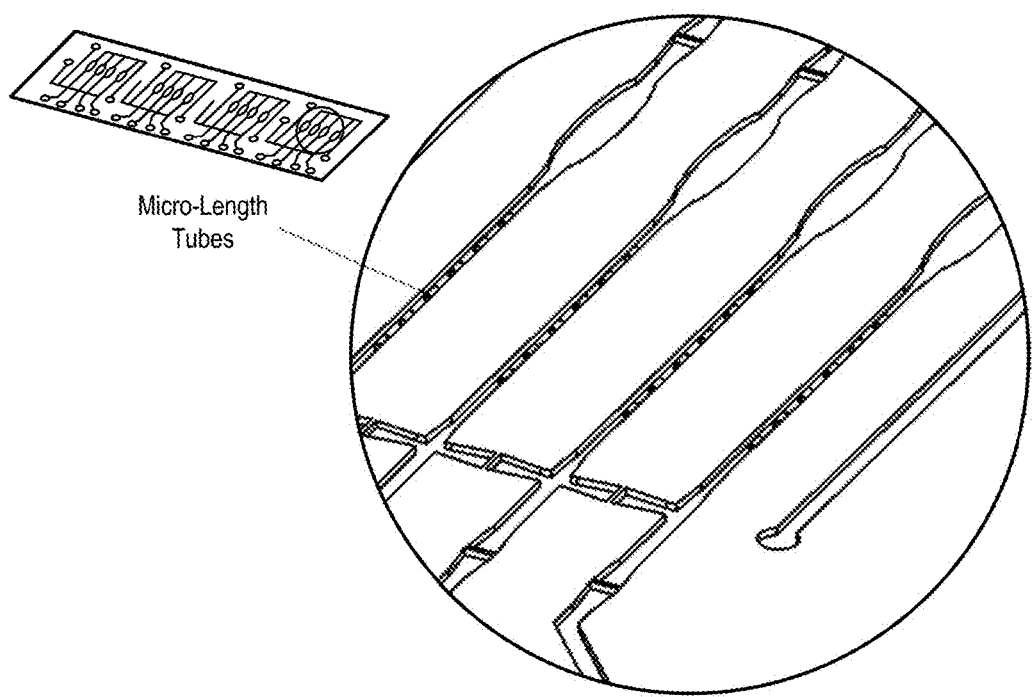
FIG. 3 is a much enlarged perspective view of a portion of the cassette, denoting four parallel channels, in each of which are fixed six micro-length tube flow elements.
Figure 4:
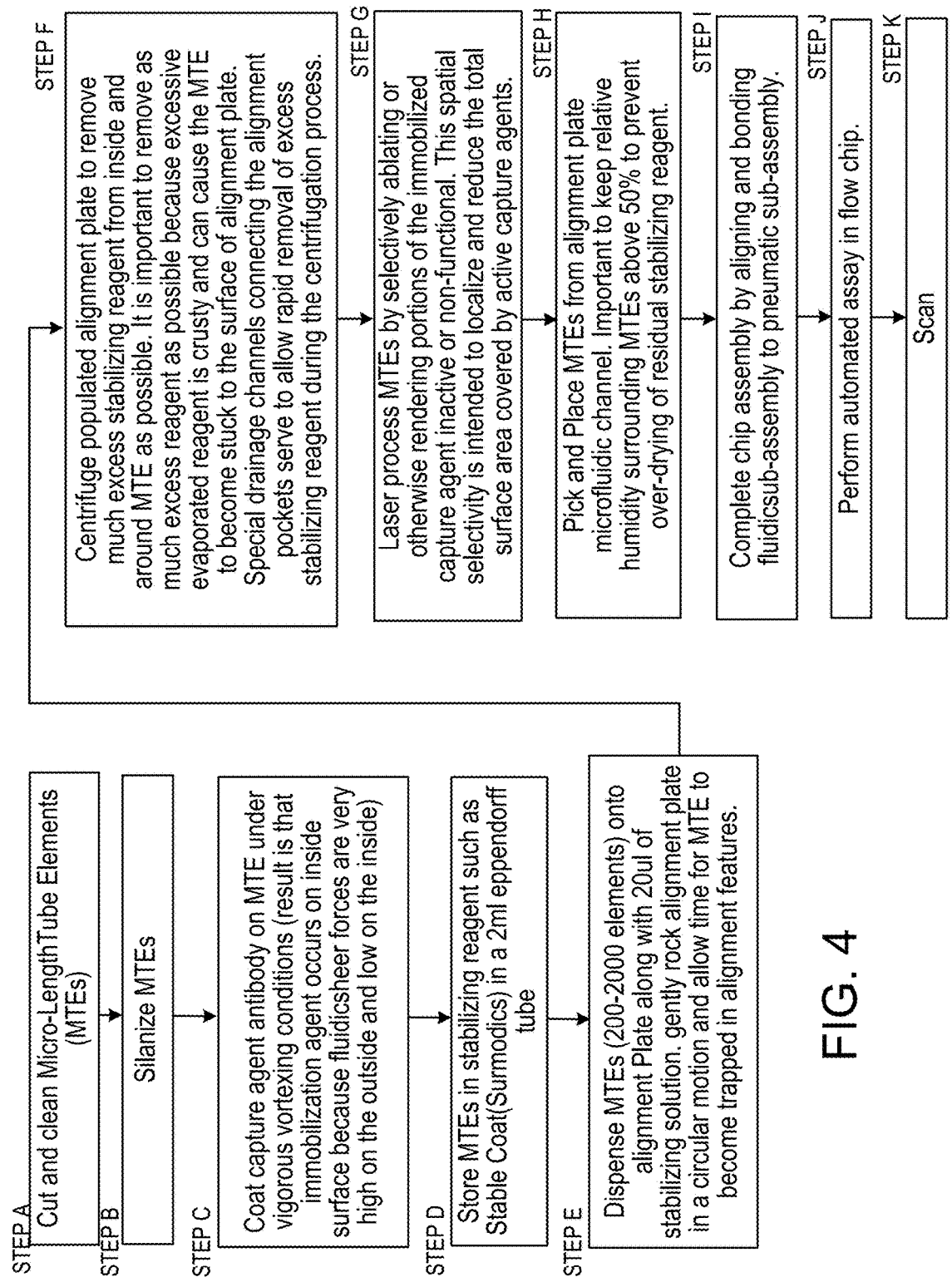
FIG. 4 is a flow diagram of steps A through K in the manufacture and use of the cassette (i.e. "flow chip") constructed according to the foregoing Figures.
Figure 6:
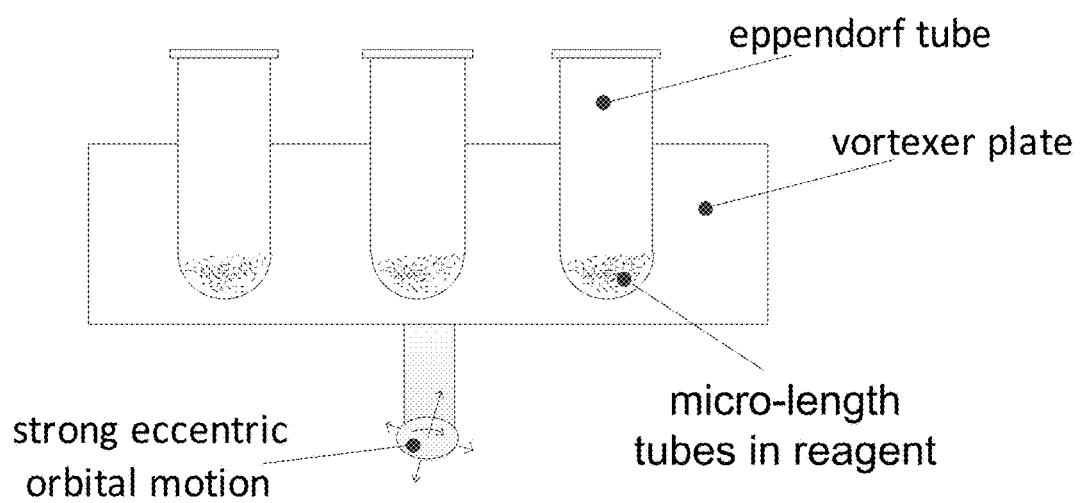
FIG. 6 depicts a device employed to aggressively agitate a suspension of micro-length tube elements in a capture agent, e.g. antibody, antigen, or oligomer-containing liquid.
Figure 7:
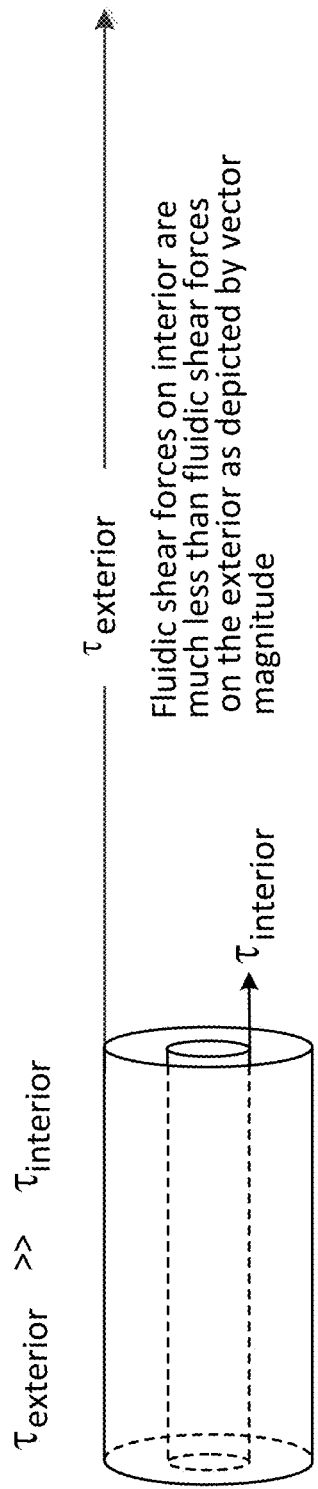
FIG. 7 illustrates diagrammatically, by vectors, sheer forces τ to which the outside and inside surfaces of the micro-tubular element are exposed.

FIG. 3 illustrates a wicking pad shown on the left top surface of the plate and having drawn the excess StabilCoat® away from the GNRs through the channels.

The micro-length tube elements while still in the plate can be further processed with a laser, preferably an ultraviolet laser, which could be an excimer laser, fluoride or krypton fluoride laser, with two beams that are spaced such that the ends and a an end margin portion or section of the micro-length tube element are exposed perpendicular to the element axis by a laser beam in a way that either ablates or denatures the capture agent, e.g. antibody, from the ends of the element as well as a section of the inside surface of the element. It is a feature of the laser configuration that the two laser beams are separated by a fixed distance that defining the desirable width of the remaining band of capture antibody surface. The micro-length tube elements within their pockets of the alignment plate can be allowed to move back and forth with a degree of liberty, while still the laser processes substantially the ends of the elements and leaves a fixed width pattern near the center of the element, plus or minus a reasonable some tolerance window.

It is possible instead to define a series of three or more laser beams, with gaps, such that the pattern produced by the various widths of laser beams in the various gaps between the laser beams defines a pattern of exposure in the tubular element that looks like and is useful as a bar code.

Further, it is realized as useful to have significant by-pass flow in a channel outside of the micro-flow element as well as through the element. One advantage is simplicity of manufacture as the element can be held but without being sealed and with no attempt to use cumbersome adhesive to adhere the element to the channel walls. Another advantage is the avoidance of the risk of totally spoiling an assay because a chance particle obstructs internal flow of one of the micro-flow elements when arranged in series in a liquid flow path. Having significant by-pass flow on the outside, e.g. a flow greater than the flow through an element, thus "short circuiting" the element, ensures that despite one element being plugged or obstructed and flow stopped, the other elements will receive flow and the assay will only be partially affected by the obstructing particle. It is realized further that with concepts presented here, enabling the avoidance of having active capture agent on either the cylindrical exterior of the micro-length tube element or on its end faces, does not result in a depletion problem. The techniques previously described, of avoiding active capture agent from adhering to the exterior cylindrical surface of the micro-length tube elements and laser treating the ends, thus contribute to the practicality of employing the by-pass flow described.

Referring to FIG. 5, in general the advantage of so treating the surfaces of the micro-length tube element, in reducing depletion, and in particular, with regard to the considerations of by-pass flow, may be understood by considering the total surface area exposed to the coating solution as represented by the sum A+2B+C where A is the internal cylindrical surface, B is the end face, and C is the external cylindrical surface area. It is pointed out that according to the concepts articulated that it is possible to reduce the depletion area to A only, that being the only area that carries meaningful information. Indeed the reduction can be extended by suitably sizing the laser beams to treat the margins of the inner cylindrical surface from which the active agent has been removed or has been deactivated can be of preselected length. For instance, in a dilute solution, it may be desirable to have more area than in a less dilute solution of the analyte. Indeed, as previously mentioned, it is possible to have the laser act upon capture agent in one or more mid regions of the area of the inner cylindrical surface, even form a code. Such patterns are not visible when only in the state of an active capture agent, but made visible or photo detectable by the captured fluorescently labeled analyte.

As previously discussed, it is very important having no capture agent on the outside surface of the micro tube elements, avoiding the potential for damaging the functional surface and negatively influencing the results of the assay. As a result of transferring the micro-length tube elements from an alignment plate to the microfluidic device or other channel it is quite possible for the outside surface to encounter contact with other hard surfaces, leading to damage of a functionalized surface. So it is beneficial to prevent binding of capture antibody to the outside surface therefore, excluding signal that might arise from the capture agent coming from the outside surface. As an example of A, B, and C, where C is the exterior surface area of the micro-length tube element having a length dimension of approximately 250 microns, interior diameter of 75 microns and an outside diameter of 125 microns, C being the exterior surface area is approximately 98,000 square microns. B which is the two-times the end face surface area is approximately 15,600 square microns, and A being the inside surface area approximately 58,000 square microns. The total of A, 2B, and C is approximately 171,000 square microns.

By cooperation of the processes, it is easy to eliminate the surface area associated with the exterior surface area of the micro-length tube element and the end face of the micro-length tube element, thereby reducing the total surface area by 66%. It is possible to further reduce the surface area of the capture antibody even on the interior surface to an arbitrarily small surface area. An example would be a narrow stripe on the inside of a 75 micron diameter tube, resulting in a total surface area of approximately 10,000 square microns.

Assays run in the microfluidic device can use various types of micro-length tube elements with different capture agent present on the inside surface of the elements. For example, one type of micro-length tube element would contain a capture antibody associated with the antibody interleukin-6 Another one could be interleukin-2, and yet a third would be interleukin-12. Each of the micro-length tube elements of respective types can be placed into different channels and or locations within that channel, thereby determining at the time of performing the assay what type or what particular antibody was used in that particular location. That is a method for identifying the type micro-length tube element for what has bound onto that surface. In addition to using location as a means for identifying a particular type of micro-length tube element, another means is using the striped code pattern created by selectively ablating or selectively denaturing antibody functionality along the length of the micro-length tube element for providing for a code, a bar code, which is then used to identify that particular type.

There are various possible ways of doing the ablation or creating the ablated pattern, within the micro-length tube element using a laser beam.

A wavelength in the range of about 193 nanometers to 250 nanometers is presently preferred. One possible way is to establish a single laser beam of a particular width and then translating micro-length tube element, then dispensing a fluence of laser to the element, turning the laser off, translating to a new position then dispensing another amount of fluence thereby eliminating or denaturing only portions of a particular tubular element. Another method, as mentioned previously, is to use an opaque mask to establish a particular pattern, and illuminate simultaneously the entire micro-length tube area with the ultraviolet light. Yet another method is to scan the micro-length tube element using a synchronized system of X, Y galvanometers.

Besides writing the code, one could scan simply the ends of the micro-length tube elements to ablate capture agent. It is anticipated that a feature size as small as 30-40 microns is possible with an ultraviolet laser. For example, a 250-micron long micro-length tube element having a feature size of 30 microns would result in 8 possible stripe zones and with 8 possible stripe zones, one could produce a number of patterns. For example, a pattern using a binary coding system would lead to a total number of combinations of 28, which are 256 possible combinations. The method:

Step (1): provide micro-length tube elements.

Step (2): apply coating, the manufacturing process, provide a coating particular of a capture antibody, Step 3 a manufacturing process that coats only the inside surface of the micro-length tuber element. Two novel ways of achieving the this: One is providing a capture agent, e.g. antibody, in a solution that contain the micro-length tube elements and agitating the liquid in an aggressive manner, generating high shear force on the exterior of the elements, whereby binding occurs only on protected inside surface of the micro-length tube elements. The second means of coating only the inside of the micro-length tube element. The agitation process would prevent coating of the antibody on the outside surface only, but not the end faces. So further reducing surface coating on the end faces would involve using a laser process. The second means of preventing coating on the outside surface (but not chopped end faces) concerns the manufacturing process at the stage of drawing and coating endless micro-bore tubing, prior to chopping to form discrete micro-flow elements or micro-length tube elements. By adding a-bond-preventing coating prior to the usual polymer coating prevents silanization of the exterior surface, preventing silane from adhering to the outside surface, and therefore defeating the ability for many capture agents, for instance antibodies and antigens, from adhering to the surface. This would further prevent antibodies from being bound to the outside surface. In either case, the polymer coating is added to the glass filament during its manufacturing process to maintain the intrinsic strength of the glass filament. The process for providing or manufacturing the micro-length tube elements, the raw elements without a coating, involve chopping the micro-bore tubing into the particular length element, which for the preferred configuration is approximately 250 microns, then removing the polymer coating using a sequence of acid and basic baths. Subsequent to the manufacturing process that coats only the inside surface of the micro-length tube element, the micro-length tube elements are then secured into a channel of a microfluidic device.

The channel of the microfluidic device is configured such that a portion of the flow is allowed to bypass the outside of the micro-length tube element. Micro-length tube elements are placed into a channel in a way that, preferably, approximately two times the flow volume proceeds around the outside of the tubular element as compared to the volume proceeding through the inside area. So the ratio of the cross-sectional areas of the by-pass flow versus the inside diameter is approximately 2:1. Micro-length tube elements are then secured into the channel whereby the channel wall is an elastomer, which allows the micro-length tube element to be placed in the channel, and the grippers used to place the element into the channel can be released because the adhesion of the elastomer is sufficient to secure the element into the channel. Any residual adhesion between the micro-length tube element and the tweezers is overcome by the larger adhesive force between the micro-length tube element and the channel. Subsequent to that step, a top is then secured over the open channel containing the micro-length tube element. The top also includes an elastomeric material. That elastomeric material is used to compress and thus secure the element in the channel because the open channel duct is of smaller depth than the outside diameter of the tubular element. The elastomeric "roof" or top thus provides a means of securing the micro-length tube elements in their locations in that channel.

Figure 8:
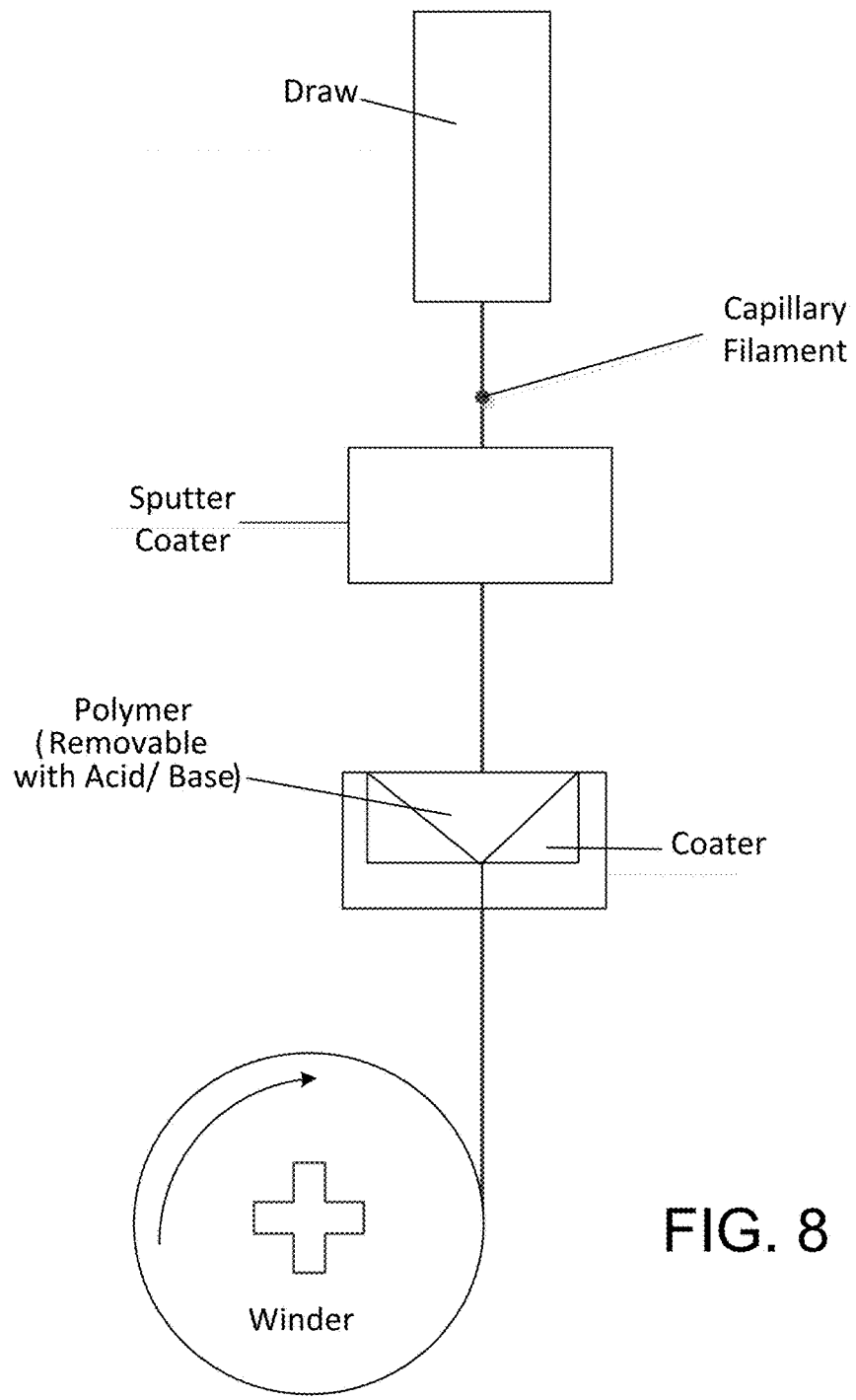
FIG. 8 illustrates a step in the manufacture of micro-tubular elements from micro-bore drawn filament.

Referring to FIG. 8 et seq., another useful technique, with considerable advantage, of completing the assembly between two pre-constructed subassemblies, in contrast to using a non-permanent bonding process, is to form permanent bonds.

It is found that low pressure operation permitted by the general organization and design just described, can so-diminish the driving pressure on the air to permeate the membrane, that the bubble problem is lessened to the extent that an elastomeric membrane, such as PDMS, is employable with significantly reduced risk of air penetration and bubbles than designs of the prior art. This has the advantages of low cost and simplicity of manufacture, and enables achieving extremely consistent and sensitive assays.

A difference in the implementations now to be described is that the membrane or the flexible layer that is actuated by vacuum or pressure to operate the valves and the pistons is made from elastomeric material and different, advantageous techniques are used to fabricate the device.

One of the problems addressed concerns the surface area associated with a hollow flow element as has been depicted and as has been described above, i.e., an element having length less than 700 micron, preferably less than 500 micron, and in many cases about 200 micron, and a bore diameter between about 75+/−50 micron, that is fixed in a flow channel and exposed to flow of liquid sample. (Such hollow flow elements and assay devices based on them are available from CyVek, Inc., Wallingford, Conn., under the trademarks "Micro-length Tube™, u-Tube™, and Mu-Tube™). Such devices are efficiently made of endlessly drawn micro-bore filament such as used to form capillary tubes, but in this case, the filament is finely chopped in length to form discrete, extremely short hollow flow elements, rather than capillary tubes. It is realized that capture agent immobilized on the surface of such a device, applied by immersion techniques, can raise a significant depletion problem. This occurs, for instance, when attempting to characterize concentrations of an analyte at low levels such as a few pico-grams per milliliter, s is desired. The phenomenon referred to as "depletion" occurs in which the concentration of analyte in the sample being measured can be disadvantageously depleted volumetrically as a result of binding to a large active area of the flow element. This results in reduction of sensitivity of the assay, and therefore its usefulness. To explain further, any analyte in an ELISA or sandwich type of amino assay on antigen will bind to a capture antibody in a way that is governed by a kinetic reaction, a dynamic process. While analyte such as an antigen binds to capture agent such as an antibody, the reverse also occurs, the bound analyte molecules unbind from the capture agent. The kinetics concern an "on" rate and an "off" rate analyte being captured and analyte being released. The capture reaction will continue, depleting the analyte in the ambient volume, and reducing its net rate of capture, until the system reaches equilibrium in which the rate of binding is equal to the rate of unbinding. The gradual action occurs according to a substantially exponential curve.

The absolute value of the equilibrium condition depends on the original concentration of the analyte in the volume of sample being assayed. Increase in concentration results in a higher signal, decrease in concentration results in a lower signal. In cases in which assay depletion occurs, the concentration of the analyte in the sample is detrimentally decreased over time. It is realized that hollow flow elements fixed in flow channel may present an excess of capture agent in the volume of liquid sample to which the element is exposed, decreasing the effective concentration of the analyte. The concentration decreases at an excessive rate, relative to initial, starting point concentration sought to be measured. While efforts to calibrate for this are helpful, such depletion ultimately lowers the sensitivity of the assay because, as the signal goes down, it approaches the noise level, and results in a lower signal-to-noise ratio, i.e. an inherent reduction of effectiveness of the assay. (Already there are significant contributors to noise i.e., background, nonspecific binding of capture antibody, fluorescence noise, electronic noise, etc.). Therefore, especially for detecting small concentrations, it is desired not to deplete the initial volume of the analyte in manner that does not contribute positively to the assay measurement. Efficient ways to do that, as by somehow limiting the amount of exposed surface have not been apparent. This may be seen as an inherent problem with use of small detection elements of various descriptions that are coated by immersion or the like and used in an immunoassay or sandwich assay or even a molecular diagnostic type of assay. One typically wishes to immerse the elements in capture agent, e.g. an antibody or some type of moiety that is a capture molecule for the analyte to be sensed or detected, to uniformly coat all surfaces of the element. One object of invention is to overcome this problem with respect to hollow flow elements characterized by an inside surface and an outside surface, or often also with two end surfaces. Adding up all surface area over which a density of capture molecules is coated can add up to a surface area on the order of over 100,000 square microns. This is the case for a preferred form of hollow flow element formed of small-bore filament, the element having on the order of about: a length of less than 700 micron, preferably about 500 micron or less, and in presently preferred implementations, 200 microns. Likewise, the inner bore is found desirable to have within a range of 50 micron+/−25 micron, for achieving uniform coating by immersion and agitation. In one preferred case, an element has an external diameter or width of 125 microns, and an internal diameter or width of 70 microns. A particular problem addressed here is to find practical approaches for accurately reducing active surface area of immersion-coated flow assay elements in general, and in particular, hollow flow elements, and in particular elements of the dimensions mentioned.

A further problem being addressed here concerns treated hollow flow elements that are to be in fixed positions in channels for exposure to flow of sample. It is desirable to expose the elements in batch, in free state to an immobilization process for applying the capture agent or antibody to the element surface, and then transfer each element mechanically to its fixed position in a channel, for instance in a channel of a multiplex micro-fluidic "chip" (or "cassette"). It is desired to use a quick and accurate placement process, for instance a pick and place device mounted on an accurate X, Y stage. For such purpose, it is desirable to physically contact the tiny element for picking it up from a surface and placing it in an open channel, which is then closed to form a micro-fluidic passage. It is desirable to employ grippers, e.g. a tweezer instrument, or a vacuum pickup that contacts the outer surface of the device. The pick and place action is made possible by pre-aligning open channels to receive the hollow flow elements and the surface on which the free elements are supplied with the automated pick-and-place instrument. This enables the grippers to pick up and place the hollow flow elements precisely from supply pockets to desired flow channel positions in which they are to be fixed. With a vacuum pick up, it is possible to serve the hollow element in end to end abutting relationship in supply grooves, and engage the outer cylindrical surface with the vacuum pick up. We recognize a problem arises with having an active capture agent, e.g. antibody, immobilized on outer surfaces of an element. Such a coating is susceptible to mechanical damage as a result of the manipulation process. Outside surfaces of micro-flow elements come in contact with (a) a supply surface, e.g. an aligning pocket or groove, (b) the transferring grippers or vacuum pickup device, and (c) surfaces of the channel in which it is being deposited. All of these contact opportunities give rise to possible damage to the fragile coated capture agent, which typically is a very thin layer of antibody or the like adsorbed to the surface of the flow element. This coating is often only a few molecules thick, thickness of the order of nanometers or tens of nanometers, and is quite fragile. The net result of damaging a capture surface of the placed hollow flow element is seen during read out of the assay. If the surface has been scratched or perturbed in any way, that can give rise to an irregular concentration or presentation of captured analyte, the signal can be irregular, and contribute to irreproducibility or poor performance of the assay.

We thus realize it is desirable not to have immobilized active capture agent on the outside surface of a hollow detection element, and especially the fine bore elements formed of micro-bore filaments, where it is susceptible to damage, and where it contributes to increasing the total surface area of the capture agent or antibody that contributes to depletion.

The features described in the claims and hereafter address these and other important problems.

Discrete hollow flow elements are immersed in liquid containing capture agent, such as antibodies or antigens, and, after coating by the liquid, are picked, and placed into channels for flow-through assays. The hollow flow elements are in preferred form of discrete elements of length less than about 700 micron, and bore diameter of 70+/−50 micron, preferably 50+/−25 micron. The flow elements are surface-treated so active capture agent, e.g. capture antibody, is not on the outside, or is of limited outside area. For this effect, the hollow flow elements are disposed in a bath of active agent and violently agitated, resulting in coating of protected inside surface, but due to extreme shear forces, a clean area on the outside surface, for instance the entire outside cylindrical surface of a round cross-section discrete element. In lieu of or in addition to this shear procedure, a special filament-manufacturing process is conceived that results in preventing coating an exterior surface of flow elements with a predetermined capture agent. Capture agent on selected coated areas are ablated or deactivated with precisely positioned laser beam, such as can be produced by a mask for simultaneous treatment of a large number of elements, leaving residual active agent of defined area on the inside surface of hollow flow elements. Residual capture agent, itself, on the inside of the elements, usefully defines a readable code related to the desired assay. Flow channel shape is sized relative to flow elements fixed in the channel to allow (a) bypass channel flow along the exposed outside of a hollow flow element to reach and flow through later elements in the channel in case of clogging of the first element, along with (b) sample and assay liquid flow through the hollow flow element to expose the surface to capture agent and other assay liquids. Lacking the need to attempt to seal the outside, the element can simply be gripped, as by an elastomeric sheet pressed against the element. Electrostatic attraction between flow element and channel wall is employed to fix the element in position, overcoming any disturbing force of the placing instrument as it is drawn away after delivery of the element. After assay, in the case of use of epi-fluorescent detection, fluorescence is excited and read by special scanning confined to the hollow flow element geometry. Locators are seeded in the recorded data, and used to locate the regions of interest in detected fluorescence data, e.g. from the elements. Code, written with the capture agent substance inside the hollow element is read through a transparent wall of the element. A number of the features are or will be found to be useful with other hollow elements, for example, longer elements.

In respect of scanning, the purpose of this invention to deliver a method for performing a fluorescence measurement of multiple immobilized elements contained in a microfluidic chip. This method provides for determining the paths to be followed during the scanning, as well as the proper focus, and camera exposure. The method is based on a known general chip layout. The method provided results in the ability to place the chip to be measured into the scanner and then start the scan without any additional manual settings required. The method does the rest, and produces the desired fluorescence measurements as the results.

Certain aspects of invention involve eliminating or preventing the occurrence of active capture agent on outside surfaces of the hollow flow elements, e.g. extended outside cylindrical surface, and/or end surfaces, while leaving active capture agent on the inside surface unperturbed, or of a desirable area or pattern. Features addressing this aspect include techniques to selectively limit the capture agent on the interior surface and steps that act in combination with outside and inside surfaces to achieve the desired result.

For the specific advantage of reducing the overall capture surface area, two aspects of invention will be described, and the effect of their combination. A first technique is employed to eliminate or prevent capture agent, e.g. antibody, from immobilizing to the outside surface of hollow flow elements. That is done during a batch coating process, and involves suspending discrete hollow elements in an Eppendorff tube or other laboratory tube with the capture agent of interest and aggressively agitating fluid to impart disrupting shear forces to the exterior surface of the elements. Preferably this is achieved by vortexing the fluid at high speed, for instance employing an instrument that orbits the container at approximately 2000 rpm of the orbiter, about an orbital path with total lateral excursion of the supporting table of the order about 0.5 cm, measured across the center of rotation of the orbiter.

The hollow flow elements are placed with a volume, e.g. a milliliter of capture agent, e.g. antibody. The appropriate vortexing speed is dependent e.g. on the nature of the suspension, e.g. the viscosity of the liquid chosen, and can be easily determined experimentally. It is set by observing whether the capture agent is effectively non-existent on the outside, long surface of the hollow flow elements, e.g. the outside cylindrical surface in the case of the body being of circular cross-section.

The physical principle involved concerns shearing force on the outside surface of the element that acts to prevent binding of the capture agent to the surface through an adsorption process. One can observe whether the vigorous agitation is sufficient to shear off any capture agent, e.g. antibody that has already been bound to that surface. At the same time, the inside surface is environmentally shielded from this shearing by virtue of the geometry which is tubular, and the micro-bore of the tube. This prevents vortexing from causing any turbulence to occur within the element. Only laminate flow conditions exist. With micro bore elements the Reynolds number is always low enough to ensure that that laminar flow condition exists on the inside surface. Under these conditions, the velocity of fluid traversing in the hollow element at the interior wall interface is by definition zero. So there is no shear force involved there, whereas the outside is in a highly turbulent, high shear force environment. The shortness of the length of the elements enables uniform coating of the inner surface, whereas longer elements, coated by immersion, are susceptible to detrimental non-uniform coating.

The observed result of aggressive agitation, e.g. vortexing, is that fluorescence which is observed by performing a sandwich assay is completely absent from the outer cylindrical surface, or other shape of a hollow element, whereas it is present in an observable way on the inside surface. In the case of square-end hollow flow elements, fluorescence is also present on the end faces of elements.

Vortexing is the presently preferred technique for producing the shear forces. The case showed here employs orbitally rotating the coated element in a very rapid manner back and forth in small circles at a rate of approximately a couple thousand rotations per minute, and an excursion of about 25 mm.

However, any type of rapid oscillation that creates a high degree of turbulence can be employed, so a back and forth motion, a circular rotation, anything that would very rapidly mix the fluids and create high shear forces will suffice.

In summary, hollow flow elements in the presence of aggressive agitation leads to removal of capture agent, e.g. antibodies, from outside surface of the elements, and prevention of their coating with the agent, but leaves the inside surface of the element in condition to immobilize capture agent, e.g. capture antibodies, for subsequent interaction with analyte of the sample.

As an alternative to the high shear technique, we conceive an alternate process in which, during the original drawing of the small bore tube, and prior to the point along the draw path that the usual removable protective polymer coating is applied to the filament, that a non-stick coating, e.g. sputtered gold, silver or graphite, is applied to the filament, e.g. by passing through a sputtering chamber. Silane or similar coating must be applied to receiving surfaces before capture agent, e.g. antibodies will attach. However, due to the properties of the sputter coating, or the like, the surface will not receive the silane or equivalent, then likewise, the active capture agent.

Another feature of invention concerns realizing the desirability and technique of removing coated capture agent from selected end surfaces of the flow elements and a margin portion or other portion of the interior surface. Preferably, following the aggressive agitation process, the elements are further processed using a laser elimination process that removes or de-activates capture agent, e.g. antibodies, from surface from which the agent was not removed by the high shear process. Those surfaces include transverse end surfaces and a selected portion of the inside surface, leaving only an annular stripe on the inside surface sized sufficient to process the assay, but small enough to reduce depletion of the analyte from the sample.

In a preferred form an ablating laser is arranged transversely to the axis of elongation of the hollow elements with the effect that the energy arrives though parallel to the end faces has a neutralizing or removal effect on the capture agent that is on those end faces, as a result of incidence of substantially parallel radiation, but also of internal reflection scattering of the radiation by the transparent substance that defines those end faces.

The net effect of two novel processes described, if used in novel combination, is to leave only a band of selected dimension, which can be small, of capture agent immobilized on the inside surface of the hollow element. This can be done in a way that leaves one or more bands separated by a space of no capture agent. Thus one can generate a single band in the center or a single band closer to one end or multiple bands distributed along the length of the element. These bands can be of different widths, can have different spacing, and can be of the form of a code, e.g. a bar code, which is useful to encode the particular flow element.

Further is a description of manufacturing techniques that have important novel features.

The short, hollow elements are first formed i.e. chopped, from previously supplied continuous small-bore filament into the short, discrete elements. They are then treated in batch manner.

A bulk of the hollow elements is then exposed in an Eppendorff tube to wash buffer. After washing processing is performed, the buffer is removed, and replaced with a silane. By use of this simple, low-cost immersion step, the silane is allowed to bind to all of the surfaces of the elements. Excess silane after a period of time is washed away with water in a buffer. Then a capture agent, e.g. antibody, in solution is added to the Eppendorff tube with the bulk of hollow elements and allowed to incubate overnight. The incubation is performed on the orbital vortexer for approximately 16 hours at 2000 rotations per minute. The order of 0.5-centimeter diametric displacement by the orbital motion. The orbital plate that contains the numerous Eppendorff tubes is approximately 6 inches in diameter, but the orbital motions is a circular pattern counterclockwise and then clockwise motion the orbiting causing the displacement of approximately 0.5 centimeters from side to side, for instance.

After the vortexing process is completed, the net result is that the capture agent has been immobilized on the inside surface of the hollow element and also on the end faces but it is not present on the outside cylindrical surface of the hollow element. The capture agent solution is removed from the Eppendorff tube, which is replaced with a wash buffer, a wash buffer solution, and the wash buffer solution is then further replaced with a stabilizing buffer, what we call a blocking buffer. In the preferred embodiment, a commercial material called StabilCoat® solution is used.

StabilCoat® blocking solution is introduced to the Eppendorff tube along with hollow flow elements, and then a portion of those elements is aspirated in a pipette along with some of the StabilCoat®, and dispensed onto an alignment plate. For tweezer pick up the alignment plate contains a series of rectangular shaped pockets, each designed to accommodate and position a single element within a small space, preferably with clearance tolerance sized in microns, a space of 10 to 50 microns between the element and the walls of the pocket. After the elements are allowed to roam on the plate, they fall into these pockets still in the presence of the buffer solution. The excess buffer solution is removed from the alignment plate containing the elements by placing their plates with elements into a centrifuge or centrifuge holder and centrifuging at approximately two thousand rpm, for 30 seconds, thereby removing all excess StabilCoat® solution from the plate and the elements. This process is facilitated by the novel design of the plate, in which drain channels extend radially from the pockets.

(In the case of vacuum pickup continuous grooves are employed to receive the treated elements, in greater density than enabled by the pockets, as the elements can be close together, end to end, since pickup will be by engaging the cylindrical surface, not the end surfaces as is the case with tweezers.)

The hollow elements while still in the plate are further processed with a laser, preferably an ultraviolet laser, which could be an excimer laser, fluoride or krypton fluoride laser, with two beams that are spaced such that the ends and an end margin portion or section of the element are exposed perpendicular to the element axis by a laser beam in a way that either ablates or denatures the capture agent, e.g. antibody, from the ends of the element as well as a section of the inside surface of the element. It is a feature of the laser configuration that the two laser beams are separated by a fixed distance that defines the desirable width of the remaining band of capture antibody surface. The hollow elements within their pockets of the alignment plate can be allowed to move back and forth with a degree of liberty, while still the laser processes substantially the ends of the elements and leaves a fixed width pattern near the center of the element, plus or minus a reasonable tolerance window.

It is possible instead to define a series of three or more laser beams, with gaps, such that the pattern produced by the various widths of laser beams in the various gaps between the laser beams defines a pattern of exposure in the hollow element that looks like and is useful as a bar code.

Further, it is realized as useful to have significant by-pass flow in a channel outside of the hollow element as well as through the element. One advantage is simplicity of manufacture as the element can be held but without being sealed and with no attempt to use cumbersome adhesive to adhere the element to the channel walls. Another advantage is the avoidance of the risk of totally spoiling an assay because a chance particle obstructs internal flow of one of the hollow-flow elements when arranged in series in a liquid flow path. Having significant by-pass flow on the outside, at least as great as 50%, in many cases 75% or larger, and in certain preferred instances 100% or more is highly useful. As least to some extent, this enables "short circuiting" the element, ensuring that despite one element being plugged or obstructed and flow stopped, the other elements will receive flow and the assay will only be partially affected by the obstructing particle. It is realized further that with concepts presented here, enabling the avoidance of having active capture agent on the exterior, i.e. for cylindrical elements, on either the cylindrical exterior of the hollow element or on its end faces, does not result in a depletion problem. The techniques previously described, of avoiding active capture agent from adhering to the exterior cylindrical surface of the hollow elements and laser treating the ends, thus contribute to the practicality of employing the by-pass flow described.

Sizing of Hollow Flow Elements

It has long been accepted knowledge that the smaller the surface area of the capture agent, e.g. antibody, the more sensitive the assay is from a theoretical point of view. The desire has always therefore been to keep the inside diameter of a hollow element as small as possible to minimize that surface area. But it has now been determined empirically that, within limits, the performance of the assay is improved as that diameter is increased to an extent. It is believed this is a direct result of non-uniform coating by the batch process desired to be employed, as well as probably some effects that occur during the assay in that it is possible that there are perturbations in the amount of volume, total volume, that actually flows through the hollow elements in cases where the tube element diameter is small compared to an element of i.e. of 75 microns. We have found that the internal diameter should be about 75+/−50, and in preferred cases, 50+25.

It is preferable that the exterior diameter have a diameter or width within the range of 1.2 and 4 times the internal diameter or width For length of the hollow flow elements, best results are obtained with lengths of less than about 700 micron, and in many cases, less than 500 micron. In a presently preferred form, the length is 250 um.

In some embodiments, it is preferable that the interior diameter have a diameter or width have a length to inner diameter of 20:1.

It has been discovered that the shorter hollow elements lead to greater uniformity of the coating of capture agent when coated by the batch process described herein, and as well, shorter hollow elements are found to be more amenable to withstanding axial tweezing forces during pick and place motions.

As previously mentioned there are significant advantages in providing two subassemblies that are each fabricated on their respective solid substrates or carriers, which are dimensionally stable, though permissibly flexible. The extremely small hollow flow elements (or other detection elements to be fixed in position within the cassette) are placed into open locations on the mating face of one of the subassemblies, prior to aligning. Once the subassemblies are aligned, the two subassemblies are brought together under bonding conditions to form one completed assembly, and fixing the embedded location of the elements. Then the two subassemblies are brought together to complete the fluidic channels. Bringing them together completes the valve and piston devices as well as embedding the detection elements. These features occur with the non-permanently bonded implementation.

Another implementation of the broad assembling concept will now be described, employing permanent bonding features. We will refer now to the Figures beginning with FIG. 27. The following is a list of components called out in FIG. 27 et seq.

20. Completed Cartridge
22. Sample Inlet wells
24. Buffer Inlet Wells
26. Waste Well Reservoir 28. Reservoir Well—Detect Antibody Reagent—Preferred Embodiment—Dried
30. Microfluidic Channels
32. Extremely Small Hollow Flow Elements ("Elements")
34. Microfluidic Valve Seats
35. Microfluidic Valve Pneumatic Chamber
36. Piston Fluidic Chamber
37. Piston Pneumatic Chamber
38. Elastomer Membrane
39. Plasma Bonded Interface
40. Arrows Depicting Flow
41. Bypass Flow Path
42. Glass Substrate
43. Bulk Material
44. Microfluidic Channel Walls
46. Control Reservoir Layer
48. Fluidic Layer Sub Assembly—No Elements
50. Fluidic Layer Sub Assembly—With Elements
52. Single Sample Four Analyte Microfluidic Network
54. Microfluidic Valve—Full Assembly
55. Piston—Full Assembly
56. Reservoir/Control Plastic Member
58. Pneumatic Interface Ports
60. Piston Control Lines
62. Valve Control Lines
64. End of arm tooling (tweezer or vacuum probe)
66. Pick and Place Arm (moves up and down)
68. Source/Target X, Y table (moves in X and Y coordinates)
70. Source of Hollow Flow Elements (groove or well plate)
72. Target Microfluidic device
74. End of arm tooling—vacuum
76. End of arm tooling—tweezer
78. Activated Surface In FIG. 27, starting from the upper side, the subassembly 46, i.e. the controls/reservoir layer 46, is comprised of two elements, the upper injection molded or machined plastic component 56 with a PDMS membrane sheet bonded to its lower surface.

The bottom fluidic layer or subassembly 50 has detection elements, e.g. hollow short cylindrical flow elements 32. The fluidic subassembly consists of a thin glass sheet 42 with a PDMS gasket or sheet permanently bonded face-wise to its upper surface, the sheet having cut-outs defining fluidic channels between channel walls 44, the channel bottomed on the glass sheet 42, FIG. 28C. Before those two subassemblies are brought together, the detection elements are dispensed, in the embodiment shown, by pick and place action, into fixed positions in the channels of the fluidic layer 48. The two subassemblies 46 and 50 are brought together and bonded in a way that provides fluid-tight and leak-free operation, but also enables the actuation of valves and pistons by portions of membrane. One novel a feature of this construction is that the two subassemblies as described, using a PDMS gasket, enables capture or embedding detection elements, here extremely short hollow flow elements, (Micro-length Tube™ elements) into channels. Combining those two subassemblies into a single assembly provides the functionality of having microfluidic channels that contain the hollow flow elements as well as functioning valves and pistons. In a fluidically robust and leak-free microfluidic structure, using the plasma-bonding process, known per se, to perform the numerous functions described, securing the detection elements in place and forming the valves and pump diaphragms in a way that completely seals the channels, together with a process to be described that defeats plasma bonding at the exposed valve seat contacted by the PDMS membrane.

The fluidic subassembly is assembled by covalently bonding PDMS to glass, and then upper assembly, the reservoir assembly is formed by covalently bonding PDMS to plastic. The dominant advantage is the placing the discrete, small detection elements, the hollow flow elements, into open channels prior to assembling.

The importance of the technique also relates to enabling the immobilization of capture agent, e.g. antibody, onto a solid substrate in an efficient batch process, thereby allowing many thousands of these elements to be fabricated in one very simple batch process, which is cost effective and highly reproducible. The process itself is absent of process parameters that would cause damage to biological content, and can be a room temperature process.

Thus features of the concept include bringing together subassemblies to capture elements in a fixed position, the capture (or detection) elements having been pre-prepared in batch process, with the final assembly, which employing a bonding process, especially the permanent plasma bonding process to join the subassemblies, and doing it in a selective way at the valve seats by repeatedly locally deflecting and bringing in contact the valving surfaces, which will now be described.

Valve Break-In Process

Connect pneumatic control input ports to externally controlled pneumatic line/s

Actuate all valves using vacuum (5-14 psi) to draw membrane up into pneumatic valve chambers.

Bring surface-activated (e.g. plasma activated) Reservoir/Control layer into conformal contact with Fluidic Layer.

Momentarily apply pressure (1-10 psi) to valve control lines to force PDMS membrane into intimate contact with the PDMS surface of the Fluidic layer. Allow contact for approximately 1-3 seconds before switching back to vacuum pressure in control lines.

Perform initial break-in of valves by rapid performing a sequence of actuations between vacuum and pressure for approximately 20 cycles, over a time period of 1-2 minutes.

Continue to cycle valves with vacuum and pressure over a period of 5-20 minutes, depending on the surface activation and thermal history of the PDMS surfaces. Once the initial break-in cycles are performed, a slower and more protracted actuation sequence is preferably used to prevent the slow inexorable bonding of the PDMS surfaces, until all inclination for bonding is prevented, which can be achieved by actuating the valve with pressure for up to 1 minute followed by intermittent actuations with vacuum so as to break any newly formed bonds. Continuing this process for up to 20 minutes has been shown to completely prevent future permanent bonding between the valve membrane and the valve seat.

Other materials which have molecular bonding capabilities when like surfaces are bought together may also be employed, and the molecular bonds destroyed at valve seats in similar manner, Description of Valve Break-In Process Native PDMS, comprised mainly of repeating groups of —O—Si(CH3)2- is hydrophobic in nature, and, without special treatment, has a tendency to adhere to, but not permanently bond to other like surfaces such as PDMS, glass and silicon. However, upon treatment with oxygen plasma or the like the methyl groups (CH3) are replaced with silanol groups (SiOH), thus forming a high surface energy, hydrophilic surface capable of bonding irreversibly with other like surfaces containing high densities of silanol groups. This irreversible bonding process occurs via condensation reaction between OH groups on each surface resulting in covalent Si—O—Si bonds with the concomitant liberation of water (H2O).

Oxygen plasma and similar techniques have control parameters such as pressure, power, and time all of which determine the concentration of surface OH groups. Higher concentrations of OH groups lead to more covalent bonds between the two surface and therefore higher mechanical bonds. Left exposed to atmosphere after oxygen plasma or similar treatment, the hydrophilic surface will undergo "recovery" back to its native hydrophobic state via migration of short, mobile polymer chains from the bulk to the surface. Full "recovery" occurs over a period of hours at room temperature and can be accelerated with increased temperature and retarded by storage in vacuum and/or low temperatures. This is accommodated by storing activated substrates at −50 C in vacuum bags for several days to lock-in the hydrophilic surface treatment prior to bonding.

Since the bonding mechanism follows a fairly slow condensation reaction, which involves the liberation of, water over a period of several minutes to a few hours before completely consuming the available OH sites, it is possible to interrupt this process before completion. Once completed, the bond strength between the interfaces is comparable to the bulk tear strength leading to an irreversible attachment of the two materials. Attempts to separate the layers at this stage will lead to bulk damage of one or both of the layers. However, interruption of the bonding process by mechanically separating the surfaces during the early stages of the bonding cycle is found to irreparably damage only the small number of formed bonds between the two surfaces. The tear strength of the bulk is considerably higher than the interface bond, therefore separation produces no irreparable damage to the bulk. Also, if the bonding process is interrupted early enough (typically in first few seconds), then the force required to separate the layers is little more than the adhesion force required to separate untreated layers. Bringing the layers back into contact for a short duration (typically a few more seconds), will initiate, and interrupt bonding again. Each time this cycle is repeated, potential bonds are incrementally eliminated until all such bond sites are consumed and the material reverts back to having the properties of the untreated material.

In a preferred novel technique, microvalves are formed between layers of PDMS by surface activating, e.g. plasma activating, the PDMS or similar surfaces, bringing them into contact and then activating the valves to open and close in such a manner that permanently disrupts bonding between the flexible membrane and the valve seat, but results in complete and robust bonding elsewhere over broad surfaces to hold the device together.

Device Manufacture

Figure 27A:
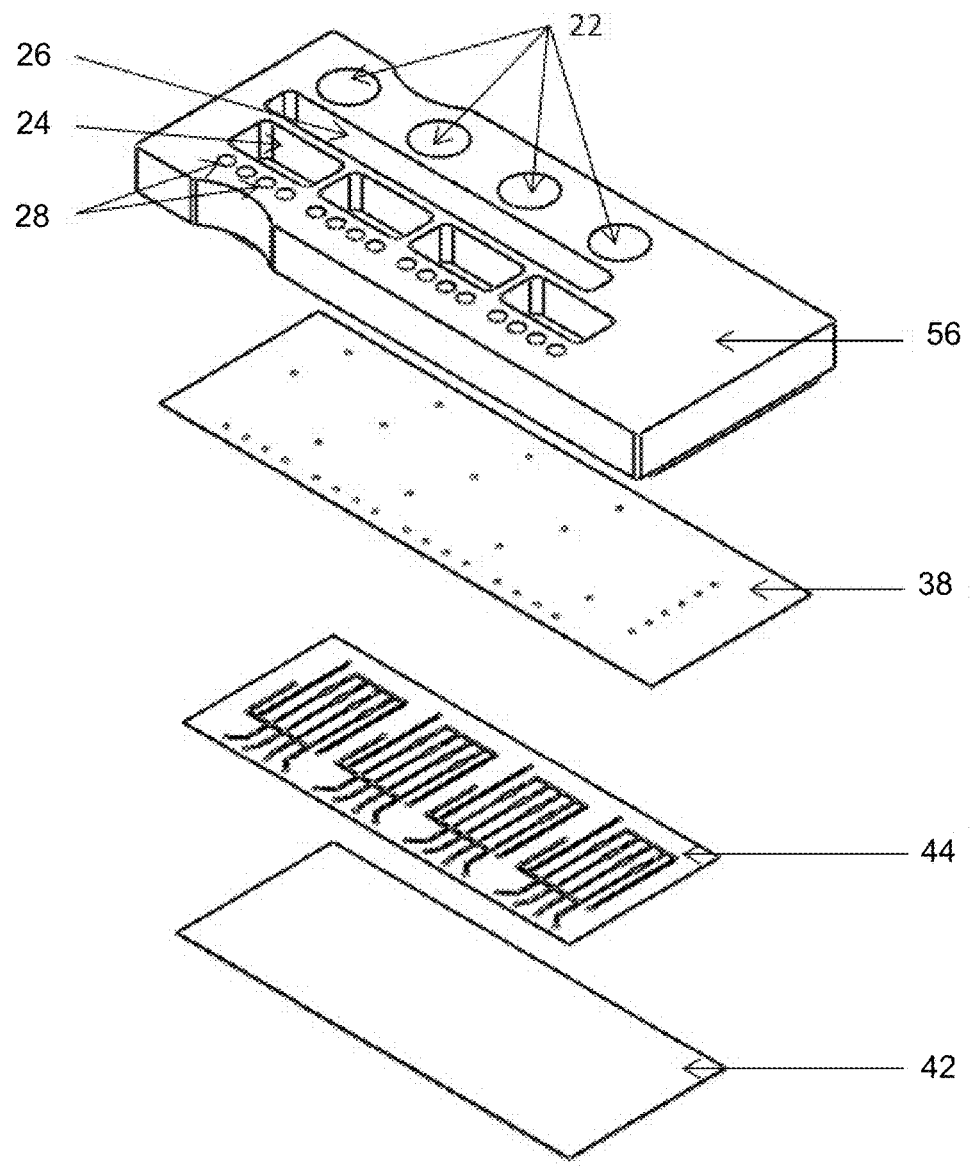
FIG. 27A is an exploded perspective view of the device of FIG. 27.

Referring to FIG. 27, a product employing the concepts described is a consumable microfluidic cartridge for the purpose of quantifying antibody concentrations in human plasma samples. The cartridge, such as shown in FIG. 27, contains on board provisions for sample inlets, in other words, a reservoir that will receive a sample to be analyzed, e.g. a blood plasma or serum sample.

A completed cartridge 20 contains sample inlet wells 22 for receiving patient plasma or serum sample or other type of bodily fluid, including cerebral spinal fluid, or urine. It will also contain a buffer inlet well 24, buffer being a reagent used during the processing of the assay, a waste reservoir well 26 designed to contain all of the reagents and sample that flow through the microfluidic channels and that are no longer needed all self-contained on the microfluidic cartridge, also containing a reservoir well 28 which has contained in it a detection antibody with a fluorescent label. The preferred embodiment, the detection antibody will be dried down in the channel or in the reservoir and rehydrated during operation using the buffered contained in buffer well 24.

Figures 28A, 28B:
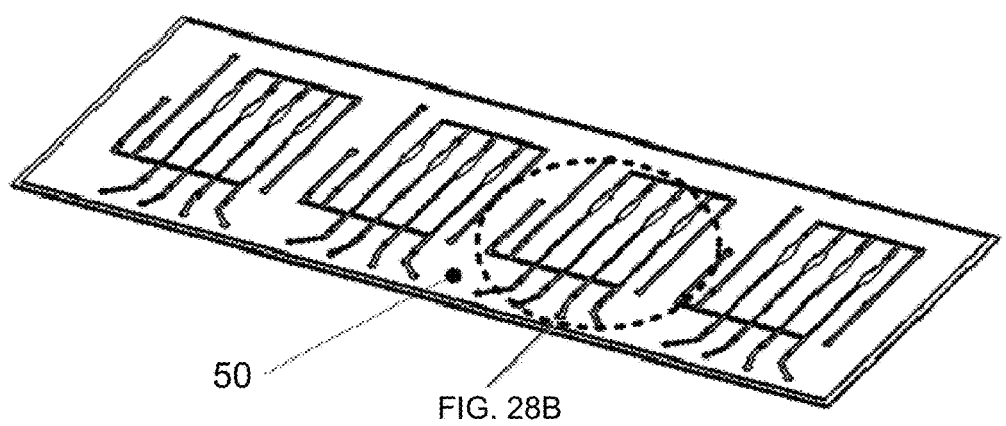
FIG. 28A is a perspective view on an enlarged scale of a fluidic channel of FIGS. 27 and 27A.
FIG. 28B is a further magnified view of a portion of FIG. 28A showing flow channels, hollow flow elements (e.g. GNRs), valve seats and pump chambers.
Figure 28B:
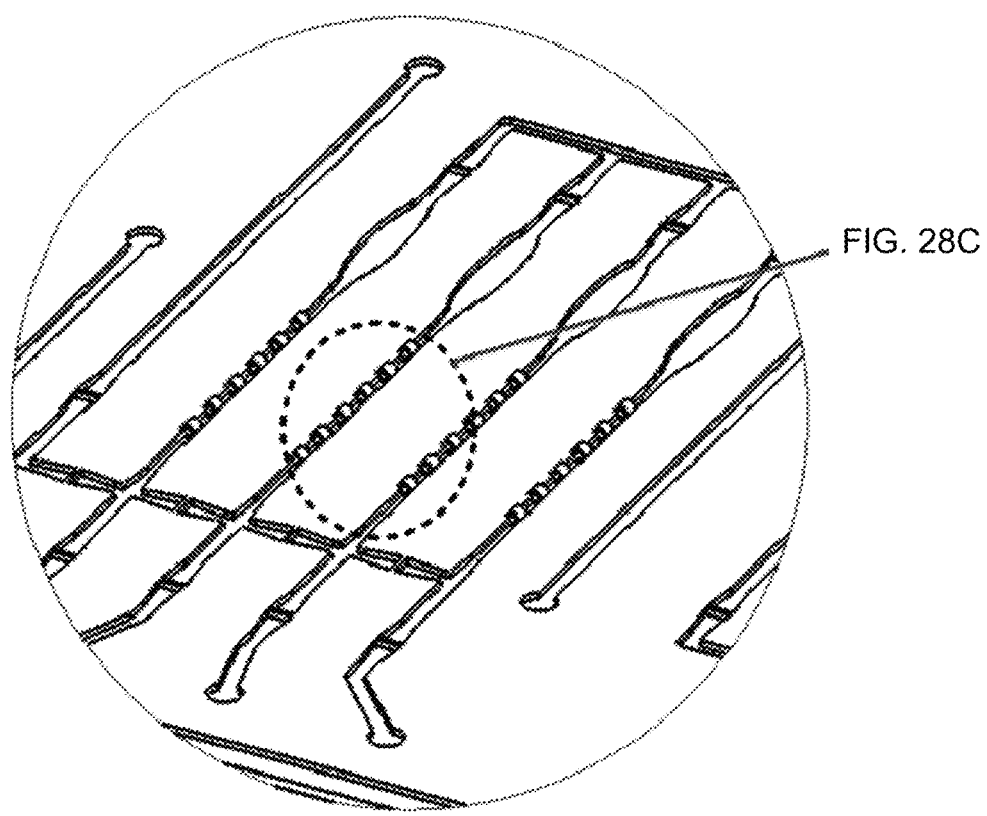
Figure 28C:
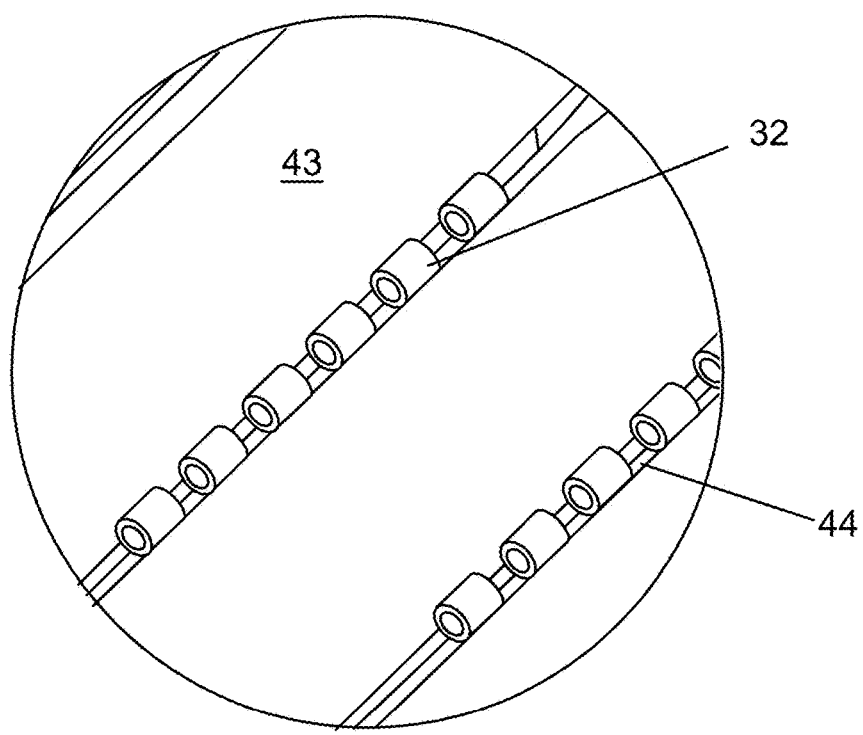
FIG. 28C is an even more greatly magnified view of sets of extremely small hollow flow elements disposed in channels of FIGS. 28A and 28B (see FIGS. 5 and 7 for a representation of a single flow element)

Referring now to FIGS. 28A, 28B and 28C, FIG. 28A shows the microfluidic channels containing 4 independent microfluidic channel groups containing the extremely small hollow fluidic flow elements, referred to hereafter as elements. FIG. 28A shows those four channel groups each containing six channels 30. There are extremely small hollow flow elements 32, microfluidic valve seats 34, and pistons 36. The extremely small hollow flow elements are formed in a batch process with a capture antibody provided on the inside surface of the elements and those elements are placed into channels 30.

Example of dimensions of the hollow elements: The length of the preferred embodiment is approximately 250 microns, the inner diameter approximately 75 microns, and an outer diameter of approximately 125 microns. FIG. 28B is a blown up schematic of the hollow elements shown in two parallel example channels.

In presently preferred practice, the channels are wider than the elements, and the elements are attracted by near electrostatic force to adhere to one channel wall, defining by-pass flow paths on the other side.

Figure 31:
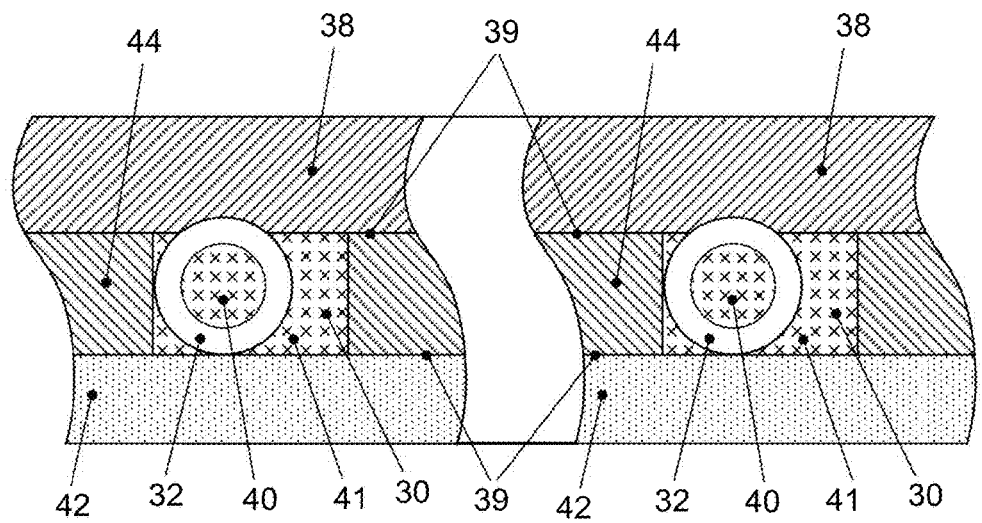
FIG. 31 is a magnified diagrammatic cross section, with parts broken away of microfluidic channels of a device, and depicting the membrane capturing a hollow flow element in the channel, lines of flow being indicated through and outside the flow element.
Figure 31A:
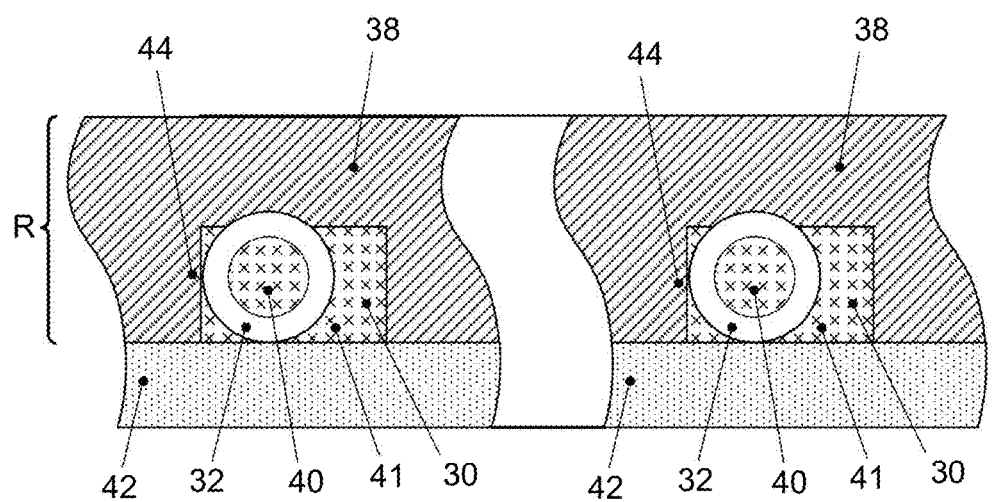
FIG. 31A is a view similar to FIG. 31 in which two layers (membrane and the layer defining the side wall of the channels), both of PDMS, have been fused by covalent bonding to close the channels and secure the hollow flow elements.
Figure 32:
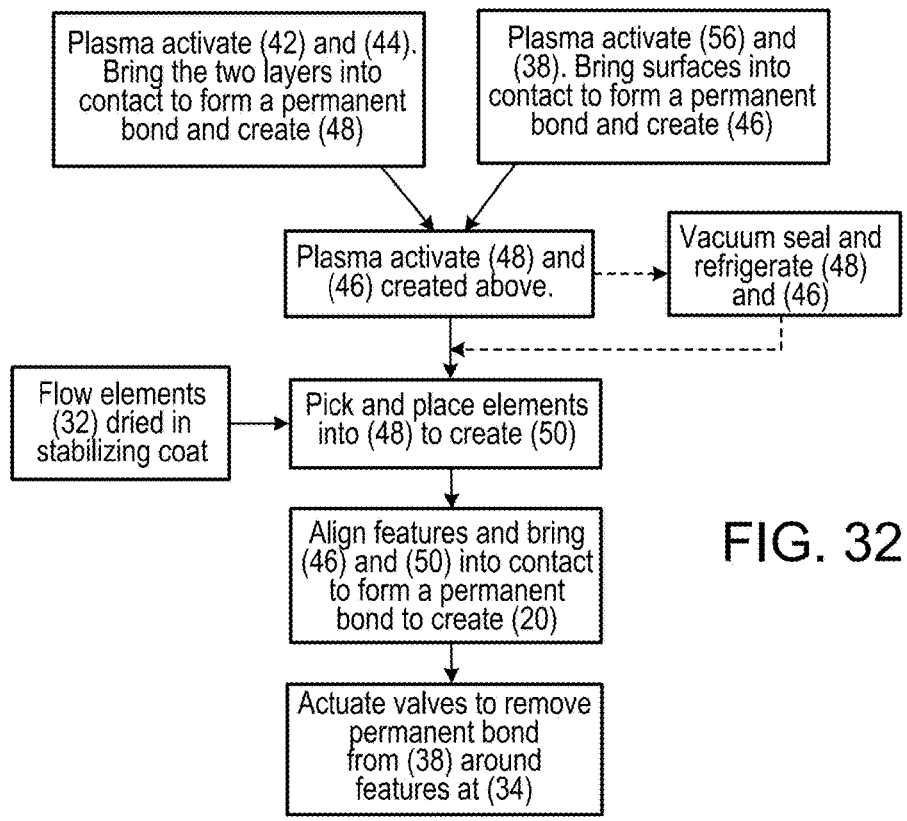
FIG. 32 is a diagram of steps in the assembly process for the device of preceding figures.
Figure 32A:
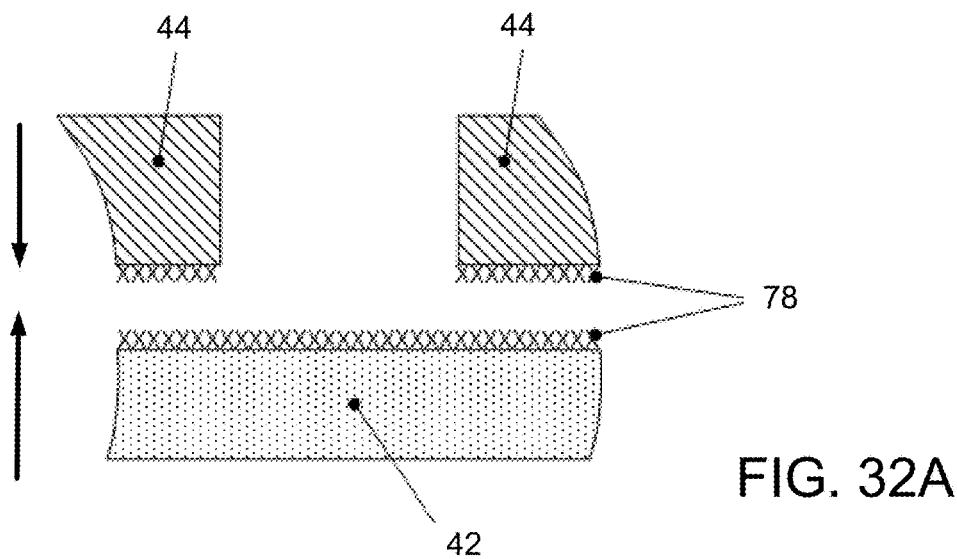
FIGS. 32A, 32B, 32C, and 32D are cross-sectional views of a microfluidic device through a hollow flow element, illustrating, diagrammatically, steps in employing PDMS surface activation and covalent bonding to form the liquid-tight channels and secure the extremely small hollow flow elements in place in the channels.
Figure 32B:
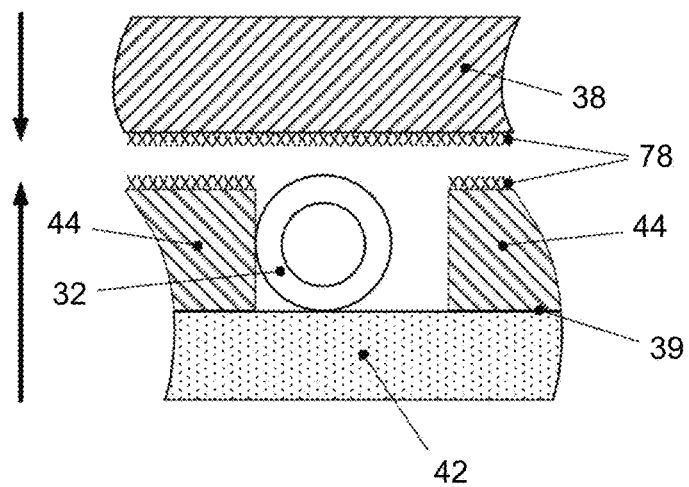
Figure 32C:
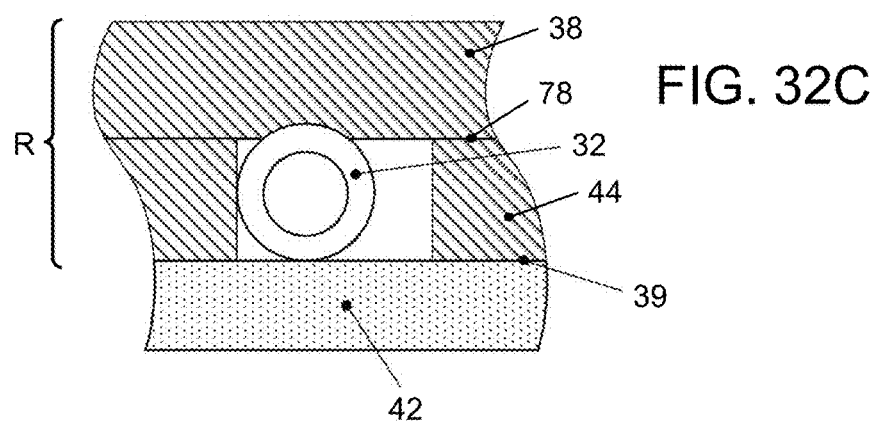
Figure 32D:
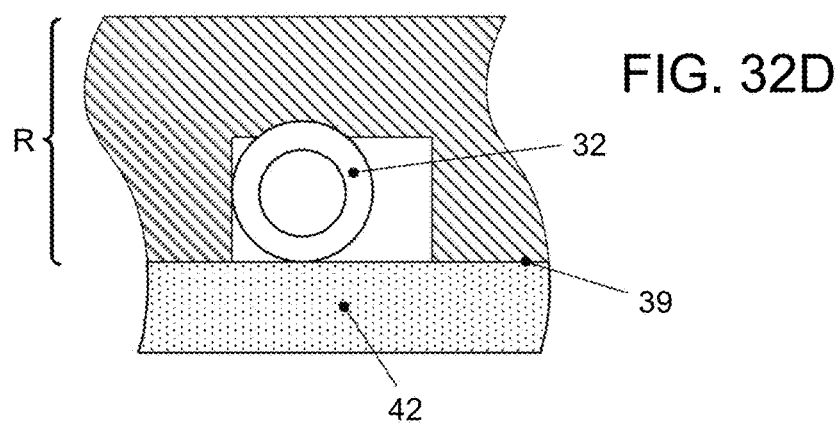

FIG. 31 shows a cross-sectional view of a hollow flow element in channel 30 with space surrounding hollow element on the outside of the element. FIG. 31 depicts hollow element 32 in microfluidic channel 30 with flow arrows 40 depicted, the hollow element as captured by the top surface elastomer membrane 38 and on the bottom surface by glass substrate element 42.

Typical dimensions for the glass substrate layer 42 are 200 microns thick of boro-silicate glass and the elastomer membrane layer element 38 has typical thickness of 100-200 microns. Also providing the channels are an elastomer, PDMS material typical 100-150 microns tall thus forming the microfluidic channel. Also shown in FIG. 31 the elastomer membrane layer continues both to the left and to the right as well as the glass substrate continuing to the left and to the right and on either side containing one or more parallel microfluidic channels also containing hollow glass elements, glass layer element 42 is bonded to elastomer wall, a micro-fluidic channel wall 44, previously formed in a sub-assembly process using a covalent bonding technique involving plasma activation of the PDMS surface and subsequent contacting and therefore bonding to the glass layer, the hollow element is inserted into that channel.

There are additional channels 30 in parallel. The purpose of parallel channels is to isolate different antibodies from each other for preventing cross-reactivity.

Channel depth is less the diameter of hollow element that are picked and placed against one of channel walls such that electrostatic forces between the element and channel walls release the placing device, e.g. tweezers or vacuum pickup, from the element. In this process, by moving in an "L" shaped motion, laterally at the end, increases the electrostatic attraction and allows the tweezer to be released from engagement with the element and tweezers to be removed. Channel 30 enclosed by bringing into contact both ends of elastic membrane 38 of control/reservoir 46. Elements are retained in channel 30 between elastomeric 38 and glass 42.

FIG. 29 shows schematically two example channels containing a series of four spaced apart elements 32 and by-pass flow space 41.

Figure 21:
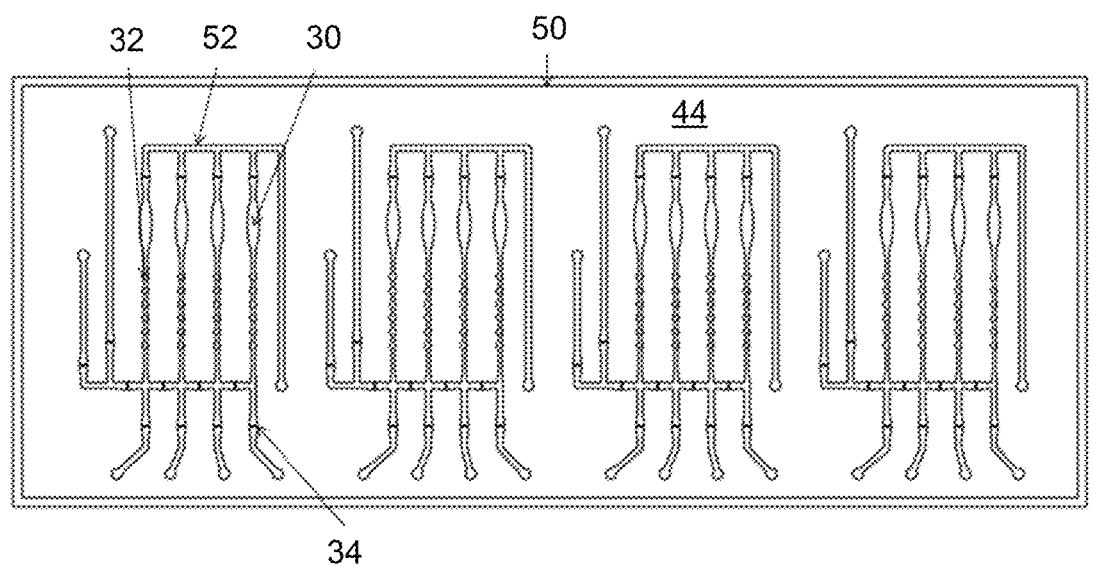
FIG. 21 is a top-view of the fluidic sub-assembly on an enlarged scale (see also FIG. 103)

FIG. 21 is a top view of the fluidic layer sub-assembly 48 with elements 32 in channels 30. The assembly 50 contains the elements.

In FIG. 21 four sets of microfluidic single sample, i.e., four analyte networks 52 are shown, each network is designed to perform an assay with its own respective sample.

FIG. 30 is a blowup schematic of a single channel 30 containing four elements 32 and microfluidic piston chamber 36, and valve 54 having seat 34, FIG. 30A.

FIG. 30 depicts by arrowheads, flow through the bypass flow path 41 around the hollow element 32 as well as through the element.

Referring to FIG. 21, the channels 30 are formed by glass substrate and micro-fluid channel walls formed by knife cutting sheet of PDMS of 110-micron thickness.

FIG. 27 shows forming the fluidic area 48 by bringing together glass sheet 42 and the unique cut-patterned PDMS sheet 44 using known techniques.

Reservoir/control plastic member 56 (containing fluidic reservoirs for sample, 22, assay buffer 24 and reagent waste 26) is bonded to PDMS membrane 38 to form control/reservoir layer 46.

FIG. 21 is a top view of the fluidic layer sub-assembly 48 with elements 32 in channels 30. The assembly 50 contains the elements.

In FIG. 21 four sets of microfluidic single sample, i.e., four analyte networks 52 are shown, each network is designed to perform an assay with its own respective sample.

Referring to FIG. 21, the channels 30 are formed by glass substrate 42 and micro-fluid channel walls formed by knife cutting sheet of PDMS of 110-micron thickness 32

Figure 22:
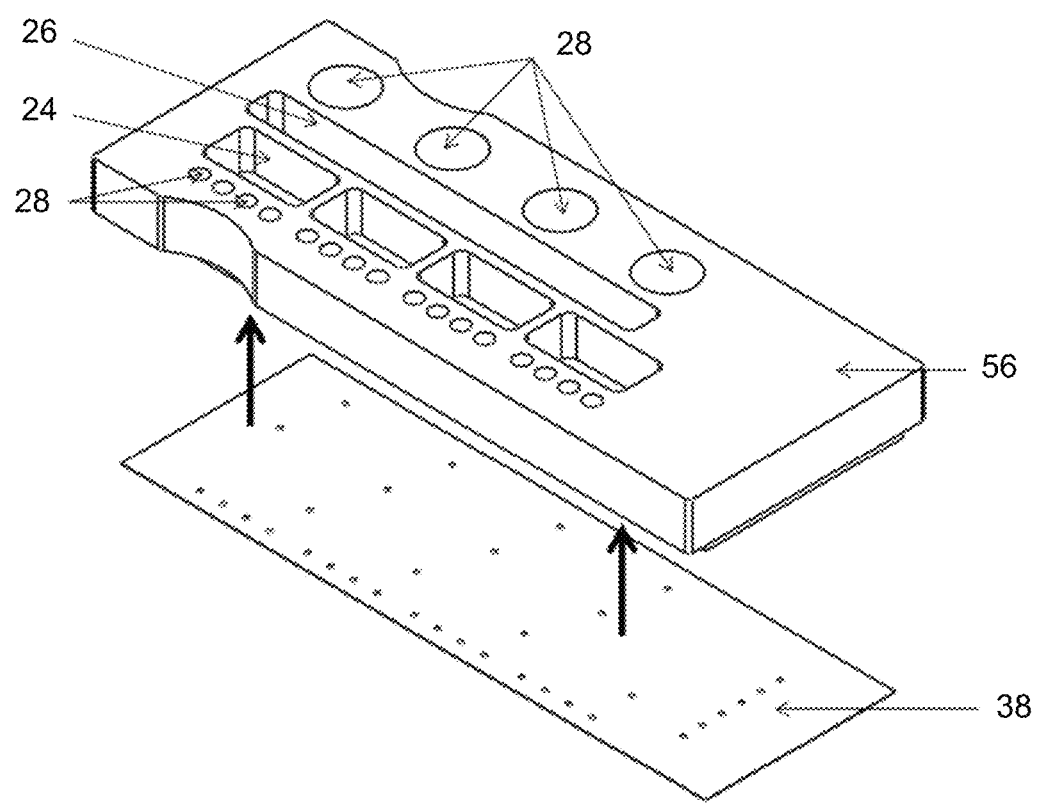
FIG. 22 is a perspective view of parts of the pneumatic sub-assembly as the PDMS sheet comes together with the reservoir/pneumatic layer.
Figure 26:
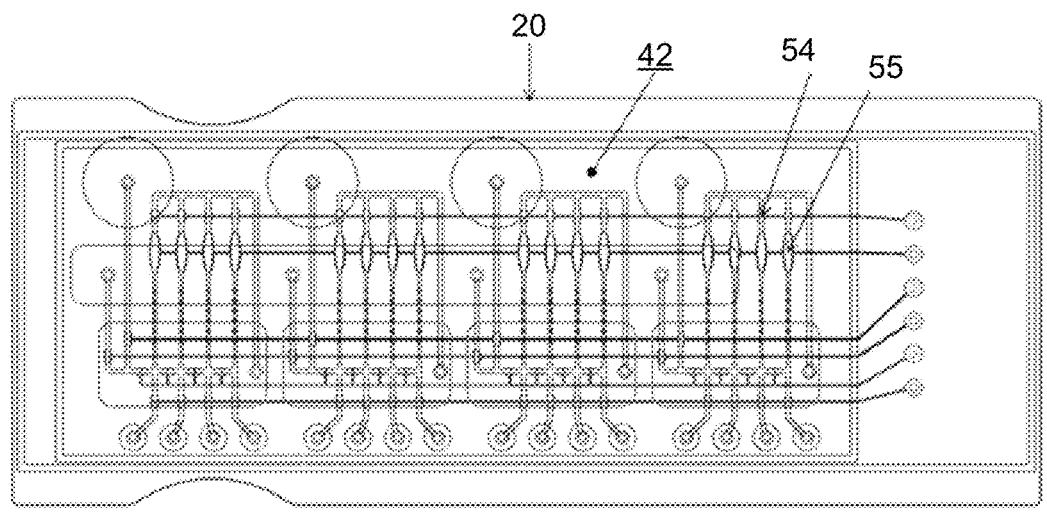
FIG. 26 is a top view of the completed assembly.

Referring to perspective of FIG. 22, layer 56 and membrane 38 are ready to be assembled by plasma-activated molecular bonding. FIG. 26 is a top view depicting final assembly. Pneumatic interface ports 58 are adapted to match with computer-controlled pneumatic control lines that provide pressure and vacuum actuation to valves 54 (formed by membrane 38 and microfluidic valve seat 34) and pistons 55 (the pistons being formed by elastomer membrane 38 lying over piston fluidic chamber 36 and piston pneumatic chamber) piston control lines 60 and valve control lines 62. The piston pump formed by membrane 38 sandwiched between 37 and 36 is activated by vacuum in one direction and pressure in the other.

For pneumatically controlled microfluidic systems, there is need for forming a fine, closely-spaced pneumatic channel network with high fidelity over an extensive area. One important use of such networks is for actuating a distribution of microfluidic valves or systems of microfluidic pistons and valves that constitute microfluidic pumps. As is well known to those in the microfluidic field, there are significant problems associated with doing this economically and reliably. The problems become more acute as the extensiveness, complexity and greater miniaturization of the microfluidic network increases. Many of the problems relate to materials, material handling and manufacturing techniques.

In the case of using high precision molds to form three-sided micro-pneumatic channels integral with a body that may perform other functions, there is extreme cost and inflexibility involved in creating the precision molds and in making mold changes required over the life of the mold. For many molded parts, there can be difficulty in achieving sufficiently intimate bonding with another material to close open channels and achieve air-tightness under both positive and negative air pressures.

In the case of forming a composite channel with walls of one material and top and bottom closures of different materials, it is difficult to find the right materials and manufacturing techniques that meet all needs. Form instability as well as difficulty in achieving intimate, air-tight, long-lasting bonds under positive and negative air pressure are among the problems. During the production of such a device, when formed of parts that need to be joined to complete the fine features of the pneumatic system, there is a particular need for the finely formed parts to have dimensional stability in handing to achieve registration and proper mating with cooperating parts. Without precise registration, desired pneumatic pressure levels may not reach microfluidic valves or pistons to operate them in proper sequence.

These considerations apply especially to microfluidic assay devices that perform multiplex assays, e.g. ELISA, in which in one device, multiple assays of bodily fluids are performed. In many cases, for instance in drug development, it is desired that multiple isolated samples be simultaneously subject to multiple assays.

There is particular need to find a combination of materials and manufacturing techniques that meet all of the many requirements of micro-pneumatic structures described here and otherwise well known in the field of microfluidics.

As a specific example, it is desired to provide a highly quantitative immunoassay device capable of receiving multiple samples, for instance approximately sixteen to sixty four samples on a single portable microfluidic cartridge, and provide, for each sample, a microfluidic network capable of quantitative determination of a number of analytes simultaneously, for instance conduct four to eight different assays, the assay cartridge having macro sized features for containing patient sample (e.g. blood serum, urine), reagents such as buffers and secondary antibodies, and waste.

Especially, it is desired to find an efficient approach to manufacturing such a portable microfluidic assay device of overall ("footprint") dimensions of, e.g., 5 inches by 3 inches. In such device it is important to have the microfluidic channels closely packed with other channels and features, of a distance of the order of four to eight times the width of a pneumatic micro-channel, with, for instance, channel sizes on the order of 100 microns or less, for instance, channel widths approximately 100-150 microns and depths of 100-150 microns, with precision in features of 10-20 microns of tolerance. In many cases, macro-size features such as sample wells and reagent reservoirs are desired to be incorporated in the portable device, typically of several millimeters in dimension, i.e. several millimeters cross-wise and several millimeters deep.

To be of practical utility, it is necessary to find a way to provide the entire assembly reliably and inexpensively despite the optimum qualities of the materials for various features being different, and the need to join them in a reliable manner while retaining full functionality.

The invention is especially useful in microfluidic assay devices which have a pneumatic channel component, a fluidic channel component, and a flexible membrane joining the two. For this type of construction, as well as more generally, we have solved the foregoing problems, in particular with respect to the pneumatic component of such system, as follows.

We found an excellent starting material for forming the pneumatic channels comprises a double sided pressure sensitive adhesive sheet having a non-fluorescent central layer formed of rigid material, non-fluorescent adhesive on each side, and peelable liner layers protecting the adhesive and we found a process for forming the pneumatic channels and features by processing this sheet by using a CO2 laser, followed by very simple bonding process. The laser is used to ablate pneumatic micro-channels and other structures by cutting entirely through the core, the adhesive layers and the liners to form the sidewalls of the desired channels and other features. Thus a pneumatic channel has a side wall formed partly of the inner core layer of the adhesive sheet, and partly by the adhesive itself, at both sides of the core layer. This technique is found to form fine precise features having sizes on the order of 100 microns or less, with channel widths approximately 100-150 microns, and depths of 100-150 microns, with precision in features of 10-20 microns of tolerance.

The dual-sided pressure sensitive adhesive sheet with suitable low fluorescence is available commercially with size up to 27 inches, for instance. It is important that the material have very low tendency to fluoresce when exposed to an excitation laser such as green laser or red laser used to excite fluorescence in the conduct of epi-fluorescent reading of fluorescent-tagged analyte at the capture sites of an assay. Mylar™ (polyester), a material often used in the manufacturing of pressure sensitive adhesive sheets as a structural component upon which the adhesive is applied, has a high degree of auto-fluorescence which interferes with the process of taking a measurement in the cartridge, and is inappropriate for use with assay cartridges intended to be ready by an epi-fluorescence or other stimulated fluorescent emission process.

It has been found that a core layer of polypropylene is excellent for this purpose. A polypropylene layer of approximately 2 mils (50 micron) thickness with the adhesive on each side of 1.8 mils or 45 microns thickness is found to perform very well with silicone adhesive layers. A suitable product is sold by Adhesive Research under the product designation AR 90880 having layers of silicon based adhesive, known as SR26 silicon adhesive.

An example of a product formed by the techniques described is a portable consumable immunoassay cartridge (cassette) constructed of several layers, the pressure sensitive adhesive with channels formed by through-laser cutting being one of the layers integrated into the cartridge. That layer, with its peel strip removed, is attached to the bottom flat surface of a rigid reservoir layer that defines the macro features previously mentioned, i.e. sample wells and buffer and reagent reservoirs. Laminated to the bottom surface of the pneumatic channel layer by the second pressure sensitive adhesive sheet, with peel strip removes, is a membrane layer which is formed on a 100 micron thick PDMS membrane containing fluidic vias that are aligned with vias in the reservoir layer and the adhesive sheet layer. This assembly is bonded to the fluidic layer, elsewhere described, that bonding being effective to capture discrete detection elements that have been introduced to the micro-fluidic channels and connect the microfluidic channels of the cartridge, though the vias, to the sample wells and reservoirs elsewhere described.

The rigid reservoir cartridge layer is either a machined plastic body approximately 6 to 14 millimeters thick or an injected molded plastic body approximately 6 to 14 millimeters thick having reservoir macro-features located on its top surface, the features approximately 3 to 6 millimeters in dimensions, and with fluidic vias from the reservoirs penetrating through the bottom of the reservoir layer, aligned with vias laser-cut in the pressure sensitive adhesive layer. The adhesive sheet with laser-through-cut pneumatic channels, vias and other features is laminated to the bottom surface of the rigid reservoir layer in alignment with the vias in the reservoir layer so that the fluidic vias are arranged to transport sample and reagents from the reservoir layer to the fluidic layer through the vias in the reservoir layer through vias in the pressure sensitive pneumatic layer and vias in the following membrane layer. To then enter into the fluidic layer Also contained in the pneumatic layer are features associated with valves and pistons in addition to the fluidic vias. These features can be ovals approximately 800 um long and 500 um wide in the case of valves, or 3000 um long and 800 wide in the case of pistons with long channels connecting these features along the entire surface of the substrate and terminating at the pneumatic actuation ports located at the end of the device in a series of pneumatic vias.

One of the challenges in creating a highly functional disposable immunoassay cartridge is in constructing one that has a large number of features which therefore provides a high degree of functionality. For example, one which is capable of running multiple samples preferably 16 to 48 different samples and for each sample the ability to precisely quantify several analytes, 4-8, on one cartridge. Such requirements often drive the complexity and the need for a high density of fluidic features, including valves, vias and piston pumps.

For each sample there is on the cartridge an independent fluidic circuit having the ability to perform measurements of up to 8 unique analytes. The independent fluidic circuit is fluidically isolated from all other fluidic circuits on the cartridge and is used to perform the same measurements in parallel on different samples. The current design squeezes as many as 20-30 different fluidic features, such as valves, piston pumps and vias into an area of approximately 200 square millimeters (10×20 mm), as well as the pneumatic channels that connect the features.

A cartridge that measures 16 individual samples would have 16 independent fluidic circuits. However the functionality of each circuit is identical which means that every circuit is architecturally identical. So across the cartridge there would be 16 buffer inlet valves (one for each circuit) as well as 16 valve banks associated with each of the detect reagents, waste outlets and pistons. Since the circuits are identical copies it's possible to share pneumatic control lines across all circuits and use a small set of independently controlled pneumatic channels, limiting the complexity of the instrument that runs the cartridge. So for example, a cartridge with 16 samples running up to 8 different analytes, could for example have as few as 7 pneumatic channels where each of those pneumatic channels connects the same set of functional features located in each of the independent fluidic circuits. The functional sets would include banks of valves for example a bank of valves that allow the detect reagents to flow at a particular time or a bank of valves designed to close off and isolate a set of fluidic channels from one another in the manifold region of the fluidic circuit, or a bank of valves located at the output or a bank of pistons. Sets of functionality are connected to each other through a single contiguous pneumatic channel which terminates at one end at the pneumatic interface and the other end at the last feature in the string of connected features. Pneumatic channels in an effort to intersect with the sets of active features at every circuit are required to serpentine back and forth across a microfluidic cartridge, never overlapping one another, in an effort to cover all of the features located on the surface of the cartridge. Long continuous channels, as long as 10 to 20 inches in length. And also as a result of the high density of pneumatic channels located on the devices it is necessary to keep channels, pneumatic channels as tightly packed as possible in order to accommodate the high degree of functionality required to run such an assay. As a result of these long channels tightly packed and located on a cartridge, and having a serpentine like path nature it was discovered that laser cutting a PSA based film for the purposes of creating these pneumatic channels had the deleterious effect of being structurally unsound. During the manufacturing process or immediately following the laser cutting process it was discovered that the substrate with such formed channels was unable to structurally support itself and retain the required necessary dimensional tolerances.

As a result, features intended to have very tight physical tolerances for the purposes of forming the precision actuation of valve and pump piston were lost as a result of having this physical instability due to the formation of the long serpentine like channels back and forth across the substrate.

The solution to the problem involved interrupting the channel formation, so rather than forming long contiguous uninterrupted channels the channel were broken into segments approximately 20 to 30 millimeters in length, and depending on the nature of the channel path if it involved turning a corner for example or channels were closely packed to one another then the segment lengths could vary from 10 millimeters to 30 millimeters. These channel interruptions were formed by making the channel path with short, un-cut gaps approximately 150 microns in length, forming bridges between the channel segments approximately 150 micron. The result is a structure that is entirely self-supporting, which can be handled without the concern of losing the registration or the intended tight dimensional tolerances. The channels now having interruptions in them and not having the continuity of air flow from the pneumatic input to the final terminal structure at the end of the channel as a result of the bridges is made functional again by deploying shunts either directly underneath the bridges in the membrane layer or directly above the bridges in the reservoir layer, as shown in FIGS. 56I and 56J.

Figure 56I:
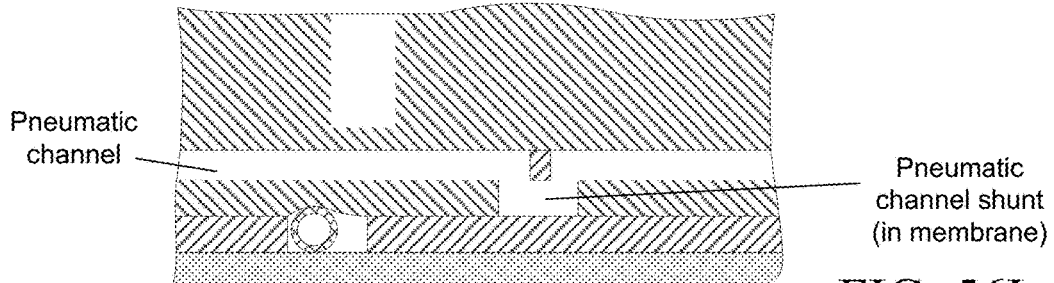
Figure 56J:
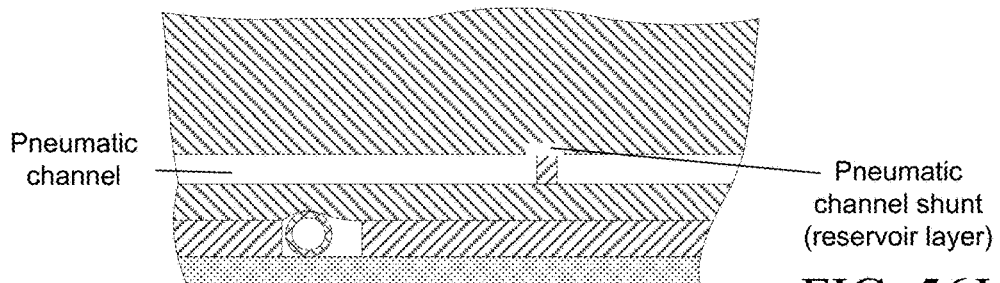

In the case of shunts being formed in the membrane layer shown in FIG. 56I a hole or a via is cut in the membrane similar to those used for the fluidic vias. In the case of the shunt being formed in the reservoir layer as shown in FIG. 56J a small pocket is machined into the bottom surface of the reservoir layer or it can be formed in the process of injection molding a piece of plastic involving the formation of the reservoir layer.

Once combined, the channel network of pneumatic channels and the shunts whose alignments overlap with the bridges form a contiguous pneumatic channel capable of actuating all of the features, such as pistons and valves, located throughout the area of the cartridge. Such channels have cross sectional dimensions of approximately 150 microns by 150 microns.

The benefits of the approach include lower cost of manufacturing and higher precision in feature locations. Because the raw material for the pressure sensitive adhesive is relatively inexpensive per cartridge (<$1/cartridge) and because the relatively high speed of manufacturing these channels also results in a relatively low cost yet high precision structure necessary to implement the precision actuated pistons and valves in a pneumatically actuated microfluidic device.

The overall cost impact as compared to injection molding or machining or other methods used for forming similarly such pneumatic channels is significant.

Although one could injection mold such a piece, there are high costs and long development times associated with developing an injection molding process as the inflexibility of an injection molding process to adapt to changing design concepts. It is anticipated that a number of variations or configurations of cartridges will be supplied resulting in the need for some flexibility in the formation of the pneumatic circuits, and with injection molding each component requires a unique mold. Whereas with respect to using the present invention, the same equipment, the laser set up can be used with a different program to execute drawings that have been made.

One of the other important benefits is, the implementation of the membrane layer, which is an integral part of the fluidic cartridge as it is responsible for a number of functions. Its responsible for closing off the channels and making them closed fluidic channels, for containing elements placed into such channels for the flexibility associated with forming microvalves and pistons. A PDMS membrane is necessary as an integral part of the microfluidic cartridge and needs to be permanently adhered to the pneumatic channel surface whatever that pneumatic channel surface is formed in. In the case of an injection molded plastic, the bonding process between the PDMS membrane and the PDMS is difficult and costly as it involves multiple steps typically, and also is limited to a small subset of plastics such as polystyrene, polycellphone, COC and COP. Some of those plastics are unsuitable for the formation of a reservoir layer that is formed in a thick such as 6-12 millimeter thick having both macro features on one side and micro features on the other side. In the case of COC and COP, the cost of such plastics makes the formation of a device such as that prohibitively expensive. Which then relegates one to a very few number of available plastics such as polystyrene.

Although some plastics such as polystyrene make good candidates for such a process, most others, such as polycarbonate and PMMA are not good candidates. So developing a cartridge around a more flexible machine process then transferring it to injection molding would be difficult because the material choices aren't well suited for both processes.

Typically one starts with a machining process to wring out the design and then transfers it to injection molding once the design has been stabilized and locked down essentially. Which is really a direct consequence of the high nonrecurring expenses associated with injection molding.

But you're bringing working towards the fact that the material for instance with pressure adhesive on both sides can be easily bonded to any Exactly, that is sort of the point, is that the pressure sensitive adhesive because it is naturally adherent or naturally adheres to nearly any clean smooth surface, the available range of plastics and processing processes are opened up widely. One can then employ polycarbonate or polystyrene or any number of plastics without regard to the bondability of the PDMS membrane to that surface of plastic.

And just as an aside, if you were to make the pneumatic layer as a part of injection molded or machined part, what is done to make it bondable to a PDMS membrane?

Well, there's a process that involves plasma activating the surface of that plastic surface and then exposing it to an intermediate bondable layer such as a silane or an organosilane type component which readily adheres to both the plastic surface and the PDMS membrane surface.

The examples of FIGS. 43A, 43B, 44A, and 45A illustrate PDMS bonding to PDMS. For a region R1 in which bonding of the bondable surfaces is not desired, FIG. 44B shows deflection of the two PDMS layers in opposite directions by elastic deformation, and dashed lines indicate the layers in region R1 relaxed, un-deflected. Adjacent regions R2 of the layers are retained in contact, either solely by initial surface-to-surface bonding, or with the added benefit of outside confinement or compression, indicated by arrows P. Thus the Figure illustrates the two conditions achieved cyclically during exercise of the make and break protocol previously described, enabling bonding at contiguous regions, but bond prevention in a selected region of the potentially bondable surfaces.

For instance, for ease of tooling and product design, instead of employing physical engagement and mechanical movement to produce the make and break conditions at region R1, it is frequently desirable that the make and break contacts be caused by application of fluid pressure differential evenly across the region R1 of each layer. (The term "fluid" is here employed in its generic sense, to cover all "fluids", i.e. liquids or gases). Use of fluid pressure assures even loading and prevention of disrupting distortion of a layer during the cyclical make and break protocol. To achieve the deflected condition, a deflection cavity at the backside of region R1 provides space for the deflection. The adjacent regions R2 of the layers are retained in contact, either solely by surface-to surface bonding, or with the added benefit of confinement or compression.

For reasons of convenience and economics in many situations, it is found desirable to employ differential gas pressure to produce the deflections. For instance, thus can be avoided the need for design of special mechanical moving devices or the need for drying associated with the use of liquid pressure. The gas pressure differential can be achieved by application of positive gas pressure to the interstitial space, as by a special channel, with the benefit of being able to use high values of pressure to speed the operation or for use where bonds are formed rapidly or are of high strength.

In many cases however, it is found desirable that gas pressure differential be produced by application of vacuum to the outside of a layer to produce its deflection. One advantage is that the manufacturer can employ channels and cavities of the device itself, such as those associated with pneumatic operation of the device during its normal use. By this the manufacturer can reduce the need for special, costly tooling and extra manufacturing steps. An example is the manufacture of microfluidic cartridge device described herein.

Referring to FIG. 44B, in the case of applying vacuum on the backside (outside surface) of a PDMS layer to produce gas pressure differential, the cavity is a closed vacuum chamber engaged upon the backside of the PDMS layer. FIG. 44B illustrates such a deflection chamber on each side of the pair of contacting membranes surfaces. The vacuum-actuated deflected state of region R1 is shown in solid lines while the dotted lines illustrate the natural relaxed and undeflected state when there is no vacuum is applied to the vacuum chambers. Preferably, indeed, positive pressure is applied to both chambers, having the effect of enhancing the momentary contact, and therefore lessening the time needed before another break phase of the cyclical is performed, thus speeding the neutralization of the layers in regions R1.

FIG. 45B illustrates a deflection chamber on only one side of the assembly, deflecting a single membrane. The opposing membrane is shown rigidly backed against a planar surface to which it may previously have been adhered, to ensure that it remain stations when region R1 pulls away.

Figure 43A:
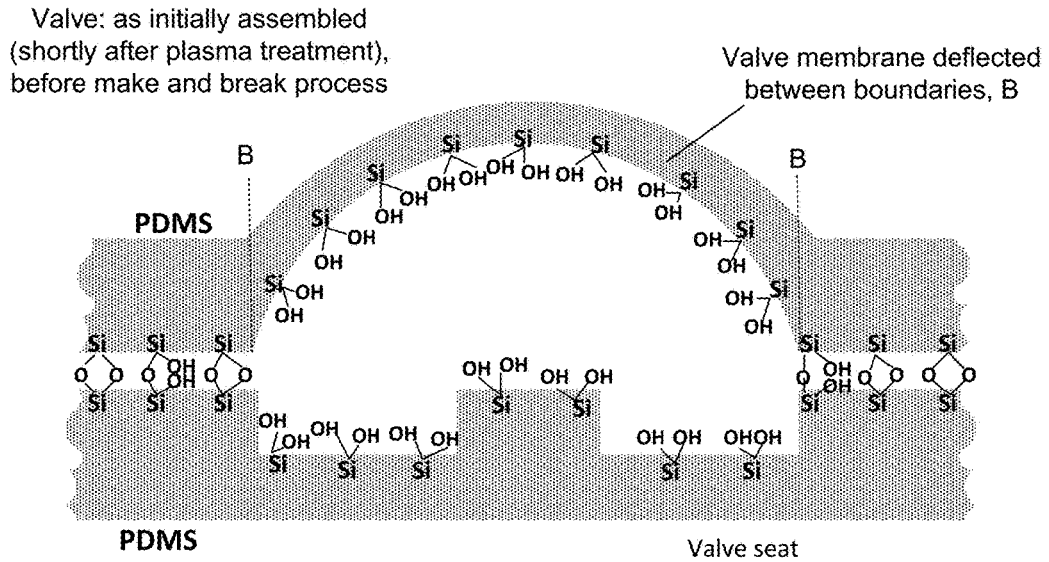
FIG. 43A, similar to parts of FIG. 41, illustrates, in diagrammatic cross-section, a valve as initially assembled, comprising two opposed layers of plasma-treated PDMS with a valve membrane portion of one layer deflected, the opposed PDMS sheet forming an opposed valve seat.
Figure 43B:
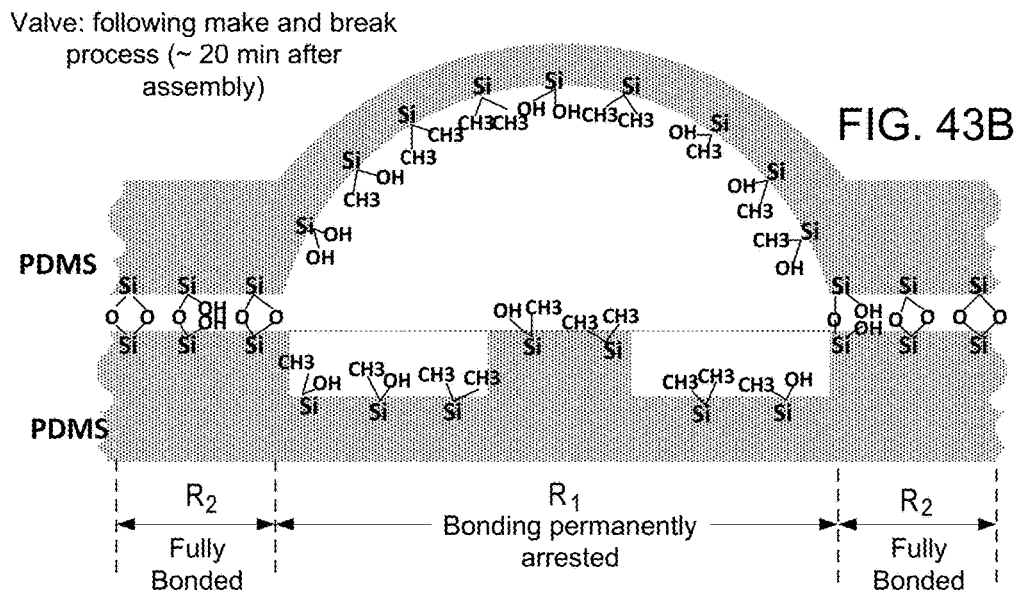
FIG. 43B is similar to FIG. 43A following make and break process after assembly.
Figure 43C:
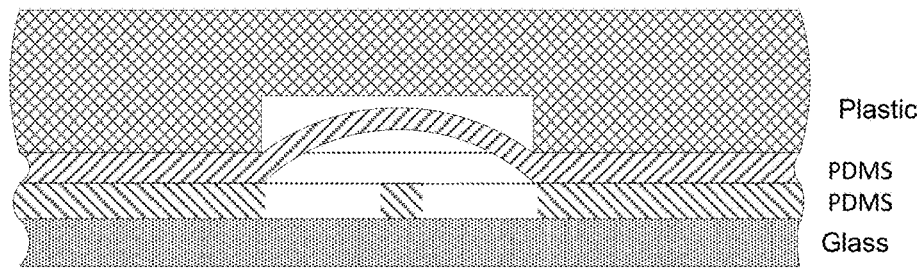

FIG. 43C illustrates a single deflection chamber and an opposing valve seat on planar surface in construction similar otherwise to that of FIG. 45B.

In all the cases of FIGS. 44B, 45B, and 43C, the deflection chamber may be formed by manufacturing tooling constructed only for that purpose and then removed. In other cases as has been shown in the examples of the microfluidic assay cartridge shown in this application, the deflection chamber is in fact part of the final microfluidic product, with numerous obvious advantages with respect to tooling cost and economy of manufacturing steps.

Figure 56K:
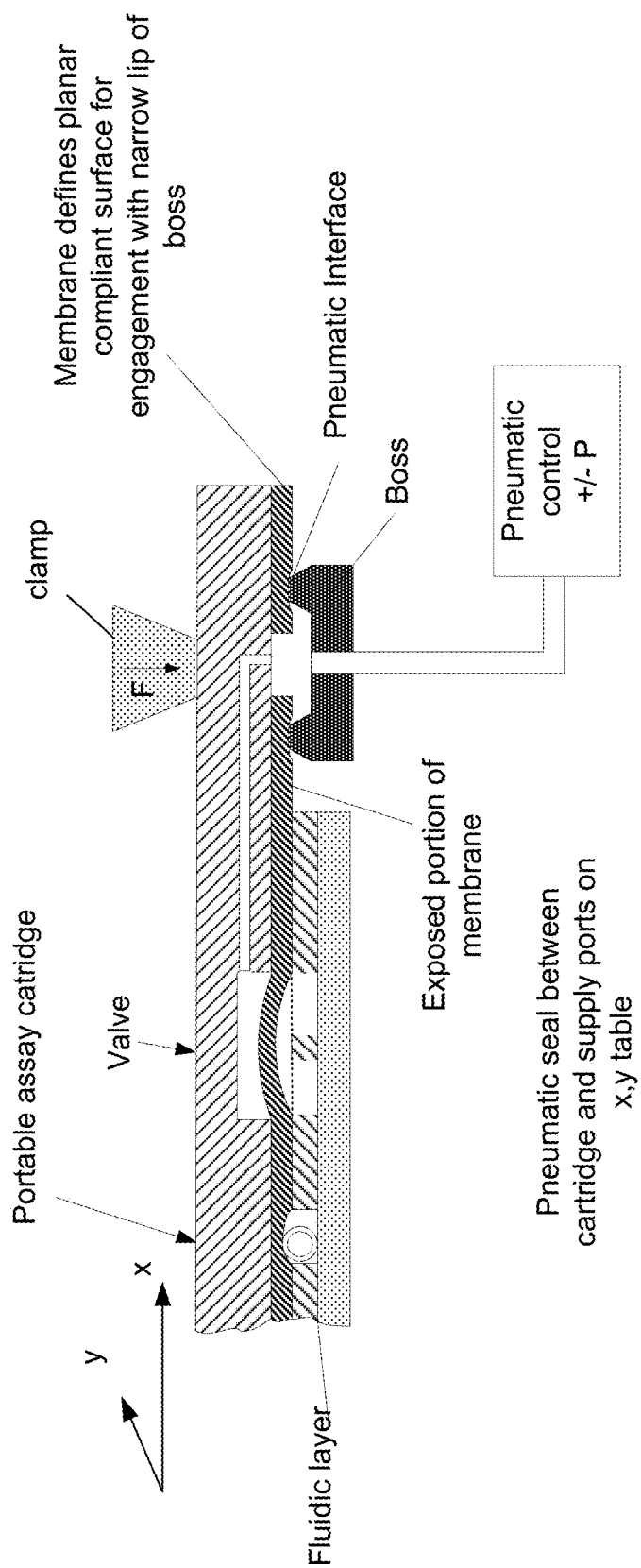

FIG. 56K diagrammatically illustrates a microfluidic cartridge having a complex microfluidic (liquid) channel network, a large number of microfluidic valves formed by the make and break protocol, and other pneumatically controlled features that are all actuated simultaneously with the valves.

There are many obvious technological advantages and beneficial effects of perform this make and break operation simultaneously on many different valves, or on many other features, such as those described below, or on combinations of many valves and many other features. For instance, from a manufacturing point of view there can be great ease with which a complicated structure can be made by applying only a simple pneumatic force in the form of a vacuum or pressure and actuating all of features at once. This of course includes the benefits of low cost and low complexity of the manufacturing process.

As has been indicated, there are numerous advantages to using cycles of pneumatic vacuum and positive pressure applied on the exterior or the nonbonding side of the flexible sheet. While such vacuum deflection of the make and break protocol in manufacture of portable microfluidic assay cartridges has great advantages, more broadly viewed the essence of the activating fluid aspects of the invention has to do with deflection of a region of a membrane layer by application of differential fluid pressure across the layer no matter what medium is employed or on which side the greater pressure is applied. In particular, there are important circumstances in which advantage is obtained in creating differential gas pressure across the layer by pneumatic forces applied between the sheet-form layers, i.e. applying positive pressure to cause the deflection of one or both layers and negative pressure between the sheet-form layers to cause collapse and contact.

One of the advantages of employing positive pressure relates to the fact that in employing vacuum to deflect the membrane, the maximum pressure that can be applied is 1 atmosphere, approximately −14 psi, which limits the deflection forces applied to a membrane whereas a positive pressure applied between the sheets is nearly unlimited in magnitude to cause separation to occur between the sheets.

In respect of applying positive pressure to produce the outward membrane deflection, two alternatives for the deflection cavity will be described, that of a deflection slot defined by walls that engage the outer surface of the layer, but that is open and un-limiting with respect to the deflection distance for the layer, and that of a chamber that also has the walls, but is closed with a ceiling. The walls of an open or closed cavity for pressurized deflection define the physical perimeter of the area of the deflection, thus defining regions R1 and R2, and hence the area over which the make or break process occurs. In the case of use of a simple open slot, the limit of deflection is a function of the elastic properties of the membrane and the pressure applied, and may be most useful in the use of moderate positive pressures, or where there is ample margin for error regarding the strength of the membrane. The use chamber which, in addition, has a ceiling creates an additional physical limit for outward deflection, which can potentially protect the membrane from deleterious effects of tearing or bursting the membrane, useful e.g. where particularly thin membranes or particularly high outward forces are to be employed.

Figure 46B:

In the discussion so far, the flexible, deflectable sheet has been monolithic, and in the examples of FIGS. 43A, 43B, 43C, 44A, 44B, 45A, 45B and 56K, it has been PDMS. A composite sheet may be used instead, comprised of multiple layers, the basic requirements being that the overall sheet is flexible to be capable of elastic deflection, and that the inner surface be bondable. While not necessary according to broad aspects of the invention, it is advantageous that the bondable surface of the composite still be surface-activated PDMS, either pre-formed as a separate sheet or as a coating on a carrier sheet which itself may be monolithic or a composite. In the example of FIG. 46A the composite comprises a bondable pre-formed layer joined to a layer of another substance. For instance the bondable layer may be surface-activated PDMS and the back layer of a pre-formed layer of a material other than PDMS, for example a sheet of PDMS laminated to a second pre-formed flexible sheet of a compatible substance, or one that can be rendered compatible by use of a treatment, such as flame or plasma treatment or by use of an intervening layer that can be bonded to both. For instance the second layer may be a pre-formed sheet of Mylar™ (PET), Polycarbonate or Polyurethane produced as blown or cast film sheet, as appropriate for the resin and the circumstances. FIG. 46B illustrates a flexible pre-formed back sheet coated with a thin coating of PDMS material typically ranging from approximately one to three microns in thickness, having its surface activated in preparation for a bonding process. The back layer for instance may be Mylar™ (PET) of thickness approximately 5 to 15 microns.

In still another implementation, not shown, an essentially monolithic layer of PDMS may carry an exterior coating of another substance, for purposes such as improving the gas-barrier properties of the composite.

FIG. 46C illustrates a laminate structure similar to that of FIG. 46B, but with a flexibility-increasing feature. It is useful for the condition in which a flexible outer sheet bonded to PDMS sheet (or it could be a flexible sheet having a PDMS surface coating) wherein the flexible sheet is less flexible than PDMS and it is desired that the composite exhibit increased flexibility, e.g. to increase the deflection capability and thus the flow capacity of a valve or pump formed by the deflectable membrane. The principle being illustrated is use of an interruption or reduction in thickness of the back layer. The interruption can be a single moat in the back layer, extending around the perimeter of the defined area R1, or, as shown, a series of concentric moats that allow a greater displacement to be generated as a result of allowing the flexibility of the PDMS to perform the majority of the stretching during an activation of either a vacuum deployed or pressure deployed activation protocol.

By way of summarizing certain technological advantages and beneficial effects of features regarding materials selection for the flexible membrane:

PDMS has the advantages of being a low cost material that is easily bonded, flexible and easily machined or otherwise easily formed into channels surfaces to cooperate with the deflectable membrane features described. In the specific case of laminated structures, including that of FIG. 46C is the ability of a material other than PDMS to block air passage or reduce the overall gas permeability coefficient of the structure. Whereas PDMS is known to have a high degree of gas permeability other plastic material such as polyester, polycarbonate and polyethylene exhibit extremely low permeability relative to PDMS. This can be of great benefit in microfluidic type devices in which positive gas pressures are used for actuating valves, preventing gas permeation through the membrane into the fluidic channels thereby creating bubbles that can have a deleterious effect. For instance, under many assay flow conditions, air bubbles that enter the reagent stream can attach to the capture agent and prevent binding; air bubbles can prevent complete wetting of surfaces, and thus inhibit the capture agent from capturing an antigen of interest; and air bubbles can also displace fluid in the microfluidic channels causing the microfluidic system to become less stiff from a fluidic point of view and also increasing the variability of flow rate, producing uncertainty of flow rat that can impair quantification assays.

With specific reference to the technological advantages and beneficial effects of the last Figure, FIG. 46C. It employs a series of narrowly defined moats or channels that are cut into the more rigid yet somewhat flexible air-impermeable backing sheet part of the flexible sheet/PDMS laminate. The moats allow the stiffer component, e.g. Mylar™ (polyester) or polyethylene to deflect using the underlying flexible PDMS to act as an expansible spring, therefore achieving greater deflection. Thus, decreased permeability of the relatively stiff backing layer, to decrease air permeability within a microfluidic valve can be obtained, while achieving enhanced membrane deflection away from a valve seat to allow adequate or improved flow across the cooperating valve seat when the membrane is deflected to open position. This is a novel feature in its own right, as such benefits can be obtained even when different approach is employed to join materials of the device.

Referring again to FIG. 45B, the single deflectable membrane implementation, a fixed bondable surface opposite to a flexible membrane PDMS bondable face is not limited to the same material, and there are circumstances in which advantages are obtained by using a different bondable surface. Referring to FIG. 47A, the deflectable membrane has a PDMS bondable surface, but the opposite bondable surface is provided by a rigid silicon based material including crystalline or amorphous silicon, amorphous silica, silicates and ceramics. Benefits of different thermal conductivity, electrical conductivity, or the ability to add electrical contacts, as in the case of silicon or having the beneficial properties of silica in the form of optical clarity low autofluorescence optical smoothness or the special hardness properties and insulating properties of ceramics can be of advantage.

FIG. 47B illustrates the accommodation of a flexible membrane with a surface-activated PDMS bondable surface to a synthetic resin or metal based device employing an intermediate bifunctional layer. For example surfaces of well-known plastics including COC (cyclical olefin polymer), COP (cyclical olefin copolymer), polycarbonate, polysulfone, polystyrene can be surface-activated or metals such as aluminum or iron that either readily form oxide layers can be employed. Such surfaces can be modified with an intermediate bifunctional layer such as an organol, to create an oxide layer.

Figure 57:
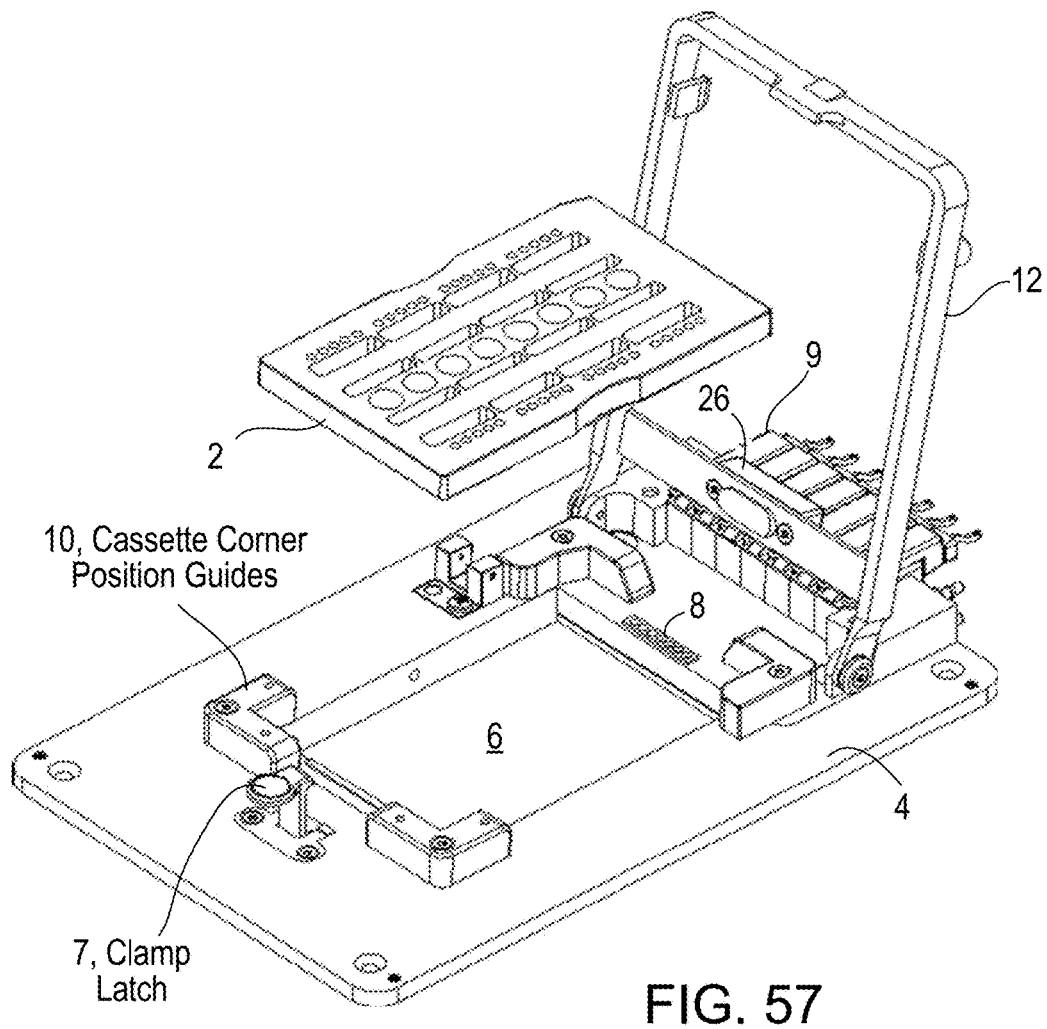
FIGS. 57 and 57A illustrate, respectively, two positions of a microfluidic cartridge relative to a carrier plate upon which it is intended that the cassette be fixed while the plate is moved on a precision X, Y stage relative to a fixed, finely focused optical detection system.
Figure 57A:
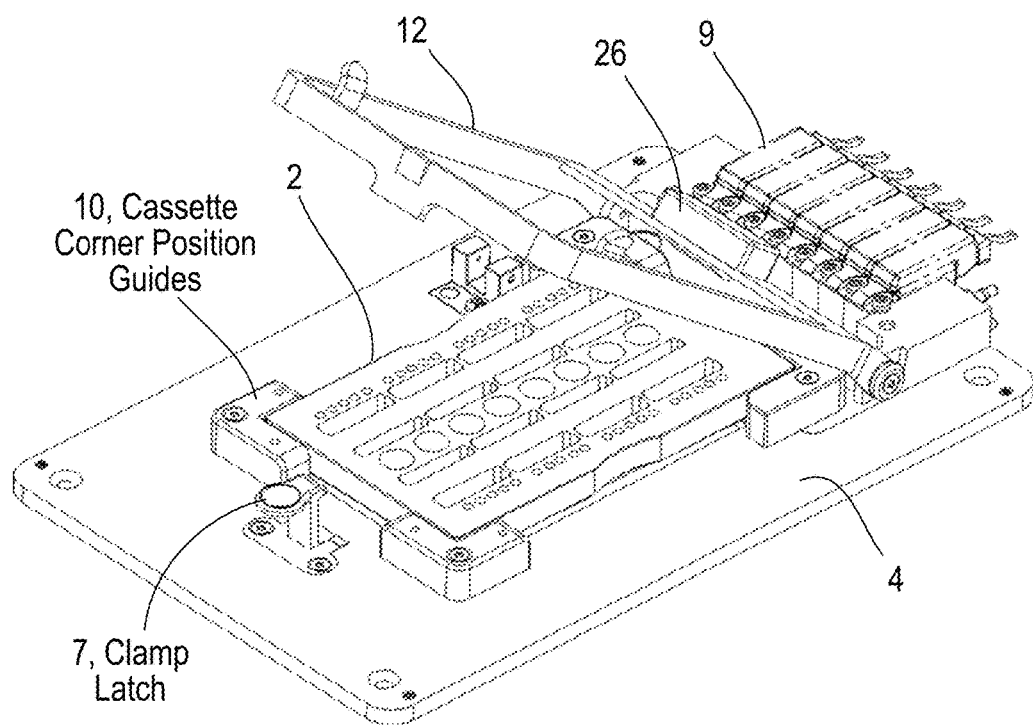
Figure 57B:
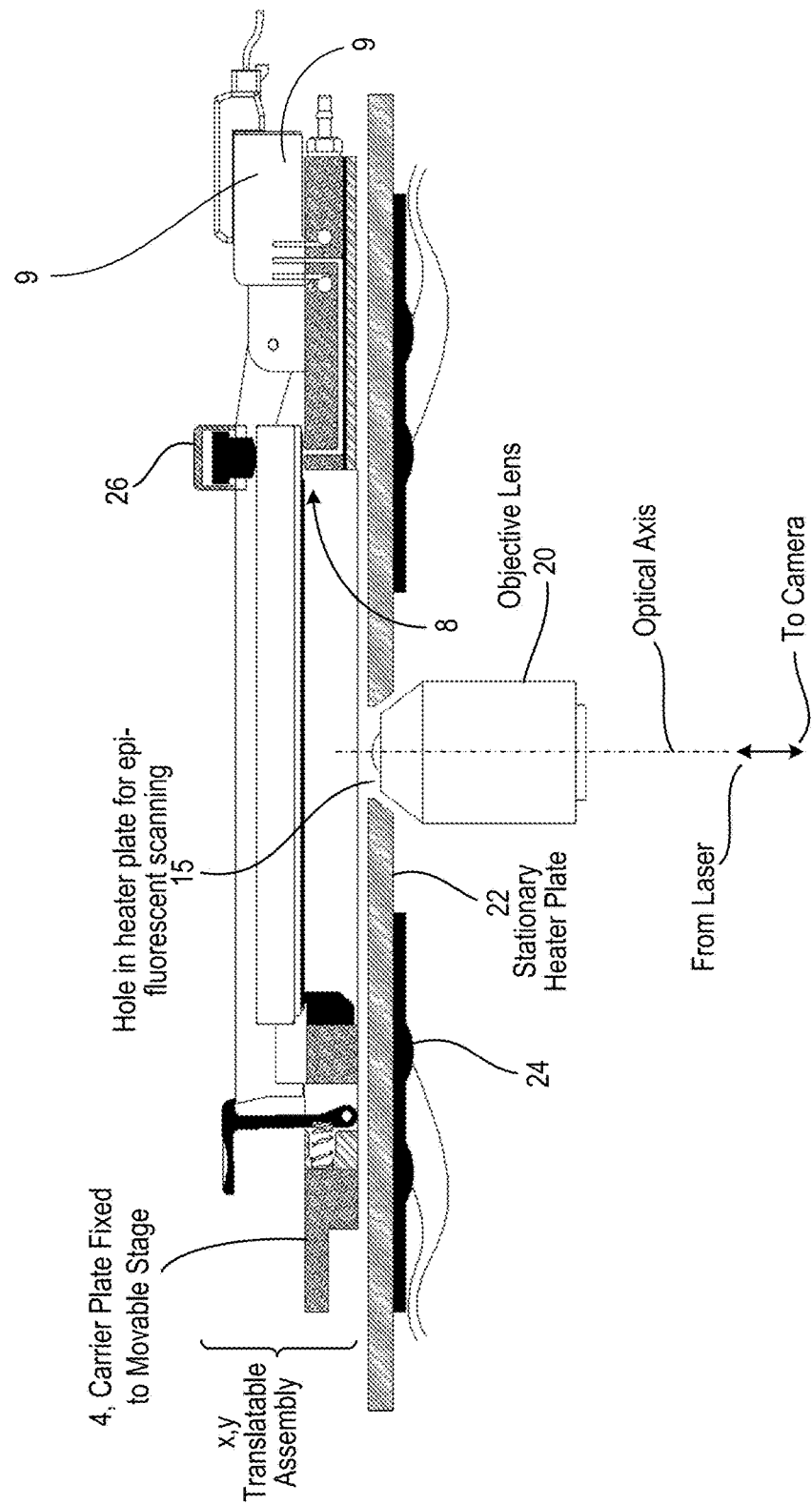
FIG. 57B is a cross-section view of the cartridge of FIGS. 57 and 57A now fixed to the carrier plate on the movable stage, to move over a fixed heater plate and optical detection system, the objective of which is exposed to the cartridge through a hole in the heater plate.

In a preferred implementation, a portable microfluidic cartridge 2 is placed into an operating and scanning instrument by the user. It enters in a receptacle or reception area 6 at which the cartridge is retained for conducting the assay while scanning A suitable receptacle is shown in FIGS. 57 and 57A, and the relationship of the receptacle and cassette when in assay/reading position is shown in FIG. 57B and the detail of FIG. 57C. An implementation of the overall system is shown in exploded view, FIG. 58. FIG. 58 includes x, y precisely movable stage 13 that moves the cartridge on its carrier relative to the stationary objective lens.

Referring to FIGS. 57 and 57A, cartridge 2 and the cartridge receptacle 6 are shown with a clamping mechanism 12 and pneumatic interface 8. A series of computer-operated solenoid valves 9 that move on the stage with the cassette apply positive and negative air pressure to ports that interface with the positioned cassette.

Figure 59:
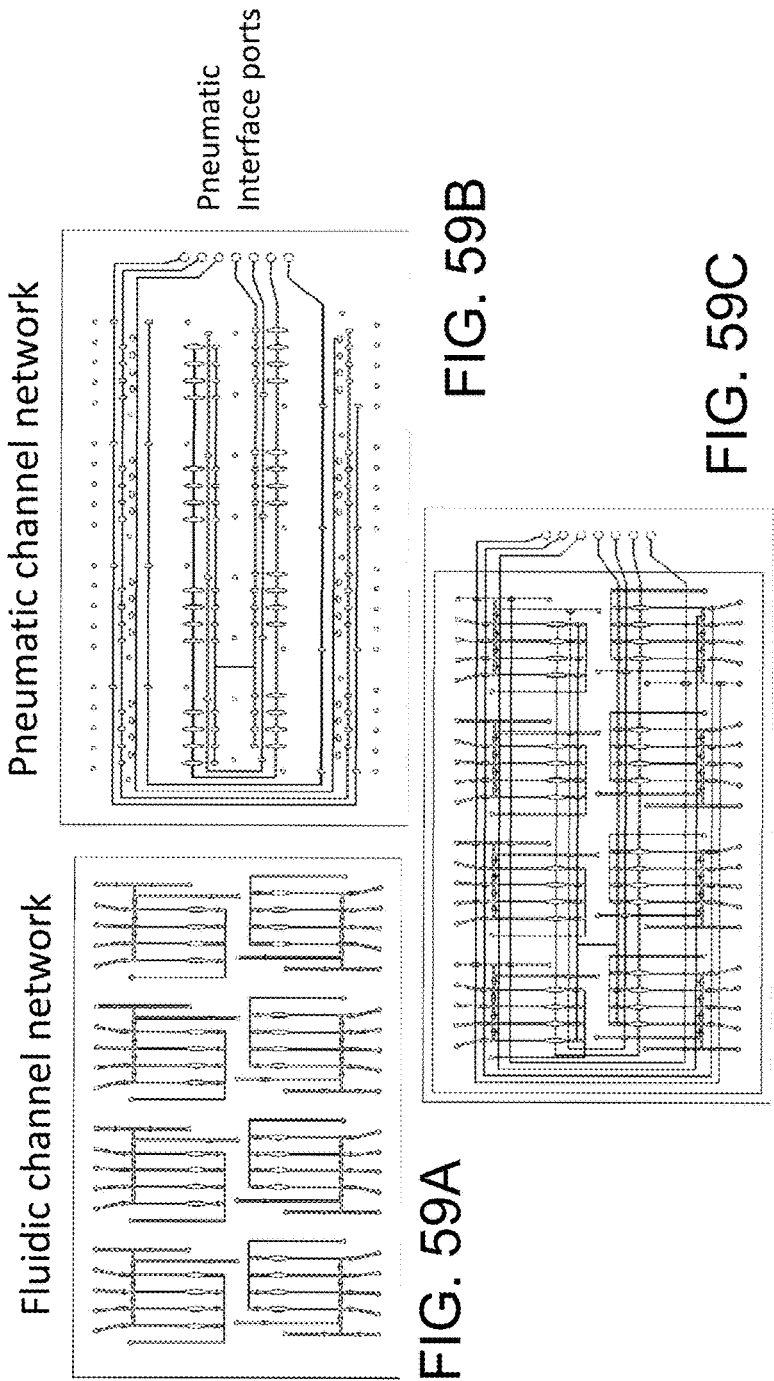
FIGS. 59A, 59B and 59C are plan views of the microfluidic and pneumatic channel architecture of the cartridge of FIGS. 57 and 57A.

FIG. 59C illustrates a microfluidic configuration within a cartridge, illustrating both a series of fluidic networks and a pneumatic channel network to actuate on-board membrane micro-valves and micro-pistons in the fluidic network. The fluidic network in FIG. 59A comprises eight discrete microfluidic circuits closed by an over-lying elastic membrane, e.g., a continuous layer of PDMS. Each of those circuits has a number of microfluidic channels, valve locations, and piston locations. Portions of this membrane are located at formations in the channel that define valve and pump cavities. The corresponding portions of the membrane define movable elements of the valves and the piston.

The pneumatic channel network FIG. 59B is shown as an overlay in FIG. 59C. It matches the fluidic network with respect to the various features that need to be actuated.

FIG. 60 is a magnified view of one of the circuits of FIG. 59C, illustrating a number of the micro-features including valves, pistons, and the various reagent or reservoir inputs including the sample, the buffer (wash), the assay reading dyes, the secondary antibodies and the waste. The four elements GNR shown in black in each of the four individual (isolatable) channels represent glass nano-reactors (GNRs) embedded in those channels. This illustrates the basic micro fluidic unit replicated a number of times in the cartridge depending on the number of samples that the cartridge is designed to accommodate. The assay protocol flow sequence shown at the left of FIG. 60 starts with the prime flow step, and is followed by sample step, wash step, secondary antibody step, another wash step, a dye step for reacting to attach reading dye to the captured moiety, and finally another wash step. This illustrates an example assay sequence capable of being performed in this microfluidic structure. Each one of the fluids: sample, secondary (e.g., secondary antibody), wash, and reactive dye is caused to flow from its respective inlet well by activation of the pumps formed by each piston and upstream and downstream valves, with the end result of captured moieties at the detection elements that are labeled with the reactive dye, ready for reading to quantify the result of the assay. Examples of volumes employed on this device include the sample at 20 microliters, a buffer of 150 microliters (as shown in the table)—the total volume of the microfluidic circuit is approximately 1.8 microliters.

Figure 98:
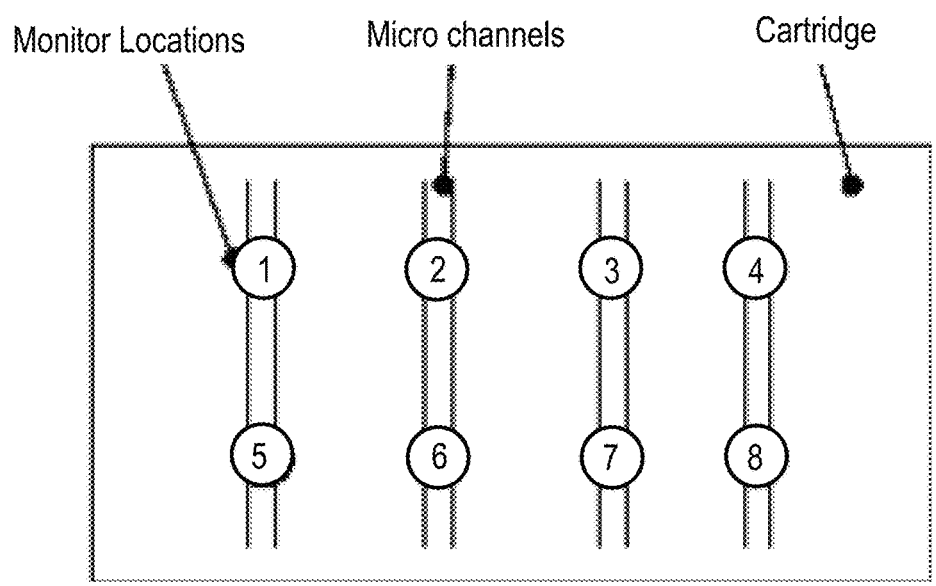
FIG. 98 depiction of a microfluidic system having microfluidic channels and monitor locations.
Figure 98A:
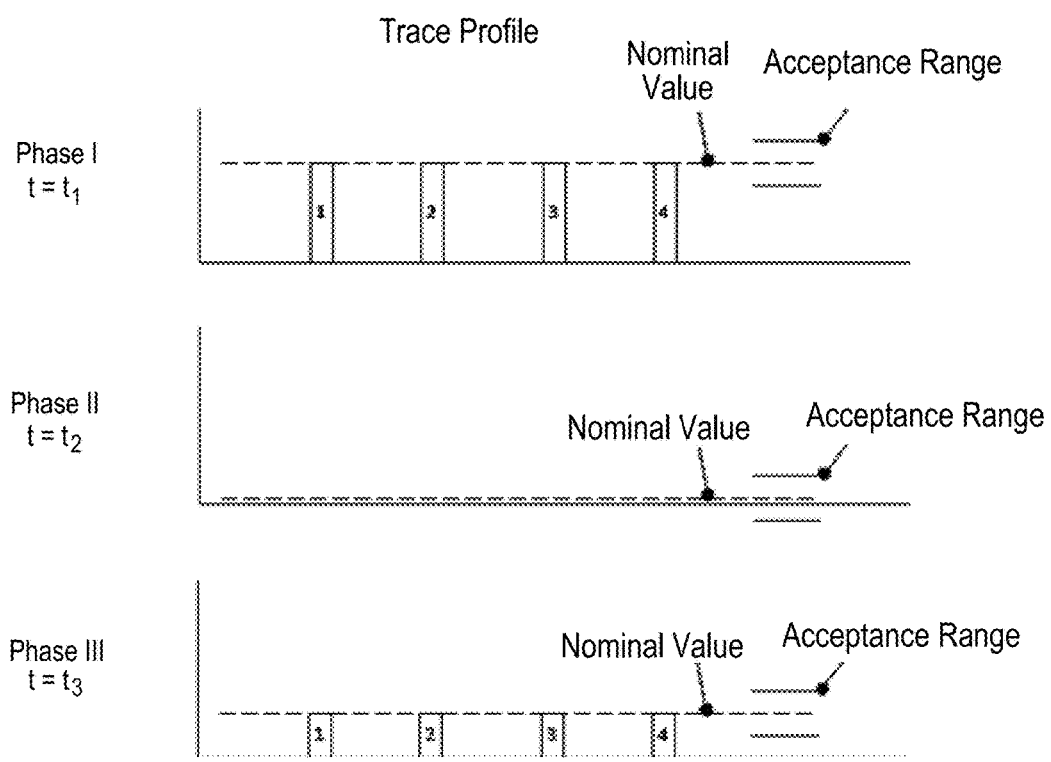
FIG. 98A depiction of signals obtained in three phases at a set of monitoring positions under three different conditions, illustrating a properly running assay.

In FIG. 98, four micro channels on a portable microfluidic cartridge are illustrated, each having two monitor positions. The further discussion relates to the first set of monitor positions 1, 2, 3, 4 in respective channels. In FIG. 98A, three different operations of an illustrative assay with discrete phases are represented by times t1, t2, and t3. In phase 1 at time t1 at four different locations on a cartridge to sample four channels, the tracer signal is detected to be at the expected nominal value within the acceptance rate. It is therefore considered a successful phase 1 disposition. Phase 2, at time t2 the nominal level is near zero, which might indicate that a buffer or some fluid that intentionally had no tracer was properly flowing in the channels at that particular phase. In phase 3, at time t3 third reagent or fluid in the channel has a tracer level that is different from that of phase one but is detected to occur at its nominal value within its acceptable and expected range. So the entire operation considering phases 1, 2, and 3 would be considered successful. This represents proper operation with no failures.

Figure 98C:
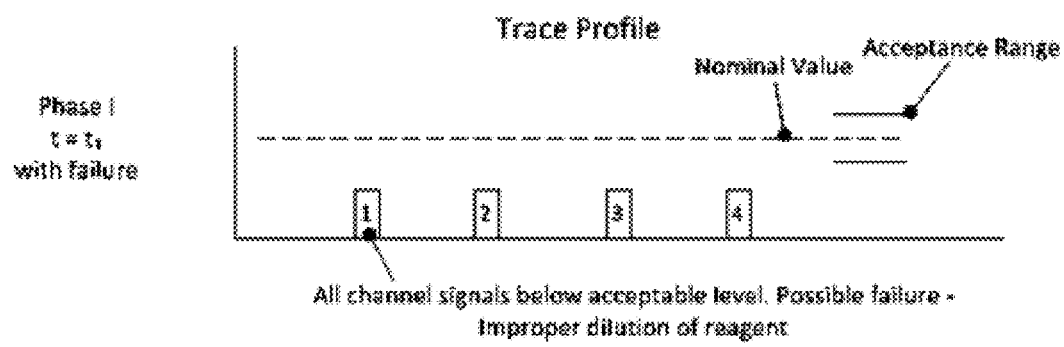
FIGS. 98B and 98C, similar to FIG. 98A, depictions of signals obtained during improperly running assays.
Figure 98B:
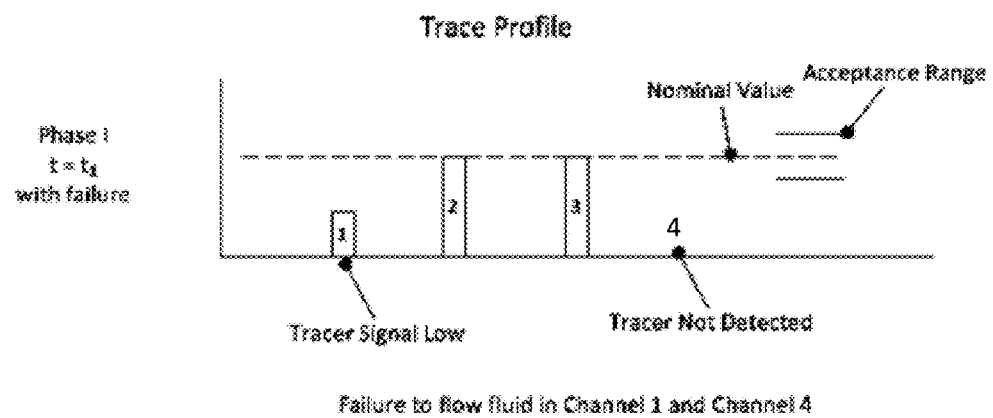

FIG. 98B illustrates another run of the same assay. In phase 1, time t1, a failure has occurred wherein the detected tracer signal occurs outside (here, below) the acceptance range. In channel 1, the tracer signal is shown present, but lower than the acceptance range, whereas in channel 4 the detected tracer value is shown as not present. In FIG. 98C at time t1 of the assay run, all four channels are shown as having a detectable tracer signal below acceptable range. But note that all four signals are equal and uniform. This indicates that there is not an independent failure mode within that cartridge but probably indicates that an improper dilution had been used to create the reagent that was used.

There are other failure modes such as the improper interface of the pneumatic seat which could lead to valves not opening fully or not closing fully or pistons not operating in full extension or lift so that their fluid volumes might not be what was anticipated. A hierarchy of signal modes can be constructed, e.g., in the simplest case a signal versus no signal, a simple digital response, and in other cases where the quantitative value of the signal does not meet expectations.

In digital response, there is no quantification. The signal is either present or not. A further level of complexity involves quantifying the level and comparing that quantity to an acceptable level where there is range of acceptable levels (acceptance range) not just on or off. That quantification technique might be used to determine whether a proper dilution or proper concentration or proper reagent was used in the proper location. Another advantageous level of sophistication is in monitoring and analyzing the signal structure over time, to obtain the temporal response of the signal relative to an expected temporal response. That requires a more detailed explanation.

Figure 99:
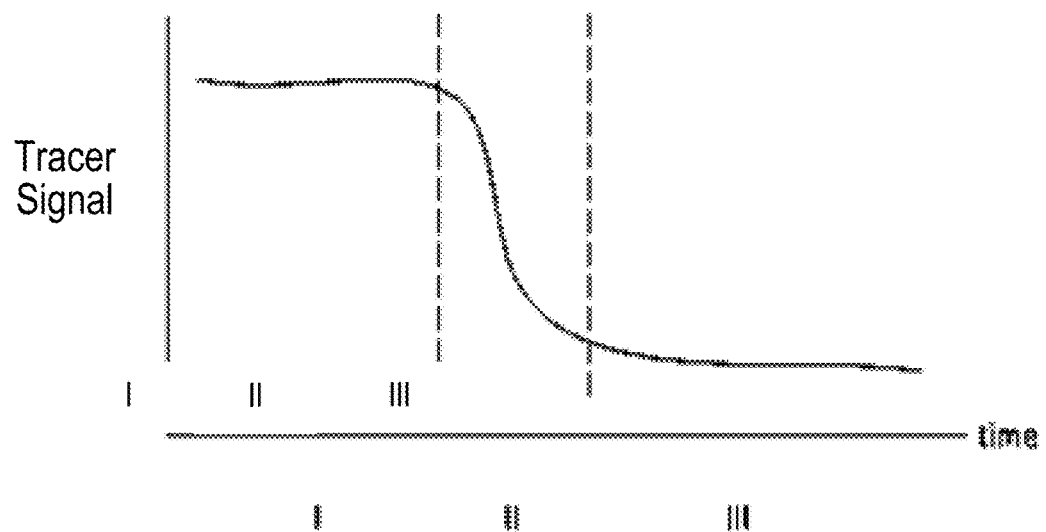
FIG. 99 diagrammatically illustrates tracer signal during monitoring a microfluidic channel at a single location, over a brief period of time over which flow changes; time response at location 1: I. Piston actuation (oscillating flow) @ full tracer concentration (no net flow); II. Pumping fluid with no tracer (in one direction, toward waste) to displace tracer-laced fluid in channel; III. Oscillating flow, no tracer.

Referring to FIG. 99, the evolution of a detected tracer signal is shown while monitoring over time a fixed location in a microfluidic channel, for example a channel approximately 100 microns wide by 100 microns deep in a length section of approximately 20-50 microns long. Thus a very specific isolated location within the channel is monitored over three different phases. The first phase shown depicts the condition of no flow occurring within the channel but the channel has present in it a reagent laced with a tracer of a certain concentration that provides a detected signal of any type, e.g., detected fluorescence. Phase 2 in FIG. 99 follows the evolution of the signal, showing that it decreases over time as the reagent with the tracer is displaced by a reagent without a tracer, for example a buffer reagent or wash liquid that has no tracer in it.

The signal evolution decays very rapidly in phase 2 as the new reagent displaces the old reagent with tracer, and the signal goes down. Then in phase 3 of FIG. 99 the displacement process stops and the signal is monitored with no net flow during phase 3. This represents successful washing of a channel.

The benefit of thus staring at one location is not only to watch the real time evolution of what is occurring at the location but also in the case of using a fluorescent dye that is photo bleachable, to look at the fine structure not shown in this trace but shown in subsequent traces that reflect details of exactly what is occurring in the microfluidic device.

Another benefit of staring at a specific location is to acquire information in the development of an optimized protocol. In the development phase for an ELISA or any other assay that involves multiple sequences of reagents and flushing followed by new reagents, it is important to know whether the displacement of the prior reagent is complete and how many cycles or how long or what type of flow rate for example is required to ensure that the next phase of the assay process is firmly established. What is called "open protocol" refers to assays that are not monitored. For such assays, it is vitally important to characterize the microfluidic system beforehand. The technique being described may be used as a tool to be used during test runs of an assay, to characterize the system and optimize the protocol. So for example if insufficient flushing or wash steps were applied, then residual reagent would be present at a phase that could be harmful to the performance of the assay. The presence of such errant reagent may be detected by presence of its respective tracer. This therefore is an advantageous technique for evaluating performance and optimizing an assay protocol.

One implementation is to provide a cassette in development on an x, y movable table. The table is indexed to any selected position relative to the detection systems, e.g., optical system, and the assay can be run while detecting signal from that position. A commercial instrument constructed to run and read an assay has substantially all of the functionality required to generate development data that is fed back into developing an optimized protocol.

Figure 100:
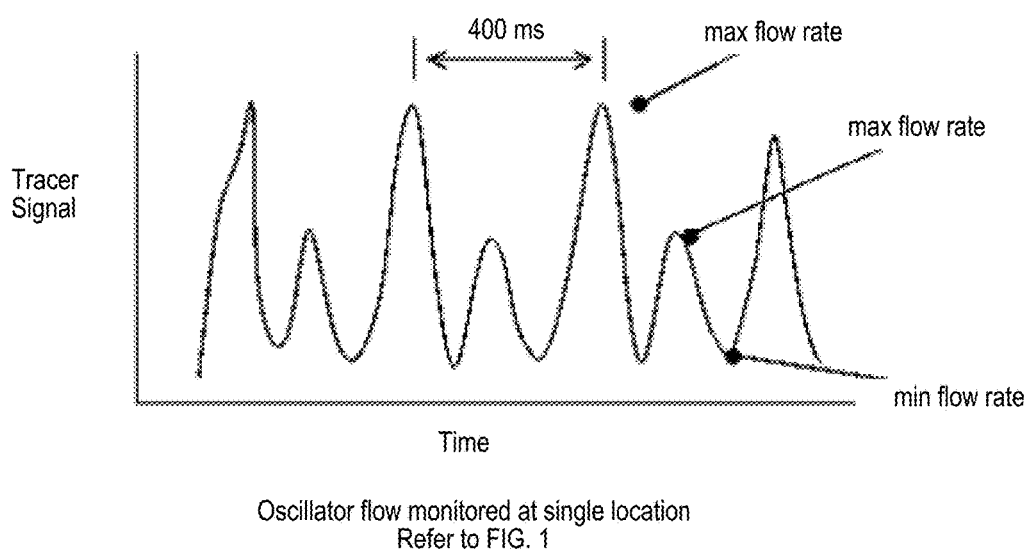
FIG. 100 is similar to FIG. 99, but diagrammatically illustrates monitoring a fluid to detect operation of a pump over many cycles of producing oscillating flow.

FIG. 100 illustrates the time response of a tracer signal while staring at a single location in a microfluidic device, referring back to FIG. 99, location 2, for example. The tracer dye present in the liquid in the channel is selected to be photo bleachable progressively over time. In an example, a red laser diode is employed to excite red-excitable fluorescent tracer material. When the fluid is stationary, a photo bleaching process is observed, the detected signal decaying as a function of time. The decay rate is dependent upon the laser power and type of the dye and the concentration.

Flow may be introduced to the channel in an oscillatory fashion. The purpose of oscillating the flow in normal operation of an assay is to enhance the interaction of the analyte present in the unknown concentrations sample with a capture moiety, e.g., an antigen in the sample with an immobilized capture antibody. A typical defined volume ("slug") of liquid is used, of fixed volume that is much larger than the volume exposed at the detection point. When portions of this oscillating slug of liquid move away, this allows time for diffusion to take place in those portions to bring the material into equilibrium before it comes back for exposure to the capture site, and back and forth. Whenever it comes back, the analyte in closest proximity to the capture moiety, e.g., some percentage of an antigen is captured and drawn out of that sub-volume of the sample—depleting that sub-volume. Then as it is flowed away, and diffusion allows that sub-volume to approximately re-equilibrate, to reach substantially equilibrium concentration—in time, it replenishes the sub-volume in the vicinity of the capture agent. And so the flow is oscillated back and forth to give maximum opportunity for all the sub-volumes to interact with the capture moiety, to substantially optimize the reaction by optimization condition with the capture moiety.

Referring back to FIG. 100, the time response of a detected tracer signal is shown from a given monitoring location in a scenario with oscillatory flow. Fluorescent dye is used that is subject to photo bleaching. One observes a peak-like nature, or an up and down signal structure with peaks and valleys at a given time sequence and periodicity, due to the oscillation frequency of the fluid back and forth. So there is no net flow of fluid away from the location, but with oscillation, there is an opportunity to replenish the photo-bleached portions of the reagent with fresh reagent. In those cases where the flow rate is maximum, passing by the excitation beam quickly, the photo bleaching decay rate is offset by replenishment of new reagent. That is shown in the peaks labeled "max flow rate." At the turnaround points where the flow rate of the oscillating flow goes to zero, the photo bleaching decay is maximum that is indicated by the valleys, labeled "min flow rate" on this graph. From detail shown in this particular graph, in addition to the frequency and the peak-like nature, one is able to see that there are two types of peaks, taller peaks and shorter peaks. The taller peaks are associated with the flow that is being driven by the piston moving fastest, in this particular fluidic device—when the piston is under vacuum actuation. The smaller peaks are generated by the piston displacement when the piston is moving slower, being actuated a positive pressure. The negative actuating pressure value is greater than the positive pressure value and therefore induces a greater rate of displacement of the piston. For example, the negative pressure for actuating the membrane diaphragm of the pump is about −8 or −10 psi, while the positive pressure actuation of the piston is under about 4 psi.

The signature shown in FIG. 100 is indicative of normal operation. In the case where a pneumatic interface was improperly sealed or seated, then these peaks heights would occur at different levels, outside of normal acceptance range, so this is a type of failure mode that could be detected. Another factor involved here is the flow rate, which depends not only on displacement volume of the piston, but also on the impedance of the fluid in the microfluidic channel. If the impedance is increased by the addition of blockage from a contamination source or some other problem, such as a detection element being misplaced in the channel, then the nature of the signature structure would be different from what is expected and shown in this graph.

Figure 23:
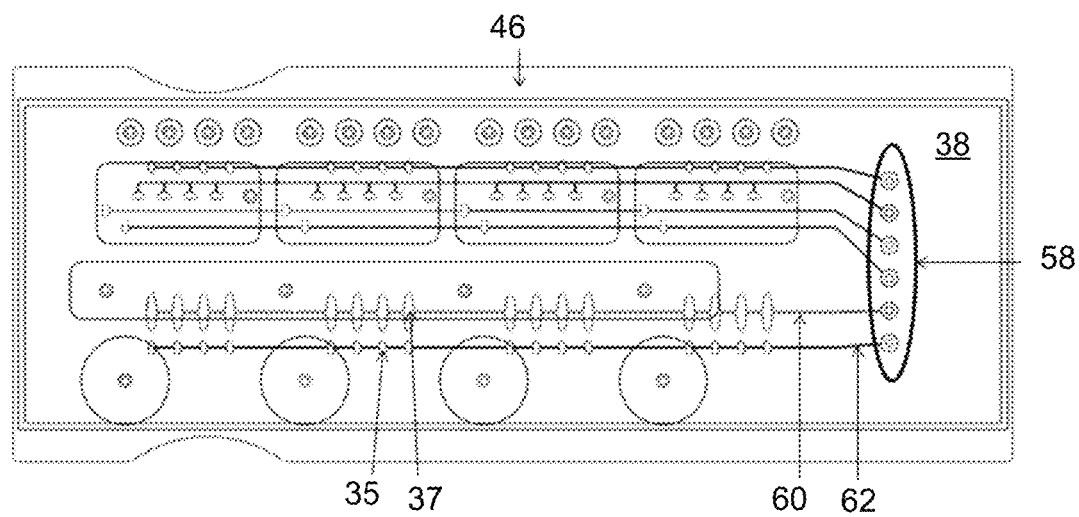
FIG. 23 is a plan view, looking up at the underside of the reservoir/pneumatic sub-assembly through its transparent PDMS membrane sheet.
Figure 24:
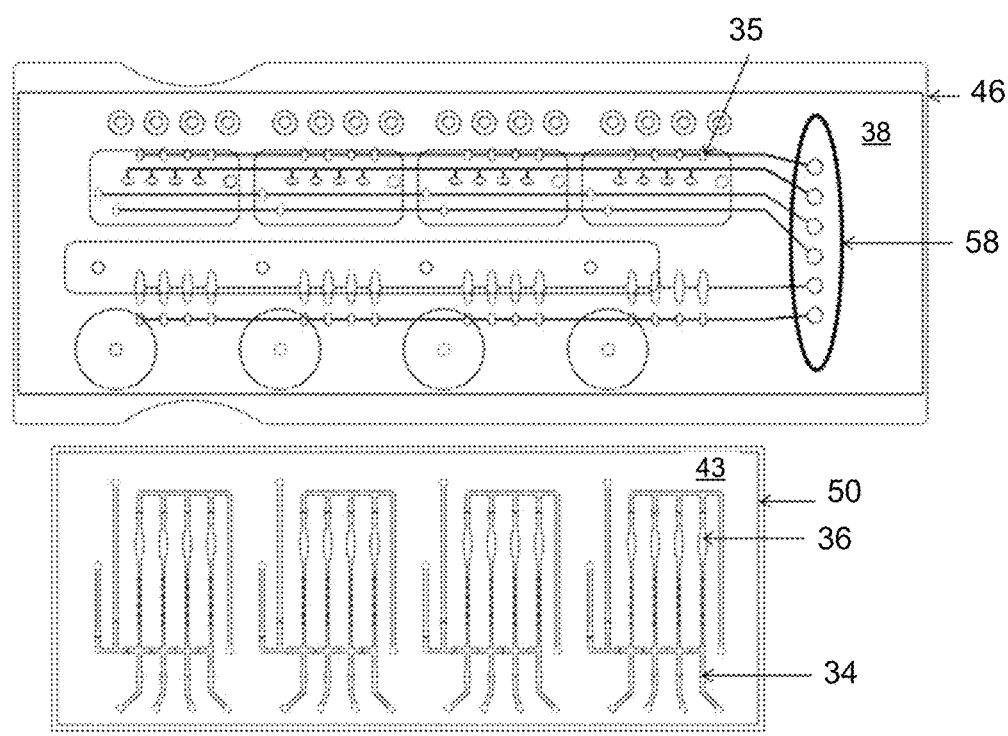
FIG. 24 is a plan view, again of the underside of the reservoir/pneumatic sub-assembly and the mating upper surface of the Fluidic Layer sub-assembly.
Figure 25:
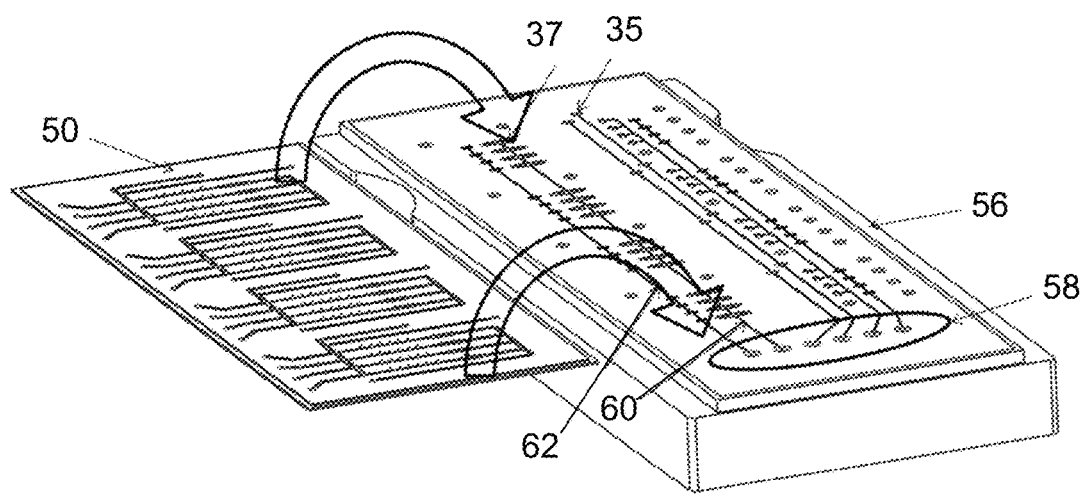
FIG. 25 is a perspective view diagrammatically illustrating the mating action of the two sub-assemblies with the micro-length tubes (e.g. GNRs) in the Fluidic Layer.
Figure 25A:
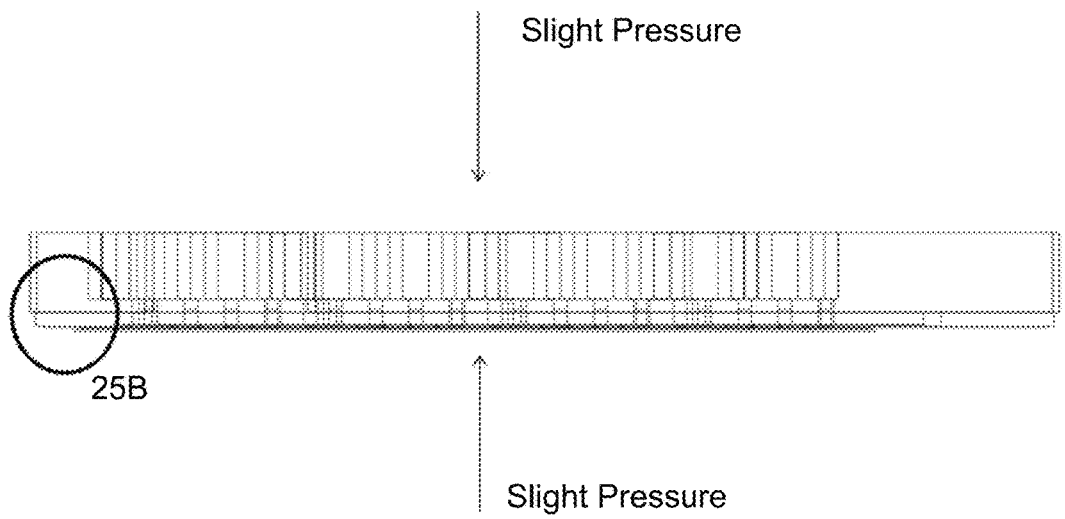
FIG. 25A is a side view illustrating the PDMS layer and the mating surface respectively of the two subassemblies (Reservoir/Pneumatic Layer and Fluidic Layer) being pressed together with slight pressure.
Figure 25B:
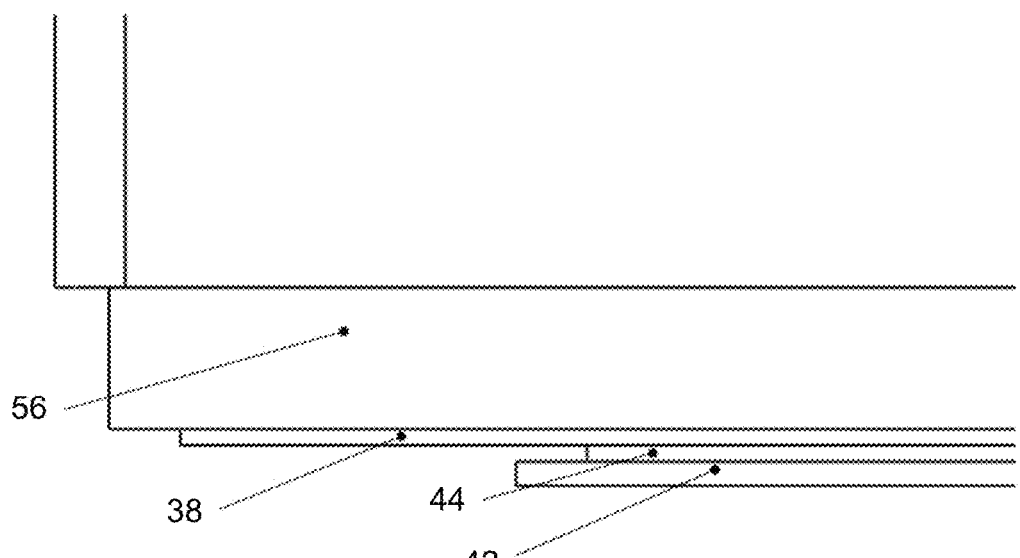
FIG. 25B is a magnified view of a portion of FIG. 25A denoted by a circle in FIG. 25A labeled 25B.
Figure 25C:
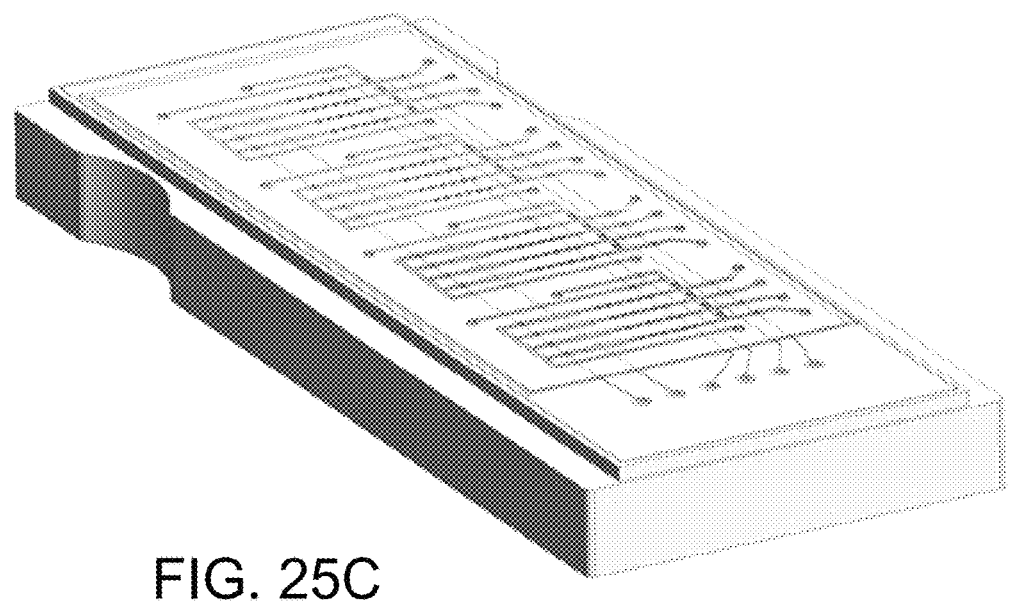
FIG. 25C is a perspective view of the completed assembly viewed from above (as assembled with the glass layer facing up)
Figure 25D:
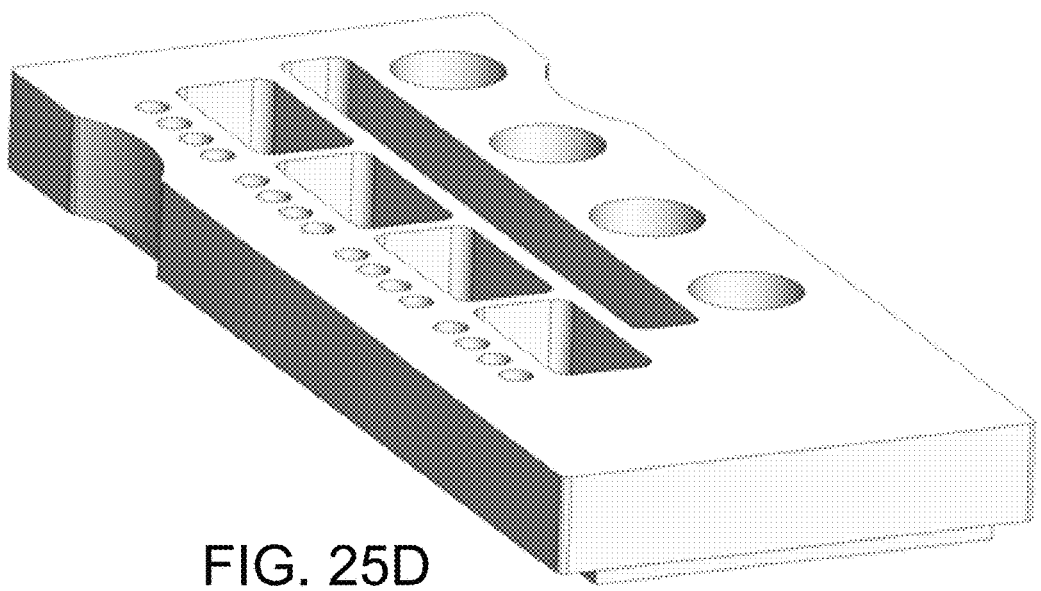
FIG. 25D is a perspective view of the completed assembly, viewed from above (after inversion, so that the reservoir layer faces up, the glass layer faces down)

The trace shown in FIG. 100 and the detected values in FIGS. 98A, 98B, 98C, and 99, are acquired by capturing the fluorescence intensity during steps of the assay by an imaging system shown diagrammatically in FIG. 23. It has an objective lens and a series of optical elements. An excitation beam from a laser is introduced to the monitoring location at a microfluidic channel, FIG. 102. The optics transform the stimulated fluorescent object, see FIG. 102, to an image plane shown as a photo detector (but in a preferred implementation, a CCD camera). The intensity of the pixels within a region of interest (ROI) captured on the camera are summed (integrated) to produce a single intensity point for that frame for that moment in time.

Figure 102:
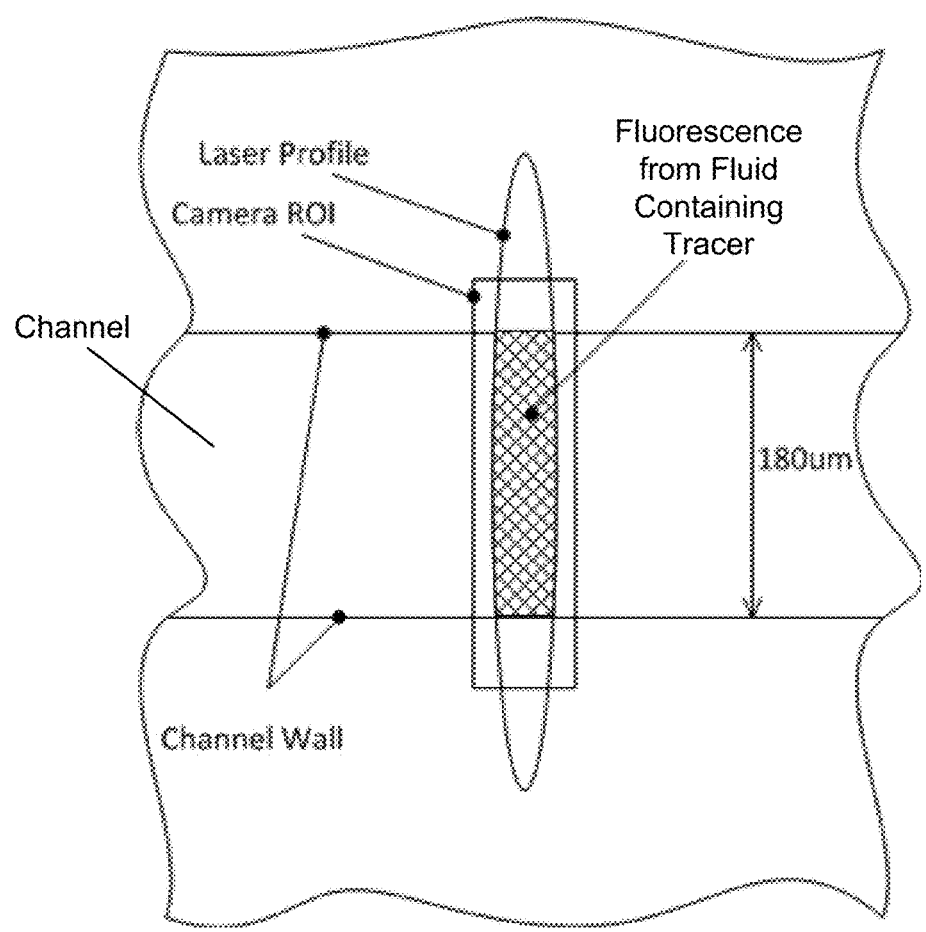
FIG. 102 illustrates the cross section of the region of interest (ROI) of the optical system of FIG. 101 in relation to the microfluidic channel and the cross-section profile of a fluorescence-exciting laser beam.

In FIG. 102 the laser beam is shown in cross-section as an oval while a rectangular box circumscribing that oval illustrates the region of interest (ROI) over which the pixel intensities are integrated to produce a single resultant signal point. That value at this point in time is plotted as a point on the graph in FIG. 100.

The scanning system is adapted, during reading of assay results, to interrogate a detection element on which assay capture agent is immobilized, see the Scanning Figures described later herein. But in monitoring mode, as depicted in FIG. 102, by relative movement between optics and microfluidic system, the system is focused on a selected monitoring point on a fluid-carrying channel at a point in which the detection element is not present.

Figure 101:
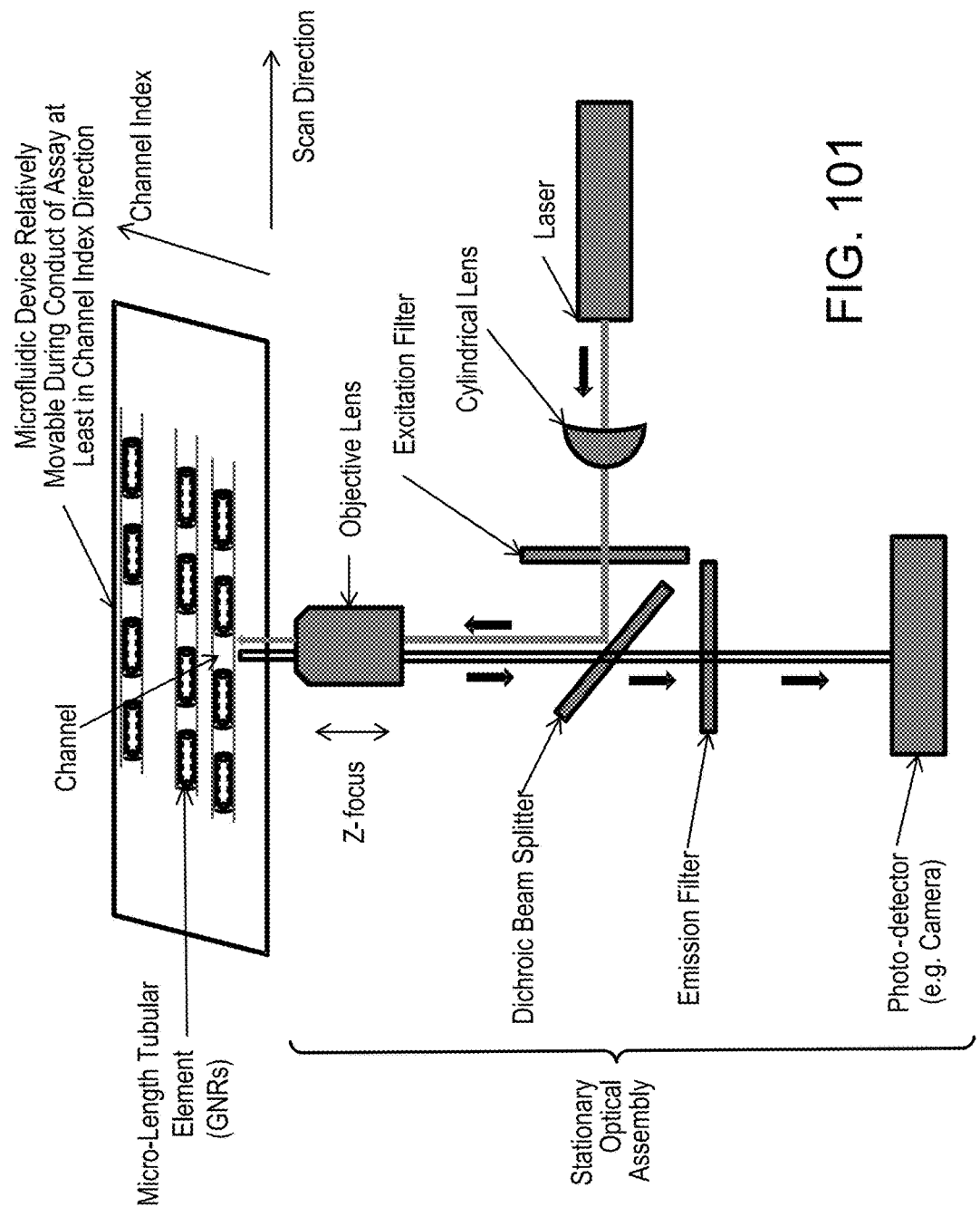
FIG. 101, similar to FIG. 65, illustrates, diagrammatically, the relation of a scanning system to a microfluidic device, shown aligned with a channel at a region that does not contain a detection element.

The optical arrangement of FIGS. 101 and 102 is used to generate the signal trace in FIG. 100 or the "snap shot" at a monitoring point in FIGS. 98A, 98B and 98C, or the measurements over time of FIG. 99.

Another important use of the novel tracer detection technique is identifying the location of microfluidic channels with high fidelity within a portable cartridge (cassette), relative to a cartridge position that is subject to some variation in position on a scale relevant to the small features of the microfluidic cassette. This is described further on, after describing a preferred implementation of a scanning/assay conducting instrument.

In a preferred implementation, a portable microfluidic cartridge 2 is placed into an operating and scanning instrument by the user. It enters in a receptacle or reception area 6 at which the cartridge is retained for conducting the assay while scanning.

Figure 57C:
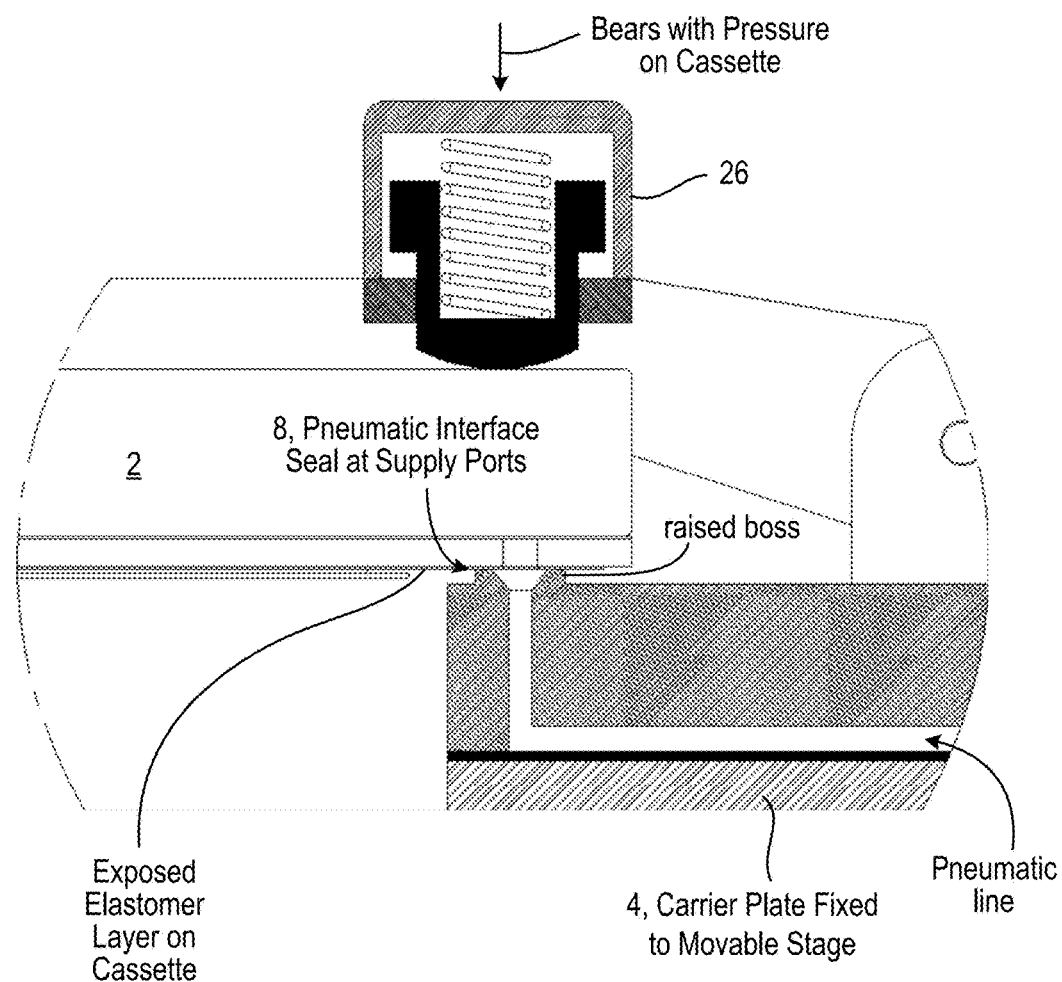
FIG. 57C is a magnified view of a portion of FIG. 57B.
Figure 58:
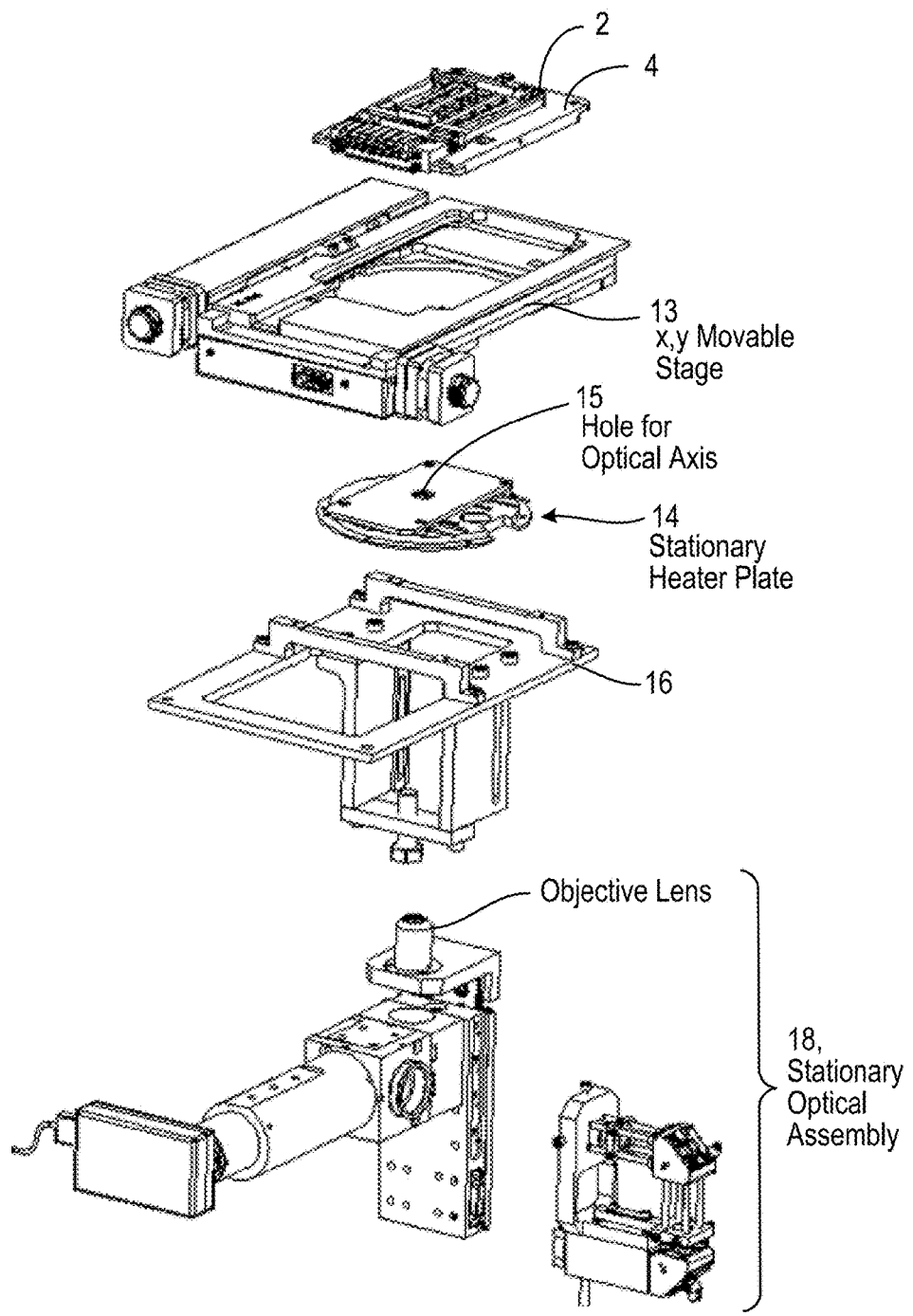
FIG. 58 is an exploded view of the assembly of a bench top operating and scanning unit for scanning the microfluidic cartridge of FIGS. 57 and 57A.

A suitable receptacle is shown in FIGS. 57 and 57A, and the relationship of the receptacle and cassette when in assay/reading position is shown in FIG. 57B and the detail of FIG. 57C. An implementation of the overall system is shown in exploded view, FIG. 58. FIG. 58 includes x, y precisely movable stage 13 that moves the cartridge on its carrier relative to the stationary objective lens.

Referring to FIGS. 57 and 57A, cartridge 2 and the cartridge receptacle 6 are shown with a clamping mechanism 12 and pneumatic interface 8. A series of computer-operated solenoid valves 9 that move on the stage with the cassette apply positive and negative air pressure to ports that interface with the positioned cassette.

Referring again to FIG. 102, for a suitable instantaneous image size, it is appropriate to use an excitation beam imaged through the objective lens to a spot size of approximately 12 microns wide by 250 microns long. The region of interest (ROI) of the camera that includes that spot has an area of approximately 35 microns width by 250 microns length. The microfluidic channel of the cassette that will be monitored has a channel width of approximately 180 microns.

Three scenarios for monitoring the tracer dye with such a beam are: (1) Continuous Scanning Modality. The microfluidic channels are scanned e.g., with substantially constant velocity across all channels of a microfluidic system, such as on a cartridge. In that case, the beam crosses over the channels and measures the fluorescence intensity as a function of position or as a function of time, as the channels are crossed. (2) A Rapidly Shift-Momentary Dwell Modality. In this case the detection axis is moved rapidly relative to the microfluidic system, to a selected location, followed by a momentary dwell, e.g., of a few seconds, in which the scanning system stops, and the optical detection system stares and collects tracer information or tracer signals as a function of time at the fixed location. The sage then moves on to another location to repeat the stare and this is done for a large number of locations over the micro-fluidic system in a short period of time. (3) Long Stare Modality. In this case a single location is selected at which the system stops and starts for an extended period of time, e.g., many seconds or even minutes. It can characterize a specific pumping or fluidic operational step. It is especially useful if there is suspicion about that particular location, determined as a result of one of the prior two scanning modalities.

The system and method have aspects useful for monitoring during operation of every assay and others that are useful as a diagnostic tool for design.

In respect of monitoring every assay, the Scanning Modality is especially useful. It is used to scan across all channels of a microfluidic system, e.g., on a cartridge, repeating this during each phase of execution of the assay. It can also stop at various locations for a short period of time to collect a trace at that location, and stop long term for staring to characterize the flow over time even in the case of monitoring usual assay function.

For a presently preferred implementation of a microfluidic cassette and how scanning can be accomplished, refer to FIGS. 59A, 59B, 59C Fluidic/Pneumatic Architecture and FIG. 60 Fluidic Architecture and Protocol.

FIG. 59A illustrates a microfluidic configuration within a cartridge, illustrating both a series of fluidic networks and a pneumatic channel network to actuate on-board membrane micro-valves and micro-pistons in the fluidic network. The fluidic network in FIG. 59A comprises eight discrete microfluidic circuits closed by an over-lying elastic membrane, e.g., a continuous layer of PDMS. Each of those circuits has a number of microfluidic channels, valve locations, and piston locations. Portions of this membrane are located at formations in the channel that define valve and pump cavities. The corresponding portions of the membrane define movable elements of the valves and the piston.

The pneumatic channel network FIG. 59B is shown as an overlay in FIG. 59C. It matches the fluidic network with respect to the various features that need to be actuated.

FIG. 60 is a magnified view of one of the circuits of FIG. 60, illustrating a number of the micro-features including valves, pistons, and the various reagent or reservoir inputs including the sample, the buffer (wash), the assay reading dyes, the secondary antibodies and the waste. The four elements GNR shown in black in each of the four individual (isolatable) channels represent glass nano-reactors (GNRs) embedded in those channels. This illustrates the basic micro fluidic unit replicated a number of times in the cartridge depending on the number of samples that the cartridge is designed to accommodate. The assay protocol flow sequence shown at the left of FIG. 60 starts with the prime flow step, and is followed by sample step, wash step, secondary antibody step, another wash step, a dye step for reacting to attach reading dye to the captured moiety, and finally another wash step. This illustrates an example assay sequence capable of being performed in this microfluidic structure. Each one of the fluids: sample, secondary (e.g., secondary antibody), wash, and reactive dye is caused to flow from its respective inlet well by activation of the pumps formed by each piston and upstream and downstream valves, with the end result of captured moieties at the detection elements that are labeled with the reactive dye, ready for reading to quantify the result of the assay. Examples of volumes employed on this device include the sample at 20 microliters, a buffer of 150 microliters (as shown in the table)—the total volume of the microfluidic circuit is approximately 1.8 microliters.

FIG. 61 illustrates the same microfluidic unit in a schematic fashion, showing four independent fluidically isolated microfluidic channels in each of which the respective piston and valves define a pump dedicated to that channel. The Figure illustrates controlled pneumatic control lines overlaid, terminating at a number of circles containing x's that represent valves. The horizontal lines with arrows labeled "Find channel scan 1" and "Find channel scan 2" illustrate the path that a scanner or a stage carrying the microfluidic system moves in order to identify the fluorescence intensity, and thus identify the location, of each of the fluidic channels. As the relative scan motion moves along that path, it will produce a trace shown adjacent to the schematic. The upper and lower black and white traces shown in the center illustrate the fluorescence intensity being high in channels 1, 2, 3, and 4 based on the peaks shown on the traces. This illustrates that the scanner while scanning across that path encounters high fluorescence because of benign tracer in liquid in each of the channels. The locations of the channels are then determined very precisely by taking the encoder information superimposed on that trace. The precise location of those channels is thus determined relative to the absolute coordinate frame of the scanning system. It is possible now to produce high resolution and highly aligned scans because the precise locations of the scans are now determined with respect to the x, y stage. Thus, while a holding system firmly fixes the position of cassette within the operating scanning position, its exact location at the level of micron accuracy need not be precise because of the trace-determined high accuracy detection. An example of a system that performs these operations is described below in relation to the scanning Figures.

The primary benefit of the approach described, of precisely identifying the location of the channels, is to relax the requirement that the cartridge be precisely aligned on the stage by the user.

It has to be fixed relative to the stage but only within a fairly course acceptance range. A benefit of the technique is that it does not require precise absolute (and costly) positioning by the user. It permits the presently preferred clamping implementation about to be described.

The apparatus for conducting the assay and simultaneously scanning for benign tracer presence will now be described with reference to FIGS. 57, 57A, 57B, 57C and 58. In FIG. 57, assay cartridge (cassette) 2 is shown above carrier plate 4, in preparation for being placed into receptacle area 6. When placed, the cartridge will make intimate contact with pneumatic interface 8, so that pneumatic controls (solenoid valves 9) can actuate appropriately to apply air pressure and vacuum via interface 8, to actuate the micro-valves and pistons on board the cassette and thus perform the assay. The cartridge is retained in the receptacle interface 6 by retaining clamp 12. In FIG. 57B, clamp 12 is shown with the cartridge in place in receptacle area 6. In FIG. 57A, the retaining clamp is shown in the process of being closed. FIGS. 57B 57C and the exploded view of FIG. 58 illustrate the relationship between the carrier plate 4 and cartridge 2 in it and the rest of the mechanical assembly of the instrument in an exploded view. The precision x, y stage 12, chassis 16, heat plate 14, and optic subassembly 18 are shown. Not shown is an enclosure for the system that excludes ambient light form the cartridge or other microfluidic assay system, and from the optical system, such that ambient light does not interference with fluorescent excitation and detection during performance of the assay and during the reading of assay results.

Referring especially to FIG. 57C, a further magnified view, the pneumatic interface and the clamping pneumatic interface 8 are shown with the cartridge 2 in intimate contact with pneumatic interface 8 while the clamping anvil 26 is resiliently compressed, providing a force compressing the cartridge against the pneumatic interface. The clamp is held in its down position by a latch.

Figure 62:
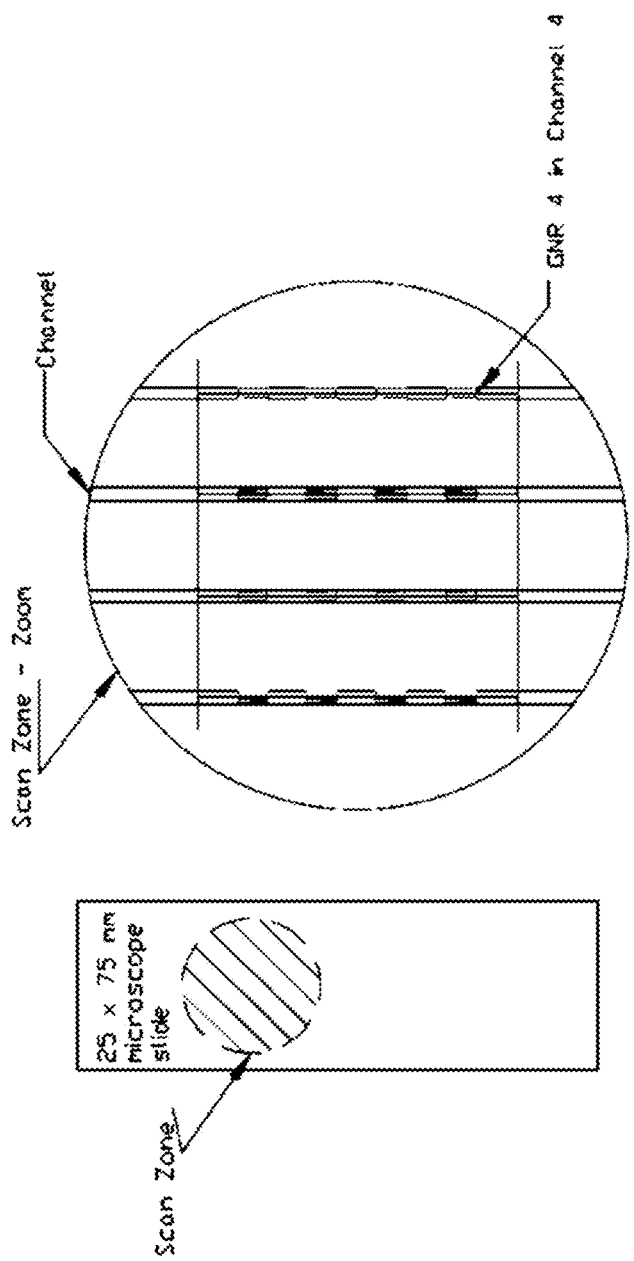
FIG. 62 illustrates the fact that the precise position of channels, for monitoring, and the location of detection elements in the channel, for later reading of results, can be accomplished in the same system.
Figure 63:
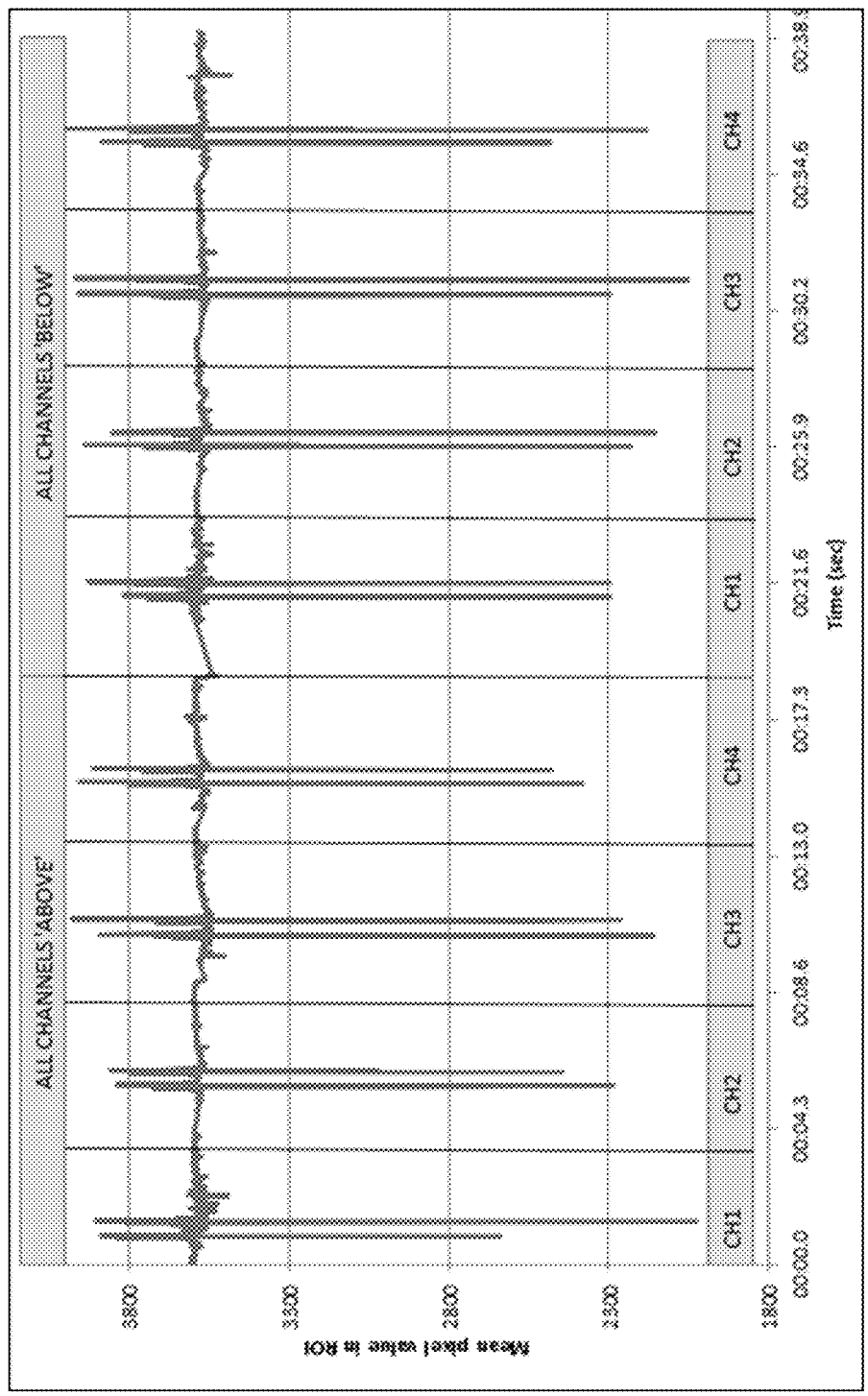
FIGS. 63 and 64 are representations repeated in the later Scanning drawings, illustrating signals obtained during position determination in the absence of trace.
Figure 64:
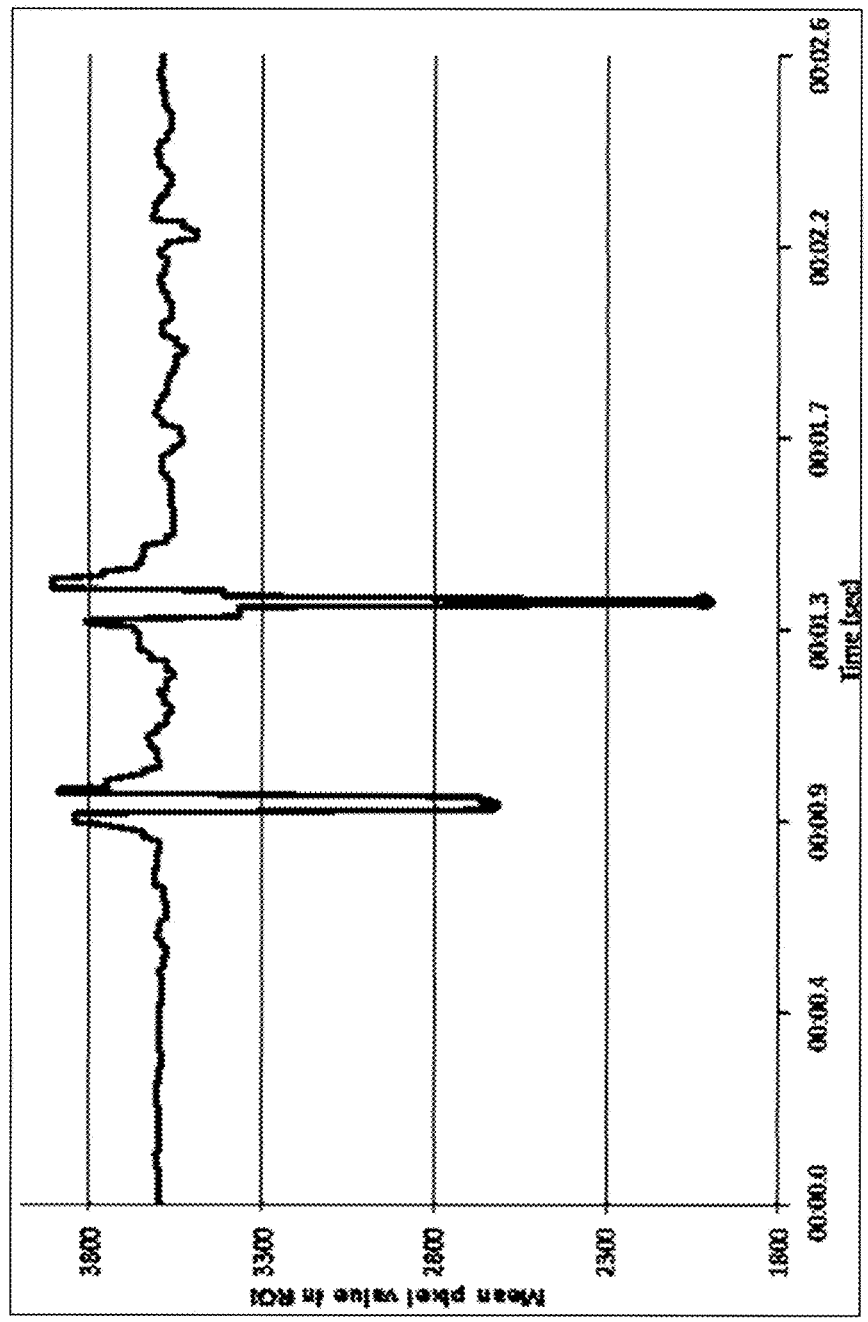
Figure 65:
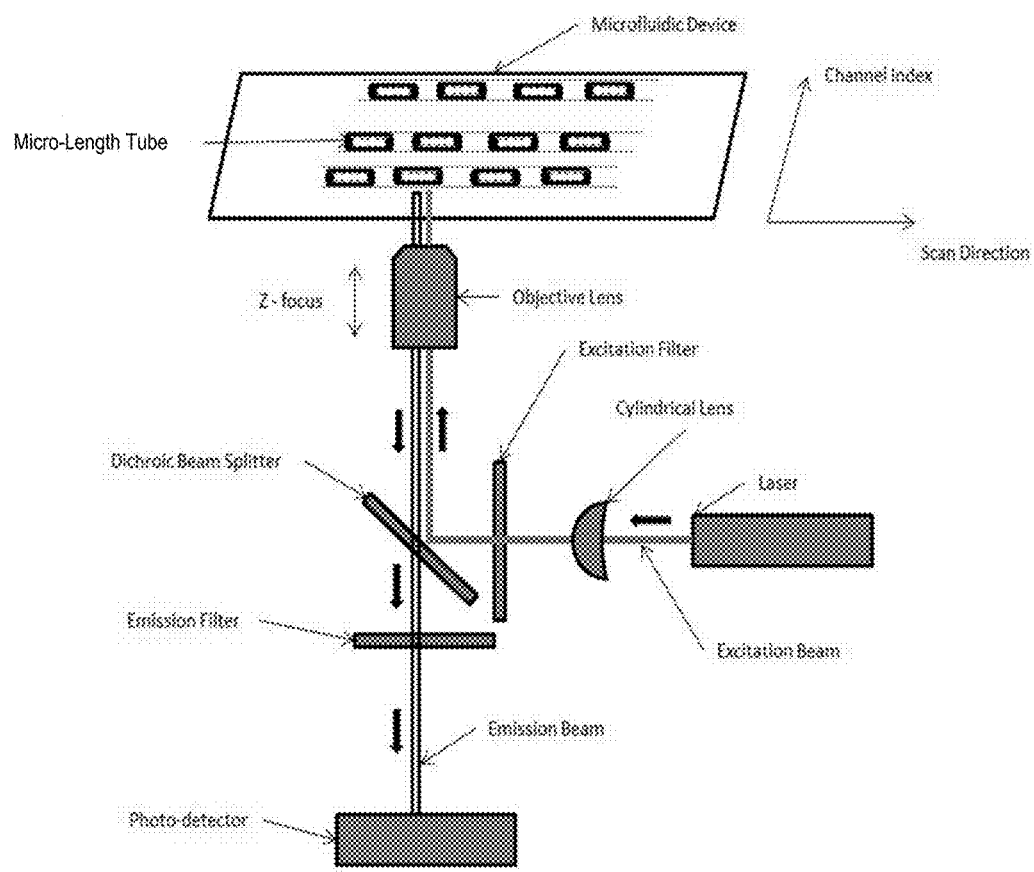
FIG. 65 General Schematic for Epi-fluorescent Scanning Microscope (similar to FIG. 101)
Figure 66:
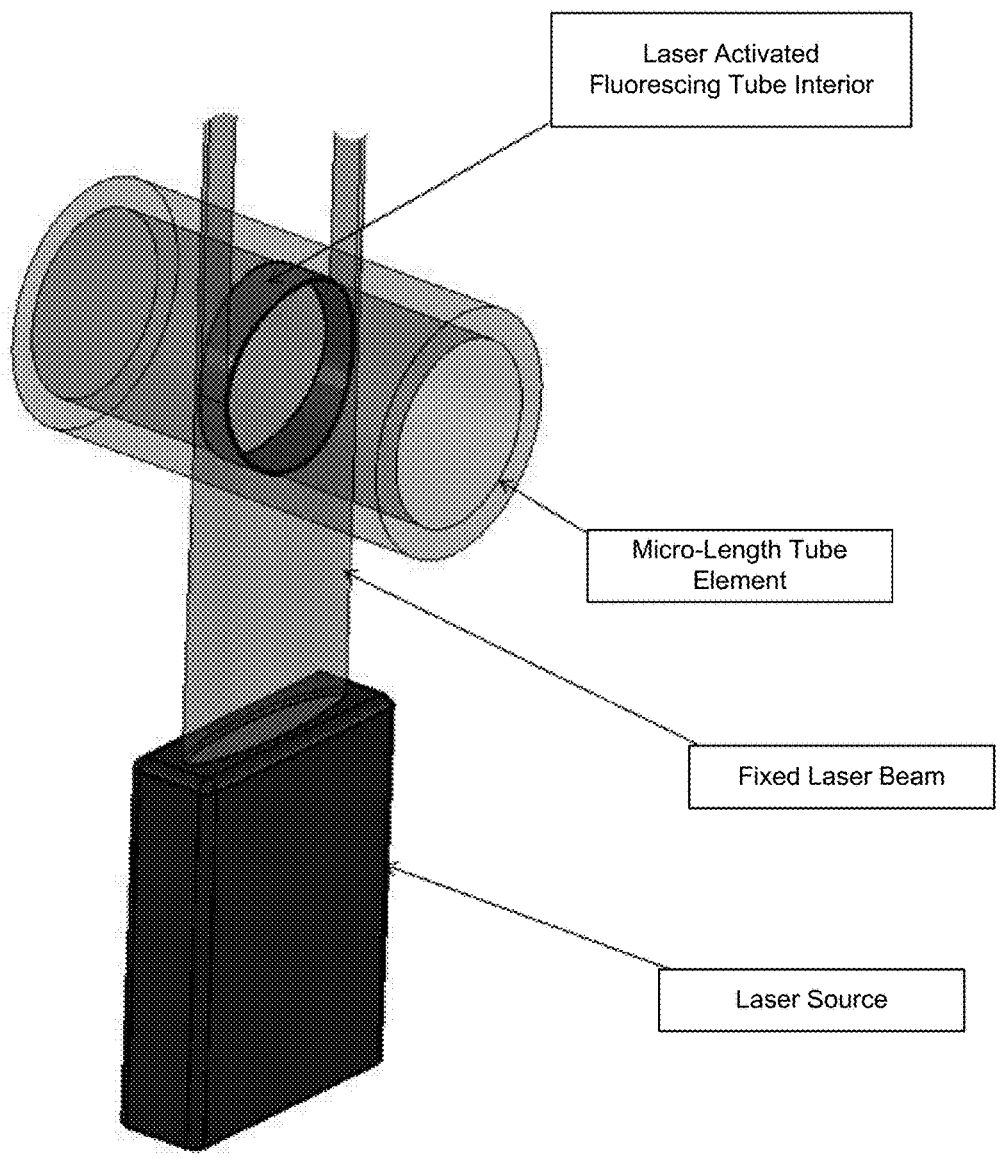
FIG. 66—Laser Beam Shape Isometric View.
Figure 67:
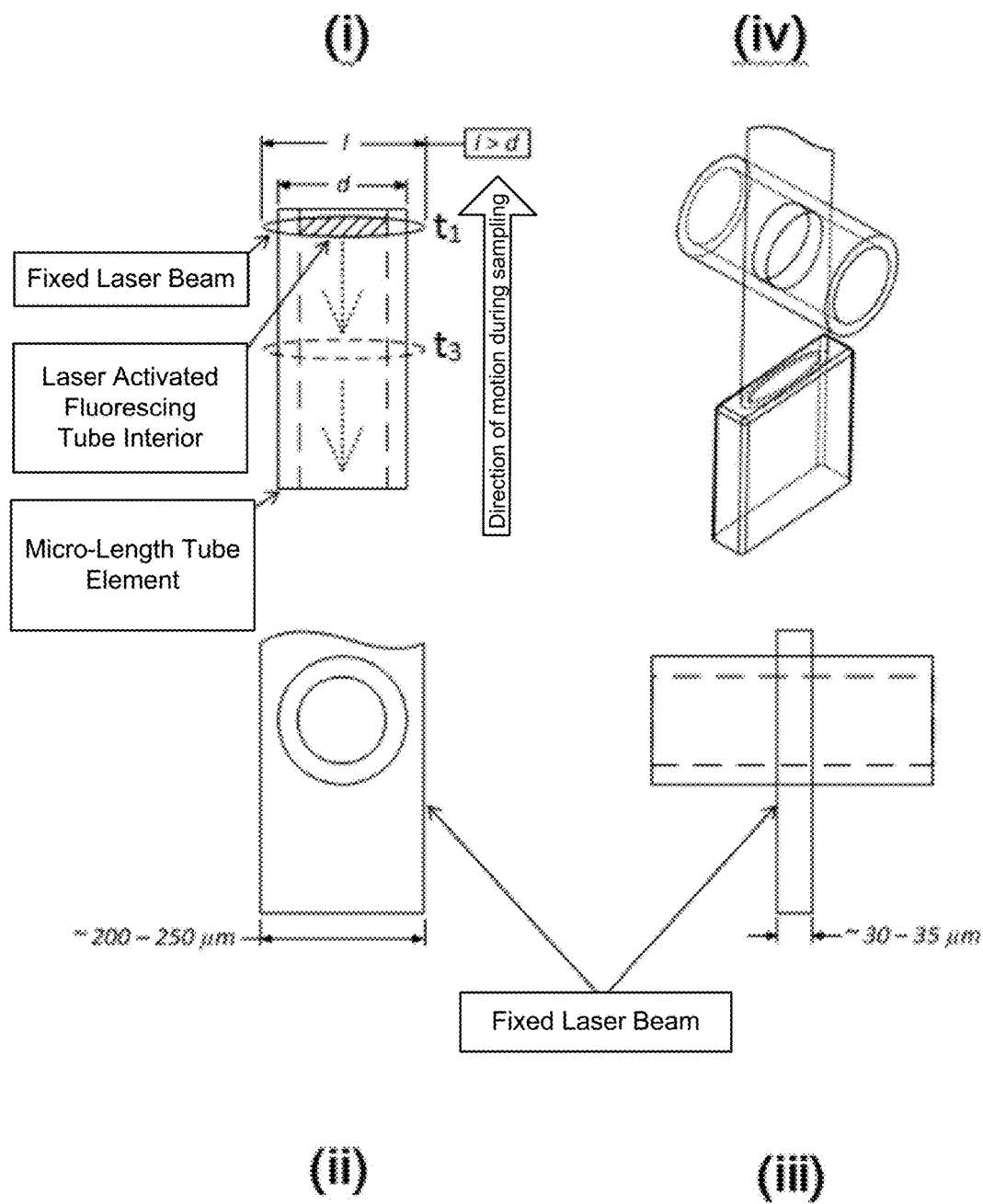
FIG. 67—Laser Beam Shape Layout View.
Figure 68:
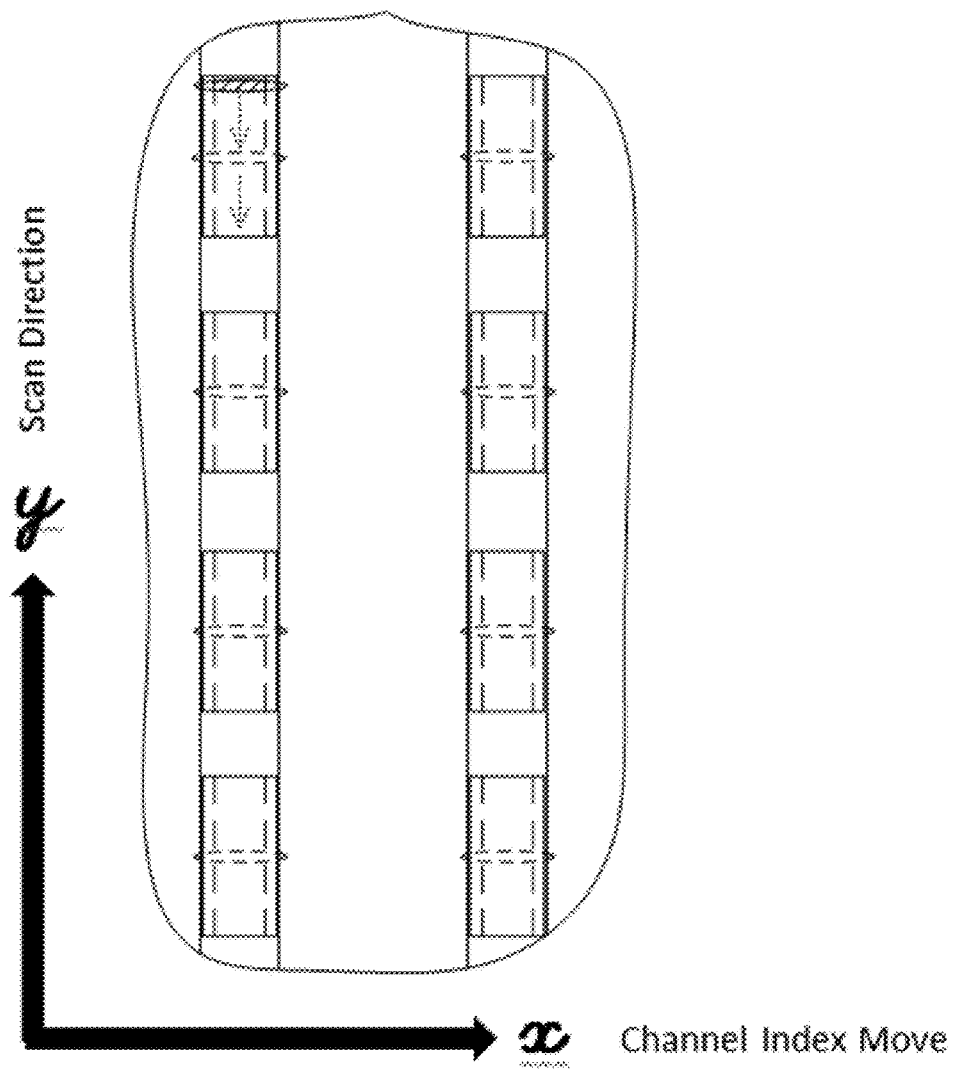
FIG. 68—Micro-length tube element scan schematic.
Figure 69:
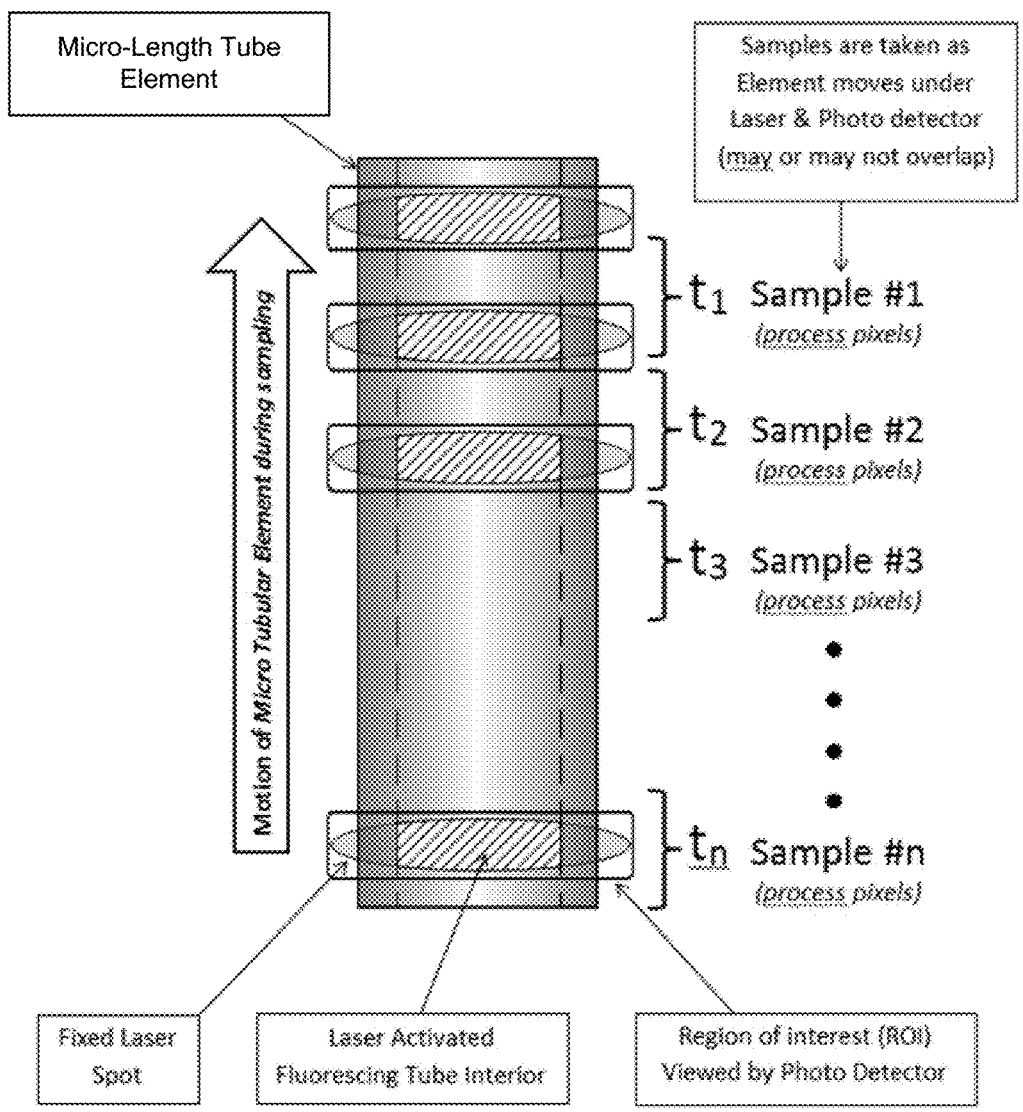
FIG. 69—Acquisition Time Series.
Figure 70:
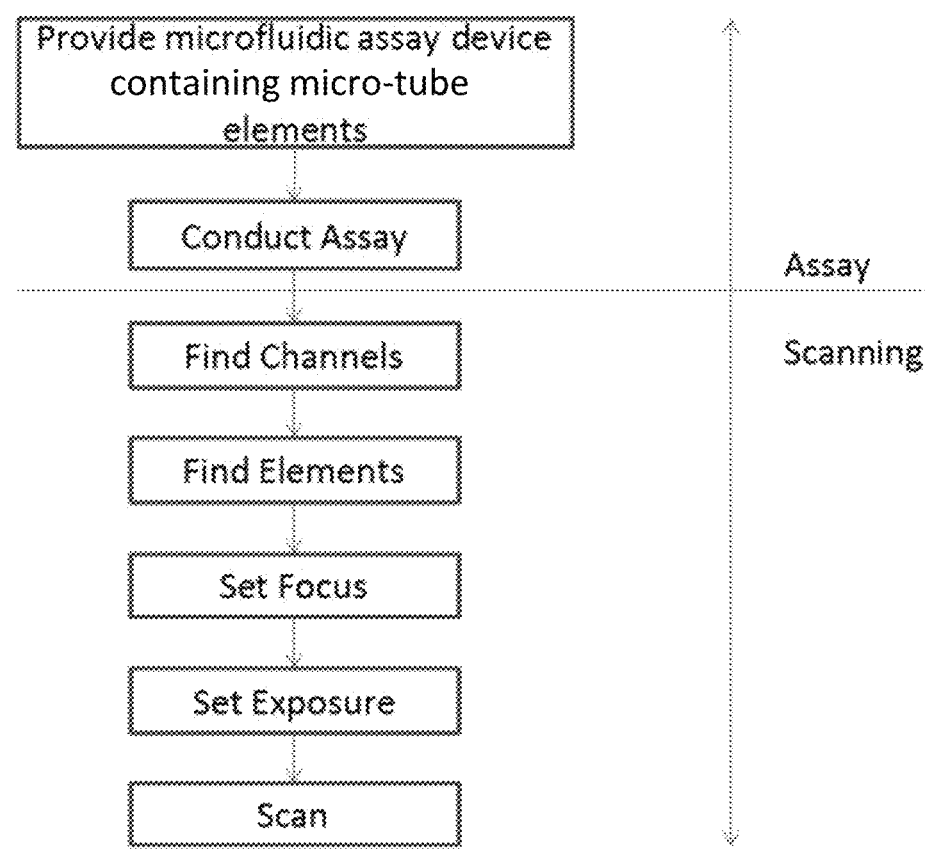
FIG. 70—Overall Scan Sequence.
Figure 71:
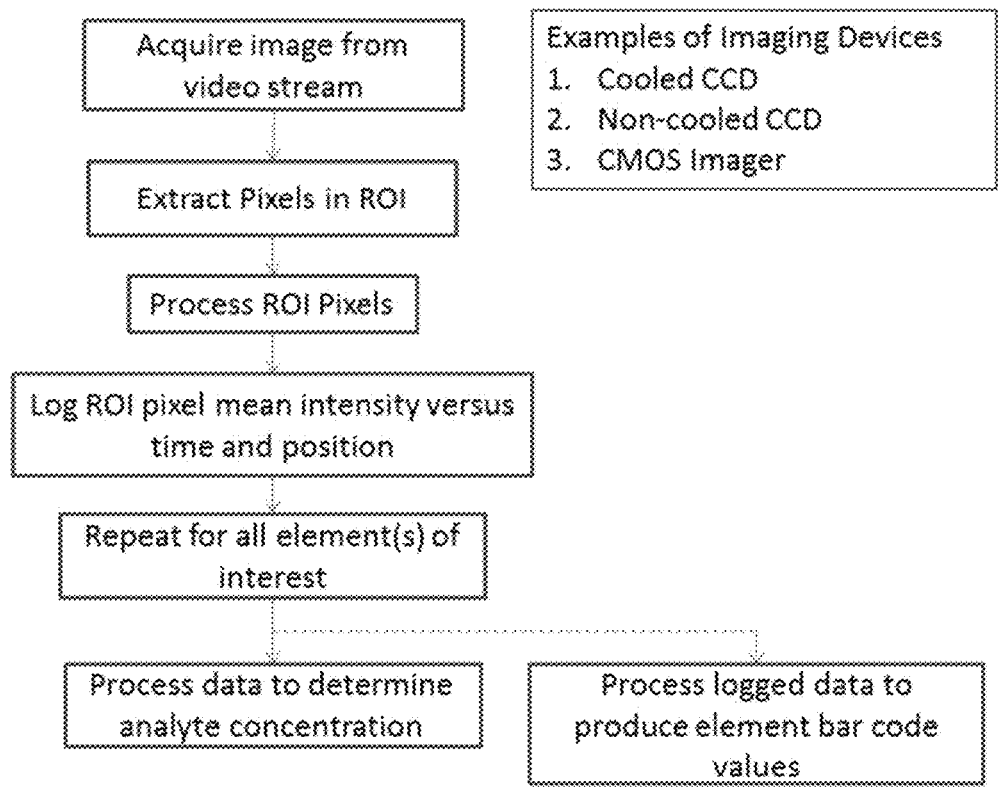
FIG. 71—Scan Sequence—Imaging.
Figure 72:
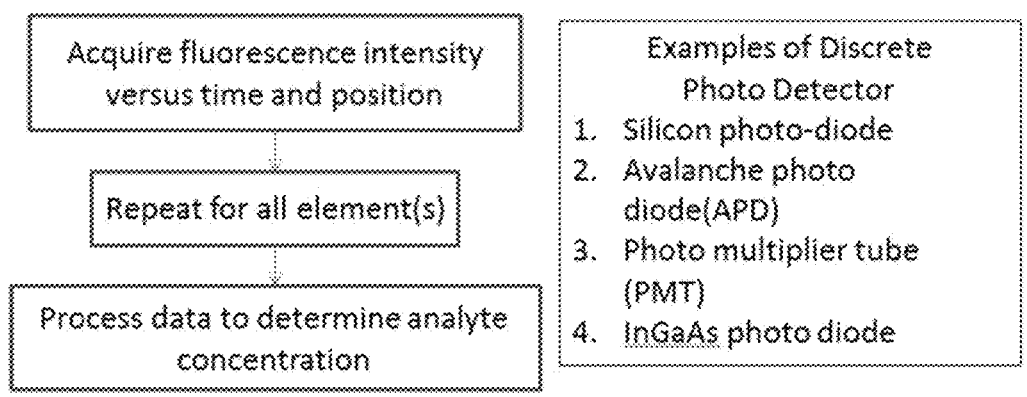
FIG. 72—Scan Sequence—Discrete photo detector.
Figure 75:
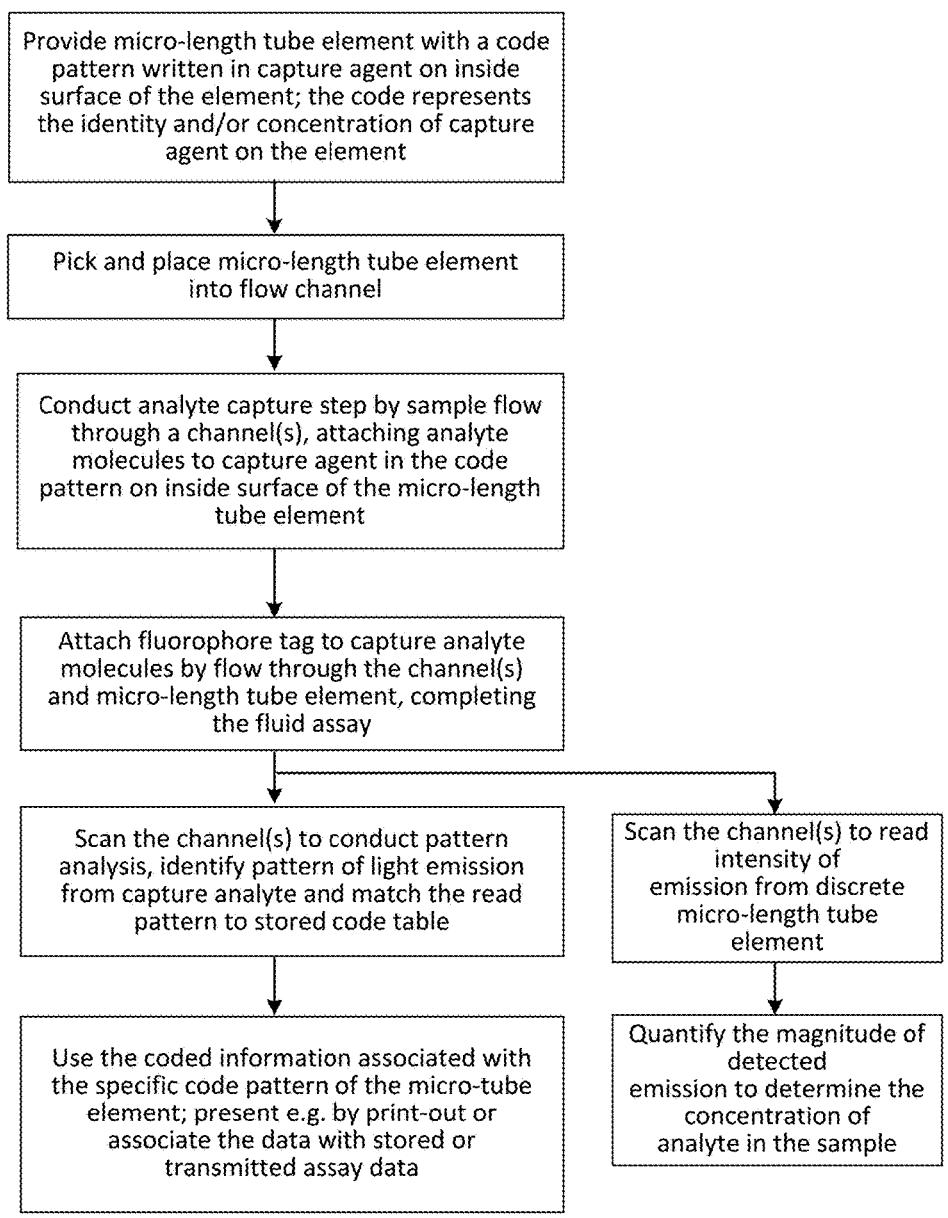
FIG. 75—Reading code and analyte quantity from micro-length tube flow element simultaneously.
Figure 76:
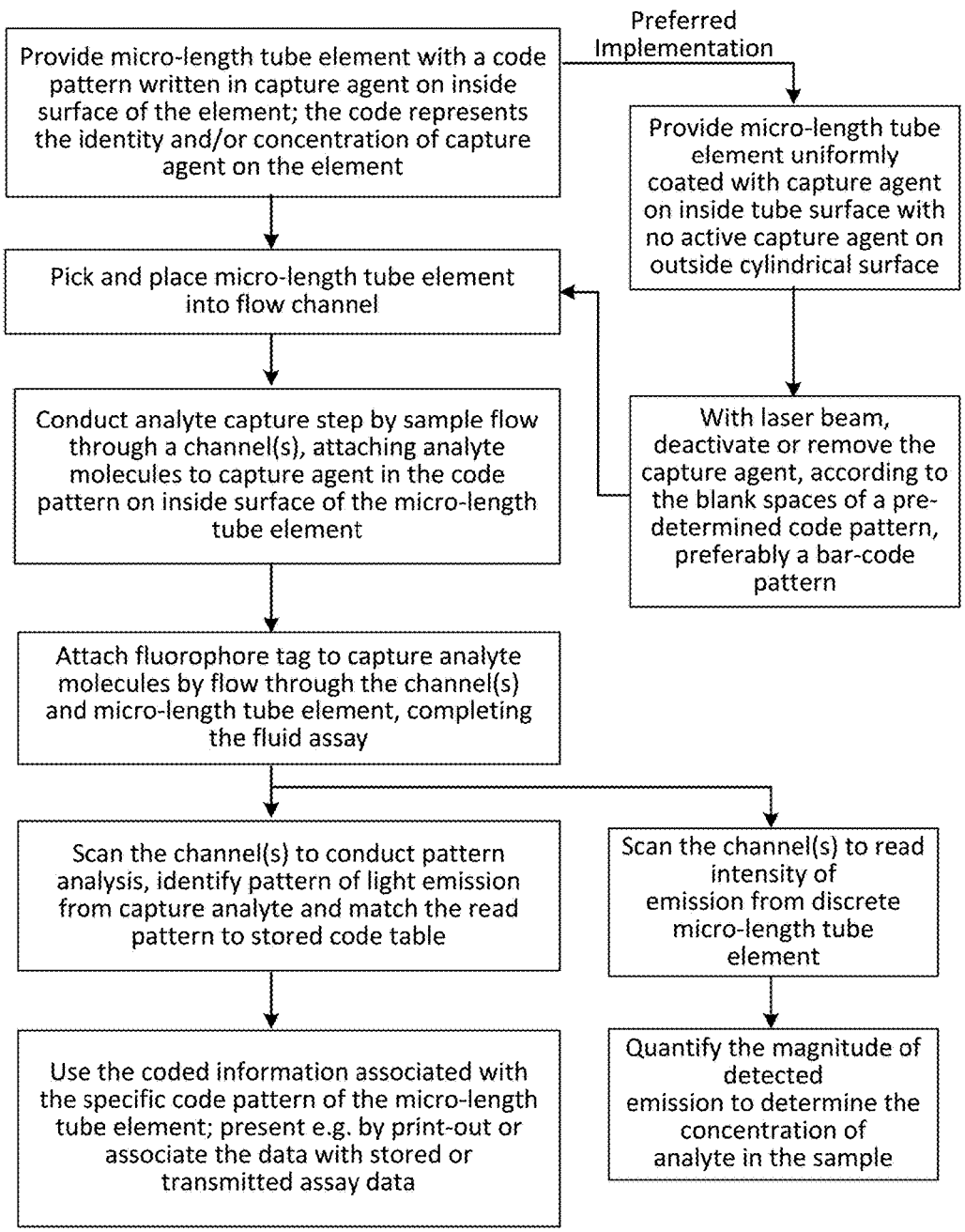
FIG. 76—Reading Code Consolidated.
Figure 80:
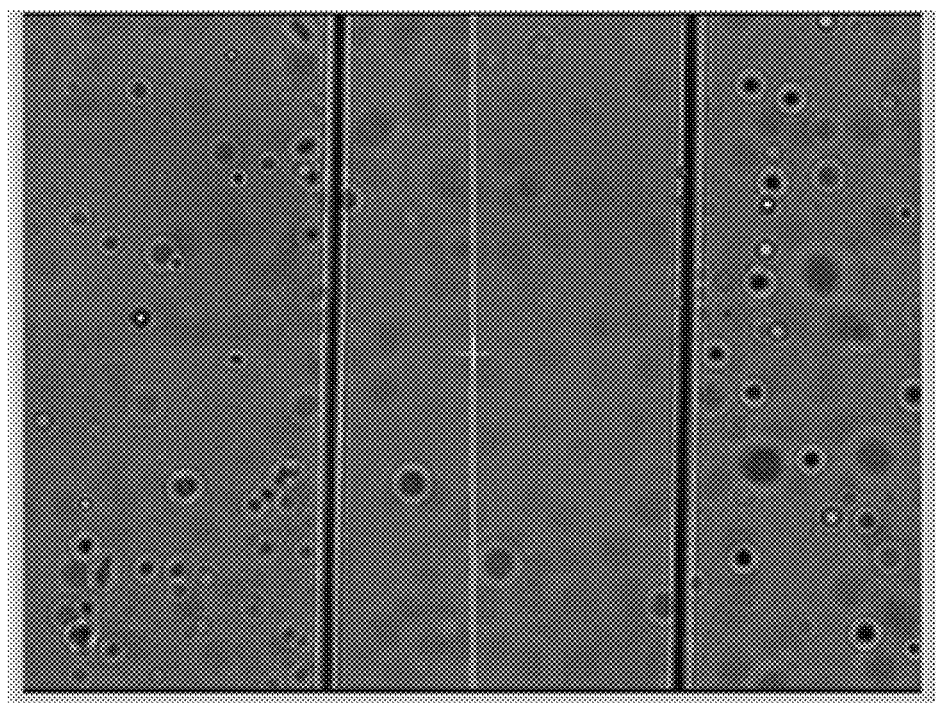
FIG. 80—Find Channels ROI.
Figure 81:
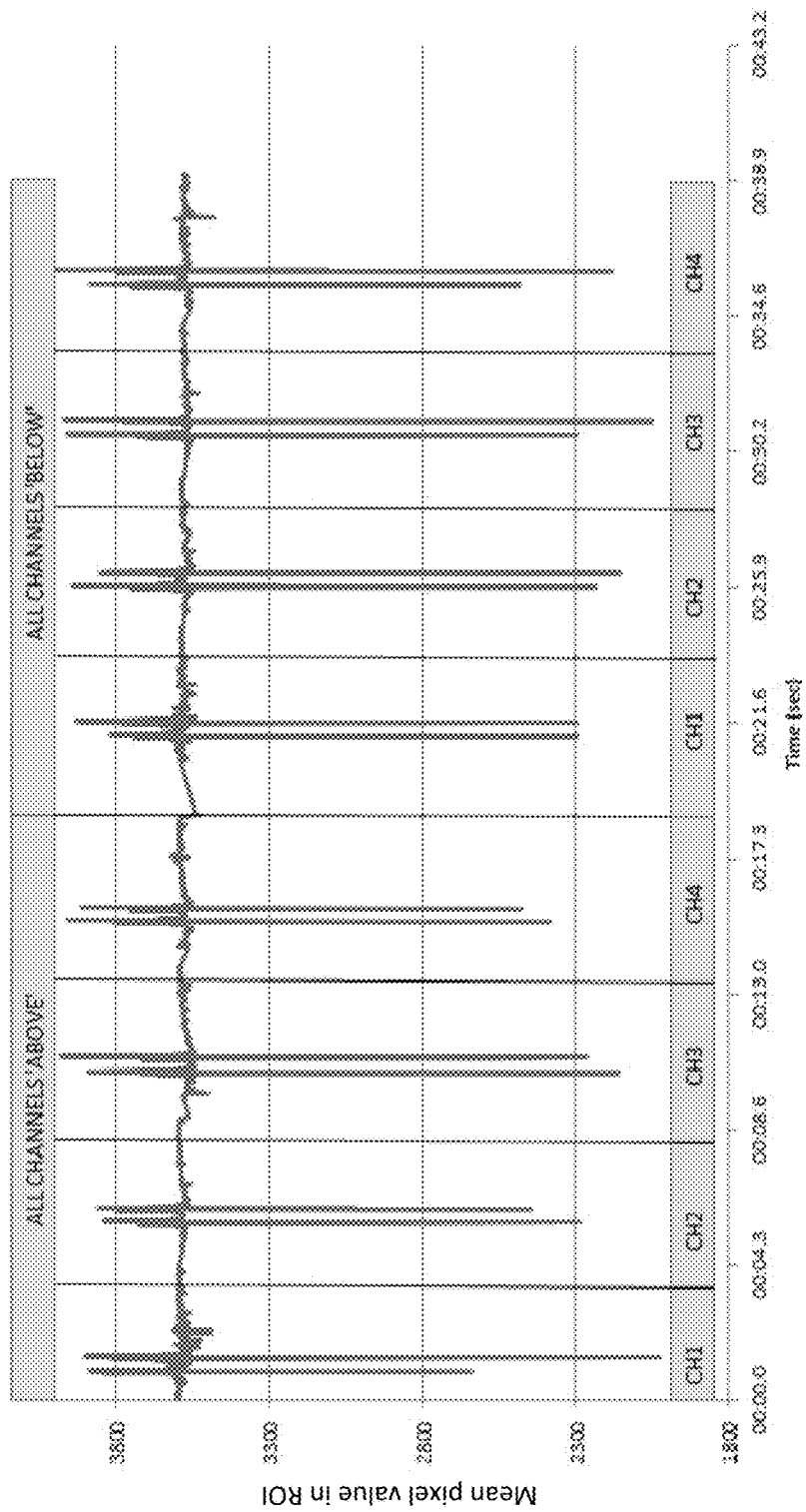
FIG. 81—Find Channels Scan Plot.
Figure 82:
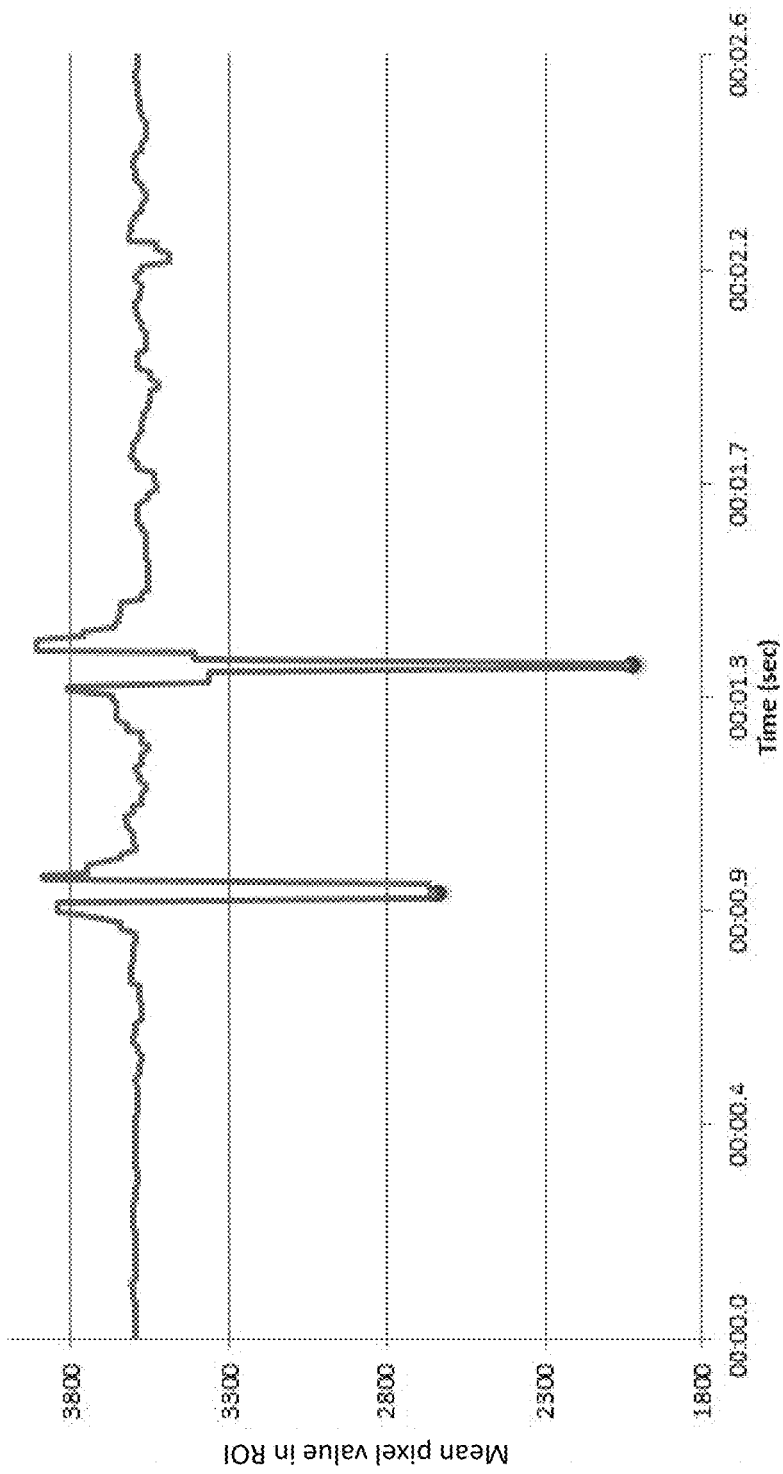
FIG. 82—Find Channels Data Segment Plot.
Figure 83:
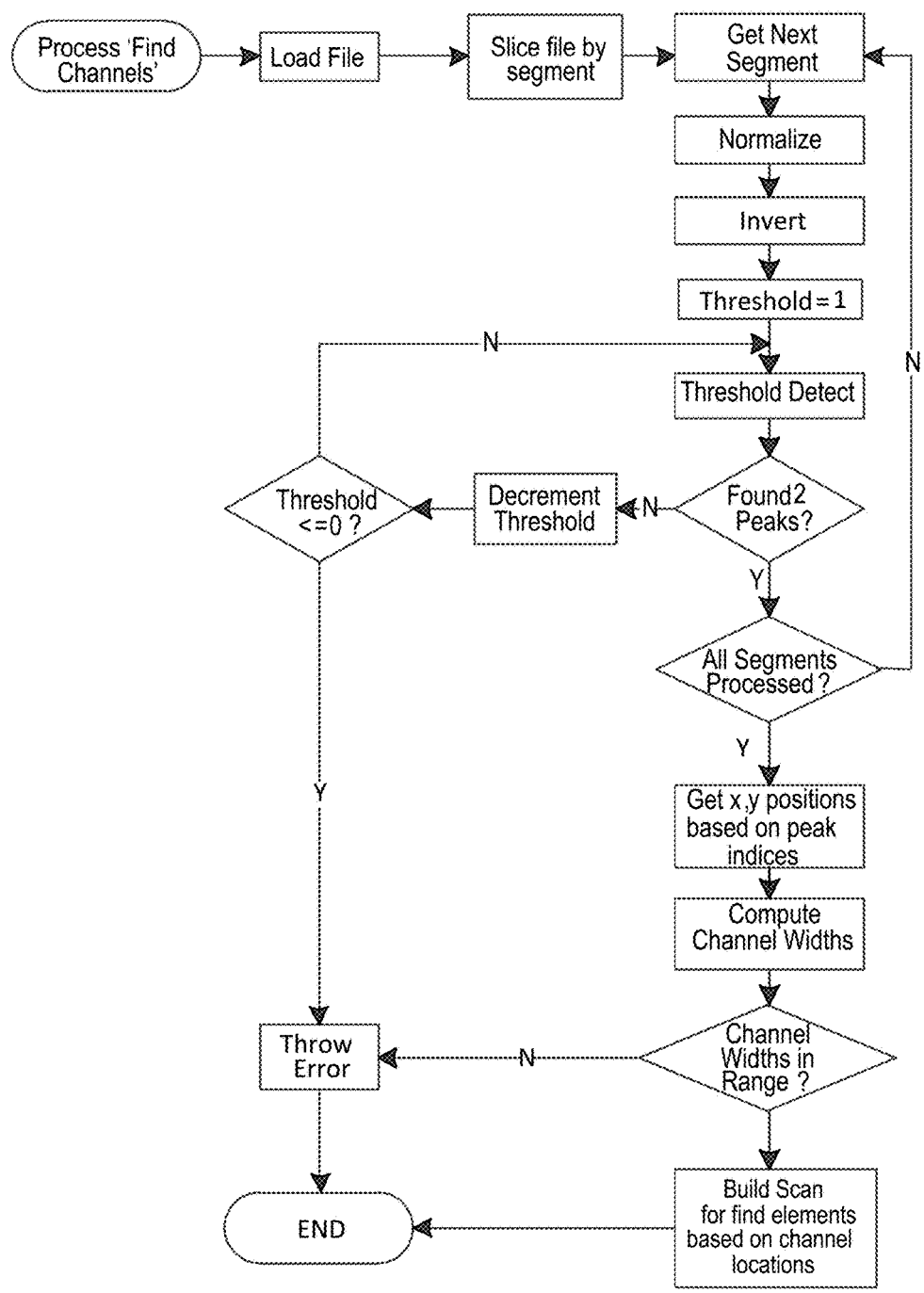
FIG. 83—Find Channels Processing Flowchart.
Figure 84:
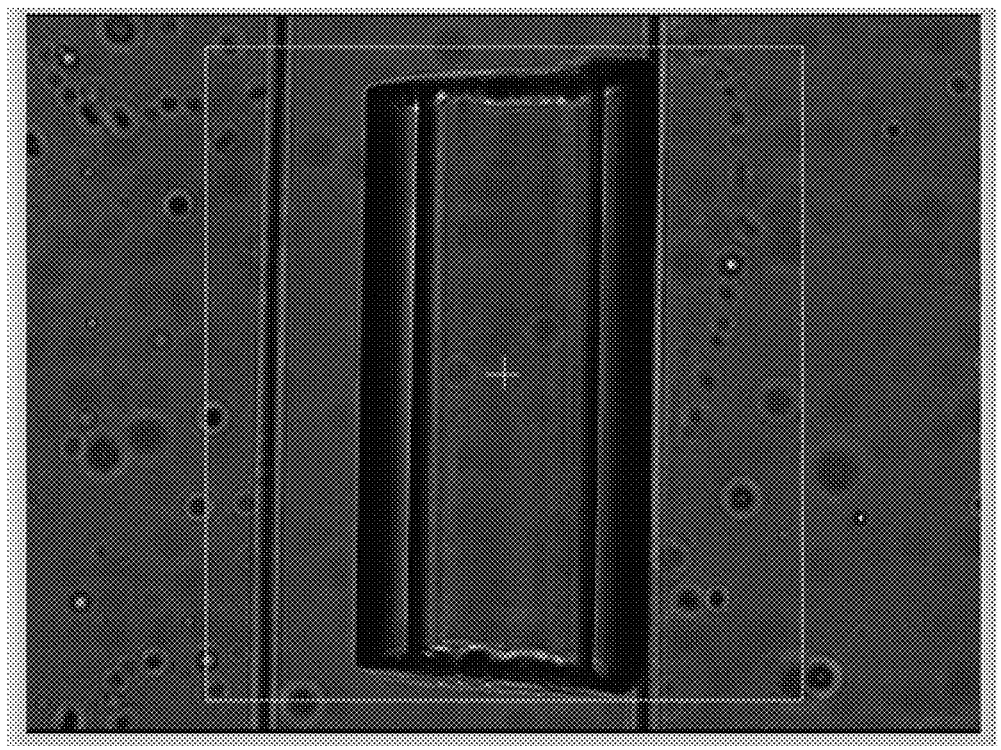
FIG. 84—Find Elements ROI.
Figure 85:
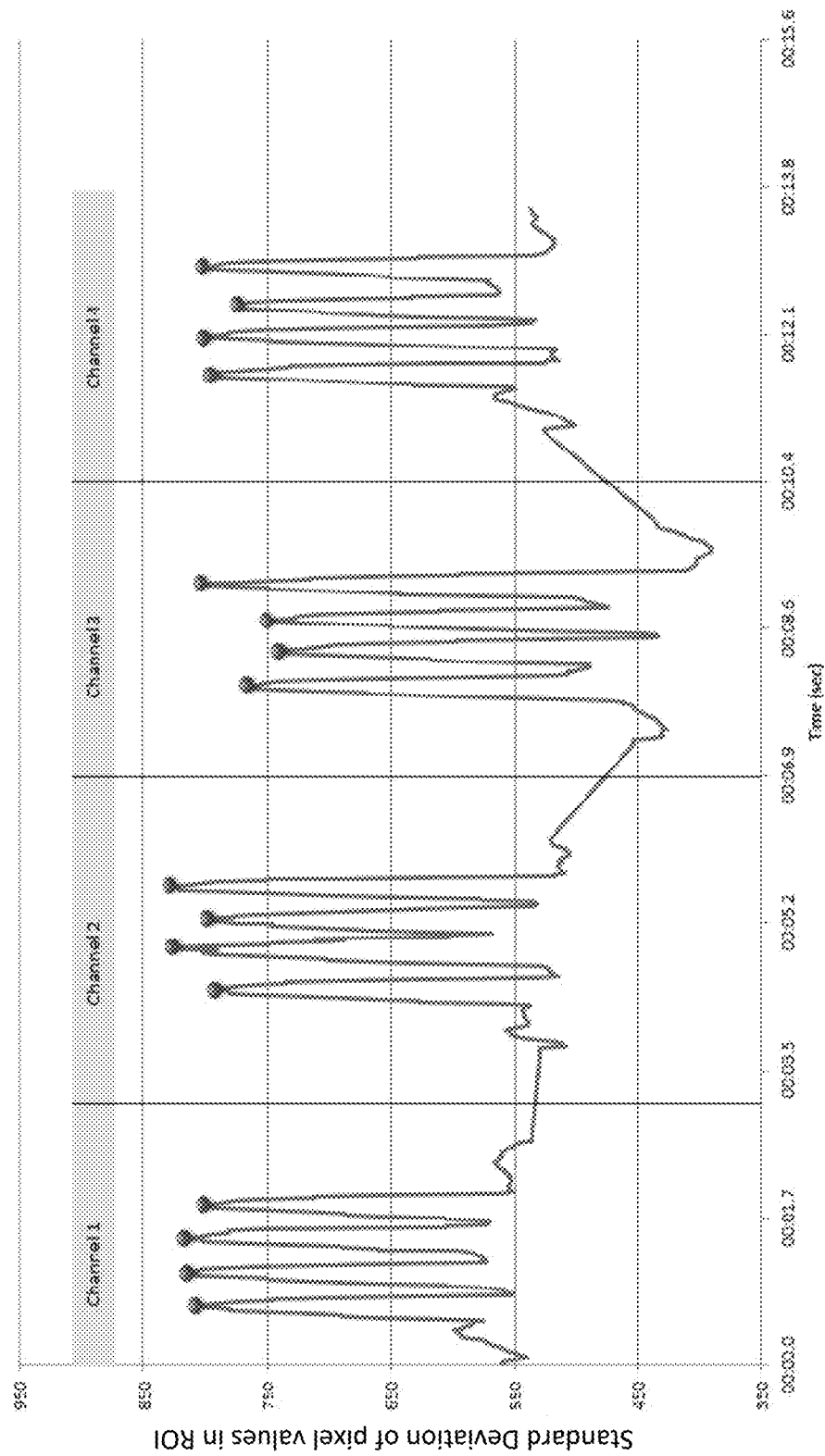
FIG. 85—Find Elements Scan Plot.
Figure 86:
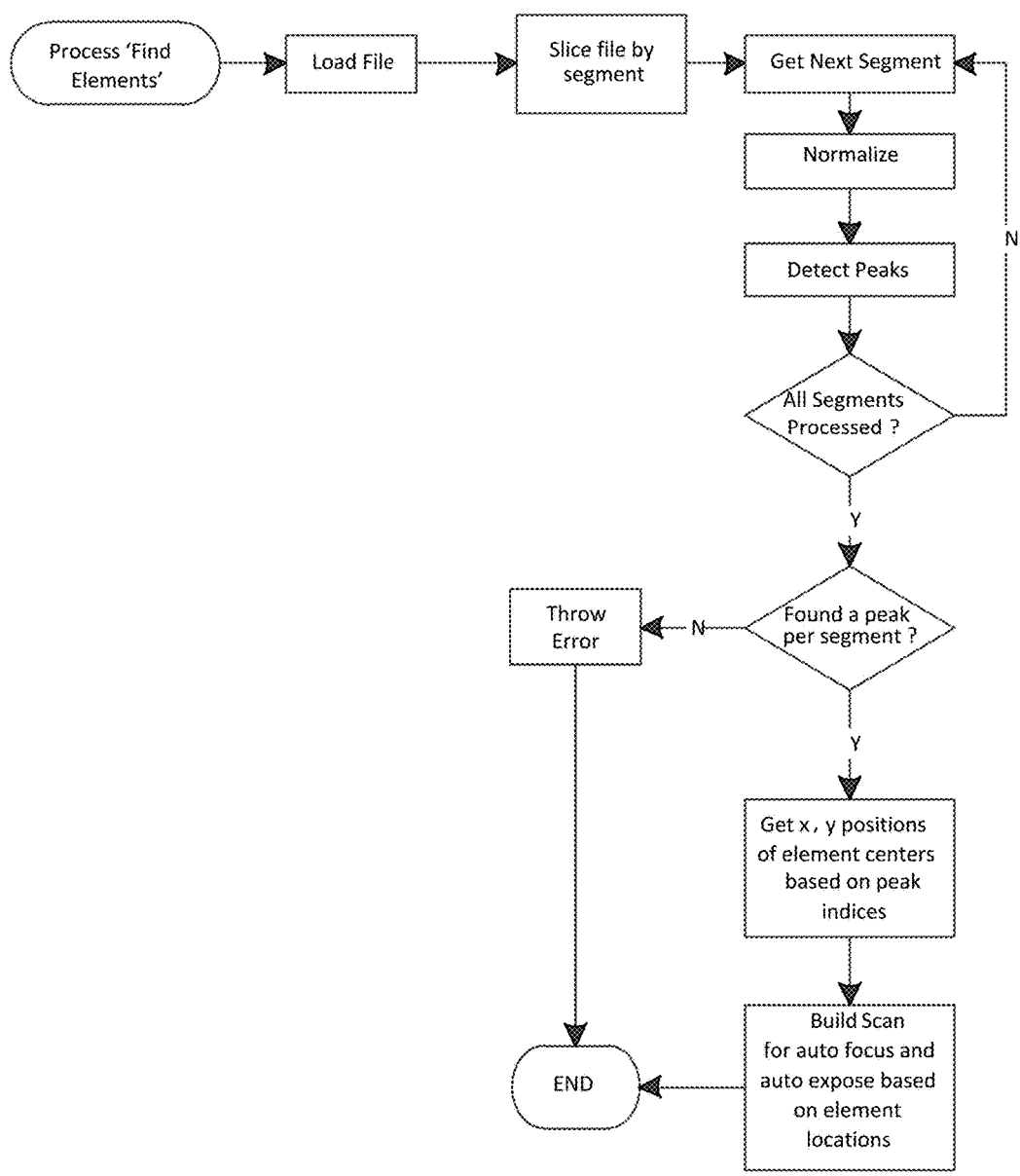
FIG. 86—Find Elements Processing Flowchart.
Figure 87:
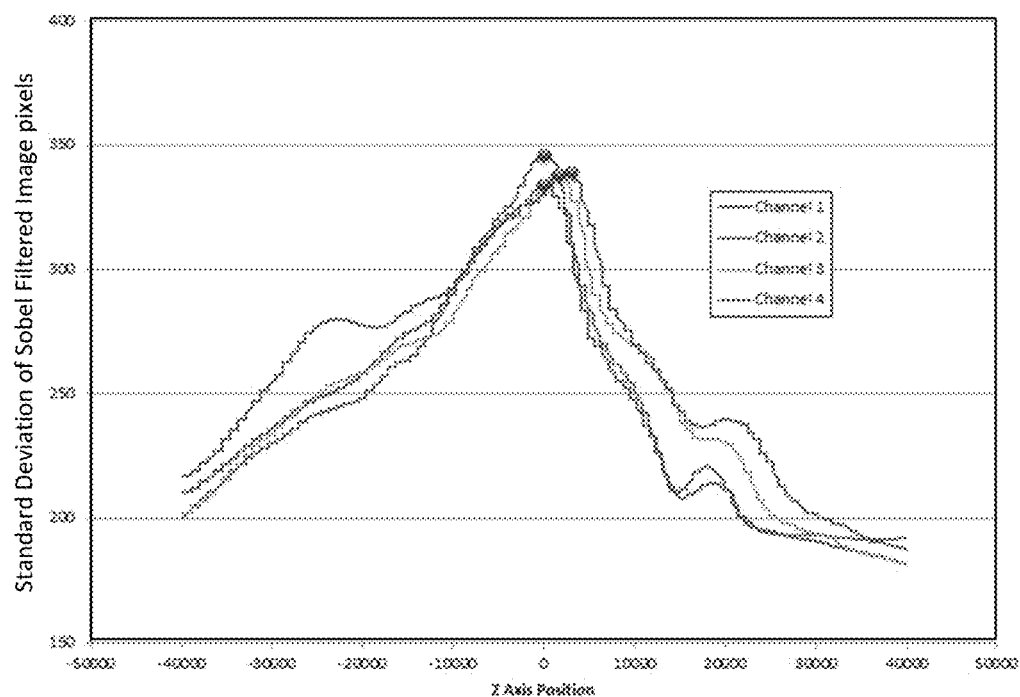
FIG. 87—Auto Focus Scan Plot.
Figure 88:
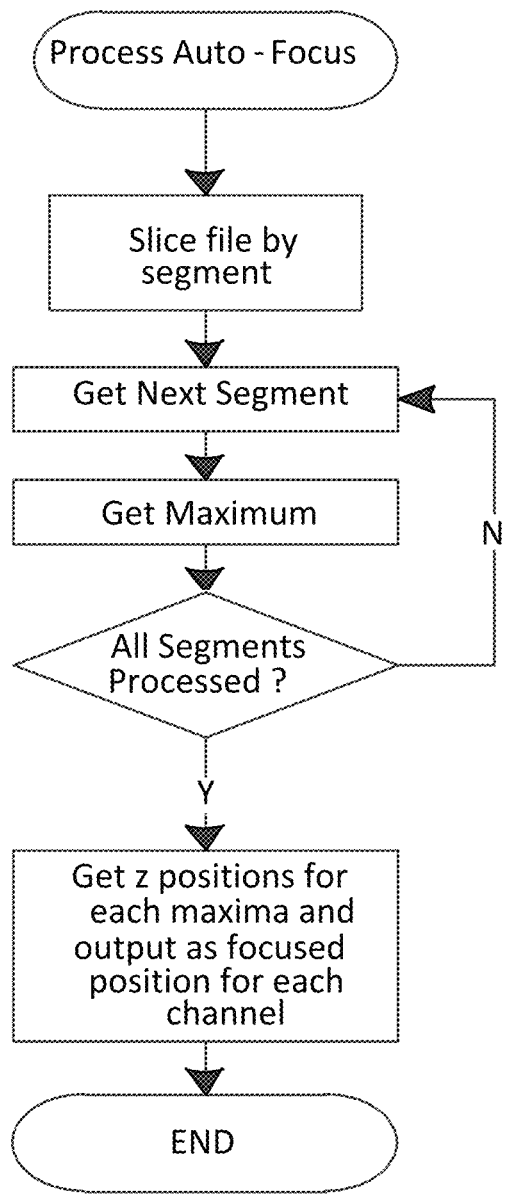
FIG. 88—Auto-Focus Processing Flowchart.
Figure 89:
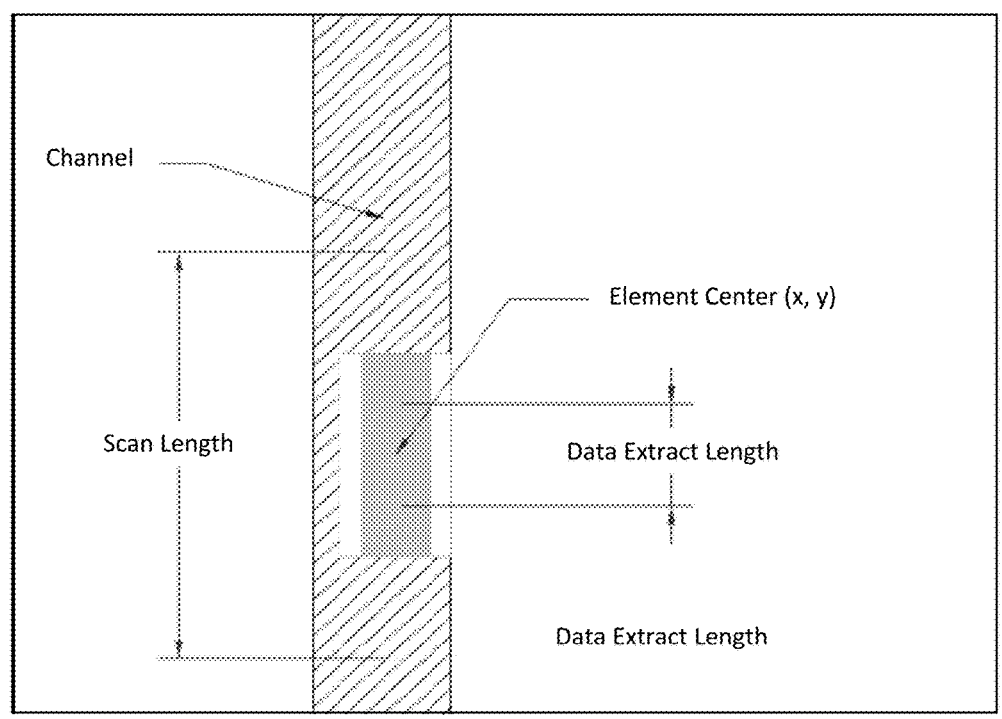
FIG. 89—Auto-Expose Schematic.
Figure 90:
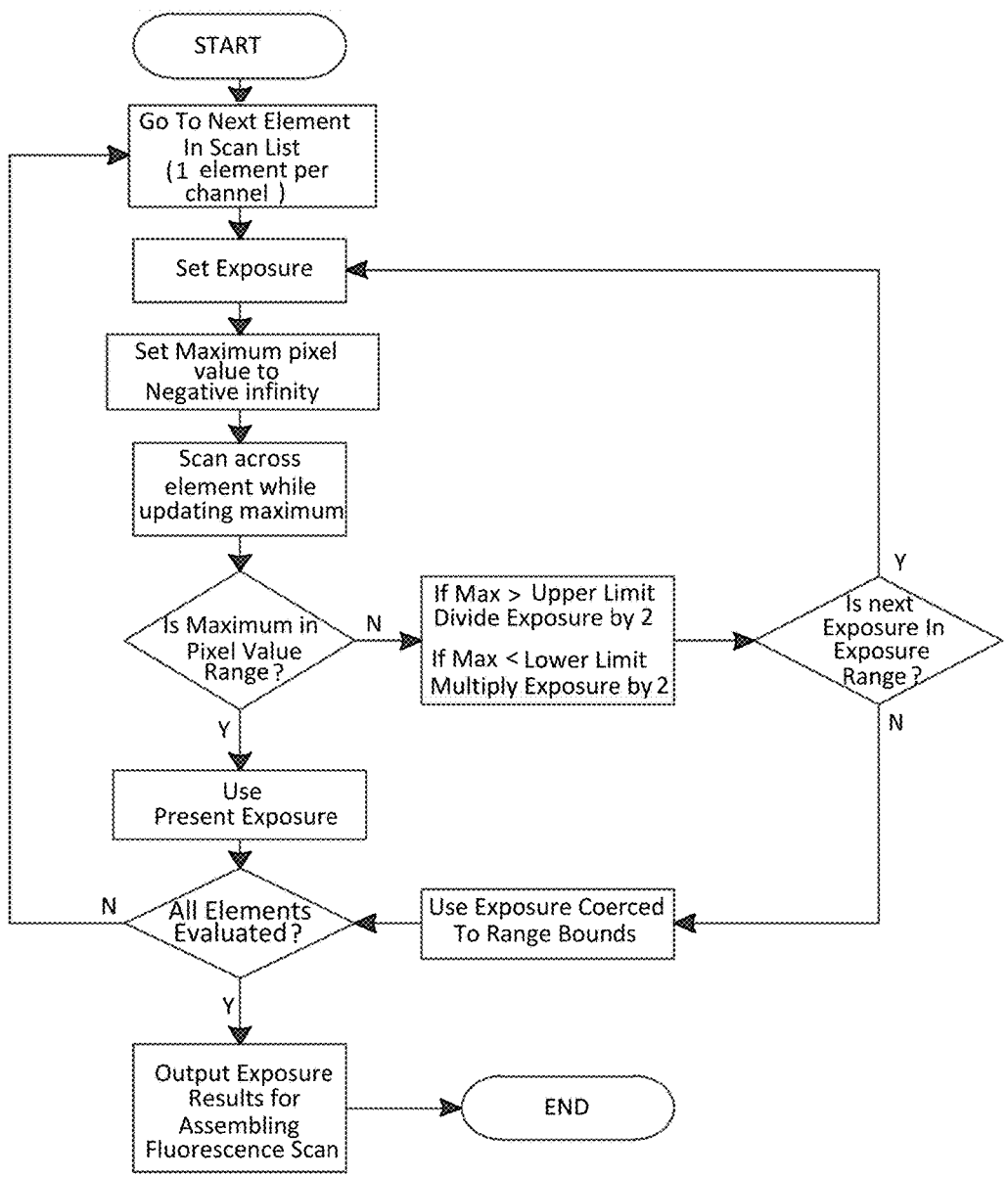
FIG. 90—Auto-Exposure Procedure Flowchart.
Figure 91:
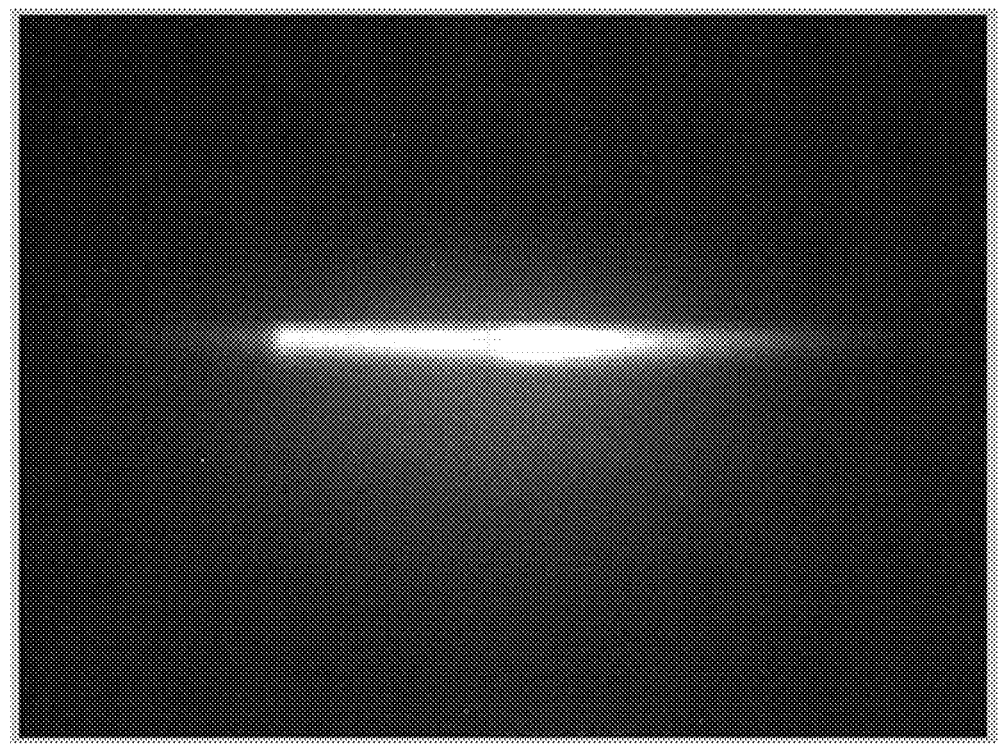
FIG. 91—Laser/ROI Alignment.
Figure 92:
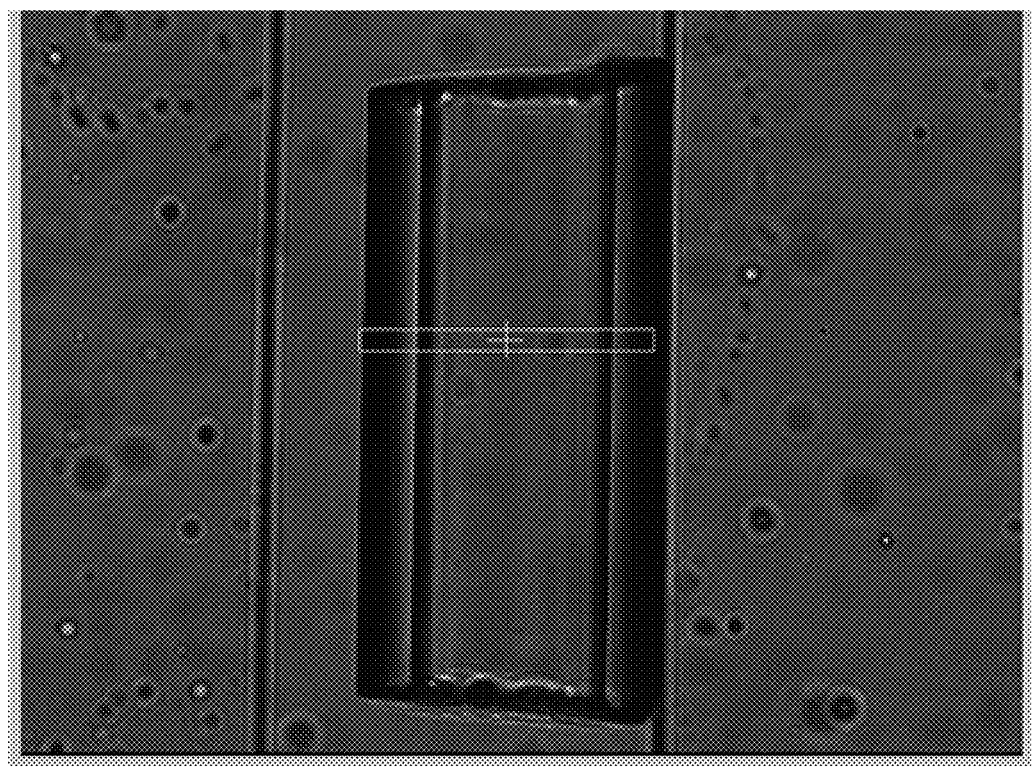
FIG. 92—Fluorescence Scan ROI, bright field.
Figure 93:
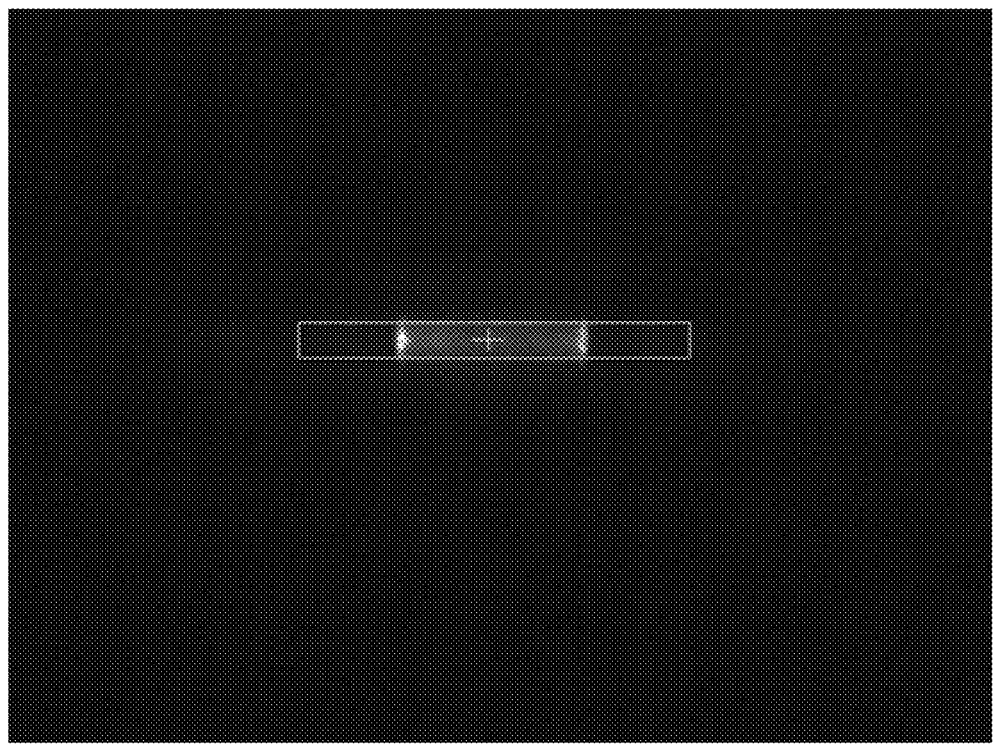
FIG. 93—Fluorescence Scan ROI, laser on, LED off.
Figure 94:
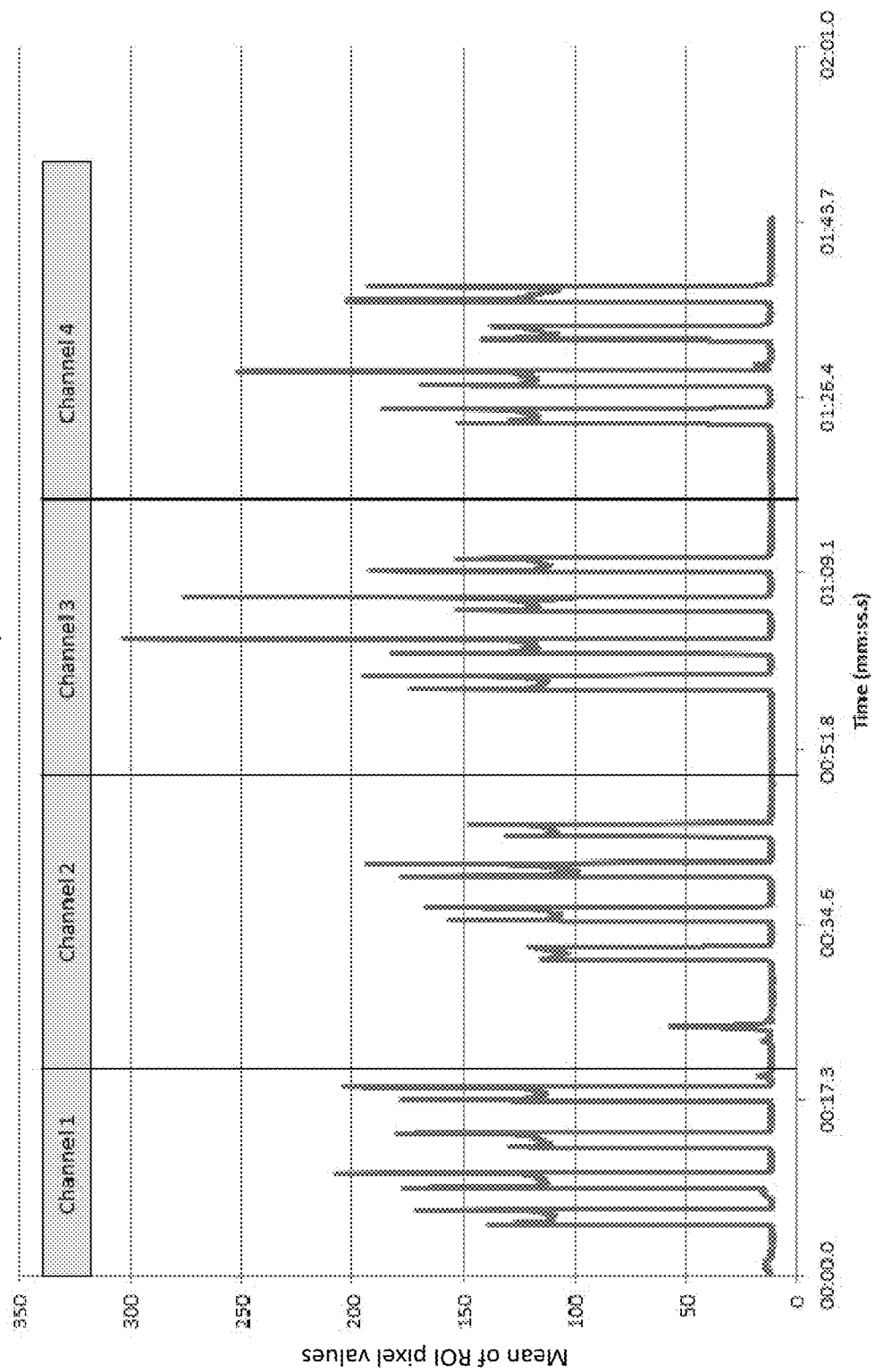
FIG. 94—Fluorescence Scan Data, Full Scan.
Figure 95:
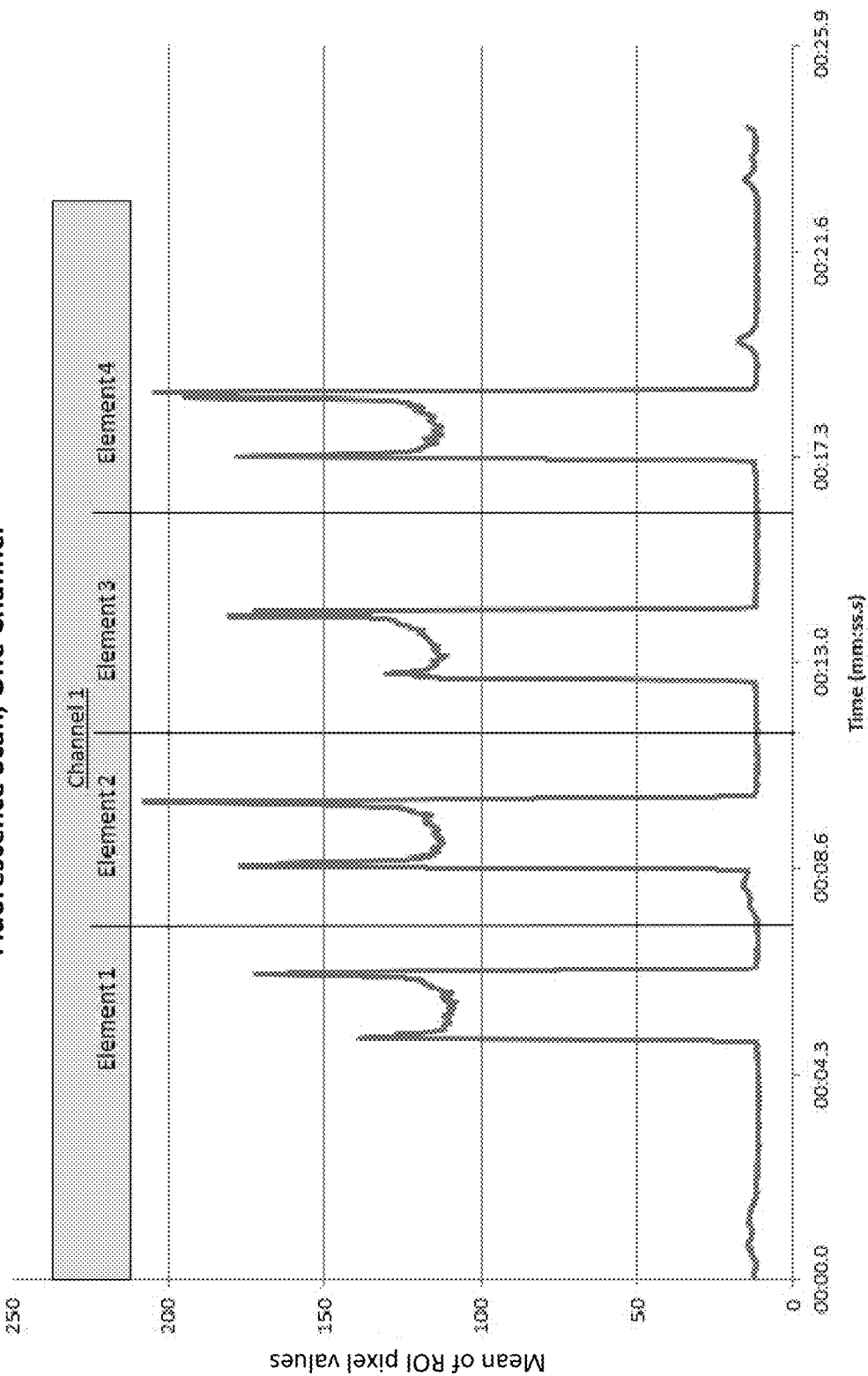
FIG. 95—Fluorescence Scan, One Channel.
Figure 96:
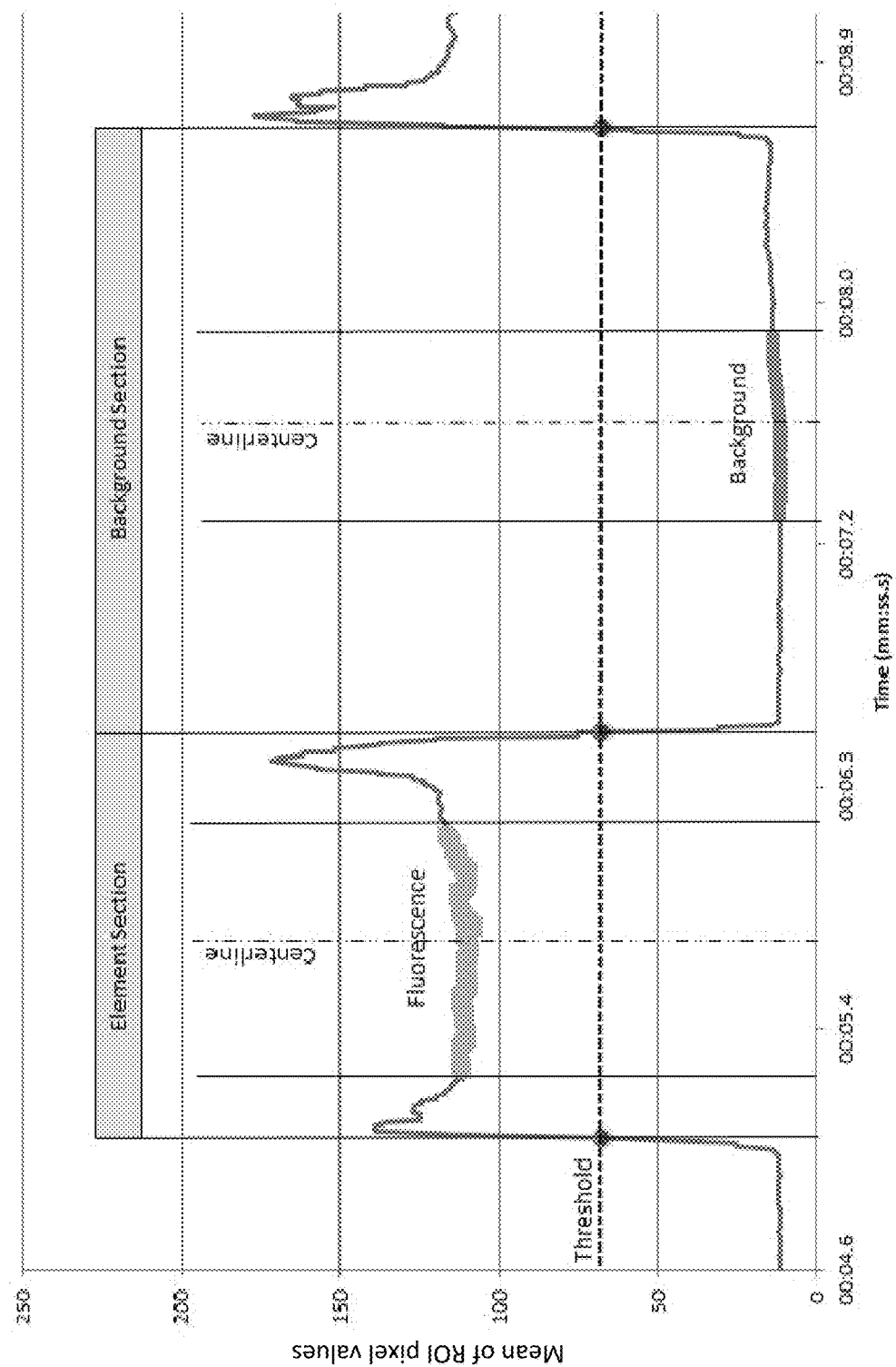
FIG. 96—Fluorescence Scan, One Element.
Figure 97:
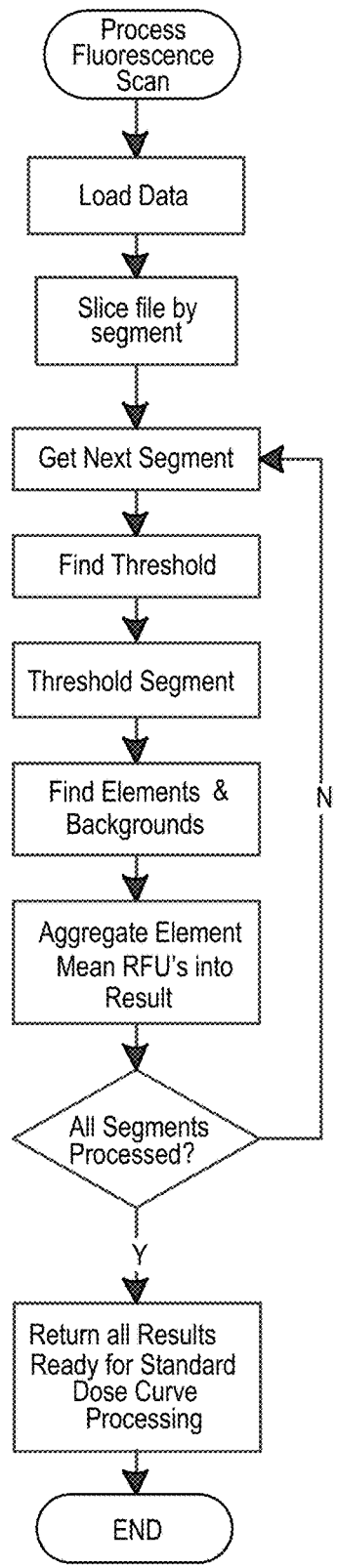
FIG. 97—Fluorescence scan data processing.

Previously described in earlier provisional application regarding the finding of the channels algorithm (as Scanning FIGS. 79, 80 and 81, below), we have FIGS. 62, 63 and 64.

FIG. 62 again illustrates four isolation channels and the path of the scanning sweep performed to identify the precise location of each of the channels. FIG. 63 shows a trace obtained by such a scan using white light illumination as opposed to using fluorescence with benign tracer, by laser-based epi-fluorescence process. The signal shown in FIG. 63 illustrates a high level of signal followed by fairly small dropouts or spikes illustrating where the edge of the channel or shadow is formed as a result of white light illumination as it impinges upon a channel. One can see in the trace that the signal change is a fairly small percentage of the overall background signal, the signal dropping from approximately 3500 counts to just under 2300 counts. This low signal makes the signal processing potentially challenging in that small aberrations or perturbations of the signal caused by other means could interfere with true identification of the channel. FIG. 64 shows a magnified view of two of those spikes illustrating both the left and right edge of a channel as the scanner proceeds across the channel. The description or the present invention utilizing a benign tracer fluorescent dye provides for much greater signal to noise level for this particular trace, and therefore is a significant improvement that can be substituted in the system. The signal level outside of the channel where there is no fluorescent dye present is only the material use in the construction of the cartridge. The fluorescence of those materials is exceedingly low whereas the fluorescence found when crossing over a channel containing liquid with fluorescence dye is exceedingly high, giving a much higher signal to noise level, and therefore greater accuracy and robustness.

In summary, a number of points of great value of the invention will be reviewed. An assay is performed under strictly controlled assay conditions, e.g., heated uniformly, and the controls (e.g., pneumatic valves and pistons) are controlled precisely. This is done while some or all of the assembly is detected, e.g., translated in x, y coordinates relative to an optical axis of a detector (e.g., camera), such that the cassette is simultaneously detected, and tracer condition determined within the various channels while the assay is run. In advantageous implementations, the very same detection instrumentation is later used to detect assay results from capture agent.

A simple technique to implement, having significant value, uses a scanner during the assay protocol to simply detect the presence or absence of the tracer dyes at the various phases of performing the assay protocol. The scanning process generates signal patterns that are compared to predetermined anticipated levels associated with the normal performance of the assay on the cartridge.

This may be readily performed by computer computations, or empirically, based on acceptance levels defined from a number of experimental runs to determine normal levels are and some acceptable range of those levels.

This tracer-based process provides great value in determining whether the assay or cartridge did what it was intended to do during the assay run.

The invention provides an entire system of monitoring methods that can be employed in coordinated fashion to address the previously described failure modes, and others. For example, another failure mode not previously discussed is in the controls based in the bench top operating and scanning instrument itself. If a control fails, e.g., a pneumatic pressure controlling solenoid valve, this failure is also detected. Thus the invention provides a generic means of detecting a host of potential failure modes during a microfluidic assay system run and especially determining whether a reagent is present or not in that channel, and if it is the proper reagent in that channel.

Similarly, the invention enables simply scanning across channels with benign fluorescent dye for the purpose of precisely locating the microfluidic channels, for setting up scan parameters, e.g. for the purpose of identifying optimal focus location, another important feature of significant value. This is in the set up process during the execution of the assay protocol that is described further within, in relation to the Scanning Figures. While the cartridge is running the assay protocol, e.g., under pneumatic protocol, the scanner system can simultaneously be used to perform a number of measurements useful to the later detection phase when the assay is completed. Those measurements include locating the channels based on the fluorescence properties of the channels containing liquid with the tracer dye. Also for determining the optimal focus location—scanning of the z-axis or the focus axis to determine the optimal location of the focus based on the fluorescence intensity profile as well. These are for use in the final scanning performed after the fluidic phase of the assay to make the quantification.

The benefits of the concept primarily pertain to making a robust operational system for making quantitative immunoassay measurements. The reproducibility and the enhanced validity of the data quality provides value for this approach.

Process controls are routinely used in the art in measurements, for example, in ELISA plates, controls are used as individual wells on an ELISA plate. Researchers when running any type of instrument always want to know or have positive verification that the measurement that they made is believable, and it is performed the way it is expected to be performed. The present invention is a means to producing that confidence in a microfluidic system and the data that the system produces.

Using the concepts herein, one may provide reliability scanners or monitoring scanners, independent of any particular type of microfluidic system. Such scanners can be used by anyone running a microfluidic assay to monitor how it is performing.

But the invention is particular beneficial to a microfluidic cartridge in which a series of reagents are flowed in different volumes and different timings, to positively identify that each one was performed properly.

The fluorescent dyes used for benign tracers inherently should not interact with the components of the assay. However if chemical interaction were found, it would be routine to chemically modify the dye to make it more inert or more benign with respect to interferences in the system. There are known conjugations that can be performed on the dye mark for such purpose.

The invention has special utility in respect of complex microfluidic based systems that run a sequence of reagents, assays where quantification is the primary outcome of the measurement Many preferred embodiments leverage what is already available in a system for making quantitative analytical measurement, e.g., existing systems in which analytical measurements are being made over a number of locations and therefore require a moving system to put the cartridge in those locations or move the detector to those locations on the microfluidic system, e.g. cartridge. Techniques following the invention can be readily retrofit into such systems. The invention is particularly applicable to situations in which the fluidic component and the optical components can perform simultaneously and the assay environmental requirements can be met. Temperature is an important parameter to be controlled during the assay protocol. The temperature is typically controlled for immunoassay systems at least to plus or minus one degree and preferably plus or minus ½ degree C. In addition, absence of ambient light or stray light is beneficial, so the assay is performed in a dark environment, as provided by an enclosure. The techniques of the preset invention are compatible with these requirements.

Some of the techniques described have accuracy beyond what ordinary blood laboratories can accomplish. For instance, the GNR's may be useful in stationary, non-portable microfluidic systems, to make very accurate measurements. Techniques of monitoring described have applicability in such instances, e.g. in high throughput blood testing.

This the inventors envision the invention applied to large, less portable higher throughput machines having a high degree of accuracy in a diagnostic type of environment. The main point is that the diagnostic measurement must come with a certain degree of certainty in its accuracy and the novel method of enhancing the degree of certainty in the outcome provided here has wide utility.

A unique assay system will now be described, which involves pneumatically actuated valves and pistons for delivering precise volumes of reagents throughout a microfluidic disposable cartridge.

It is desired to have a bench top operating and reading instrument that can operate the assay cartridge to conduct an assay through timed operation of pneumatic valves on the cartridge that cause flows of fluids that have been placed on the cartridge prior to the assay, and to thereafter read the results.

The instrument needs to have significant robustness in terms of the useful life of the instrument.

It is advantageous to provide the cartridge instrument interface on a movable stage capable of transporting the cartridge in X, Y scanning motions relative to a fixed axis of the optical system that determines location of the cartridge and fluidic channels in it, and monitors progress of the assay and reads the results.

A key requirement is that the cartridge must interface with a pneumatic control component on the instrument in reliable fashion so that no pneumatic leaks occur between the cartridge and the pneumatic actuation system. The valves and pistons on the cartridge are controlled by pressure and vacuum provided by the instrument, and if a leak were to occur at the interface between the cartridge and the reader, those valves would not actuate precisely and reliably. The result would be imprecise control of the flow of reagents on the cartridge and uncertain results with regard to the assay. This is because the assay depends upon precisely timed actuation and metering of reagents, precise volumes and precise times for exposure of the unknown sample to the capture agent, the subsequent flushing and washing of the sample prior to mixing, and exposure with secondary capture agent and then followed by the subsequent washing of that component followed by exposure to a fluorescent dye, or regarding the last two steps, alternatively, exposure to a fluorescently labeled secondary agent.

The concept for reliably making that pneumatic interface involves a compliance component as part of the cartridge. In its preferred form, it is in the form of silicone rubber layer as part of the cartridge that mates with a robust, rigid port component contained in the instrument. The rigid component contains a number of vias through which the pneumatic actuation is provided in the form of pressurized air or vacuum.

One of the important features is the novel arrangement by which both a compliant component and a rigid component are provided, that are brought together under force to form an airtight seal. The beneficial relationship is that the compliant component is located on the disposable element and not on the non-disposable side of the reader. The benefit is that the rigid component has a much longer life than a compliant component, as the rigid component would not undergo deformation over time, whereas a compliant component such as silicone rubber and other forms of rubber or even plastics would undergo inelastic deformation which eventually would lead to failure mode in the form of a pneumatic leak.

In the preferred implementation, the rigid component located on the operating instrument is metal, either aluminum or steel, and the compliant component is PDMS or silicone rubber carried by the assay cartridge.

The rubber is exposed and advantageously is provided as an extension of one of the layers within the cartridge. It is provided on the bottom surface of the cartridge, while the wells and reservoirs of the cartridge are provided on the top surface. The thickness of the silicone rubber is approximately 100 microns. In the preferred implementation it spans the entire surface area of the cartridge which could be 120 millimeters by 85 millimeters, and its durometer is about 30 shore A. A clamping system is provided to place pressure to bring the two together to form a seal that is maintained at numerous pneumatic vias. In the example, there are seven vias positioned in close proximity. For example the spacing between vias is approximately 2 millimeters and the via diameter is approximately one millimeter.

One of the important features of the pneumatic manifold interface is that the rigid component on the instrument is constructed to have a small cross-sectional area of contact. In this manner, only a small force is required to create significant physical pressure upon the compliant material. The pressure locally compresses the compliant material, thereby providing assurance of a leak-tight seal. The small area is achieved by providing a pneumatic manifold interface with very small dimensions in both the length and the width. In the example, the entire width of the interface seat is approximately 3 or 4 millimeters wide by 10 millimeters long, that includes all seven of the vias. When the cartridge is in operating position on the operating/reading instrument, its end with pneumatic interface vias rests on the rigid pneumatic interface part of the instrument, the other end of the cartridge being s supported by a fixed seat which holds the cartridge in location. X, Y direction constraint is provided by a set of four corner retaining stands, these being tapered to enable easy insertion of the cartridge into the thus-formed receptacle pocket.

Pressure is applied to the cartridge only in one location to obtain stability in the Z coordinate. The force is applied downward through the cartridge in one embodiment by a roller connected to a leaf spring, the roller arranged to contact the top surface the cartridge and provide a downward force which compresses the compliant material on the cartridge against the pneumatic manifold. In another implementation, as shown here, a simple releasable clamp applies the pressure.

There are alternate techniques to achieve the clamping force as will be understood by a skilled person, including spring-loaded mechanisms, roller mechanisms, and motorized rack and pinion. A pneumatic solenoid or an electrical solenoid can similarly apply force to maintain the connecting pressure.

Cost effectiveness and simplicity are usually the objective when designing the clamping mechanism. A motorized roller is a convenience from a user point of view, but a swing bar as shown is simple, effective, and avoids potential failure modes.

The other significant feature on the movable stage is the pneumatic interface manifold. The pneumatic control lines, the seven different pneumatic control lines in this implementation, are controlled by solenoid valves that are carried on the X, Y stage and connected via flexible hose to a pneumatic manifold in pneumatic communication with a vacuum pump and a pressure pump.

An important advantage of putting the pneumatic valves on the stage is that only two flexible pneumatic lines and a flexible electrical control cable are required to move during the motion process of the stage, so that the pneumatic channels connecting the solenoid valves to the cartridge are hard fixed channels as part of the pneumatic interface. One of the advantages is reliability of using fixed machined channels in a robust metal or plastic component compared with flexible tube connectors that over time tend to fail. Another beneficial feature of having the pneumatic interface as a fixed machined component mounted on the stage is its contribution to the desired speed of the assay. This relates to the ability to minimize the dead volumes of the pneumatic passages. This is important in the operation of the cartridge because the valves and the pistons change states as a result of switching from either a vacuum state to a pressurized state. The speed at which that occurs is directly proportional to the dead volumes in those channels. For example, switching from pressure to vacuum requires the vacuum to be completely drawn on whatever volume is contained downstream of the solenoid valves. Using the features just described, all of the downstream channels from the solenoid valves are extremely small, and the distance between the solenoid valves and the chip is maintained in a very short distance. Yet another advantage of having the pneumatic interface as a fixed machined component mounted on the stage having a low dead volume is in the ability to use low flow rate, and therefore inexpensive vacuum and pressure pumps. Since the volume of the pneumatic lines downstream of the solenoid valves and the rate of states changes determine the average flow rate, it is desirable to keep the dead volume low so as to allow the use of smaller, low flow rate pumps.

Speed is important because a large number of actuations must occur throughout the assay protocol. There can be tens of thousands of actuations and even tens of milliseconds or hundreds of milliseconds difference can add up to a substantial loss of time.

There are two different active components on the cartridge, valves and pistons. The purpose of the valves is to determine which reagents flow and to which channels they flow. The pistons are the primary components for motivating the fluid. They provide the positive and negative displacement to the reagents located on the cartridge, and so are the primary elements for motivating fluid.

The features contained on the stage are the pneumatic interface with the solenoid valves and cartridge and the clamping device. That is all that is on the stage that moves. The cartridge on the movable stage is exposed to a fixed heater plate underneath, supported only 4 or 5 millimeters below the surface of the cartridge and exposed face-to-face for radiant heat transfer. The bottom surface of the cartridge where the active capture elements are contained in the microfluidic channels must be maintained at a constant temperature between 35 and 37 degrees C. The heater plate extends in the dimension that is actually slightly larger than the surface area of the cartridge to cover its range of travel.

A uniform temperature profile is thus maintained over the surface of the cartridge. The biggest advantage of that is that the temperature of the cartridge is easily maintained without having to control the temperature of the entire reader enclosure. Thus there is no concern about heating the electronics and other sensitive components within the enclosure. Temperature control and stability is only provided at the critical surface.

Further, it is easier to control the temperature much more precisely in this fashion, using radiant heat, than it is using a convective process. It also enables temperature stabilization to be achieved much quicker than by a convective process. This is important for antibody kinetics. Antibody binding is temperature dependent so accurately controlling that temperature is an improved way of controlling the rate of the kinetics.

This is particularly important because many of the assays desired to be run are "single point assays". The assay is run for a fixed amount of time and the resulting fluorescence signal is proportional to the concentration of the analyte in the sample. Any other parameters that affect the fluorescence needs to be controlled precisely so that the variable is the concentration of the analyte. Temperature is a significant parameter that affects the binding kinetics between the antigens and the capture antibodies. And so that needs to be controlled so that potential source of variation it is taken out of the equation. Also, a convenient feature for a user to be able to just turn the instrument on and within a minute or two provide their cartridge and execute an assay run.

One of the features of the instrument is to excite a fluorescence signal using a laser and then capture that fluorescence with an objective lens while the stage is translated. A well-known epifluorescence configuration is employed in which the excitation signal, provided by a laser or laser diode, is sent through an objective lens and then the returning fluorescence is captured by the same objective lens and sent to an imaging CCD camera. The heater plate which held fixed directly underneath the cartridge is provided with a hole that allows both the excitation and the emission signal to propagate through to the fixed optical system.

All objective lenses have a so-called "working distance." Key features of an objective lens include numerical aperture and magnification, which will determine the ability of the objective to capture the fluorescence intensity in a very efficient manner and image that back to the CCD camera. The working distance for typical 10× objectives is somewhere between 5 and 12 millimeters. It is important to maintain a distance of somewhere between 5 and 12 millimeters between the objective and the bottom surface of the cartridge.

This critical distance is achieved despite the intervening presence of the heater plate. This is achieved by the heater plate being a thin aluminum plate, about one eighth of an inch thick with very thin heater strips, e.g., $\frac{1}{32}$" thick, adhesively attached to the aluminum heater plate.

The total distance between the objective and bottom of the cartridge is approximately 12 millimeters, the thickness of the plate is a small fraction of that, it is 4-6, and the plate itself has a hole that allows the light to transmit through. The hole is sized such that the objective is brought up into the hole itself, fitting partially into the plate.

Sequence of Operation

The sequence begins with placing the cartridge onto the cartridge receptacle pocket, then sealing that cartridge using a clamping mechanism, then after warm-up, actuating the pneumatic valves which forces the reagents including the buffers and the samples and the detection antibodies to flow in a very specific sequence for a specific period of time allowing incubation to occur. The incubation results in the binding of the unknown antigen in the sample to the capture moieties contained in the cartridge. The various reagents flow in a given sequence with intermediate wash steps followed finally by a fluorescence scanning process In some cases, the stage remains stationery throughout the entire incubation process. In other cases, described herein, the stage is moved during incubation to enable visual monitoring by use of tracers in the fluid. The final reagent process is to flow detection dye or fluorescent dye through the channels which then binds to the immobilized secondary antibody. During this process, if not previously done using tracer dyes, it is necessary to move the stage because it is during this process that the fluorescence dye found in the channels is used as an identification beacon for identifying the location of the channels. The optical system is actually used in coordination with motion control system to identify the location of the channels by exciting with the laser the fluorescence in those channels and the locations of those channels are identified as a result of an increased signal where the channels come through.

The bench top unit implementation described here contains no liquids and no liquids flow between cartridge and the bench top unit.

In the following, we describe other novel details of a preferred bench top unit.

Referring to the Figures, the bench top unit has just a few key subsystems. The subsystem that holds the cartridge. The cartridge is placed into a little receptacle area and located in that receptacle area is the pneumatic interface boss that has limited end surface area ("lip area") for contact with the cartridge. It protrudes off of the surface, that is the highest surface. One end of the cartridge sits on that boss. The other end of the cartridge sits on a small rail on the other side of this containment area. These are corner guides that make it easier to place the cartridge. A small arm contains on it a little spring loaded containment clamp. The spring loaded clamp bar comes down and rests on the top surface of the cartridge, and pushes the cartridge down on to the pneumatic boss.

On the opposite end is a lock and catch that holds the device in its clamping position. The user pulls down on part of the arm until it clicks and locks into the catch. Because of leverage, the user need not apply great force. A force of 4 or 5 pounds is effective to push the cartridge down against the pneumatic boss sufficient to guarantee a sound pneumatic interface seal.

Also on the subassembly are, not shown here, there are a number of pneumatic channels that lead back to the manifold with valves located on it, carried by the X, Y stage. These are the ports for vacuum and pressure. Each of the actuation ports is controlled by a solenoid valve in the valve bank. It can switch each one of these ports to either vacuum or pressure.

In the epi-fluorescent optical system is a laser diode, red laser diode, a collimator lens, a cylindrical lens, and three filters. An excitation filter ensures any of the excitation light is within a certain wavelength band. There is a dichroic beam splitter which has a high reflectivity for the red of excitation 640 nanometers, but very low reflectivity for the deeper red that comes back as a result of the fluorescence, around 680-690 nanometers. The reflects 640, but 680 transmits. The 680 coming through hits another filter, the emission filter. This allows only a small band—it blocks all red, and it allows a small band. Following this is a focusing lens onto a camera, called a tube lens.

A cylindrical lens in the infinity space between the collimator and the injector provides a stigmatic beam at the target. This produces a laser beam at target of very long elliptical profile. The beam is approximately 500 microns long by about 8 microns thick. It is like a line. The instrument scans that line down the channels to illuminate the whole width of the channel.

Scanning an Array of Fixed Micro-Flow Elements

The novel arrays of elements described above are useful only if effectively read after the fluid assay is performed. The following scanning apparatus, procedures and methods for automatically scanning a microfluidic chip effectively solves the problem with arrays of micro-flow elements, and in particular, micro-length tube elements.

2 Scanner Description
2.1 The Scanner
2.2 The Scan
2.3 Chip Layout
2.4 Find Channels
2.5 Find Elements
2.6 Auto—Focus
2.7 Auto—Exposure
2.8 Fluorescence Scan
2.9 Scan Data Processing
2.9.1 Load Data
2.9.2 Break data into segments
2.9.3 Thresholding
2.9.4 Locate Elements and Background in time history
2.9.5 Aggregate element mean RFU's into results
Introduction—Scanner The general scanning concepts of invention are given in the block diagrams and flow charts. These are followed by description of a specific, novel implementation. As a precursor to the specific method to be described, the general capabilities of the scanner, a scan, and the general microfluidic chip layout will be described first. These three sections are then followed by each sub-procedure in sequence that contributes to the overall method for automatically scanning a microfluidic chip.

The Scanner

The scanner utilized in this method is a fixed, inverted epifluorescent microscope equipped with a three axis (x, y, and z) stage for motion of the chip to be read, a CCD camera for bright field imaging and fluorescence detection, a diode-pumped solid-state laser for excitation, and a white LED for bright field illumination. A cylindrical lens is used in the laser optical path prior to any filters to expand the beam size. This allows the excitation of a larger surface area in a single pass and allows for some flexibility when placing the elements in the flow channel during chip manufacturing. All of these scanner components are controllable via a computer as follows: on command x, y, z motion, image acquisition/imaging settings, laser on/off, and LED on/off. The method described herein uses various sequences and combinations of the scanner control/acquisition to orchestrate the automatic scan. See Scanning for a general schematic of the scanner.

The Scan

A scan is comprised of a sequence of steps configured with start/end (x, y) positions, z (focus) position, velocity, and a segment number. When the end position of a step in the sequence is not the start position of the next step, the stage will make a full speed move to the x, y, z position of the start of the next step in the sequence, and no data is collected during this rapid move. While executing one of the steps (moving from start to end in x, y at a fixed z) data is collected versus time. The data that is collected includes time, the step segment number (assigned while configuring a scan step), the present x and y positions, the camera settings (gain, exposure etc.), and information extracted from the images in the video stream from the camera. The information extracted from the camera video is based on a region of interest (ROI). An ROI is defined as a rectangle somewhere in the image. The pixels within the ROI are processed to extract information from the image. For example the mean, median, standard deviation, max, min, etc. of the pixels inside the ROI from a given image are computed and included in the data collected during a step move. At the conclusion of a scan, the data collected throughout the sequence of steps that comprise the scan is written to a file (see sample in) that may then be processed to extract desired information.

The ability to flag various steps in a scan with a unique segment number that is subsequently written into the scan data file ("seeded into the file") greatly facilitates processing of scan data files and significantly improves the robustness of the various signal processing algorithms. This capability is uniquely made use of a number of times throughout the auto-scan method.

All of the sub-procedures described in the subsequent sections are based on the scan just described above, with the exception of the Auto-Focus sub-procedure.

Chip Layout

A priori knowledge of the chip features/layout is necessary to facilitate automatic scanning A chip layout is depicted in Scanning. In this Figure, the chip itself is a 25×75 mm standard microscope glass slide. Within the chip is the scan zone that contains the elements of interest. The 'scan zone-zoom' provides more detail. In particular, Scanning shows that there are a number of fluidic channels (1 thru n left to right in the Figure) and there are a number of elements per flow channel (1 thru n top to bottom in the Figure). It is the elements that are fluorescing are to be scanned in detail. The vertical lines in the middle of the flow channels depict the scan moves that are executed for the purposes of locating the channels, and the horizontal lines above and below the elements depict the scan moves that are executed for the purposes of locating the elements and subsequently performing the fluorescence measurements.

Find Flow Channels

The first step in the automatic scan is to determine where the channels are located relative to the stage x, y positions, and to also determine the skew of the chip in the event that the channels are not exactly parallel with the vertical axis. Predefined x, y positions based on a previously complete homing of the scanner stage are sufficient for guaranteeing that the scan executed will, in fact, pass over all the channel edges, given that the chip is mechanically referenced to the stage. The issue is then to determine precisely where the channel edges are relative to the x, y stage positions. To this end, a 'find channels' scan is executed following the horizontal lines in the middle of the channels shown in Scanning More specifically, the find channels scan is broken into distinct steps such that there is a step across each individual channel at the 'top' and the 'bottom' of the scan zone that is tagged with a unique segment number in order to facilitate subsequent data processing. Further, the scan is done in bright field (i.e. laser off, LED on), the ROI used is very narrow in width and extends the full height of the image (as show in Scanning), and the z position is intentionally 'defocused' from a nominal focused z position of zero, as established by homing the stage.

Alternatively, the 'Find Channels' routine can be done during the 'detect' flow phase of the chip assay. In this mode, the channels are filled with fluorescent dye. The scan to find the channels is then done as described above but the scanner is in fluorescence mode (i.e. laser on, LED off). This has the advantage that the signal to noise ratio is very high.

An example of the data collected during a 'find channels' scan is given in Scanning and a zoom in to a single channel scan is given in Scanning. In this example the 'find channels' scan has eight steps, one for each channel crossing above and below the elements.

A scan data file from a find channels scan is processed on a per scan segment basis. Consequently, the data processing operates on a set of data as depicted. The data processing proceeds as shown in Scanning. In the Figure, the data processing will produce a scan configuration that can be used for the find micro-length tube elements procedure, or it will throw an error that will halt the auto-scan procedure. The information collected during this procedure is useful for:

Defining the Find Elements Scan.
Defining the Fluorescence Scan.
Collecting Chip Quality Control data about:
Variations in channel width
Variations in channel to chip reference edge
Find Micro-length tube Elements The primary goal of find elements is to locate the first micro-length tube element in each flow channel. This information is then subsequently used for executing the auto-focus and auto-exposure procedures. The find channels procedure must be a precursor to this procedure in that the scan utilized by find elements is built via knowledge of the channel positions. The find elements scan is broken into a segment per channel and follows the horizontal lines as depicted in Scanning. This scan is done in bright field (i.e. laser off, LED on), and the ROI used is wider than a channel in width and has a height greater than the length of a micro-length tube element. This ROI is shown in Scanning. Further, the scan z position is intentionally 'defocused' from a nominal focused z position of zero, as established by homing the stage.

An example of the data collected during a 'find elements' scan is given in Scanning, and the processing sequence of the 'find elements' scan data is given as a flowchart in Scanning. The results of processing this scan data are the x, y position of each element in each channel. The information collected during this procedure is useful for: The x, y positions to execute Auto-Focus.

The x, y positions to execute Auto-Exposure.
The x, y positions for processing a Fluorescence Scan.
Validating that the predetermined number of elements are in fact present on the chip.
Collecting Chip Quality Control data about element placement.
Auto-Focus This procedure takes as input the x, y positions of the first micro-length tube element in each channel as determined by the 'find elements' procedure. For each of these positions the procedure moves to the given x, y position and conducts a sweep of z from a negative position thru zero to a positive position. While the z sweep is taking place the full images from the camera video stream are run thru a Sobel edge detect filter and then the resulting image standard deviation is computed. The end result is a set of data as shown in Scanning. For each segment (i.e. at the x, y position of an element), the resulting z position versus standard deviation plot is then used to find the z position at the maximum value of the standard deviation (See Scanning for details). The z positions, at the maximum standard deviation, from each segment are the 'in focus' z positions for each channel on the chip. The information collected during this procedure is useful for: Setting the focus for the Fluorescence Scan, Gauging the degree to which the chip/and or stage is not flat with respect to the optical system.
Auto-Exposure The purpose of this procedure is to select the appropriate camera exposure setting in order to efficiently utilize the range of the camera given the fluorescence level of the micro-length tube elements. Too short of an exposure will lead to dark images, poor signal to noise, and underutilizes the camera range. Too long of an exposure will lead to saturated images that cannot be used for collecting a fluorescence measurement. The degree to which a micro-length tube element fluoresces is dependent on the concentration of the targeted capture agent, e.g. antibody, in the sample under investigation and therefore will not necessarily be known in advance. As a result, the best exposure setting must be determined in-situ, for each fluid channel in the chip.

This procedure takes as input:
The x, y positions of the first micro-length tube element in each channel as determined by the 'find elements' procedure.
Maximum pixel value range
Exposure range and start value
Scan Half Length
Data Extract Half Length From this input, a scan, as depicted in Scanning, is constructed. The auto-expose procedure then follows the sequence given in Scanning. The ROI used for this procedure is the same as that used for the fluorescence scan discussed in the next section. This procedure is done with the LED off and the Laser on. To avoid significant photo-bleaching effects the velocity of this scan is selected to minimize the laser exposure incurred by the element. The end result of this process is the optimal exposure setting per channel to be used in the fluorescence scan discussed next.

Fluorescence Scan

Using the (x, y) positions, z (focus) and camera exposure settings found from the results of the 'Channel Find', 'Element Find', 'Auto-Focus', and 'Auto-Exposure' the Fluorescence Scan (FS) can be constructed. As with all measurements from the scanner, an ROI is used to collect pixel intensity values. The ROI for the fluorescence scan is a rectangle oriented with the long side perpendicular to the flow channel and positioned in the image on top of the laser cross section (Scanning & 28. The size of the ROI is determined by the size of the laser spot, the width of the fluorescent region on the micro-length tube element, the width of the channel containing the element, the number of pixels needed for a measurement and the scan speed. These parameters can be predetermined and optimized empirically and therefore do not change for each FS. The FS starts at a location upstream of the first micro-length tube element in the channel to be scanned. The scanner is put into fluorescence mode (LED: Off, Laser: On) and the camera exposure time and z position (focus) are set. A scan is performed (see section 0). Scanning depicts a snapshot of an element during a FS.

Scan Data Processing
This sections discussion is available as a flowchart shown in Scanning
Load Data
The data collected from the FS is loaded into memory and the mean ROI value is plotted vs. time (Scanning) This Figure depicts the mean ROI value for all the channels scanned vs. time.

Break Data into Segments

To process this data, it is broken up into segments where each segment consists of one flow channel's worth of data ( ). A peak detection algorithm is used to determine the element positions in the channel with respect to the background signal. The micro-length tube element positions found during the 'Element Find' can also be used to locate the elements in the segment.

Thresholding

Since the relative signal intensities for all micro-length tube elements in one channel are approximately equal, k-means clustering can be used to separate the pixels associated with the background from the pixels associated with the micro-length tube element. The outputs of the clustering algorithm are centroids representing the mean background value and the mean element value. The mid-point between these two centroids is used as a threshold. Thresholding must be done on a channel-by-channel basis due to differing background and exposure settings per fluid channel.

Locate Elements and Background in Time History

Once a suitable threshold is found, the mean time history gets filtered using a Savitzky-Golay (SG) filter and the peak detect algorithm identifies all threshold crossings larger than a predetermined width, thereby rejecting of most of the high frequency noise in the data. Using the found threshold crossings the time history is further broken up into an element signal component and a background signal component. The element signal component comes from the section of the channel with the fluorescent micro-length tube element in it. The background component comes from the 'empty' section of the channel adjacent to, but downstream of the fluorescent element ( ). This allows each micro-length tube element to have its own background-offset correction. The center of each component is found and the data points +/−25% of the element width are then extracted to create an average value for each component (See the highlighted points in Scanning) Only points about the center of the element and background are used in order to eliminate element edge effects. Since the signal rides on a background offset, the average of the background points is subtracted from the average of the element points and the result is normalized for camera exposure and finally stored as that element's mean RFU (Relative Fluorescence Unit). This is performed for each micro-length tube element in each channel on the chip.

Aggregate Element Mean RFU's into Results

Statistics are done on all micro-length tube elements' mean RFUs for each channel and outliers are removed by finding the lowest % CV among all combinations of element means. A minimum number of micro-length tube elements must be retained for statistical purposes. These result values can now be applied to a standard dose curve to determine capture agent, e.g. antibody, concentration.

A number of embodiments of the invention have been described. Nevertheless, it will be understood that various modifications may be made without departing from the spirit and scope of the invention.

PDMS Membrane-Confined Nucleic Acid and Antibody/Antigen-Functionalized Micro-Length Tube Capture Elements, System Employing Them, and Methods of Their Use"

Introduction:

Assay devices constructed with functionalized micro-length tubes as have been described, and particularly glass nano-reactors (GNRs), have important uses with respect to nucleic acid detection, to DNA assays and generally to the field of genomics detection (For uses see Mastichiadis C, Niotis A E, Petrou P S, Kakabakos S E, Misiakos K. Capillary-based immunoassays, immunosensors and DNA sensors—steps towards integration and multi-analysis. TrAC Trends in Analytical Chemistry 2008; 27: 771-84.))

Many of these uses employ fluorescent dyes that produce fluorescence when stimulated by excitation energy, in particular, by epi-fluorescent detection, and especially when a laser is the excitation source.

Detection of Hybridized DNA:

While we refer to DNA probes immobilized on GNRs to detect DNA molecules in solution, it is understood that this extends more broadly to nucleic acids in general, and can include RNA probes immobilized on GNRs to hybridize RNA molecules in solution, DNA probes to capture RNA in solution and RNA probes to capture solution-phase DNA molecules.

Implementations employ functionalizing a GNR with an appropriate DNA capture agent (or probes) and spiking in a known concentration of DNA oligomers (or targets). Those DNA targets are then flowed with the sample (or other fluid of interest) through the system and hybridized to the complementary strands immobilized on the DNA GNRs. At sufficient concentrations and using suitable detection systems, these hybridized molecules can generate a detectable fluorescent signal indicating that flow has occurred across the GNR, or an indication of the quantification of that flow.

Detection Systems and Processes:

This hybridized DNA is typically a synthetic molecule custom synthesized from any of the commercially available oligo supply houses (e.g. Integrated DNA Technologies IDTDNA.com), or an amplicon, the end-product of an amplification reaction such as PCR, or various isothermal reactions (Hyberbranched Amplification, Helicase reactions, qPCR, cold-PCR, etc), as these methods can easily generate the relatively high concentrations of DNA required for fluorescent detection. These higher concentration DNA hybridization events can be visualized either by the use of an intercalating agent such as Sybrgreen (Life Technologies) or Ethidium Bromide. Those dyes, when excited as by laser, generate a signal if they have become inserted between the strands of a DNA double helix, but generate no, or reduced, signal when present with only a single strand. Alternatively, the DNA strands in solution can be directly fluorescently labeled either during commercial synthesis, or using any of the chemical or enzymatic methods known to those practiced in the art (e.g. PCR with labeled nucleotides, etc). In this manner DNA strands that are sufficiently complimentary to the "capture" strands immobilized on the GNR are bound to the GNR, and thus confer fluorescent signal when excited by a laser.

In other cases, the DNA immobilized on the GNR is modified to generate signal following hybridization. DNA strands known in the art as hairpin probes (including so-called molecular beacons, scorpion probes and the like) are specifically designed to fluoresce, or increase in fluorescence, following the hybridization of a complimentary molecule. Although there can be modifications, a typical design includes a DNA molecule that possess a fluorescent dye and a quencher molecule located on different bases of the molecule, typically at the distal ends of the strand. These probes are typically self-complementary; hence normally found in a closed, hairpin confirmation wherein the fluor and the quencher are in close proximity and non-fluorescent. When the probes binds to a complimentary sequence, however, the molecule becomes linear and double stranded, separating the fluor from the quencher and fluorescence results.

We understand that it is also possible to generate detectable, quantifiable fluorescence resulting from lower concentration DNA hybridization events, such as those typically seen with populations of native, unamplified DNA, or levels seen circulating in the bloodstream even without DNA amplification. In such cases the signal resulting from a hybridization event is amplified, as opposed to amplifying the hybridizing DNA itself. Examples of this include, but are not limited to, the use of Quantum Dots, which have extremely high levels of fluorescence per molecule, and other processes including Tyramide Signal Amplification (TSA) Systems (PerkinElmer), 3DNA Array Detection (Genisphere, LLC) and Rolling Circle Amplification that generate multiple fluors per individual binding event.

Applications:

One application is in the context of a protein assay device, as in a portable cartridge constructed for protein assays. This useful mode of utilization of DNA employs, in a single channel through which sample or other fluid of interest flows, one or more GNR's functionalized for one or more protein assays, and one or more additional GNRs functionalized for capture detection of a given DNA strand. Here the capture and detection of a DNA tracer is used as a run control, a confirmation of appropriate fluid flow through the channel, and proper operation of the device (not for informational purpose from the sample). With a selected functionalization for DNA, one achieves an orthogonal tracer that has no influence or cross-reactivity with ambient protein. This meets the monitoring need for situations in which adding or spiking-in an additional protein to the sample fluid for monitoring purposes would produce risk of cross-reaction or would otherwise be objectionable. A similar application utilizes a single sample flowing through multiple parallel channels, in which at least one channel is devoted to only one or more protein assay GNRs, but another channel has one or more GNRs functionalized to DNA for monitoring purposes, that channel having only one or more GNRs functionalized for DNA or also including GNRs for other purposes, such as protein assay mentioned earlier.

This has direct application in the clinical research market as it gives clinicians a process to confirm whether the cartridge functioned as intended. It is simply a validation that the cartridge functioned properly. This allows them to read negative results as likely a true negative rather than a false negative resulting from an assay failure.

In other applications the DNA is employed as a signal calibrator, where the fluorescent signal from the DNA is compared to an expected signal, and the observed signal is either corrected to match the expected signal (the difference presumably due to differences in fluid flow rates, laser intensity or focus), or is simply confirmed to be within a predefined range, and hence acceptable, or outside the range, and thus unacceptable, thus alerting the user of possible poor quality data.

In other iterations, multiple types of GNRs are produced, each complimentary to an individual population of DNA targets. These distinct GNRs can all be placed in the same channel, or can be spread across multiple channels. When the various DNA target populations are spiked into the sample at different concentrations, the data is used to generate a calibration curve. This calibration curve is either used in conjunction with pre-determined relationships between DNA signal and protein concentration to determine the concentration of proteins detected by antibody-coated GNRs, or can be used to calibrate the signal from one instrument with another, thus ensuring that data generated on one system is equivalent with that generated on another.

Capture of Native DNA from Samples:

GNR-based DNA capture also enables the detection or monitoring detect of the levels of a specific DNA sequence or sequences in a sample, whether it be solely DNA detection, or a hybrid system in which protein and DNA are simultaneously detected using respective GNRs in a single system. In either case populations of GNRs are made with capture strands complementary to the sequence of interest, for instance a sequence in circulating blood or in cell lysate. As with the previous example of the calibration curves, multiple different populations of GNRs, specific for different DNA target populations can be generated and employed within a single channel, or cartridge provided sufficient discrimination exists between hybridization conditions for the various target sequences. In situations where a high concentration of DNA is available, DNA amplification is not required. The utility of non-amplified systems depends upon how many copies are present in the sample. For example when one is looking at specific viral loads, depending on the level of a virus present in a patient, one may encounter suitably high levels of DNA. Also in the case of transgenic organisms, multiple copies of specific genes introduced into the transgene are often present a high level.

For lower levels, amplification independent detection systems (TSA, RCA, 3D-array) have been previously described. Alternatively, DNA targets can either be amplified prior to analysis on the system the many processes known to those versed in the art (PCR, etc) or a system of amplification is provided to enable amplification within the cartridge channels themselves (described later under CARTRIDGE DESIGN CONSIDERATIONS).

Regardless of whether DNA amplification is required, this technology has application for monitoring and/or quantifying populations of organisms based on their genetics. For example, genetically modified organisms can be monitored both by detecting the genes spliced into the organism through the engineering process itself, but also the presence of proteins that the introduced genes cause the organism to express. This provides value in several ways; one is in confirming the presence of a genetically-modified organism if one was interested in promoting or monitoring that—for example in ensuring that seeds sent to farmers where successfully modified, confirming that harvested crops expressed the beneficial traits that the engineering was intended to provide (e.g. the increased nutritional value in golden rice) or in determining to what extent the traits are expressed in the final product (i.e. the relative success of the engineering process). Alternatively, the process can be employed to ensure organic crops are free of engineered seed. This is of particular interest to the organic farming profession as a whole, and certain geographic areas such as Europe. This invention addresses the requirement to test multiple samples and analytes (DNA or protein) simultaneously with a relatively small footprint and high ease of use. This type of system is employed at transportation hubs, ports of entry and other areas where the crops are concentrated after harvest (grain silos, etc.).

Diagnostic applications include the ability to monitor disease progression via the patient's biological response (protein production, e.g. cytokines) and the level of the infectious agent (by DNA signature). For example, in the case of flu outbreaks, one can simultaneously monitoring a patient's cytokine levels while quantifying the relative abundance of flu strains as indicated by GNR's specific diagnostic DNA sequences for the major flu subtypes.

The DNA-based GNR system can also be used as an enrichment application, where capture probes are immobilized to the GNR, and a sample is flowed through the channel, with complimentary sequence binding to the GNRs. The capture can be employed for one of two purposes. Either the captured material can be released in a subsequent wash step, and recovered for downstream manipulation of the enriched nucleic acid, such as next-gen sequencing. Conversely, the capture process can be employed to REMOVE unwanted sequence from a sample, as a form of subtractive hybridization. Here a high concentration, possibly confounding DNA species can be removed from the sample to enable downstream manipulation of the residual nucleic acid.

Cartridge Design Considerations:

The ability to intermingle the DNA and antibody GNRs in the same channel or place them in discrete channels provides the ability to either maximize plexity (the number of distinct analytes measured in one assay) or to employ substantially different reagents for the different detection systems if required. For example, if DNA detection requires buffers and conditions that are not amenable to antibody based detection, separate channels can be employed, while if the two systems utilize similar conditions the two assays can be combined, saving real estate and enabling more assays to be run per cartridge. DNA binding rates and specificities can be controlled through buffer composition and the presence of additives such as salt, DMSO, TMAC/TMAO and free Mg++ to mention a few. Individually addressable channels permit the use of channel-specific additives or hybridization buffers designed to ensure maximal hybridization conditions for the DNA probes.

When assays are separated by channels, additional opportunities arise for tailoring the specific reaction conditions in a channel by channel manner. For example, localized heating of microfluidic chips is known to the field employing strategies including, but not limited to, diodes, resistive heaters, flexible heating tape (e.g. kapton heaters), peltier heating blocks, resistance heating of etched indium tin oxide coated slides, and IR light exposure. Hybridization temperatures of given nucleic acids are determined by a number of factors, mainly the sequence length and base content (the relative amount of A, C, T and G nucleotides). If the temperature is too far above the hybridization temperature, the complimentary strands will not anneal. If it is too low, non-specific binding of non-complimentary strands can result. Thermal control is allows the hybridization temperature of a given channel to be tailored to the optimized temperature for the nucleic acid hybridizing in the channel.

Not only can the channel temperature be controlled, but the spatial channel separation, possibly in conjunction with thermal isolation/insulation strategies including air gaps, insulating foam or rubber or peltier cooling pads, allow the temperature of a given channel to be shifted dramatically relative to the temperature of a neighboring channel. This provides a variety of benefits. Reaction temperatures are easily adjusted to ensure optimal DNA hybridization temperatures, providing optimal specificity for DNA capture probes in each individual channel. Also, thermal control of the individual channel permits combination of thermally stabile and thermally labile assays. Assays that require or benefit from elevated temperature (such as nucleic acid hybridizations) can be run concurrently with assays that require stabile or reduced temperatures such as protein assays by isolating thermal exchange from one channel to the next.

Benefits of GNRs for DNA-Based Detection

Physical characteristics of the GNR itself provide substantial benefits for nucleic acid-based applications relative to substrates typically used in the industry. One significant advantage GNRs provide to any application (DNA or antibody based) is that they are easily manufactured in large, low cost batches. This enables quality control testing of a statistically relevant portion of the manufactured lot, and performance-based acceptance PRIOR to placement in cartridge. This is not possible in platforms that rely on spotted capture antibodies or DNA probes such as microarray. Spots can only be QC'd after the microarray is completed, and the spotting process itself is a variable one, with spot diameter and spotted concentrations changing during the manufacturing run. After the run is completed, a small section of the completed microarrays are sampled, and the entire run is accepted or rejected based on those results, with high material and labor costs incurred when scrappage occurs.

An additional advantage is seen when GNRs are compared to the various types of beads used in other commercial platforms. These bead based platforms typically employ either a relatively dense pack of nonporous beads in kind of a column layer, relatively large, porous, agarose or some sort of scaffolded bead comprised of cross linked polymers resemble a whiffle ball or a dandelion. While it is possible to achieve high concentrations of immobilized material on these beads, problems arise when they are exposed to samples containing biological debris, such as tissue chunks, blood clots, or cellular, or even contaminants from the everyday world such as threads, lint, dust or particulate matter. Due to their porous nature, bead-based platforms are susceptible to clogging. For example, the pore diameters in these porous beads are typically described in terms of angstroms, through which even soluble proteins can exhibit difficulty passing. Cellular debris and other particulates quickly clog the bead pores and impede the flow of any reagent through the bead, inhibiting the assay process and increasing the backpressure in the system, sometimes with catastrophic results.

In comparison, the GNR is designed as a straight pipe with an internal diameter of 75 microns, (750000 angstroms), roughly 10 times the diameter of a red blood cell. As a result, the GNR is extremely tolerant of particulate material, which readily passes through the GNR and out into waste without impeding analyte diffusion to the capture probes immobilized on the walls of the GNR.

It should also be noted that large particular matter is easily filtered the inclusion of a membrane filter directly under sample wells. In this manifestation, even particulates sufficiently large to block the 75 micron GNR would be easily prevented from entering the system. This has significant value in that it enables the use of whole blood as a sample, preventing the passage of clots, etc. into the system microfluidics, and eliminating time consuming and laborious centrifugation steps prior to analysis of clinical samples.

Lastly, the process through which DNA and antibodies are immobilized on the GNRs results in capture moieties attached to the internal surfaces, but not the external surfaces of the GNR. This enables robotic or other pincer-based mechanical systems to physically place GNRs in the channels of the cartridge during the manufacturing process without concern for damaging the immobilized capture molecules. The fact that the immobilization surface is protected, physically shielded by the outside of the GNR tube, protected from any sort of mechanical damage or insult whether it is in pick and place or handling in any form.

Figures 104, 105:
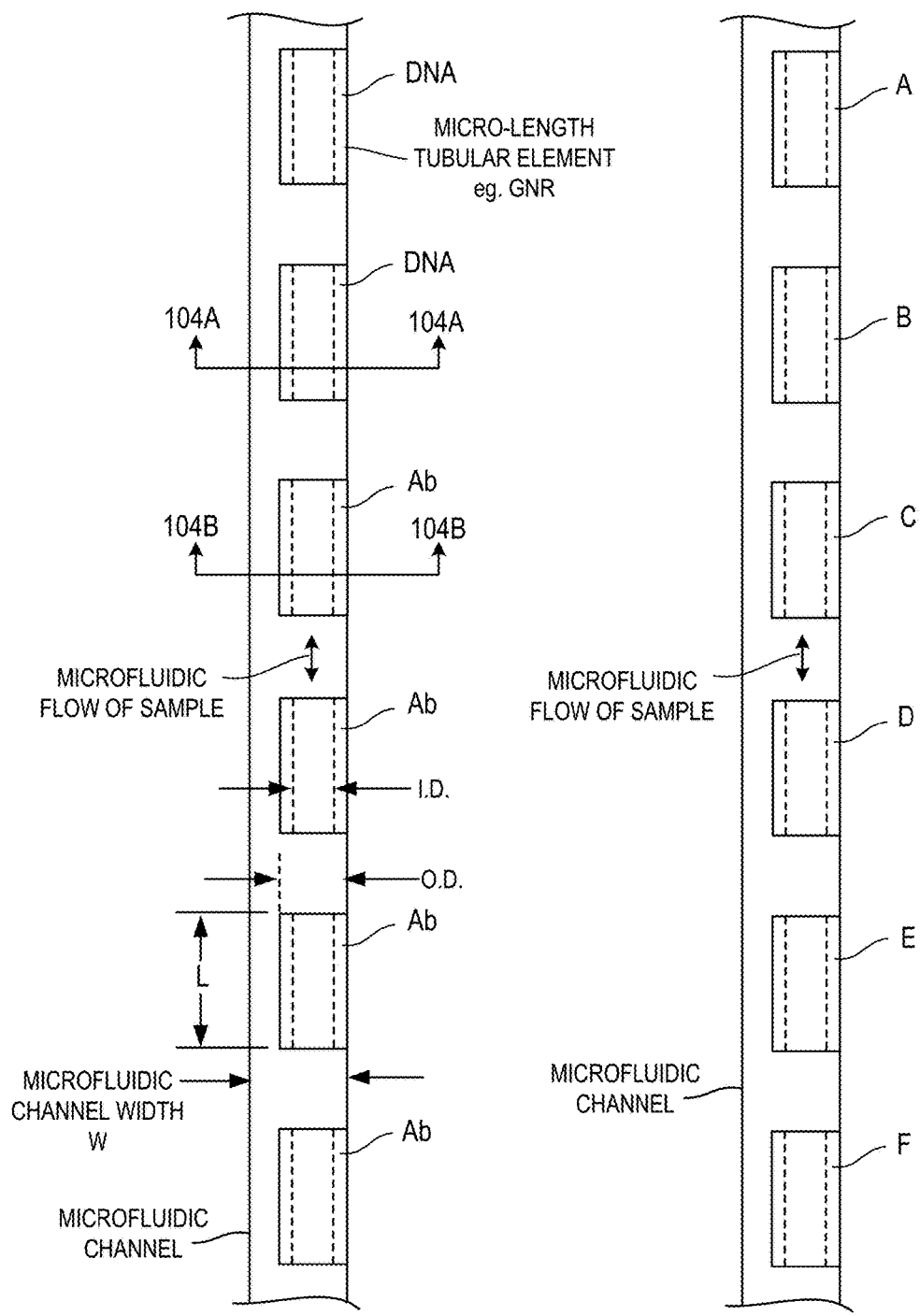
Figure 104A:
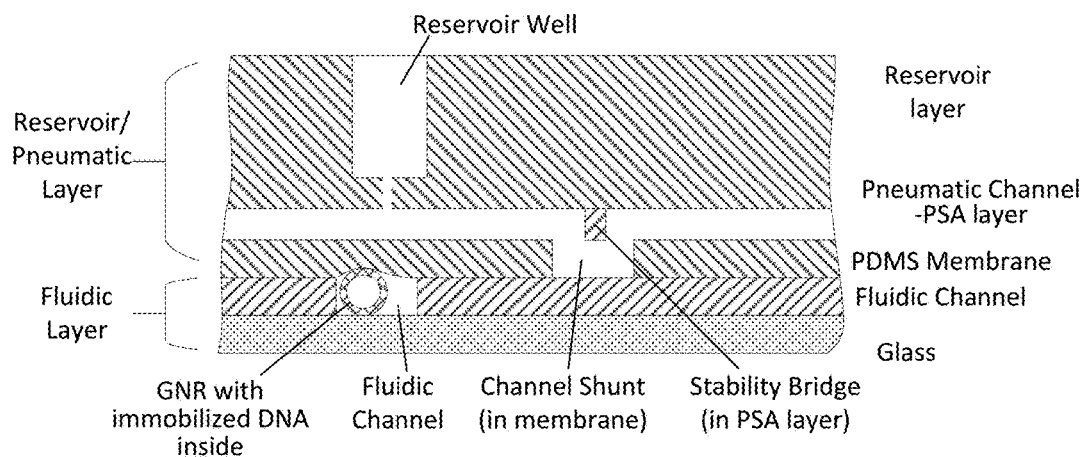
FIGS. 104A and 104B are partially broken away cross sectional views of a device implementing FIG. 104, taken at respective lines indicated in FIG. 104.
Figure 104B:
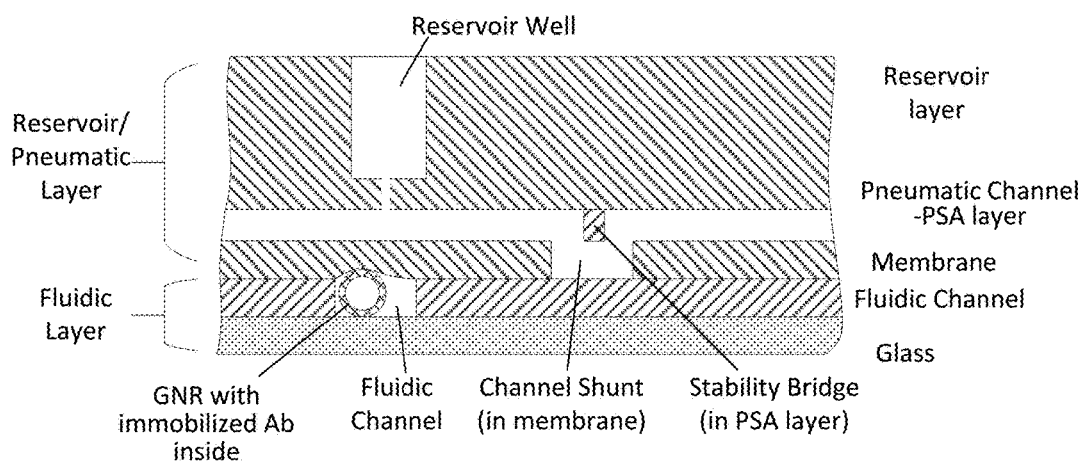

Novel systems employ the PDMS-confined micro-length tube elements with nucleic acid, antibody or antigen capture agent (i.e., probe) immobilized on internal surfaces of the elements: Besides those previously described in the many examples above, are the following:

In a given microfluidic channel, a combination of (a) one or more micro-length tubes are internally functionalized with nucleic acid capture agent and (b) one or more micro-length tubes are internally functionalized with capture agent for antibody-antigen binding. The agents are selected, and present within the micro-length tubes in sufficient number of each type element, with active agent in sufficient concentrations, to enable the nucleic-acid functionalized elements to detect a complementary tracer and serve as an assay control or in a monitoring system for an antibody-antigen assay conducted by successive back- and forth flows within the microfluidic channel. An example arrangement is illustrated in FIGS. 104, 104A and 104B.

The reverse can also be usefully employed. That implementation uses a tracer for antibody-antigen binding with respect to a nucleic acid assay. As well, a tracer of one nucleic acid can be employed with respect to an assay for another nucleic acid, using appropriately functionalized micro-length tubes for capture of the tracer and for the assay.

Typically, in any of these cases, more micro-length tube elements are provided for the assay than for tracer detection. In a preferred implementation, the micro-length tubes of each functionalization are pre-formed en masse, as by dicing long drawn tubing, batch functionalized with respective capture agents, and micro-length tube elements from the batch are located in the micro-fluidic channel. This can be done by a pick-and-place instrument, such as tweezer or vacuum tip instrument, which may be manual or under automated control as previously described.

The microfluidic system may be provided in a portable cartridge, devoted to a single sample, or multiple microfluidic networks may be provided, having respectively different sample wells or sources.

The capture protocol is preferably implemented with flows of successive sample, wash and reagent(s), each flow phase including a succession of back and forth movements of a given slug of a given fluid, slug dimension of the order of 100 times the length of a micro-length tube element, with sufficient number of successive slugs of that fluid to carry out the intended phase of the assay, before the next fluid of the assay sequence is introduced.

Figure 106:
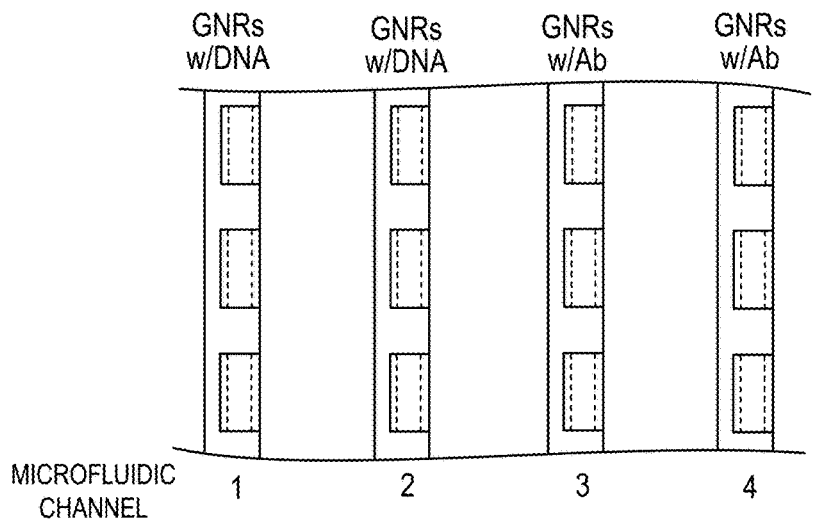
FIG. 106 is a diagrammatic view of four parallel microfluidic channels containing micro-length tubes, on the insides of which are immobilized capture agent; in channels 1 and 2 the capture agent is DNA and in channels 3 and 4, the capture agent is antibody.
Figure 107:
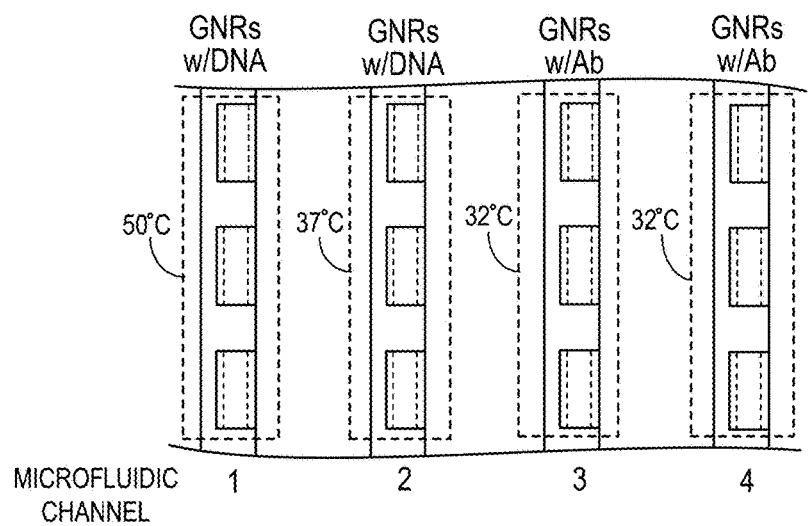
FIG. 107 is a is a diagrammatic view of four parallel microfluidic channels containing micro-length tubes, on the insides of which are immobilized capture agent, in channels 1 and 2 the capture agent is DNA and in channels 3 and 4, the capture agent is antibody, and with zones heated at different respective temperatures.

In a given microfluidic channel, a series of micro-length tube elements immobilizing a nucleic acid capture agent to their interior surfaces are provided for passive (i.e. without amplification) analytical detection of a native nucleic acid (or more than one) in a sample. An example is given in FIG. 105. In some cases, a tracer as described in (1) is also included. Again, in preferred implementations, the micro-length tubular elements are pre-formed en masse, batch functionalized with respective capture agents, and elements from the batch are located in the channel, e.g. by a pick-and-place instrument, which may be manual or under the automated control shown. The microfluidic system may be provided in a portable cartridge, devoted to a single sample, or multiple microfluidic networks may be provided, having respectively different sample sources;

Using a plurality of parallel, isolated micro-channels connected to receive portions of the same sample, differing sets of internally functionalized micro-length tube elements are provided, for conducting multiple independent assays on the same sample, each as described for (2), with or without a tracer as described in (1), at least some of the micro-length tube elements being functionalized with nucleic acid. An example is shown in FIG. 106. In preferred implementations, two or more parallel channels receive sample from the same source and discharge to a common waste receptacle, as shown previously. In a particularly important implementation of (3), multiple channels are provided with nucleic acid immobilized within micro-length tubes, the nucleic acids being different species in the respectively different channels, and provisions are made for applying different reaction conditions to the respectively different channels, for instance, different temperature conditions. An example is shown in FIG. 107.

In an antibody-antigen assay device having multiple parallel channels receiving portions of the same sample, one or more nucleic acid probes may be incorporated in each channel to detect a tracer, according to feature (1) above, thus to obtain indication of proper operation of each channel, which may be conducting a different assay from the rest. An example is given in FIG. 108.

In FIGS. 104, 104A, 104B, 105, 106, 107 and 108, for purposes of illustration, but by no means limiting, the nucleic acids illustrated in the figures are shown as DNA (i.e. single strand DNA), but like examples can be employed with other forms of nucleic acid, for instance single strand RNA or mRNA. Similarly, the immobilized capture agent for antibody-antigen binding are shown as an antibody, but antigens can alternatively be immobilized as capture agents against antibody targets. Micro-length tubes of various compositions can be used, for instance transparent plastic with low fluorescence, but the presently preferred form is glass, forming glass nano-reactors (GNRs), and those are shown in the following examples. In any case the tubes are preferably sections of drawn form, with the smooth internal surface characteristics of the drawing process, in which the material is progressively drawn from a heated ingot or progressively emerges through a stationary die.

Where employed for fluorescent assays, the substance is chosen to be transparent to the wavelengths of fluorescence passing outwardly, and in the case of stimulated fluorescent emission, also to the wave length of the stimulating radiation passing inwardly. In other cases, in which the micro-length tubes are employed to capture a target for extraction for other forms of assay or processing, the micro-length tubes need not be transparent.

FIGS. 104, 104A and 104B illustrate a microfluidic channel that is part of a microfluidic network having micro-valves and micro-pistons, all as previously described herein, that produce flows in the channel. The microfluidic channel is of width W, for instance 180 micron. A series of micro-length tube elements, e.g. GNR's, are held immobilized in the channel by a PDMS membrane that forms the top of the channel. For instance the GNR's may have an outside diameter O.D. of 125 micron, inside diameter I.D. of 75 micron, and length L. of 250 micron. (The further examples can employ similar dimensions, for example). Other regions of the same PDMS membrane form pneumatically deflectable portions of pneumatically actuated valves and pistons that produce the indicated channel flow in response to positive and negative pneumatic pressure applied to respective deflection chambers, controlled by a network of pneumatic channels connectible to a pneumatic controller, all as previously described.

In the series of GNRs in the micro-fluidic channel, the inner surface of the first two GNRs carry immobilized DNA for capturing a target tracer and the following four GNRs carry immobilized antibodies, e.g. for assay. This arrangement is useful in an antibody detection platform in which the DNA-immobilized GNRs are used as a control for the execution of the assay, i.e. to determine that the right fluid has flowed at the right rate and right duration. This arrangement is also useful to passively detect (i.e. without amplification) native DNA occurring at high enough concentrations not requiring biological or signal amplification. In this particular case both DNA and antibody detection occur in a single channel using immobilized GN's.

In the case of use for control, a tracer is spiked into the sample containing a complementary nucleic acid strand, e.g., a DNA strand to bind to an immobilized DNA strand on the internal surface of the GNR.

For monitoring, a specific complementary strand of nucleic acid, e.g. RNA or DNA, is spiked into a fluid, for example one of the reagents used for the execution of a quantitative antibody test. At the end, presence of the complementary strand is determined using fluorescent detection. The resultant signal detected from the nucleic acid immobilized GNRs is compared to a defined acceptable range of values for the determination of proper execution of the related step of the assay. Falling within acceptance limits would be a positive indication that the respective reagent was present and the protocol in this respect was executed properly.

Another use with respect to nucleic acid, concerns immobilizing nucleic acid to the surface of the GNRs for capture of a native nucleic acid in a sample. Referring to FIG. 105, a series of 6 GNRs are placed in a single channel, the internal surface of each GNR having immobilized DNA for capture of native nucleic acid in a sample. The nucleic acid species may be the same for the set of GNRs, e.g. for purpose of assay redundancy, or different, to detect different species. In this case it is preferable that the GNR-immobilizing PDMS membrane be permanently bonded to structure forming the walls of the channel, to achieve a robust assay device. This may be by use of PDMS activated surface bonding previously described herein, using the make and break technique at the associated micro-valves. An alternative use for the arrangement shown is to capture DNA for extraction and assay by other means or for further processing. In this case, the PDMS membrane is not surface-activated during manufacture, and forms a removable bond with a cooperating surface such as another layer of un-surface-activated PDMS in which channels sides are cut or glass forming the channel sides.

In FIG. 106, instead of having a single channel with immobilized nucleic acid GNR's, a series of channels is provided, illustrated here by 4 parallel channels, in which a selected combination of nucleic acid-immobilized GNRs and antibody-immobilized GNRs are placed. For example, FIG. 106 illustrates channels 1 and 2 having nucleic acid-immobilized GNRs and channels 3 and 4 having antibody-immobilized GNRs.

FIG. 107 again has 4 parallel channels with nucleic acid-immobilized GNRs in channels 1 and 2 and antibody-immobilized GNRs in channels 3 and 4, with the addition of selected channels being uniquely heated. In the example, channel 1 is shown to be heated to a temperature of 50 degrees Celsius, channel 2 to a temperature of 37 degrees Celsius, and the remaining two channels heated to 32 degrees Celsius. The specific elevated heating of channels 1 and 2 are for the purpose of optimizing the specificity of the nucleic acid binding properties for the particular nucleic acids that are used in those channels.

Figure 108:
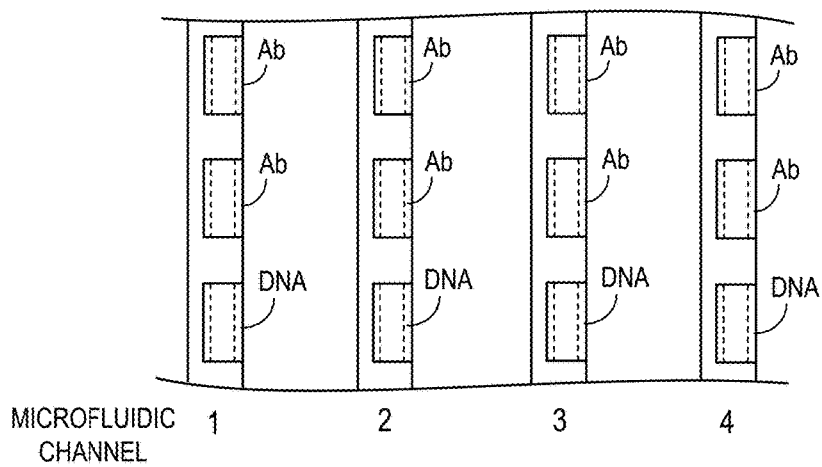
FIG. 108 is a diagrammatic view of four parallel microfluidic channels containing micro-length tubes, on the insides of which are immobilized capture agent, each channel containing micro-length tubes, two having inside surfaces functionalized with antibody and one functionalized with DNA.

FIG. 108 illustrates 4 channels with 3 GNRs in each channel, the first 2 GNR's in each channel having antibodies immobilized on the GNRs while the $3^{rd}$ GNR in each channel has nucleic acid immobilized on the GNR for the purpose of running control using the nucleic acid GNRs or, in the alternative, for the purpose of passive detection of native DNA.

In all those cases involving assay detection of a captured target, one of the many known techniques of detecting by fluorescence, and especially stimulated fluorescent signal is employed, in many cases using laser-excited epi-fluorescent scanning or imaging.

Figure 109:
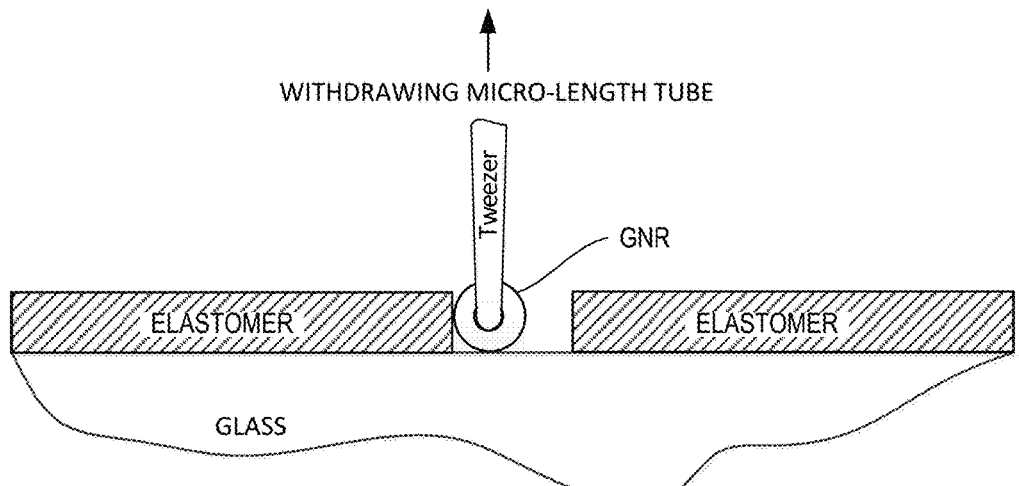
FIGS. 109 and 109A are diagrammatic views from the end and side of a micro-length tube element being plucked by tweezers for removal from an open fluidic channel of larger width than the element, using tweezers the same as those shown respectively in FIGS. 18B and 21.
Figure 109A:
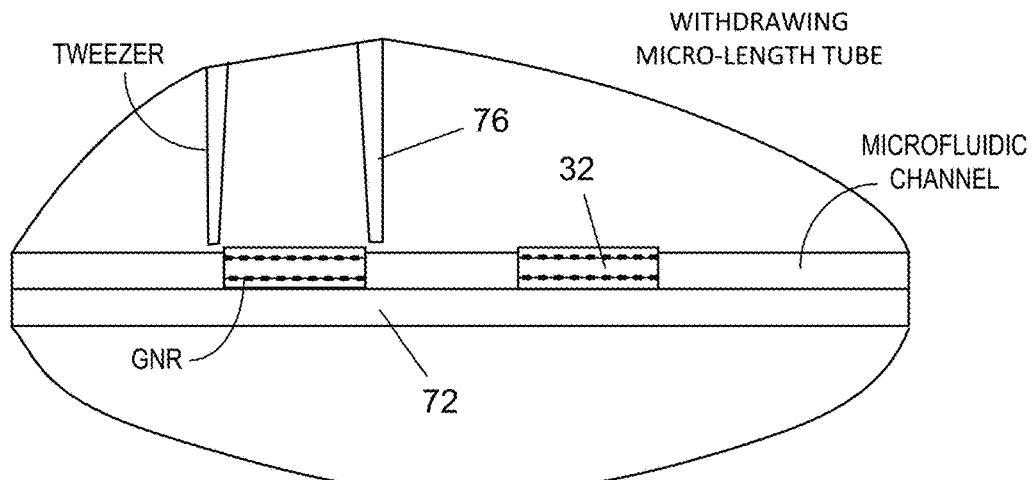
Figure 110:
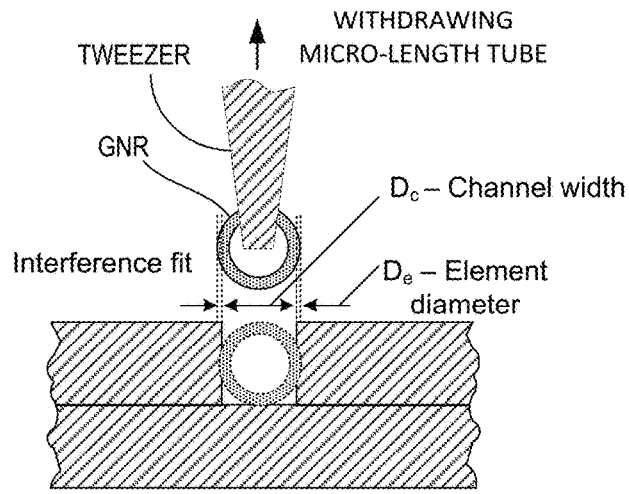
FIG. 110 is a diagrammatic view from the end of a micro-length tube element being plucked from an open fluidic channel of smaller width than the element, using a tweezer the same as shown in FIG. 9G.

In other cases, as previously mentioned, it is desired to employ the unique system for harvesting the captured species or analyte for assay by other means or for further processing. In this case the PDMS membrane, un-surface activated, serves the useful purpose of forming a detachable bond to a like surface of PDMS or other surface such as glass. After the capture or assay procedure is run, the membrane is removed, preferably it being a bonded part to a pneumatically control layer removed with it. This exposes for removal the GNRs carrying internally the captured material, nucleic acid, antibody or antigen (or with other functionalized elements, other captured entity). A useful means of removing the elements is using tools the same or similar to those used in placing the elements in the first place, whether hand tools or automated tools. FIGS. 109, 109A and 110 illustrate use of the same tools previously described with respect to placing the elements, FIGS. 109 and 109A illustrating removal of a micro-length element with tweezers in the case of channel width being greater than width of the microtubes, while FIG. 110 illustrate removing a GNR with tweezers for a channel in which the micro-length elements have been force-fit.

In general, a theory regarding ambient analyte optimization, is described by Roger Ekin, in certain papers, including: R. P. Ekins, "Towards immunoassays of greater sensitivity, specificity, and speed: an overview", in: A. Albertini, R. Ekins (Eds.), "Monoclonal Antibodies and Developments in Immunoassay", Elsevier/North-Holland, Biomedical, Amsterdam, 1981, pp. 3-21, which is incorporated herein by reference to the extent necessary to understand the present invention, makes several key predictions, and is contingent upon choosing assay conditions such that the reaction kinetics proceed in the ambient analyte regime. The requirements for, and various benefits of, operating in ambient analyte ("a.a.") regime, include the following: There is superior signal-to-noise and limits of detection, which maximizes the detection signal relative to background noise; the assay results are not affected by variations in sample volume, such as pipetting errors or other variations; the assay results are not affected by variations of capture surface area, typically based on surface area variations caused by manufacturing of the GNRs; the ambient analyte (a.a.) condition is approximated by the relationship: # of binding sites on the GNR<0.1 VKd (where V=Sample Volume, and Kd=the equilibrium dissociation constant); for a GNR having dimensions (in microns) of 265(L)×125(OD)×75(ID), the Number of binding sites on the GNR is approximately 0.6 VKd, which is close to (i.e., approaching) the desired ambient analyte condition but not fully in that condition.

As is known, the ambient analyte ("a.a.") theory is shown by the below equation for f and optimization occurs when f (fractional occupancy of binding sites) is maximized in the below equation, where f is dependent on surface density of binding sites, surface area, reaction volume, equilibrium dissociation constant and the analyte concentration.

$$f = \frac{(a+b+1) - \sqrt{(a+b+1)^2 - 4ab}}{2b}$$

$$b = \frac{S\Gamma_m}{VKd}$$

$$a = \frac{A_0}{Kd}$$

$f$ = fractional occupancy $\Gamma/\Gamma_m$ $S$ = Surface Area $\Gamma_m$ = max surface concentration of occupied receptors (moles/cm$^2$)

$\Gamma$ = surface concentration of occupied receptors (moles/cm$^2$)

$V$ = reaction volume($L$)

$A_0$ = Analyte concentration (moles/$L$)

$Kd$ = Equilibrium dissociation constant($M$)

Figure 111:
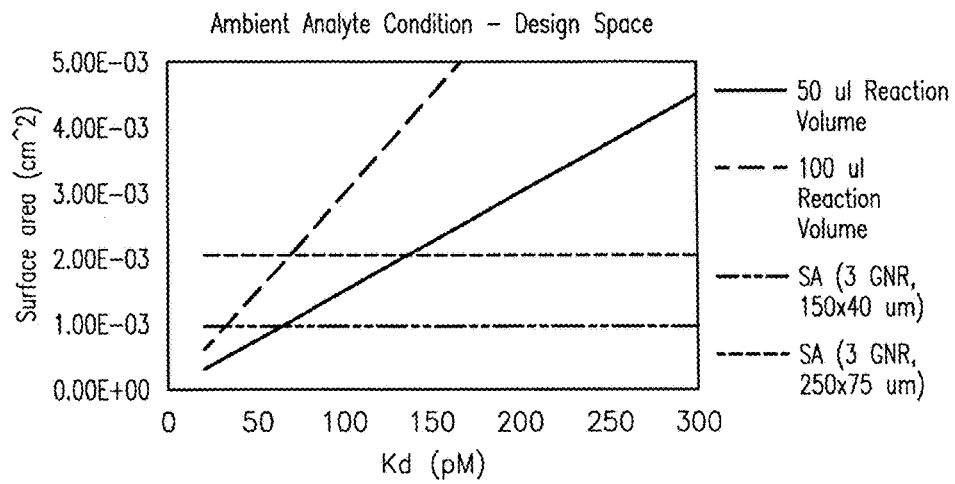
FIGS. 111 and 112 are line drawings showing the ambient analyte design space, in accordance with embodiments of the present invention.
Figure 112:
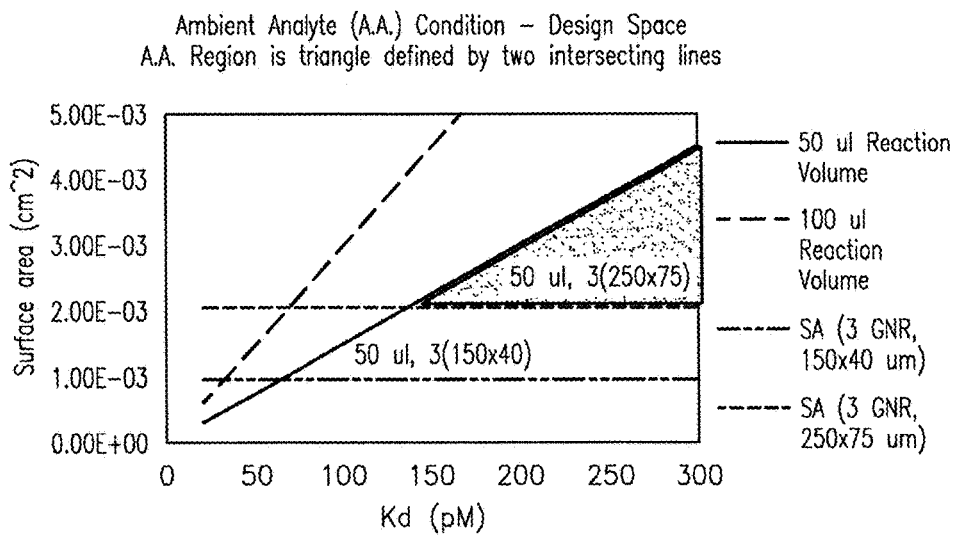

Referring to FIGS. 111 and 112, the ambient analyte design condition is shown. In particular, users typically desire to use the least amount of precious sample possible. Also, 50 ul (microliters) was chosen as the minimum reaction volume required by a user to make multi-analyte measurement. Ultra high affinity antibodies have Kd's around 10-50 pM (picomoles). It is desirable to use these in the a.a. region to realize the full benefit of these highly sensitive antibodies. Also, high affinity Ab's require less surface area to remain in the ambient analyte region. For present configuration (3 GNRs, 250×75 um and 50 ul reagent volume) the minimum Kd still in the a.a. region is 130 pM. Accordingly, reducing the GNR size to about 150×40 um would decrease the minimum Kd from 130 pM to about 60 pM. Also, increasing the minimum reagent volume to 100 ul would decrease the minimum Kd to about 25 pM. Any or all of the above can be done to further improve assay performance and get even closer to the ambient analyte condition. Other sample volumes can be used if desired, depending on the performance requirements of the assay in view of that discussed herein.

Figure 113:
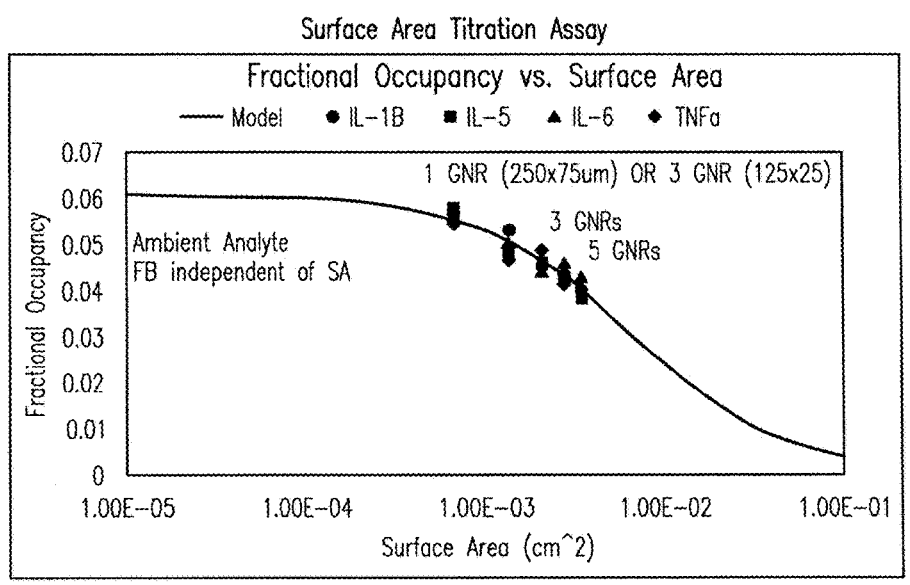
FIG. 113 is a graph of fractional occupancy vs. surface area, in accordance with embodiments of the present invention.

Referring to FIG. 113, the curve shows results of a surface area titration assay, showing the fractional occupancy vs. surface area. In particular, for this experiment: Surface Area (SA) varied by populating channels with either 1, 2, 3, 4 or 5 GNRs. Present configuration uses 3 GNRs (as seen on graph, not ambient analyte region). Total Surface Area (SA) ~2e5 sq. um (or 2e-3 sq. cm). This shows that for 1 GNR (with dimensions 250×75) OR 3 GNRs (with dimensions 150×25), and an OD of 125 microns for both, the assay is essentially in the ambient analyte ("a.a.") regime for Kd=60 pM. Estimated SA variance due to manufacturing processes ~7e3 sq. um. Sensitivity to SA variation ~2.5e-6%/sq. um. Anticipated % CV due to GNR surface area fluctuation is about <1%, which is a desirable result. Even though the assay in this example is not operating in the full ambient analyte region, the GNR surface area is tightly controlled enough in the GNR manufacturing processes to sufficiently reduce signal variation due to GNR surface area variation. Thus, decreasing the surface area of the GNRs from 250×125×75 to a smaller surface area, would further reduce sensitivity to surface area variation and optimize performance with even high affinity Ab's (antibodies), as discussed herein.

An estimate of Antibody surface density for the GNR is as shown in the below table:

| Ab dia | 8 nm |
| Ab diam | 0.008 um |

| area | 5.02655E-05 um$^2$ |
| density | 19,894 per um$^2$ |
| % of sites active | 20% |
| active density | 3,979 per um$^2$ |
| mass | 15,000 Da |
| density | 6.6E-21 moles/um$^2$ |
| density | 6.6E-13 moles/cm$^2$ |
| Surface Density | 3979 Sites/um$^2$ |

Figure 114:
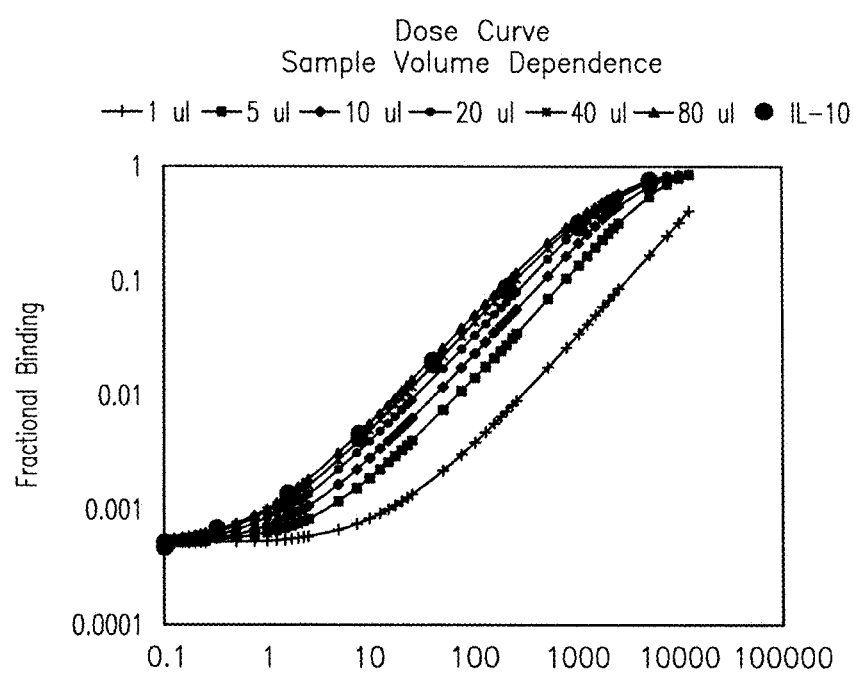
FIG. 114 is a graph of a family of dose curves for fractional binding and sample volume dependence, in accordance with embodiments of the present invention.

Referring to FIG. 114, the graph shows the dose curve dependence on reaction volume. In particular, a rapid decrease in curve sensitivity occurs for reaction volumes less than 20 ul. Also, curve shape remains nearly unaffected for reaction volumes greater than 40 ul. Therefore, a minimum reaction volume of about 40 ul is desired to perform the assay and meet the desired performance criteria discussed herein. Other sample volumes may be used; however, the performance may be degraded. The model parameters for graph shown are: Kd=60 pM; Surface Density=3,000 sites/SQ. um; and Surface Area (SA)=0.002 sq. cm for 3 GNRs, at 250×75 um.

Figure 115:
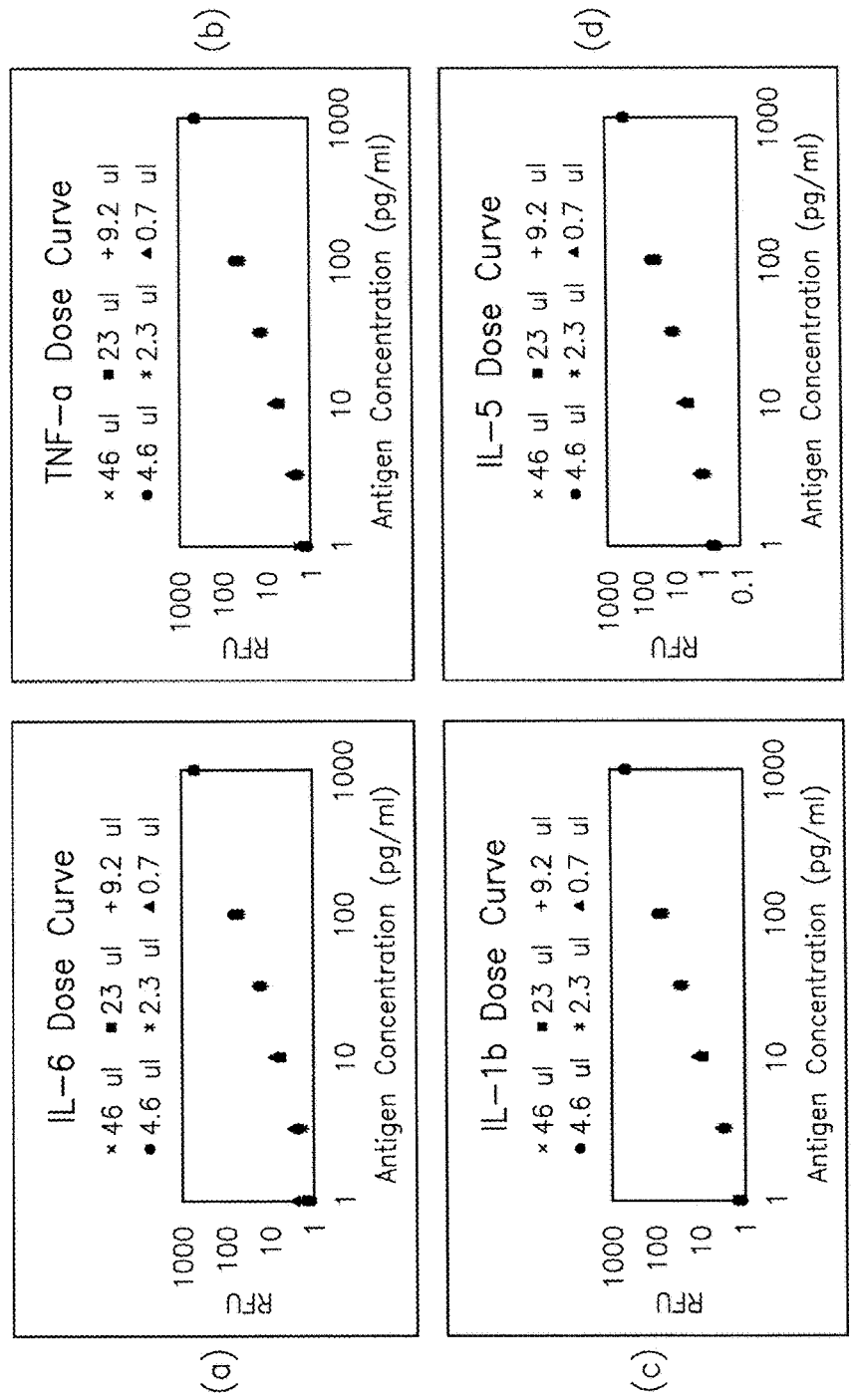
FIG. 115, illustrations (a)-(d), are graphs of dose curves for four different antigens, in accordance with embodiments of the present invention.

Referring to FIG. 115, illustrations (a)-(d), for the dose curves shown, the assays appears to be substantially insensitive to consumed sample volume. Accordingly, the GNR capture surface has full access to reaction volume and sample homogenization (or mixing or equilibrating) is occurring as a result of piston reciprocation.

Figure 116:
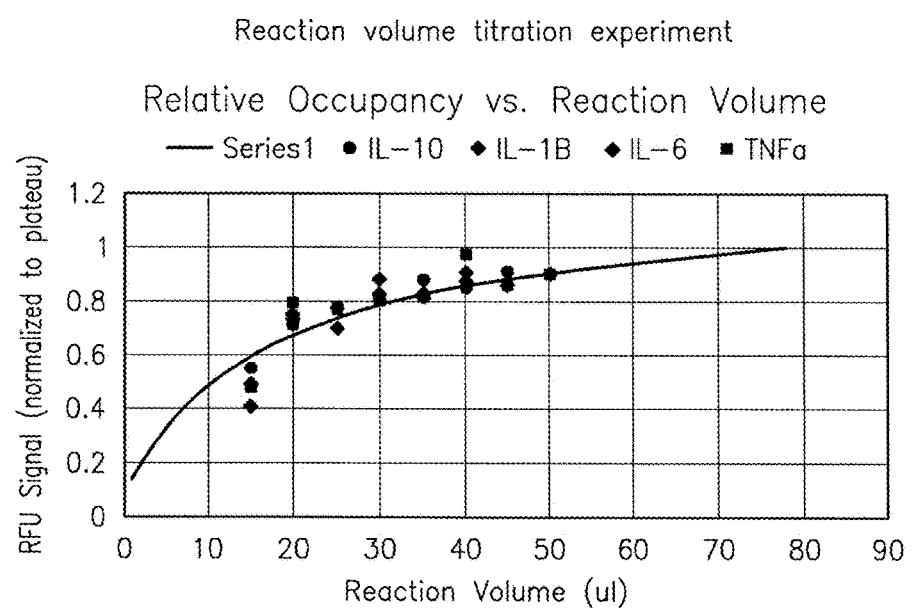
FIG. 116 is a graph of RFU signal vs. reaction volume, in accordance with embodiments of the present invention.

Referring to FIG. 116, in performing a reaction volume titration experiment, we found the following: decreasing reaction volumes result in decreasing signal, especially below 40 ul; the signal becomes almost independent of reaction volume above 50 ul; in this experiment with 3 GNRs (250×75) and 4 analytes, the consumed volume less than 5 ul, and varied volume of sample in reservoir from 15 to 50 ul. Also, from a mathematical model, Kd=60 pM, 3000 capture sites/sq. um, for 3 GNRs (250×75 um).

In view of the analysis shown herein regarding ambient analyte, we have found that to further optimize approaching the ambient analyte condition the GNRs may be made on the order of about 150 microns long, about 125 microns outer diameter (or possibly about 100 microns), and about 25 microns inner diameter. Such dimensions would be achievable with current manufacturing limitations (drawing, dicing). This also takes into account potential end face effects of about 20% of the length and a limiting the inner diameter to a minimum of about 25 microns to avoid potential clogging issues. In that case the Surface Area (SA) is reduced from about 0.02 sq. cm (with a GNR of 250(L)×125(OD)×75(ID) microns) to about 0.0007 sq. cm (with a GNR of 150(L)×125(OD)×25(ID) microns). Other dimensions may be used but may not optimize these parameters.

Figure 117:
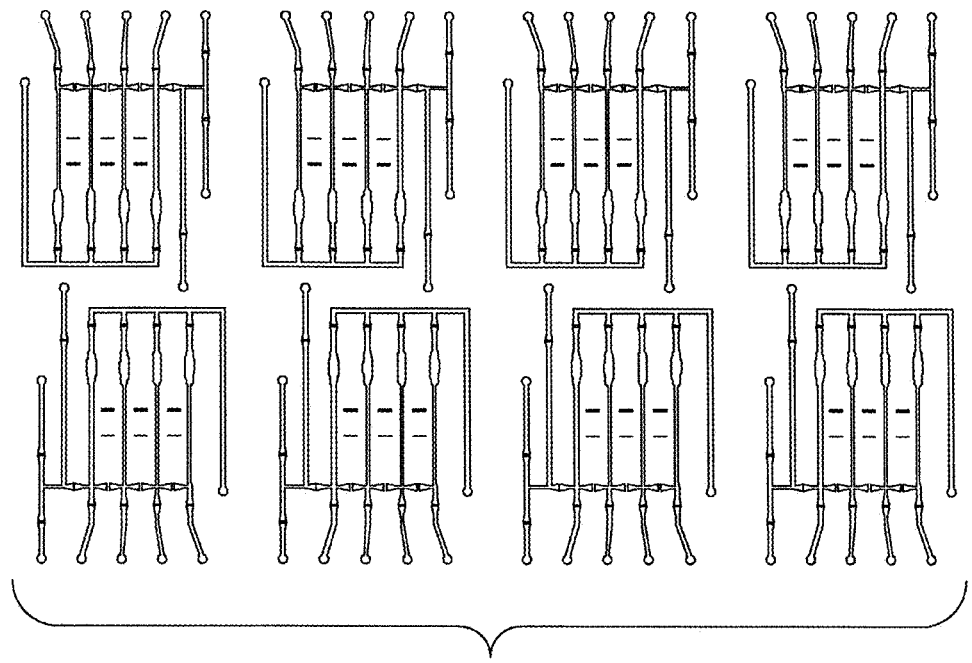
FIG. 117 is a top view of eight fluidic circuits, in accordance with embodiments of the present invention.
Figure 118:
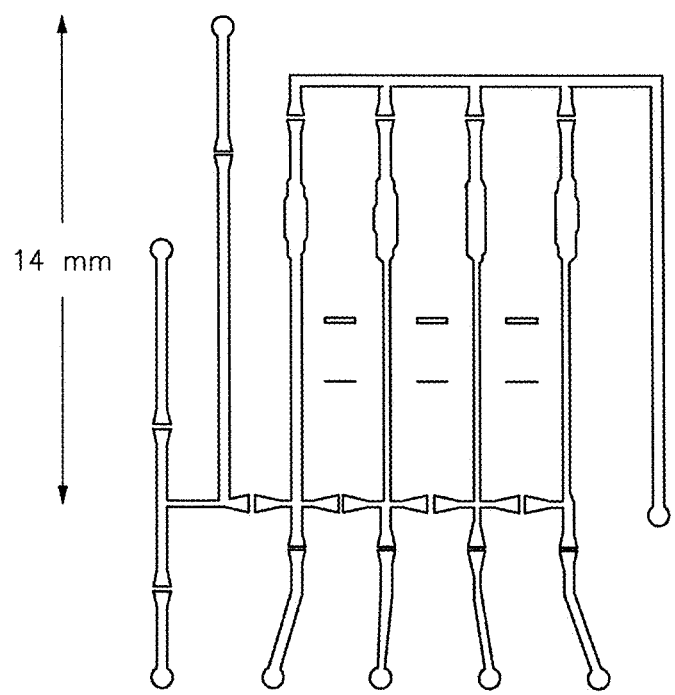
FIG. 118 is a top view of an exploded view of one fluidic circuit, in accordance with embodiments of the present invention.

FIGS. 117 and 118, shows the fluidic architecture for some of the analysis performed herein, which includes: 8 circuit fluidic layer (2 fluidic layers per cartridge); Circuits are fluidically isolated from one another; Each circuit contains 4 isolation channels with 3 GNRs each; and Each isolation channel is used to measure a unique analyte; and the piston volume is 0.3 microliters.

Figure 119:
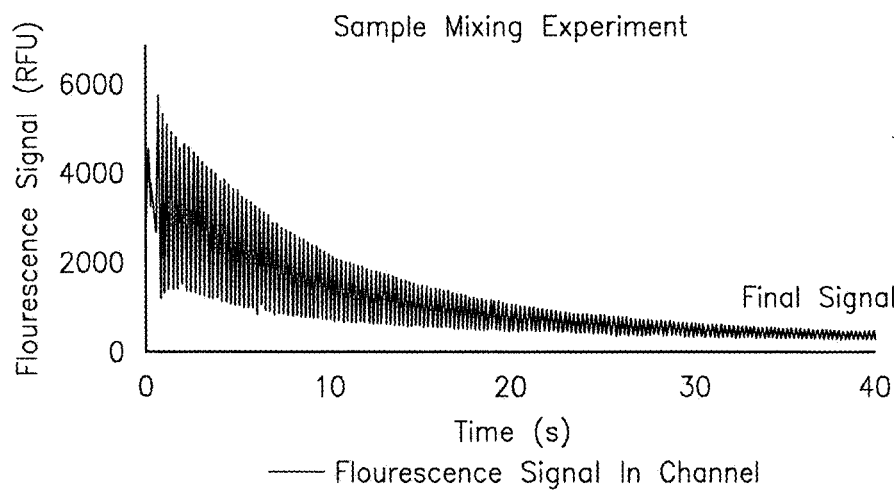
FIG. 119 is a graph of fluorescent signal vs. time for a sample mixing experiment, in accordance with embodiments of the present invention.
Figure 120:
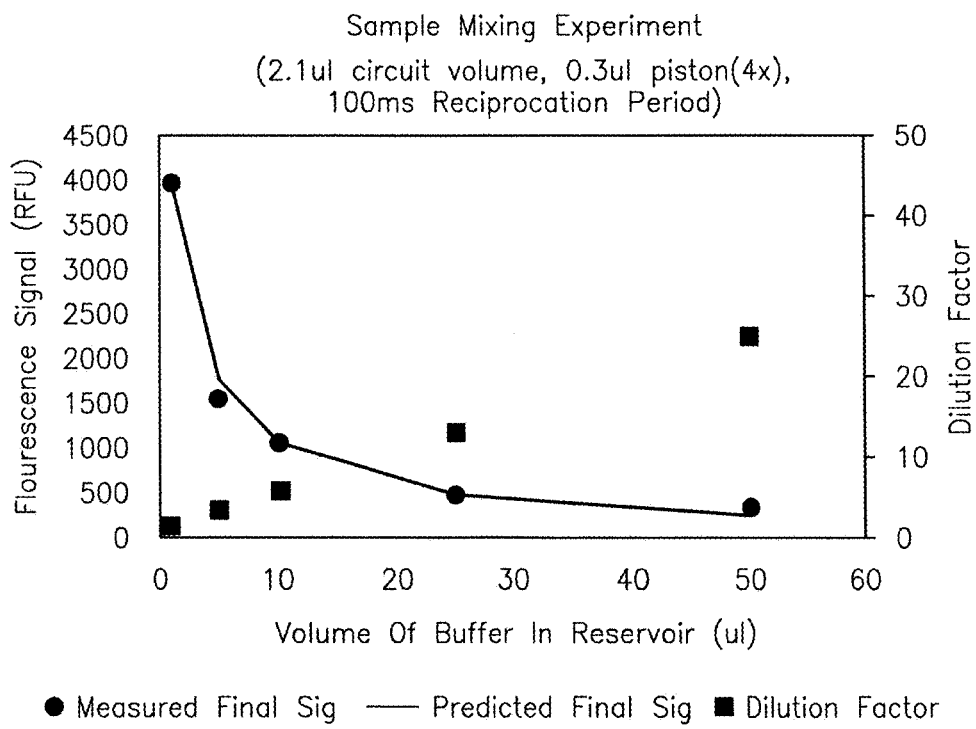
FIG. 120 is a graph of fluorescent signal vs. volume of buffer in reservoir for a sample mixing experiment, in accordance with embodiments of the present invention.

FIGS. 119 and 120, show the results of a mixing experiment where: Circuit Volume=2.1 ul; Fluidic circuit initially filled with fluorescent dye; Sample reservoir initially filled with clear buffer (50 ul); Piston actuation: 100 ms open state followed by 100 ms closed state; Continuous piston actuation for 60 seconds; Fluorescence interrogated near GNR location.

The observations from this experiment were as follows: Peak signal for each piston stroke decays over time, indicating that the buffer and the dye are mixing over time; Final fluorescence signal is asymptotically reached at about 40 seconds, indicating that buffer and dye are completely mixed in 40 sec.; Final signal level is predicted by scaling initial signal by dilution factor; DF (Dilution Factor)=(circuit volume+sample volume)/circuit volume. Accordingly, we have shown that for at least one embodiment of the system of the present invention, complete mixing of the sample volume occurs.

In one embodiment, reagent reciprocation (also referred to herein as piston sloshing, includes the following parameters: Pulse volume=1.2 ul (4×0.3 ul); Pulse Duration=50 ms; AVG volumetric Flow Rate=24 ul/s; Slosh Period=200 ms (open to close states); piston volume=0.3 microliters.

Accordingly, reagent reciprocation provides full access to the bulk sample volume and eliminates sample diffusion limitations near the surface of capture surface of the GNRs. More specifically, we have found that in a stationary condition, where a portion of the sample volume is brought into the reaction channel and allowed to sit undisturbed and in contact with the capture surface for a period of time, the analyte concentration would become depleted as a result of rapid binding to the capture surface. This is exacerbated in microfluidic channels due to their very large length to width aspect ratios. Since diffusion distances may realistically only be about 3 mm over the span of a 40 min incubation period and the fact that the channel volume is very low, typically about 1.0 ul, only a small portion of the reaction volume would interact with the GNR capture surface. Rapid reciprocation serves to replenish the concentration locally by carrying the depleted sample back to the sample reservoir where it is homogenized (or equilibrated) with the full reaction volume, thereby removing diffusion limitations on the reaction kinetics and thus maximizing the utilization of the sample reaction volume.

The micro-length tube element 32 may also be referred to herein as a "GNR" (glass nano reactor), a species of micro-length tube, or as "micro-flow element", "microtube", or "micro-bore tube", all intended to refer to a tubular element of micro length; a micro-length tube in the context of a detection element captured in a channel, which can be regarded as an unique and advantageous species of a "micro element", a "microparticle" or a "micro-length particle".

As referred to herein, a "batch" (or bulk number) of the GNRs 32, is typically the amount of GNRs located in the Eppendorff tube (or other tube capable of performing the functions described herein) that is exposed to the capture agent, and is at least thousands, e.g., typically about 75,000 to 150,000. In that case, each tube of GNRs 32 constitutes a "batch."

Regarding removal of capture agent from the exterior of the GNR 32 (as discussed herein), it is known for typical particle assays to use gentle agitation of the particles (in this case the GNRs) during silanization and functionalization, e.g., using magnetic stir bars, a rotisserie, gentle rocking, gentle vortexing, or other techniques to move the GNRs around in the fluid (or fluid around the GNRs), to achieve good mixing. However, we found that when gentle vortexing was done during GNR functionalization, some of the capture agent was removed from the outer surface of the GNR 32. This caused further experimentation, which resulted in the discovery that all of the capture agent can be removed from the exterior cylindrical surface of the GNRs 32 by vigorous vortexing as described herein.

The appropriate vortexing speed and diameter, is dependent on the nature of the suspension liquid, e.g., the viscosity of the liquid chosen, and size of the GNRs 32, and can be easily determined experimentally. It is set by observing whether the capture agent is effectively non-existent on the outside, long surface of the GNRs 32 (e.g., the outside cylindrical surface in the case of the body being of circular cross-section), while also ensuring that the internal coating along the axial length of the GNR 32 is substantially uniform (as discussed herein).

After the GNRs 32 are allowed to roam on the alignment plate 70, they fall into the alignment pockets still in the presence of the stabilizing solution. The alignment plate 70 may be gently rocked or agitated, to facilitate the GNR capture process. For example, the plate 70 may be first rocked about the longitudinal axis of the pockets allowing many of the GNRs to fall into the pockets, then rocked about an axis perpendicular (or other orientation) to the axis of the pockets to redistribute the remaining GNRs, then switch back to the longitudinal axis, and repeat until the GNRs populate most (e.g., more than 95%) of the pockets on the plate 70.

We have found that an accurate and repeatable biochemical assay with highly sensitive quantitative results can be achieved without removing the capture agent from the end faces of the GNR 32 (e.g., without ablating the ends faces or otherwise removing capture agents from the end faces). In particular, this occurs because the surface area of the end faces are not significant enough to cause depletion problems, and, thus, can maintain a condition that substantially approaches or nears the ambient analyte theory conditions, and because the optical signal from the end faces are ignored (or filtered out) by the optical reader (as discussed hereinafter), and, thus, it does not contribute in an appreciable way to the optical noise floor.

Referring to FIG. 121, illustrations (a)-(d), regarding the length L, we have found that the shorter the length L of the GNR 32, the greater the uniformity of the coating density of capture agent molecules along the internal length L of the GNR 32 when coated by immersion as described herein. In particular, when the length L of the GNR 32 is on the order of about 1 mm or 1,000 microns (illustration (a)), an axial coating density curve (or profile) 610 showing the capture agent molecule coating density along the internal axial (or longitudinal) length of the GNR 32, shows a significant portion of the axial length (near the middle of the GNR length) with very low coating density, which is very detrimental to obtaining sufficient binding to detect reagents and thus to obtaining sufficient optical signal for assay measurement readings/results. When the GNR 32 has a length of about 750 microns, the axial coating density profile 610 also shows a low coating density near the middle of the GNR length, but not as severe as the 1 mm length (illustration (b)).

We have found that as the length L of the GNRs 32 gets shorter than about 750 microns, the uniformity of the capture agent coating density curve 610 of the inner surface of the GNR 32 improves significantly. In particular, the coating density curve 610 becomes more uniform when the length L is about 500 microns, but still exhibits a decrease in coating density (illustration (c)) near the middle of the GNR length. When the length L is about 250 microns or less (illustration (d)), the coating density curve 610 is substantially constant along the entire length L of the GNR 32, thereby providing maximum binding to detect reagents and, thus, maximum optical signal for the assay measurement results.

We have also found that even if the axial coating density curve 610 for a given GNR length L is not completely uniform (or flat) over the entire GNR length, it will not adversely affect the performance or quality of the assay results, provided the coating density profile is consistent from one GNR to the next (for a given GNR batch) and any non-uniformity does not have any substantial negative effects on the optical measurement of the assay results.

In addition to the axial coating density decreasing significantly for longer GNR lengths, there are also optical edge effects caused by capture agent on the two end faces of the GNR and possibly other optical effects, such as reflection or refraction of incident light from the edge faces. Such effects can distort the optical measurement signal for the assay results. As a result of these edge effects, a certain distance from the end of the GNR 32 (e.g., about 15 microns) may not be usable for assay measurement purposes, as indicated by the vertical dashed lines 612. Accordingly, the usable region of flat or uniform coated inner surface of the GNR 32 is further reduced by the edge effects 612.

In addition, another advantage of shorter GNRs is that they are more amenable to withstanding axial tweezing forces during pick and place motions.

Referring to FIGS. 122 and 123, an assay cartridge creation process and a process for running an assay with the present invention is shown.

Referring to FIG. 124, a top view of the fluidic and pneumatic channels are shown for a cartridge having 16 sample wells, 16 fluidic circuits (each having 4 channels with GNRs) and 64 detection analyte input ports. It also shows how the fluidic and pneumatic channels intersect with the valve and piston features of the present invention. Referring to FIG. 125, a top view of the pneumatic channels laser cut (or otherwise machined or formed) on the underside of the reservoir member is shown for the channels. More specifically, the pneumatic channels provide paths for actuating the internal valves and pistons for moving fluids, as described herein. The pneumatic channels are closed by a double-sided adhesive sheet (PSA layer), pressure sensitive adhesive layer, which lies between the PDMS membrane and the reservoir layer. The PSA layer has cut-outs (or through holes of various geometries), that define pneumatic cavities for the valves and pistons, into which the membrane deflects in response to pneumatic negative pressure (or vacuum) applied by the pneumatic channels which are cut into the reservoir layer, as described hereinabove.

As discussed herein, bypass flow is provided around the GNRs 32 of the present multi-analyte detection system, in which multiple channels discharge sample fluid back to the sample chamber for mixing. Such bypass flow has several benefits. In particular, it enables full sample mixing, thereby allowing the entire sample volume to be used in the assay, which allows the sample volume to be substantially independent of the number of analyte channels, and allows the system to be sized for minimum sample volume. In addition, it decouples the overall channel flow impedance from the GNR internal flow impedance, thereby enabling both flow effects to be optimized. In addition, having such bypass flow does not impact the repeatability and consistency of the measurement.

In particular, the flow mixing of the present invention provides a single source volume (e.g., 50 microliters) of a multi-analyte sample in the well, which can be used with N separate and different analyte test channels (or branches), where the sample volume is substantially independent of the number of analyte channels, provided the sample volume is a least as large as the total dead volume of the fluidics circuit. This is because of mixing of the entire sample volume that occurs between sample flowing in the channels with GNRs and the sample well, through the reciprocating flow, which is caused by repeated actuation of the dedicated piston in each branch of the multi-analyte assay.

Regarding flow impedance, the local flow impedance around the GNR 32 in the channels 30 is has two portions with very different impedances: i) the narrow internal detection passage along the inside of the GNR 32 which has a high flow impedance; and ii) the by-pass flow outside the GNR 32 along a non-analyte-capturing path which has a generally lower flow impedance.

This arrangement creates an overall low impedance to flow through the branch, which enables the sample liquid to flow at a relatively high velocity (highest velocity being near the center of the channel 30) when it is flowing back toward the sample well. This high velocity flow enables high efficiency mixing with the sample well contents upon each reciprocation of the piston. As a result of such mixing, the sample liquid in each trip through the particular branch contains a refreshed concentration of the particular analyte molecules, such concentration being of the order of the original sample concentration, thereby creating a condition that approaches the ambient analyte detection conditions. Accordingly, it is desirable for the channel flow impedance to be low to allow such high velocity flow to occur easier.

The high impedance portion of the flow that passes through the inside of the GNR 32 and past the immobilized capture agent, enables molecular capture to occur under quiescent flow conditions. This enables a high attachment efficiency of the analyte molecules and also avoids disturbing the molecular binding activity. In general, the internal diameter is desired to be small to reduce the assay surface area to achieve the desired assay performance, as discussed herein. As a result, the internal GNR flow impedance is relatively high to allow optimize these conditions.

Thus, this arrangement decouples the internal GNR flow impedance (which is relatively high), from the overall channel flow impedance (which is desired to be small), thereby allowing the design parameters of both to be optimized for their respective functions.

According to the present invention, in a multiplex microfluidic assay device for determining concentration of multiple molecular analytes in a sample fluid, for use with an assay system that includes microfluidic pump and valves, respective actuating controller for pumps and valves, and an assay reader, the assay device comprises: a sample well for receiving sample fluid to be analyzed, a plurality of fluidically parallel detection channels, each defining a microfluidic volume connectable by a manifold to the sample well by an associated inlet path, and each detection channel containing an immobilized capture agent specific to at least one of the plurality of analytes, the volume of each detection channel and its associated inlet path being a minor portion of the combined volume of the well, inlet path and, a plurality of secondary reagent channels connectible to respective detection channels to introduce respective secondary reagents specific to the assays to be performed in the respective detection channels, the detection channels being isolated or isolatable from one another during presence of respective secondary reagents to avoid cross-reactions, each of the plurality of detection channels associated with a dedicated reciprocal microfluidic pump operable by the operating system in repetitive cycles, each cycle having an intake stroke that defines the volume of a fluid segment and a discharge stroke, the pumps each constructed, during an analyte capture stage of the assay, in its intake stroke to move a microfluidic segment of sample from the common sample well through the respective detection channel for exposure to the immobilized capture agent, and in a discharge stroke move the sample segment backwardly past the immobilized capture agent toward the inlet passage for further exposure to the immobilized capture agent, the device constructed to determine concentration of the respective analytes in the sample on the basis of capture of analytes substantially dependent on the concentration value of analyte in the sample, wherein each reciprocal pump has intake stroke volume and velocity such that during each discharge stroke of the pump, at least a portion of the previously withdrawn fluid is returned beyond the respective detection channel for mixing with segments from other channels that are likewise returned, such that during the analyte capture stage of the assay the concentration of analyte in repeated segments of fluid sample passing through a given detection channel is not substantially depleted of the respective analyte due to previous sample capture cycles performed on segments of liquid in that microfluidic channel.

According further to the invention, a multiplex assay device for determining concentrations of multiple analytes in a sample, the device having multiplicity of microfluidic channels containing capture agent for respectively different analytes, each channel fed a portion of the fluid sample from a common reservoir to expose the portions of the sample to the respective capture agents, the device constructed, for each channel, following exposure of the flow to the respective capture agents, to direct at least a portion of the respective flows to return to a common volume in which it is mixed with flows from the other channels, thus to provide a supply of substantially undepleted concentration of the analytes for repetitive flows through the channels, the device constructed to determine concentration of the respective analytes in the sample on the basis of capture of the respective analytes in quantity substantially dependent on the concentration value of the analyte in the original sample.

According further to the invention, wherein the common volume is at least partly defined by a common manifold passage, and/or wherein the common volume is defined at least in part by the common reservoir. Still further according to the present invention, wherein the flow paths for the return flows comprise reverse direction flow in conduits originally introducing sample to the respective channels containing the capture agents.

A number of embodiments of the invention have been described. Nevertheless, it will be understood that various modifications may be made without departing from the spirit and scope of the invention.

What is claimed is:

1. An operating and reading instrument for performing an assay employing a portable microfluidic assay cartridge, the instrument comprising a translatable table under automated control, the translatable table carrying a receiving region for the portable cartridge and carrying a port system connectible to the cartridge, the port system having at least one remotely automated source valve arranged to apply air at positive or negative pressures at selected times to the cartridge to operate micro-valves in the cartridge to perform the assay while the cartridge is on the translatable table and is connected to the port system;

a stationary planar radiant heater plate having a planar radiant heater surface mounted in close proximity to, and parallel with, a planar cartridge surface of the cartridge on the translation table, the planar cartridge surface being adjacent to enclosed microfluidic channels in the cartridge, there being an air gap between the planar radiant heating surface and the planar cartridge surface, the heater plate having a size sufficiently larger than the portable cartridge so that the fluidic portion of the cartridge is always adjacent to the radiant heater surface throughout a range of translation of the cartridge;

a stationary optical system constructed to inspect the cartridge along an optical inspection axis; and the heater plate having an aperture through which the optical inspection axis extends.

2. The instrument of claim 1 in which the supply valve or valves on the translatable table are solenoid-operated.

3. The instrument of claim 1 in which a flexible hose or hoses connect the supply valve or valves on the translatable table to a fixed pressure source.

4. The instrument of claim 1 in which the port system on the translatable table comprises a raised rigid boss with an engaging rim constructed to engage a compliant surface at a receiving port of the portable cartridge to form a fluid tight seal.

5. The instrument of claim 1 in which there are a plurality of adjacent receiving ports on the portable cartridge and the port system on the translatable table comprises a ganged set of rigid bosses having engaging rims lying in the same plane, constructed to engage a planar compliant surface on the cartridge.

6. The instrument of claim 1 including a clamp mechanism constructed to clamp the portable cartridge against the porting system carried on the translatable table.

7. The instrument of claim 6 in which the clamp mechanism comprises a lever mounted on a pivot axis, having a manual operating portion and a load applying portion for pressing the cartridge against the porting system, the manual operating portion spaced substantially further from the pivot axis than the load applying portion.

8. The instrument of claim 1 wherein the stationary optical system is constructed to inspect the cartridge during movement of the table, and the table is constructed to move the cartridge across the fixed optical axis to enable imaging different regions of the cartridge.

9. The instrument of claim 1 in which the optical instrument is constructed to inspect the cartridge by epi-fluorescence.

10. The instrument of claim 1 in which the table is movable in X and Y orthogonal coordinates.

11. The instrument of claim 1 constructed and programmed to translate the cartridge for inspection during conduct of the fluid flow portions of the assay for monitoring or determining location of portions of the microfluidic system.

12. The instrument of claim 1 constructed and programmed to translate the cartridge for inspection after conduct of the fluid flow portions of the assay for reading the results of the assay.

13. The instrument of claim 1 constructed and programmed to perform an immunoassay on the cartridge.

14. The instrument of claim 1 constructed and programmed to perform ELISA on the cartridge.

15. The instrument of claim 1 in which the only fluid connections to the cartridge are pneumatic connections.

16. The instrument of claim 1 wherein the port system comprises a manifold having at least one rigid pneumatic channel that connects the at least one supply valve to the cartridge, the channel having a predetermined dead volume and distance between the supply valve and the cartridge, the dead volume and distance being small enough to not affect the speed of the assay performed in the cartridge.

17. The instrument of claim 1 wherein the supply valve rapidly switches from positive pressure to negative pressure.

18. The instrument of claim 1 wherein the supply valve switches from positive pressure to negative pressure greater than ten thousand times during the performance of the assay.

19. An operating and reading instrument for performing an assay employing a portable microfluidic assay cartridge, the instrument comprising a translatable table under automated control, the translatable table carrying a receiving region for the portable cartridge and carrying a port system connectible to the cartridge, the port system having at least one remotely automated source valve arranged to apply air at positive or negative pressures at selected times to the cartridge to operate microvalves in the cartridge to perform the assay while the cartridge is on the translatable table and is connected to the port system;
- the port system comprising a manifold having at least one pneumatic channel that connects the at least one supply valve to the cartridge, the channel having a predetermined dead volume and distance between the supply valve and the cartridge, the dead volume and distance being small enough to not affect the speed of the assay performed in the cartridge;
- a stationary planar radiant heater plate having a planar radiant heater surface mounted in close proximity to, and parallel with, a planar cartridge surface of the cartridge on the translation table, the planar cartridge surface being adjacent to enclosed microfluidic channels in the cartridge, there being an air gap between the planar radiant heating surface and the planar cartridge surface, the heater plate having a size sufficiently larger than the portable cartridge so that the fluidic portion of the cartridge is always adjacent to the radiant heater surface throughout a range of translation of the cartridge;
- a stationary optical system for inspecting the cartridge along an optical inspection axis; and
- the heater plate having an aperture through which the optical inspection axis extends.

20. An operating and reading instrument for performing an assay employing a portable microfluidic assay cartridge, the instrument comprising a translatable table under automated control, the translatable table carrying a receiving region for the portable cartridge and carrying a port system connectible to the cartridge, the port system having at least one remotely automated source valve arranged to apply air at positive or negative pressures at selected times to the cartridge to operate microvalves in the cartridge to perform the assay while the cartridge is on the translatable table and is connected to the port system;
- a stationary planar radiant heater plate having a planar radiant heater surface mounted in close proximity to, and parallel with, a planar cartridge surface of the cartridge on the translation table, the planar cartridge surface being adjacent to enclosed microfluidic channels in the cartridge, there being an air gap between the planar radiant heating surface and the planar cartridge surface, the heater plate having a size sufficiently larger than the portable cartridge so that the fluidic portion of the cartridge is always adjacent to the radiant heater surface throughout a range of translation of the cartridge;
- a stationary optical system constructed to inspect the cartridge during movement of the table, the optical system having a fixed optical axis and the table constructed to move the cartridge across the fixed optical axis to enable imaging different regions of the cartridge; and
- the heater plate having an aperture through which the optical inspection axis extends.

* * * * *

UNITED STATES PATENT AND TRADEMARK OFFICE
CERTIFICATE OF CORRECTION

PATENT NO. : 9,651,568 B2
APPLICATION NO. : 14/479290
DATED : May 16, 2017
INVENTOR(S) : Martin A. Putnam et al.

It is certified that error appears in the above-identified patent and that said Letters Patent is hereby corrected as shown below:

On the Title Page

In the References Cited, under U.S. Patent Documents please insert --U.S. Publication 2006/0053732 A1, Watson et al.--

Signed and Sealed this
Twentieth Day of March, 2018

Andrei Iancu
*Director of the United States Patent and Trademark Office*